US006927287B1

(12) United States Patent
Gruskin et al.

(10) Patent No.: US 6,927,287 B1
(45) Date of Patent: Aug. 9, 2005

(54) NUCLEIC ACID ENCODING EXTRACELLULAR MATRIX PROTEIN OR FRAGMENT THEREOF

(75) Inventors: Elliott A. Gruskin, Killingworth, CT (US); Douglas D. Buechter, Wallingford, CT (US); Guanghui Zhang, Guilford, CT (US); Kevin Connelly, Los Angeles, CA (US)

(73) Assignee: United States Surgical Corporation, Norwalk, CT (US)

( * ) Notice: Subject to any disclaimer, the term of this patent is extended or adjusted under 35 U.S.C. 154(b) by 343 days.

(21) Appl. No.: 10/153,469

(22) Filed: May 22, 2002

Related U.S. Application Data

(63) Continuation of application No. 09/169,768, filed on Oct. 9, 1998, now Pat. No. 6,492,508, which is a continuation-in-part of application No. 08/655,086, filed on Jun. 3, 1996, now Pat. No. 5,821,089.

(51) Int. Cl.[7] .................. C07H 21/02; C12Q 21/04; C07K 14/435
(52) U.S. Cl. .................. 536/23.5; 536/23.1; 530/350; 530/356
(58) Field of Search .................. 536/23.1, 23.5; 530/350, 356

(56) References Cited

U.S. PATENT DOCUMENTS 6,083,902 A * 7/2000 Cederhom-Williams ....... 514/2
6,492,508 B1 * 12/2002 Gruskin et al. ............ 536/23.5

FOREIGN PATENT DOCUMENTS

WO        WO 9003438        4/1991

OTHER PUBLICATIONS

Martin et al. Gene. Mar. 1995. 94: 159–166.*
Tan et al, "Proline Analogues Inhibit Human Skin Fibroblast Growth and Collagen Production in Culture", Journal of Investigative Dermatology, 80:261–267 (1983).
Noren et al, "A General Method for Site–Specific Incorporation of Unnatural Amino Acids Into Proteins", Science, vol. 244, pp. 182–188 (1989).
Dougherty et al, "Synthesis of a Genetically Engineered Repetitive Polypeptide Containing Periodic Selenomethionine Residues", Macromolecules, vol. 26, No. 7, pp. 1770–1781 (1993).
Uitto et al, "Procollagen Polypeptides Containing cis–4–Hydroxy–L–proline Are Overglycosylated and Secreted as Nonhelical Pro–y–Chains", Archives of Biochemistry and Biophysics, 185:1:214–221 (1978).
Papas et al, "Analysis of the Amino Acid Binding to the Proline Transfer Ribonucleic Acid Synthetase of *Escherichia coli*", Journal of Biological Chemistry, 245:7: 1588–1595 (1970).

Deming et al, "In Vitro Incorporation of Proline Analogs into Artificial Proteins", Poly.Mater.Sci.Engin.Proceed., vol. 71 (1994) pp. 673–674.
Ellman et al, "Site–Specific Incorporation of Novel Backbone Structures into Proteins", Science, 255:197–200 (1992).
Chung et al., "Probing the Role of Loop 2 in Ras Function with unnatural Amino Acids", Proc.Natl.Acad.Aci.USA 90 (1993) pp. 10145–10149.
Randhawa et al, "Incorporation of Norleucine at Methionine Positions in Recombinant Human Macrophage Colony Stimulating Factor (M–CSF, 4–153) Expressed in *Escherichia coli*; Structural Analysis", Biochemistry, vol. 33, No. 14 (1994) pp. 4352–4362.
Kiode et al, "Receptor–Binding Affinities of Human Epidermal Growth Factor Variants Having Unnatural Amino Acid Residues in Position 23", Biochemistry, vol. 33, No. 23 (1994) pp. 7470–7476.
Cornish et al, "Site–specific Incorporation of Biophysical Probes into Proteins", Proc. Natl.Acad.Sci.USA vol. 91 (1994) pp. 2910–2914.
Ellman et al, "Biosynthetic Method for Introducing Unnatural Amino Acids Site–Specifically into Proteins", Methods in Enzymology, vol. 202 (1991) pp. 301–336.
Kohne et al, "Non–protein Amino Acid Furanomycin, Unlike Isoleucine in Chemical Structure, Is Charged to Isoleucine tRNA by Isoleucyl–tRNA Synthetase and Incorporated into Protein", Journal of Biological Chemistry, vol. 265 (1990) pp. 6931–6935.
Richmond, "The Effect of Amino Acid Analogues on Growth and Protein Synthesis in Microorganisms", vol. 26 (1962) pp. 398–420.
Takeuchi et al, "Biosynthesis of Abnormal Collagens with Amino Acid Analogues", Biochimica et Biophysica Acta 175 (1969) pp. 156–164.
Uitto et al, "Incorporation of Proline Analogs into Procollagen", Archives of Biochemistry and Biophysics 181 (1977) pp. 293–299.
Rosenbloom et al., "Incorporation of 3, 4–Dehydropoline into Protocollagen and Collagen", The Journal of Biological Chemistry, vol. 245 pp. 3361–3368.

(Continued)

Primary Examiner—Carla J. Myers

(57) ABSTRACT

Incorporation of certain amino acid analogs into polypeptides produced by cells which do not ordinarily provide polypeptides containing such amino acid analogs is accomplished by subjecting the cells to growth media containing such amino acid analogs. The degree of incorporation can be regulated by adjusting the concentration of amino acid analogs in the media and/or by adjusting osmolality of the media. Such incorporation allows the chemical and physical characteristics of polypeptides to be altered and studied. In addition, nucleic acid and corresponding proteins including a domain from a physiologically active peptide and a domain from an extracellular matrix protein which is capable of providing a self-aggregate are provided. Human extracellular matrix proteins capable of providing a self-aggregate collagen are provided which are produced by prokaryotic cells. Preferred codon usage is employed to produce extracellular matrix proteins in prokaryotics.

2 Claims, 97 Drawing Sheets

OTHER PUBLICATIONS

Wilson et al, "Incorporation of Modified Amino Acids into Proteins in Vivo", Biochimica et Biophysica Acta, 781 (1984) pp. 205–215.

Christner et al., "Inhibition of the Assembly and Secretion of Procollagen by Incorporation of a Threonine Analogue, Hydroxynorvaline", The Journal of Biological Chemistry, vol. 250, No. 19 (1975) pp. 7623–7630.

Iouye et al, "Effects of the Stereo–Configuration of the Hydroxyl Group in 4–Hydroxyproline on the Triple–Helical Structures Formed by Homogeneous Peptides Resembling Collagen", Biochimica et Biophysica Acta 420 (1976) pp. 133–141.

Nolan et al, "Studies on the Mechanism of Reduction of Prolyl Hydroxylase Activity by D,L–3,4 Dehydroproline", Archives of Biochemistry and Biophysics, vol. 189, No. 2 (1978) pp. 448–453.

Jimenez et al, "Decreased Thermal Stability of Collagens Containing Analogs of Proline of Lysine", Archives of Biochemistry and Biophysics 163, (1974) pp. 459–465.

Uitto et al, "Incorporation of Proline Analogues into Collagen Polypeptides", Biochimica et Biophysica Acta, 336 (1974) pp. 234–251.

Uitto et al, "Incorporation of cis–hydroxyproline into collagen by tendon cells. Failure of the Intracellular Collagen to Assume a Triple–Helical Conformation", Biochimica et Biophysica Acta, 278 (1972) pp. 601–605.

Harsch et al, "Metabolism by Isolated Fibroblasts of Abnormal Collagens Containing Analogues of Proline or Lysine", FEBS Letters, vol. 26, No. 1 (1972) pp. 48–52.

Christner et al, "Effects of Incorporation of trans–4, 5–Dehydrolysine on Collagen Biosynthesis and Extrusion in Embryonic Chick Tibiae", The Journal of Biological Chemistry, vol. 246, No. 24 (1971) pp. 7551–7556.

Lane et al., "Effect of the Proline Analogue Azetidine–2–Carboxylic Acid on Collagen Synthesis In Vivo", Biochimica et Biophysica Acta 236 (1971) pp. 517–527.

Takeuchi et al., "Biosynthesis of Abnormal collgens with Amino Acid Analogues" Biochimica et Biophysica Acta 175 (1969) pp. 156–164.

Molenaar et al, "Characteristics and Osmoregulatory Roles of Uptake Systems or Proline and Glycine Betaine in Lactococcus Lactis", Journal of Bacteriology, vol. 175, No. 17 (1993) pp. 5438–5444.

Cayley et al, "Origins of the Osmoprotective Properties of Betaine and Proline in *Escherichia coli* K–12", Journal of Bacteriology, vol. 174, No. 5 (1992) pp. 1586–1595.

Uitto et al, "Inhibition of Collagen Acumulation by Proline Analogues; The Mechanism of Their Action".

Prockop et al, "The Biosynthesis of Collagen and Its Disorders", New England Journal of Medicine (1983) vol. 301, No. 1 pp. 13–22, No. 2 pp. 77–85.

Inouye et al, "Effects of the Stereo–Configuration of the Hydroxyl Group in 4–Hydroxyproline on the Triple–Helical Structures Formed by Homogeneous Peptides Resembling Collagen", Biochimica et Biophysica Acta, 420 (1976) pp. 133–141.

Venugopal et al, "Electrostatic Interactions in Collagen–like Triple–Helical Peptides", Biochemistry, vol. 33, No. 25 (1964) pp. 7948–7956.

Bella et al, "Crystal and Molecular Structure of a Collagen––Like Peptide at 1.9 A Resolution", Science, vol. 266 (1994) pp. 75–81.

Uitto et al., "Incorporation of Proline Analogs into Procollagen, Assay for Replacement of Imino Acids by cis–4–Hydroxy–L–Proline and cis–4–Fluoro–L–Proline", Archives of Biochemistry and Biophysics 181, pp. 293–299, 1977.

Takeuchi et al., "Biosynthesis of Abnormal Collagens with Amino Acid Analogues", Biosynthesis of Abnormal Collagens, pp. 142–155.

Takesako et al., "Precursor Directed Biosynthesis of Aureobasidins", The Journal of Antibiotics, vol. 49, No. 7, pp. 676–681, Jul. 1996.

* cited by examiner

5'- CAGCTGTCTT ATGGCTATGA TGAGAAATCA ACCGGAGGAA TTTCCGTGCC
TGGCCCCATG GGTCCCTCTG GTCCTCGTGG TCTCCCTGGC CCCCCTGGTG
CACCTGGTCC CCAAGGCTTC CAAGGTCCCC CTGGTGAGCC TGGCGAGCCT
GGAGCTTCAG GTCCCATGGG TCCCCGAGGT CCCCAGGTC CCCCTGGAAA
GAATGGAGAT GATGGGGAAG CTGGAAAACC TGGTCGTCCT GGTGAGCGTG
GGCCTCCTGG GCCTCAGGGT GCTCGAGGAT TGCCCGGAAC AGCTGGCCTC
CCTGGAATGA AGGGACACAG AGGTTTCAGT GGTTTGGATG GTGCCAAGGG
AGATGCTGGT CCTGCTGGTC CTAAGGGTGA GCCTGGCAGC CCTGGTGAAA
ATGGAGCTCC TGGTCAGATG GGCCCCGTG GCCTGCCTGG TGAGAGAGGT
CGCCCTGGAG CCCCTGGCCC TGCTGGTGCT CGTGGAAATG ATGGTGCTAC
TGGTGCTGCC GGGCCCCTG GTCCCACCGG CCCCGCTGGT CCTCCTGGCT
TCCCTGGTGC TGTTGGTGCT AAGGGTGAAG CTGGTCCCCA AGGGCCCCGA
GGCTCTGAAG GTCCCCAGGG TGTGCGTGGT GAGCCTGGCC CCCCTGGCCC
TGCTGGTGCT GCTGGCCCTG CTGGAAACCC TGGTGCTGAT GGACAGCCTG
GTGCTAAAGG TGCCAATGGT GCTCCTGGTA TTGCTGGTGC TCCTGGCTTC
CCTGGTGCCC GAGGCCCCTC TGGACCCCAG GGCCCCGGCG GCCCTCCTGG
TCCCAAGGGT AACAGCGGTG AACCTGGTGC TCCTGGCAGC AAAGGAGACA
CTGGTGCTAA GGGAGAGCCT GGCCCTGTTG GTGTTCAAGG ACCCCCTGGC
CCTGCTGGAG AGGAAGGAAA GCGAGGAGCT CGAGGTGAAC CCGGACCCAC
TGGCCTGCCC GGACCCCCTG GCGAGCGTGG TGGACCTGGT AGCCGTGGTT
TCCCTGGCGC AGATGGTGTT GCTGGTCCCA AGGGTCCCGC TGGTGAACGT
GGTTCTCCTG GCCCCGCTGG CCCCAAAGGA TCTCCTGGTG AAGCTGGTCG
TCCCGGTGAA GCTGGTCTGC CTGGTGCCAA GGGTCTGACT GGAAGCCCTG
GCAGCCCTGG TCCTGATGGC AAAACTGGCC CCCCTGGTCC CGCCGGTCAA
GATGGTCGCC CCGGACCCCC AGGCCCACCT GGTGCCCGTG GTCAGGCTGG
TGTGATGGGA TTCCCTGGAC CTAAAGGTGC TGCTGGAGAG CCCGGCAAGG
CTGGAGAGCG AGGTGTTCCC GGACCCCCTG GCGCTGTCGG TCCTGCTGGC
AAAGATGGAG AGGCTGGAGC TCAGGGACCC CCTGGCCCTG CTGGTCCCGC
TGGCGAGAGA GGTGAACAAG GCCCTGCTGG CTCCCCCGGA TTCCAGGGTC
TCCCTGGTCC TGCTGGTCCT CCAGGTGAAG CAGGCAAACC TGGTGAACAG
GGTGTTCCTG GAGACCTTGG CGCCCCTGGC CCCTCTGGAG CAAGAGGCGA
GAGAGGTTTC CCTGGCGAGC GTGGTGTGCA AGGTCCCCCT GGTCCTGCTG
GACCCCGAGG GGCCAACGGT GCTCCCGGCA ACGATGGTGC TAAGGGTGAT
GCTGGTGCCC CTGGAGCTCC CGGTAGCCAG GGCGCCCCTG GCCTTCAGGG
AATGCCTGGT GAACGTGGTG CAGCTGGTCT TCCAGGGCCT AAGGGTGACA
GAGGTGATGC TGGTCCCAAA GGTGCTGATG GCTCTCCTGG CAAAGATGGC
```

FIG. 3A

```
GTCCGTGGTC TGACCGGCCC CATTGGTCCT CCTGGCCCTG CTGGTGCCCC
TGGTGACAAG GGTGAAAGTG GTCCCAGCGG CCCTGCTGGT CCCACTGGAG
CTCGTGGTGC CCCCGGAGAC CGTGGTGAGC CTGGTCCCCC CGGCCCTGCT
GGCTTTGCTG GCCCCCTGG TGCTGACGGC CAACCTGGTG CTAAAGGCGA
ACCTGGTGAT GCTGGTGCCA AAGGCGATGC TGGTCCCCCT GGGCCTGCCG
GACCCGCTGG ACCCCCTGGC CCCATTGGTA ATGTTGGTGC TCCTGGAGCC
AAAGGTGCTC GCGGCAGCGC TGGTCCCCCT GGTGCTACTG GTTTCCCTGG
TGCTGCTGGC CGAGTCGGTC CTCCTGGCCC CTCTGGAAAT GCTGGACCCC
CTGGCCCTCC TGGTCCTGCT GGCAAAGAAG GCGGCAAAGG TCCCCGTGGT
GAGACTGGCC CTGCTGGSCG TCCTGGTGAA GTTGGTCCCC CTGGTCCCCC
TGGCCCTGCT GGCGAGAAAG GATCCCCTGG TGCTGATGGT CCTGCTGGTG
CTCCTGGTAC TCCCGGGCCT CAAGGTATTG CTGGACAGCG TGGTGTGGTC
GGCCTGCCTG GTCAGAGAGG AGAGAGAGGC TTCCCTGGTC TTCCTGGCCC
CTCTGGTGAA CCTGGCAAAC AAGGTCCCTC TGGAGCAAGT GGTGAACGTG
GTCCCCCCGG TCCCATGGGC CCCCCTGGAT TGGCTGGACC CCCTGGTGAA
TCTGGACGTG AGGGGGCTCC TGCTGCCGAA GGTTCCCCTG GACGAGACGG
TTCTCCTGGC GCCAAGGGTG ACCGTGGTGA GACCGGCCCC GCTGGACCCC
CTGGTGCTCC TGGTGCTCCT GGTGCCCCTG GCCCCGTTGG CCCTGCTGGC
AAGAGTGGTG ATCGTGGTGA GACTGGTCCT GCTGGTCCCG CCGGTCCCGT
CGGCCCCGCT GGCGCCCGTG GCCCCGCCGG ACCCCAAGGC CCCCGTGGTG
ACAAGGGTGA GACAGGCGAA CAGGGCGACA GAGGCATAAA GGGTCACCGT
GGCTTCTCTG GCCTCCAGGG TCCCCCTGGC CCTCCTGGCT CTCCTGGTGA
ACAAGGTCCC TCTGGAGCCT CTGGTCCTGC TGGTCCCCGA GGTCCCCCTG
GCTCTGCTGG TGCTCCTGGC AAAGATGGAC TCAACGGTCT CCCTGGCCCC
ATTGGGCCCC CTGGTCCTCG CGGTCGCACT GGTGATGCTG GTCCTGTTGG
TCCCCCCGGC CCTCCTGGAC CTCCTGGTCC CCCTGGTCCT CCCAGCGCTG
GTTTCGACTT CAGCTTCCTC CCCCAGCCAC CTCAAGAGAA GGCTCACGAT
GGTGGCCGCT ACTACCGGGC T-3'
```

*FIG. 3B*

```
5'-  CAGCTGTCTT ATGGCTATGA TGAGAAATCA ACCGGAGGAA TTTCCGTGCC
     TGGCCCCATG GGTCCCTCTG GTCCTCGTGG TCTCCCTGGC CCCCCTGGTG
     CACCTGGTCC CCAAGGCTTC CAAGGTCCCC CTGGTGAGCC TGGCGAGCCT
     GGAGCTTCAG GTCCCATGGG TCCCCGAGGT CCCCCAGGTC CCCCTGGAAA
     GAATGGAGAT GATGGGGAAG CTGGAAAACC TGGTCGTCCT-3'
```

*FIG. 5*

```
GGA TCC ATG GGG CTC GCT GGC CCA CCG GGC GAA CCG GGT
CCG CCA GGC CCG AAA GGT CCG CGT GGC GAT AGC GGG CTC
CCG GGC GAT TCC TAA TGG ATC C
```

FIG. 7

```
Gly-Leu-Ala-Gly-Pro-Pro-Gly-Glu-Pro-Gly-Pro-Pro-
Gly-Pro-Lys-Gly-Pro-Arg-Gly-Asp-Ser
```

FIG. 8

5'- CAGCGGGCCA GGAAGAAGAA TAAGAACTGC CGGCGCCACT CGCTCTATGT
    GGACTTCAGC GATGTGGGCT GGAATGACTG GATTGTGGCC CCACCAGGCT
    ACCAGGCCTT CTACTGCCAT GGGGACTGCC CCTTTCCACT GGCTGACCAC
    CTCAACTCAA CCAACCATGC CATTGTGCAG ACCCTGGTCA ATTCTGTCAA
    TTCCAGTATC CCCAAAGCCT GTTGTGTGCC CACTGAACTG AGTGCCATCT
    CCATGCTGTA CCTGGATGAG TATGATAAGG TGGTACTGAA AAATTATCAG
    GAGATGGTAG TAGAGGGATG TGGGTGCCGC      -3'

FIG. 10

```
         10         20         30         40         50         60
QLSYGYDEKS TGGISVPGPM GPSGPRGLPG PPGAPGPQGF QGPPGEPGEP GASGPMGPRG 70         80         90        100        110        120
PPGPPGKNGD DGEAGKPGRP GERGPPGPQG ARGLPGTAGL PGMKGHRGFS GLDGAKGDAG 130        140        150        160        170        180
PAGPKGEPGS PGENGAPGQM GPRGLPGERG RPGAPGPAGA RGNDGATGAA GPPGPTGPAG 190        200        210        220        230        240
PPGFPGAVGA KGEAGPQGPR GSEGPQGVRG EPGPPGPAGA AGPAGNPGAD GQPGAKGANG 250        260        270        280        290        300
APGIAGAPGF PGARGPSGPQ GPGGPPGPKG NSGEPGAPGS KGDTGAKGEP GPVGVQGPPG 310        320        330        340        350        360
PAGEEGKRGA RGEPGPTGLP GPPGERGGPG SRGFPGADGV AGPKGPAGER GSPGPAGPKG 370        380        390        400        410        420
SPGEAGRPGE AGLPGAKGLT GSPGSPGPDG KTGPPGPAGQ DGRPGPPGPP GARGQAGVMG 430        440        450        460        470        480
FPGPKGAAGE PGKAGERGVP GPPGAVGPAG KDGEAGAQGP PGPAGPAGER GEQGPAGSPG 490        500        510        520        530        540
FQGLPGPAGP PGEAGKPGEQ GVPGDLGAPG PSGARGERGF PGERGVQGPP GPAGPRGANG 550        560        570        580        590        600
APGNDGAKGD AGAPGAPGSQ GAPGLQGMPG ERGAAGLPGP KGDRGDAGPK GADGSPGKDG 610        620        630        640        650        660
VRGLTGPIGP PGPAGAPGDK GESGPSGPAG PTGARGAPGD RGEPGPPGPA GFAGPPGADG 670        680        690        700        710        720
QPGAKGEPGD AGAKGDAGPP GPAGPAGPPG PIGNVGAPGA KGARGSAGPP GATGFPGAAG 730        740        750        760        770        780
RVGPPGPSGN AGPPGPPGPA GKEGGKGPRG ETGPAGRPGE VGPPGPPGPA GEKGSPGADG 790        800        810        820        830        840
PAGAPGTPGP QGIAGQPGVV GLPGQRGERG FPGLPGPSGE PGKQGPSGAS GERGPPGPMG 850        860        870        880        890        900
PPGLAGPPGE SGREGAPAAE GSPGRDGSPG AKGDRGETGP AGPPGAXGAX GAPGPVGPAG 910        920        930        940        950        960
KSGDRGETGP AGPAGPVGPA GARGPAGPQG PRGDKGETGE QGDRGIKGHR GFSGLQGPPG 970        980        990       1000       1010       1020
PPGSPGEQGP SGASGPAGPR GPPGSAGAPG KDGLNGLPGP IGPPGPRGRT GDAGPVGPPG 1030       1040       1050       1060       1070       1080
PPGPPGPPGP PSAGFDFSFL PQPPQEKAHD GGRYYRARSQ RARKKNKNCR RHSLYVDFSD 1090       1100       1110       1120       1130       1140
VGWNDWIVAP PGYQAFYCHG DCPFPLADHL NSTNHAIVQT LVNSVNSSIP KACCVPTELS 1150       1160       1170       1180       1190       1200
AISMLYLDEY DKVVLKNYQE MVVEGCGCR*  .......... ..........
```

*FIG. 13*

```
              10         20         30         40         50         60
       gggaaggatt tccatttccC AGCTGTCTTA TGGCTATGAT GAGAAATCAA CCGGAGGAAT 70         80         90        100        110        120
       TTCCGTGCCT GGCCCCATGG GTCCCTCTGG TCCTCGTGGT CTCCCTGGCC CCCCTGGTGC 130        140        150        160        170        180
       ACCTGGTCCC CAAGGCTTCC AAGGTCCCCC TGGTGAGCCT GGCGAGCCTG GAGCTTCAGG 190        200        210        220        230        240
       TCCCATGGGT CCCCGAGGTC CCCCAGGTCC CCCTGGAAAG AATGGAGATG ATGGGGAAGC 250        260        270        280        290        300
       TGGAAAACCT GGTCGTCCTG GTGAGCGTGG GCCTCCTGGG CCTCAGGGTG CTCGAGGATT 310        320        330        340        350        360
       GCCCGGAACA GCTGGCCTCC CTGGAATGAA GGGACACAGA GGTTTCAGTG GTTTGGATGG 370        380        390        400        410        420
       TGCCAAGGGA GATGCTGGTC CTGCTGGTCC TAAGGGTGAG CCTGGCAGCC CTGGTGAAAA 430        440        450        460        470        480
       TGGAGCTCCT GGTCAGATGG GCCCCCGTGG CCTGCCTGGT GAGAGAGGTC GCCCTGGAGC 490        500        510        520        530        540
       CCCTGGCCCT GCTGGTGCTC GTGGAAATGA TGGTGCTACT GGTGCTGCCG GGCCCCCTGG 550        560        570        580        590        600
       TCCCACCGGC CCCGCTGGTC CTCCTGGCTT CCCTGGTGCT GTTGGTGCTA AGGGTGAAGC 610        620        630        640        650        660
       TGGTCCCCAA GGGCCCCGAG GCTCTGAAGG TCCCCAGGGT GTGCGTGGTG AGCCTGGCCC 670        680        690        700        710        720
       CCCTGGCCCT GCTGGTGCTG CTGGCCCTGC TGGAAACCCT GGTGCTGATG GACAGCCTGG 730        740        750        760        770        780
       TGCTAAAGGT GCCAATGGTG CTCCTGGTAT TGCTGGTGCT CCTGGCTTCC CTGGTGCCCG 790        800        810        820        830        840
       AGGCCCCTCT GGACCCCAGG GCCCCGGCGG CCCTCCTGGT CCCAAGGGTA ACAGCGGTGA 850        860        870        880        890        900
       ACCTGGTGCT CCTGGCAGCA AAGGAGACAC TGGTGCTAAG GGAGAGCCTG GCCCTGTTGG 910        920        930        940        950        960
       TGTTCAAGGA CCCCCTGGCC CTGCTGGAGA GGAAGGAAAG CGAGGAGCTC GAGGTGAACC 970        980        990       1000       1010       1020
       CGGACCCACT GGCCTGCCCG GACCCCCTGG CGAGCGTGGT GGACCTGGTA GCCGTGGTTT 1030       1040       1050       1060       1070       1080
       CCCTGGCGCA GATGGTGTTG CTGGTCCCAA GGGTCCCGCT GGTGAACGTG GTTCTCCTGG 1090       1100       1110       1120       1130       1140
       CCCCGCTGGC CCCAAAGGAT CTCCTGGTGA AGCTGGTCGT CCCGGTGAAG CTGGTCTGCC 1150       1160       1170       1180       1190       1200
       TGGTGCCAAG GGTCTGACTG GAAGCCCTGG CAGCCCTGGT CCTGATGGCA AAACTGGCCC 1210       1220       1230       1240       1250       1260
       CCCTGGTCCC GCCGGTCAAG ATGGTCGCCC CGGACCCCCA GGCCCACCTG GTGCCCGTGG
```

*FIG. 14A*

```
        1270       1280       1290       1300       1310       1320
   TCAGGCTGGT GTGATGGGAT TCCCTGGACC TAAAGGTGCT GCTGGAGAGC CCGGCAAGGC
        1330       1340       1350       1360       1370       1380
   TGGAGAGCGA GGTGTTCCCG GACCCCCTGG CGCTGTCGGT CCTGCTGGCA AAGATGGAGA
        1390       1400       1410       1420       1430       1440
   GGCTGGAGCT CAGGGACCCC CTGGCCCTGC TGGTCCCGCT GGCGAGAGAG GTGAACAAGG
        1450       1460       1470       1480       1490       1500
   CCCTGCTGGC TCCCCCGGAT TCCAGGGTCT CCCTGGTCCT GCTGGTCCTC CAGGTGAAGC
        1510       1520       1530       1540       1550       1560
   AGGCAAACCT GGTGAACAGG GTGTTCCTGG AGACCTTGGC GCCCCTGGCC CCTCTGGAGC
        1570       1580       1590       1600       1610       1620
   AAGAGGCGAG AGAGGTTTCC CTGGCGAGCG TGGTGTGCAA GGTCCCCCTG GTCCTGCTGG
        1630       1640       1650       1660       1670       1680
   ACCCCGAGGG GCCAACGGTG CTCCCGGCAA CGATGGTGCT AAGGGTGATG CTGGTGCCCC
        1690       1700       1710       1720       1730       1740
   TGGAGCTCCC GGTAGCCAGG GCGCCCCTGG CCTTCAGGGA ATGCCTGGTG AACGTGGTGC
        1750       1760       1770       1780       1790       1800
   AGCTGGTCTT CCAGGGCCTA AGGGTGACAG AGGTGATGCT GGTCCCAAAG GTGCTGATGG
        1810       1820       1830       1840       1850       1860
   CTCTCCTGGC AAAGATGGCG TCCGTGGTCT GACCGGCCCC ATTGGTCCTC CTGGCCCTGC
        1870       1880       1890       1900       1910       1920
   TGGTGCCCCT GGTGACAAGG GTGAAAGTGG TCCCAGCGGC CCTGCTGGTC CCACTGGAGC
        1930       1940       1950       1960       1970       1980
   TCGTGGTGCC CCCGGAGACC GTGGTGAGCC TGGTCCCCCC GGCCCTGCTG GCTTTGCTGG
        1990       2000       2010       2020       2030       2040
   CCCCCCTGGT GCTGACGGCC AACCTGGTGC TAAAGGCGAA CCTGGTGATG CTGGTGCCAA
        2050       2060       2070       2080       2090       2100
   AGGCGATGCT GGTCCCCCTG GGCCTGCCGG ACCCGCTGGA CCCCCTGGCC CCATTGGTAA
        2110       2120       2130       2140       2150       2160
   TGTTGGTGCT CCTGGAGCCA AAGGTGCTCG CGGCAGCGCT GGTCCCCCTG GTGCTACTGG
        2170       2180       2190       2200       2210       2220
   TTTCCCTGGT GCTGCTGGCC GAGTCGGTCC TCCTGGCCCC TCTGGAAATG CTGGACCCCC
        2230       2240       2250       2260       2270       2280
   TGGCCCTCCT GGTCCTGCTG GCAAAGAAGG CGGCAAAGGT CCCCGTGGTG AGACTGGCCC
        2290       2300       2310       2320       2330       2340
   TGCTGGACGT CCTGGTGAAG TTGGTCCCCC TGGTCCCCCT GGCCCTGCTG GCGAGAAAGG
        2350       2360       2370       2380       2390       2400
   ATCCCCTGGT GCTGATGGTC CTGCTGGTGC TCCTGGTACT CCCGGGCCTC AAGGTATTGC
        2410       2420       2430       2440       2450       2460
   TGGACAGCGT GGTGTGGTCG GCCTGCCTGG TCAGAGAGGA GAGAGAGGCT TCCCTGGTCT
        2470       2480       2490       2500       2510       2520
   TCCTGGCCCC TCTGGTGAAC CTGGCAAACA AGGTCCCTCT GGAGCAAGTG GTGAACGTGG
```

FIG. 14B

```
      2530       2540       2550       2560       2570       2580
TCCCCCCGGT CCCATGGGCC CCCCTGGATT GGCTGGACCC CCTGGTGAAT CTGGACGTGA 2590       2600       2610       2620       2630       2640
GGGGGCTCCT GCTGCCGAAG GTTCCCCTGG ACGAGACGGT TCTCCTGGCG CCAAGGGTGA 2650       2660       2670       2680       2690       2700
CCGTGGTGAG ACCGGCCCCG CTGGACCCCC TGGTGCTCNT GGTGCTCNTG GTGCCCCTGG 2710       2720       2730       2740       2750       2760
CCCCGTTGGC CCTGCTGGCA AGAGTGGTGA TCGTGGTGAG ACTGGTCCTG CTGGTCCCGC 2770       2780       2790       2800       2810       2820
CGGTCCCGTC GGCCCCGCTG GCGCCCGTGG CCCCGCCGGA CCCCAAGGCC CCCGTGGTGA 2830       2840       2850       2860       2870       2880
CAAGGGTGAG ACAGGCGAAC AGGGCGACAG AGGCATAAAG GGTCACCGTG GCTTCTCTGG 2890       2900       2910       2920       2930       2940
CCTCCAGGGT CCCCCTGGCC CTCCTGGCTC TCCTGGTGAA CAAGGTCCCT CTGGAGCCTC 2950       2960       2970       2980       2990       3000
TGGTCCTGCT GGTCCCCGAG GTCCCCCTGG CTCTGCTGGT GCTCCTGGCA AAGATGGACT 3010       3020       3030       3040       3050       3060
CAACGGTCTC CCTGGCCCCA TTGGGCCCCC TGGTCCTCGC GGTCGCACTG GTGATGCTGG 3070       3080       3090       3100       3110       3120
TCCTGTTGGT CCCCCCGGCC CTCCTGGACC TCCTGGTCCC CCTGGTCCTC CCAGCGCTGG 3130       3140       3150       3160       3170       3180
TTTCGACTTC AGCTTCCTCC CCCAGCCACC TCAAGAGAAG GCTCACGATG GTGGCCGCTA 3190       3200       3210       3220       3230       3240
CTACCGGGCT agatccCAGC GGGCCAGGAA GAAGAATAAG AACTGCCGGC GCCACTCGCT 3250       3260       3270       3280       3290       3300
CTATGTGGAC TTCAGCGATG TGGGCTGGAA TGACTGGATT GTGGCCCCAC CAGGCTACCA 3310       3320       3330       3340       3350       3360
GGCCTTCTAC TGCCATGGGG ACTGCCCCTT TCCACTGGCT GACCACCTCA ACTCAACCAA 3370       3380       3390       3400       3410       3420
CCATGCCATT GTGCAGACCC TGGTCAATTC TGTCAATTCC AGTATCCCCA AAGCCTGTTG 3430       3440       3450       3460       3470       3480
TGTGCCCACT GAACTGAGTG CCATCTCCAT GCTGTACCTG GATGAGTATG ATAAGGTGGT 3490       3500       3510       3520       3530       3540
ACTGAAAAAT TATCAGGAGA TGGTAGTAGA GGGATGTGGG TGCCGCTAAa agctt.....
```

*FIG. 14C*

```
          10         20         30         40         50         60
    QLSYGYDEKS TGGISVPGPM GPSGPRGLPG PPGAPGPQGF QGPPGEPGEP GASGPMGPRG 70         80         90        100        110        120
    PPGPPGKNGD DGEAGKPGRP GERGPPGPQG ARGLPGTAGL PGMKGHRGFS GLDGAKGDAG 130        140        150        160        170        180
    PAGPKGEPGS PGENGAPGQM GPRGLPGERG RPGAPGPAGA RGNDGATGAA GPPGPTGPAG 190        200        210        220        230        240
    PPGFPGAVGA KGEAGPQGPR GSEGPQGVRG EPGPPGPAGA AGPAGNPGAD GQPGAKGANG 250        260        270        280        290        300
    APGIAGAPGF PGARGPSGPQ GPGGPPGPKG NSGEPGAPGS KGDTGAKGEP GPVGVQGPPG 310        320        330        340        350        360
    PAGEEGKRGA RGEPGPTGLP GPPGERGGPG PRGFPGADGV AGPKGPAGER GSPGPAGPKG 370        380        390        400        410        420
    SPGEAGRPGE AGLPGAKGLT GSPGSPGPDG KTGPPGPAGQ DGRPGPPGPP GARGQAGVMG 430        440        450        460        470        480
    FPGPKGAAGE PGKAGERGVP GPPGAVGPAG KDGEAGAQGP PGPAGPAGER GEQGPAGSPG 490        500        510        520        530        540
    FQGLPGPAGP PGEAGKPGEQ GVPGDLGAPG PSGARGERGF PGERGVQGPP GPAGPRGANG 550        560        570        580        590        600
    APGNDGAKGD AGAPGAPGSQ GAPGLQGMPG ERGAAGLPGP KGDRGDAGPK GADGSPGKDG 610        620        630        640        650        660
    VRGLTGPIGP PGPAGAPGDK GESGPSGPAG PTGARGAPGD RGEPGPPGPA GFAGPPGADG 670        680        690        700        710        720
    QPGAKGEPGD AGAKGDAGPP GPAGPAGPPG PIGNVGAPGA KGARGSAGPP GATGFPGAAG 730        740        750        760        770        780
    RVGPPGPSGN AGPPGPPGPA GKEGGKGPRG ETGPAGRPGE VGPPGPPGPA GEKGSPGADG 790        800        810        820        830        840
    PAGAPGTPGP QGIAGQRGVV GLPGQRGERG FPGLPGPSGE PGKQGPSGAS GERGPPGPMG 850        860        870        880        890        900
    PPGLAGPPGE SGREGAPAAE GSPGRDGSPG AKGDRGETGP SGPPGAXGAX GAPGPVGPAG 910        920        930        940        950        960
    KSGDRGETGP AGPAGPVGPA GARGPAGPQG PRGDKGETGE QGDRGIKGHR GFSGLQGPPG 970        980        990       1000       1010       1020
    PPGSPGEQGP SGASGPAGPR GPPGSAGAPG KDGLNGLPGP IGPPGPRGRT GDAGPVGPPG 1030       1040       1050       1060       1070       1080
    PPGPPGPPGP PSAGFDFSFL PQPPQEKAHD GGRYYRARSA LDTNYCFSST EKNCCVRQLY 1090       1100       1110       1120       1130       1140
    IDFRKDLGWK WIHEPKGYHA NFCLGPCPYI WSLDTQYSKV LALYNQHNPG ASAAPCCVPQ 1150       1160       1170       1180       1190       1200
    ALEPLPIVYY VGRKPKVEQL SNMIVRSCKC S*..  ..... .......... ..........
```

*FIG. 15*

```
          10         20         30         40         50         60
    gggaaggatt tccatttccC AGCTGTCTTA TGGCTATGAT GAGAAATCAA CCGGAGGAAT 70         80         90        100        110        120
    TTCCGTGCCT GGCCCCATGG GTCCCTCTGG TCCTCGTGGT CTCCCTGGCC CCCCTGGTGC 130        140        150        160        170        180
    ACCTGGTCCC CAAGGCTTCC AAGGTCCCCC TGGTGAGCCT GGCGAGCCTG GAGCTTCAGG 190        200        210        220        230        240
    TCCCATGGGT CCCCGAGGTC CCCCAGGTCC CCTGGAAAAG AATGGAGATG ATGGGGAAGC 250        260        270        280        290        300
    TGGAAAACCT GGTCGTCCTG GTGAGCGTGG GCCTCCTGGG CCTCAGGGTG CTCGAGGATT 310        320        330        340        350        360
    GCCCGGAACA GCTGGCCTCC CTGGAATGAA GGGACACAGA GGTTTCAGTG GTTTGGATGG 370        380        390        400        410        420
    TGCCAAGGGA GATGCTGGTC CTGCTGGTCC TAAGGGTGAG CCTGGCAGCC CTGGTGAAAA 430        440        450        460        470        480
    TGGAGCTCCT GGTCAGATGG GCCCCCGTGG CCTGCCTGGT GAGAGAGGTC GCCCTGGAGC 490        500        510        520        530        540
    CCCTGGCCCT GCTGGTGCTC GTGGAAATGA TGGTGCTACT GGTGCTGCCG GGCCCCCTGG 550        560        570        580        590        600
    TCCCACCGGC CCCGCTGGTC CTCCTGGCTT CCCTGGTGCT GTTGGTGCTA AGGGTGAAGC 610        620        630        640        650        660
    TGGTCCCCAA GGGCCCCGAG GCTCTGAAGG TCCCCAGGGT GTGCGTGGTG AGCCTGGCCC 670        680        690        700        710        720
    CCCTGGCCCT GCTGGTGCTG CTGGCCCTGC TGGAAACCCT GGTGCTGATG GACAGCCTGG 730        740        750        760        770        780
    TGCTAAAGGT GCCAATGGTG CTCCTGGTAT TGCTGGTGCT CCTGGCTTCC CTGGTGCCCG 790        800        810        820        830        840
    AGGCCCCTCT GGACCCCAGG GCCCCGGCGG CCCTCCTGGT CCCAAGGGTA ACAGCGGTGA 850        860        870        880        890        900
    ACCTGGTGCT CCTGGCAGCA AAGGAGACAC TGGTGCTAAG GGAGAGCCTG GCCCTGTTGG 910        920        930        940        950        960
    TGTTCAAGGA CCCCCTGGCC CTGCTGGAGA GGAAGGAAAG CGAGGAGCTC GAGGTGAACC 970        980        990       1000       1010       1020
    CGGACCCACT GGCCTGCCCG GACCCCCTGG CGAGCGTGGT GGACCTGGTA GCCGTGGTTT 1030       1040       1050       1060       1070       1080
    CCCTGGCGCA GATGGTGTTG CTGGTCCCAA GGGTCCCGCT GGTGAACGTG GTTCTCCTGG 1090       1100       1110       1120       1130       1140
    CCCCGCTGGC CCCAAAGGAT CTCCTGGTGA AGCTGGTCGT CCCGGTGAAG CTGGTCTGCC 1150       1160       1170       1180       1190       1200
    TGGTGCCAAG GGTCTGACTG GAAGCCCTGG CAGCCCTGGT CCTGATGGCA AAACTGGCCC 1210       1220       1230       1240       1250       1260
    CCCTGGTCCC GCCGGTCAAG ATGGTCGCCC CGGACCCCCA GGCCCACCTG GTGCCCGTGG
```

*FIG. 16A*

```
           1270       1280       1290       1300       1310       1320
     TCAGGCTGGT GTGATGGGAT TCCCTGGACC TAAAGGTGCT GCTGGAGAGC CCGGCAAGGC 1330       1340       1350       1360       1370       1380
     TGGAGAGCGA GGTGTTCCCG GACCCCCTGG CGCTGTCGGT CCTGCTGGCA AAGATGGAGA 1390       1400       1410       1420       1430       1440
     GGCTGGAGCT CAGGGACCCC CTGGCCCTGC TGGTCCCGCT GGCGAGAGAG GTGAACAAGG 1450       1460       1470       1480       1490       1500
     CCCTGCTGGC TCCCCCGGAT TCCAGGGTCT CCCTGGTCCT GCTGGTCCTC CAGGTGAAGC 1510       1520       1530       1540       1550       1560
     AGGCAAACCT GGTGAACAGG GTGTTCCTGG AGACCTTGGC GCCCCTGGCC CCTCTGGAGC 1570       1580       1590       1600       1610       1620
     AAGAGGCGAG AGAGGTTTCC CTGGCGAGCG TGGTGTGCAA GGTCCCCCTG GTCCTGCTGG 1630       1640       1650       1660       1670       1680
     ACCCCGAGGG GCCAACGGTG CTCCCGGCAA CGATGGTGCT AAGGGTGATG CTGGTGCCCC 1690       1700       1710       1720       1730       1740
     TGGAGCTCCC GGTAGCCAGG GCGCCCCTGG CCTTCAGGGA ATGCCTGGTG AACGTGGTGC 1750       1760       1770       1780       1790       1800
     AGCTGGTCTT CCAGGGCCTA AGGGTGACAG AGGTGATGCT GGTCCCAAAG GTGCTGATGG 1810       1820       1830       1840       1850       1860
     CTCTCCTGGC AAAGATGGCG TCCGTGGTCT GACCGGCCCC ATTGGTCCTC CTGGCCCTGC 1870       1880       1890       1900       1910       1920
     TGGTGCCCCT GGTGACAAGG GTGAAAGTGG TCCCAGCGGC CCTGCTGGTC CCACTGGAGC 1930       1940       1950       1960       1970       1980
     TCGTGGTGCC CCCGGAGACC GTGGTGAGCC TGGTCCCCCC GGCCCTGCTG GCTTTGCTGG 1990       2000       2010       2020       2030       2040
     CCCCCCTGGT GCTGACGGCC AACCTGGTGC TAAAGGCGAA CCTGGTGATG CTGGTGCCAA 2050       2060       2070       2080       2090       2100
     AGGCGATGCT GGTCCCCCTG GGCCTGCCGG ACCCGCTGGA CCCCCTGGCC CCATTGGTAA 2110       2120       2130       2140       2150       2160
     TGTTGGTGCT CCTGGAGCCA AAGGTGCTCG CGGCAGCGCT GGTCCCCCTG GTGCTACTGG 2170       2180       2190       2200       2210       2220
     TTTCCCTGGT GCTGCTGGCC GAGTCGGTCC TCCTGGCCCC TCTGGAAATG CTGGACCCCC 2230       2240       2250       2260       2270       2280
     TGGCCCTCCT GGTCCTGCTG GCAAAGAAGG CGGCAAAGGT CCCCGTGGTG AGACTGGCCC 2290       2300       2310       2320       2330       2340
     TGCTGGACGT CCTGGTGAAG TTGGTCCCCC TGGTCCCCCT GGCCCTGCTG GCGAGAAAGG 2350       2360       2370       2380       2390       2400
     ATCCCCTGGT GCTGATGGTC CTGCTGGTGC TCCTGGTACT CCCGGGCCTC AAGGTATTGC 2410       2420       2430       2440       2450       2460
     TGGACAGCGT GGTGTGGTCG GCCTGCCTGG TCAGAGAGGA GAGAGAGGCT TCCCTGGTCT 2470       2480       2490       2500       2510       2520
     TCCTGGCCCC TCTGGTGAAC CTGGCAAACA AGGTCCCTCT GGAGCAAGTG GTGAACGTGG
```

FIG. 16B

```
          2530       2540       2550       2560       2570       2580
     TCCCCCCGGT CCCATGGGCC CCCCTGGATT GGCTGGACCC CCTGGTGAAT CTGGACGTGA 2590       2600       2610       2620       2630       2640
     GGGGGCTCCT GCTGCCGAAG GTTCCCCTGG ACGAGACGGT TCTCCTGGCG CCAAGGGTGA 2650       2660       2670       2680       2690       2700
     CCGTGGTGAG ACCGGCCCCG CTGGACCCCC TGGTGCTCNT GGTGCTCNTG GTGCCCCTGG 2710       2720       2730       2740       2750       2760
     CCCCGTTGGC CCTGCTGGCA AGAGTGGTGA TCGTGGTGAG ACTGGTCCTG CTGGTCCCGC 2770       2780       2790       2800       2810       2820
     CGGTCCCGTC GGCCCCGCTG GCGCCCGTGG CCCCGCCGGA CCCCAAGGCC CCCGTGGTGA 2830       2840       2850       2860       2870       2880
     CAAGGGTGAG ACAGGCGAAC AGGGCGACAG AGGCATAAAG GGTCACCGTG GCTTCTCTGG 2890       2900       2910       2920       2930       2940
     CCTCCAGGGT CCCCCTGGCC CTCCTGGCTC TCCTGGTGAA CAAGGTCCCT CTGGAGCCTC 2950       2960       2970       2980       2990       3000
     TGGTCCTGCT GGTCCCCGAG GTCCCCCTGG CTCTGCTGGT GCTCCTGGCA AAGATGGACT 3010       3020       3030       3040       3050       3060
     CAACGGTCTC CCTGGCCCCA TTGGGCCCCC TGGTCCTCGC GGTCGCACTG GTGATGCTGG 3070       3080       3090       3100       3110       3120
     TCCTGTTGGT CCCCCCGGCC CTCCTGGACC TCCTGGTCCC CCTGGTCCTC CCAGCGCTGG 3130       3140       3150       3160       3170       3180
     TTTCGACTTC AGCTTCCTCC CCCAGCCACC TCAAGAGAAG GCTCACGATG GTGGCCGCTA 3190       3200       3210       3220       3230       3240
     CTACCGGGCT agatctGCCC TGGACACCAA CTATTGCTTC AGCTCCACGG AGAAGAACTG 3250       3260       3270       3280       3290       3300
     CTGCGTGCGG CAGCTGTACA TTGACTTCCG CAAGGACCTC GGCTGGAAGT GGATCCACGA 3310       3320       3330       3340       3350       3360
     GCCCAAGGGC TACCATGCCA ACTTCTGCCT CGGGCCCTGC CCCTACATTT GGAGCCTGGA 3370       3380       3390       3400       3410       3420
     CACGCAGTAC AGCAAGGTCC TGGCCCTGTA CAACCAGCAT AACCCGGGCG CCTCGGCGGC 3430       3440       3450       3460       3470       3480
     GCCGTGCTGC GTGCCGCAGG CGCTGGAGCC GCTGCCCATC GTGTACTACG TGGGCCGCAA 3490       3500       3510       3520       3530       3540
     GCCCAAGGTG GAGCAGCTGT CCAACATGAT CGTGCGCTCC TGCAAGTGCA GCTGAtctag 3550       3560       3570       3580       3590       3600
     a.........  .........  .........  .........  .........  .........
```

FIG. 16C

```
         10         20         30         40         50         60
QLSYGYDEKS TGGISVPGPM GPSGPRGLPG PPGAPGPQGF QGPPGEPGEP GASGPMGPRG 70         80         90        100        110        120
PPGPPGKNGD DGEAGKPGRP GERGPPGPQG ARGLPGTAGL PGMKGHRGFS GLDGAKGDAG 130        140        150        160        170        180
PAGPKGEPGS PGENGAPGQM GPRGLPGERG RPGAPGPAGA RGNDGATGAA GPPGPTGPAG 190        200        210        220        230        240
PPGFPGAVGA KGEAGPQGPR GSEGPQGVRG EPGPPGPAGA AGPAGNPGAD GQPGAKGANG 250        260        270        280        290        300
APGIAGAPGF PGARGPSGPQ GPGGPPGPKG NSGEPGAPGS KGDTGAKGEP GPVGVQGPPG 310        320        330        340        350        360
PAGEEGKRGA RGEPGPTGLP GPPGERGGPG SRGFPGADGV AGPKGPAGER GSPGPAGPKG 370        380        390        400        410        420
SPGEAGRPGE AGLPGAKGLT GSPGSPGPDG KTGPPGPAGQ DGRPGPPGPP GARGQAGVMG 430        440        450        460        470        480
FPGPKGAAGE PGKAGERGVP GPPGAVGPAG KDGEAGAQGP PGPAGPAGER GEQGPAGSPG 490        500        510        520        530        540
FQGLPGPAGP PGEAGKPGEQ GVPGDLGAPG PSGARGERGF PGERGVQGPP GPAGPRGANG 550        560        570        580        590        600
APGNDGAKGD AGAPGAPGSQ GAPGLQGMPG ERGAAGLPGP KGDRGDAGPK GADGSPGKDG 610        620        630        640        650        660
VRGLTGPIGP PGPAGAPGDK GESGPSGPAG PTGARGAPGD RGEPGPPGPA GFAGPPGADG 670        680        690        700        710        720
QPGAKGEPGD AGAKGDAGPP GPAGPAGPPG PIGNVGAPGA KGARGSAGPP GATGFPGAAG 730        740        750        760        770        780
RVGPPGPSGN AGPPGPPGPA GKEGGKGPRG ETGPAGRPGE VGPPGPPGPA GEKGSPGADG 790        800        810        820        830        840
PAGAPGTPGP QGIAGQPGVV GLPGQRGERG FPGLPGPSGE PGKQGPSGAS GERGPPGPMG 850        860        870        880        890        900
PPGLAGPPGE SGREGAPAAE GSPGRDGSPG AKGDRGETGP AGPPGAXGAX GAPGPVGPAG 910        920        930        940        950        960
KSGDRGETGP AGPAGPVGPA GARGPAGPQG PRGDKGETGE QGDRGIKGHR GFSGLQGPPG 970        980        990       1000       1010       1020
PPGSPGEQGP SGASGPAGPR GPPGSAGAPG KDGLNGLPGP IGPPGPRGRT GDAGPVGPPG 1030       1040       1050       1060       1070       1080
PPGPPGPPGP PSAGFDFSFL PQPPQEKAHD GGRYYRARSD EASGIGPEVP DDRDFEPSLG 1090       1100       1110       1120       1130       1140
PVCPFRCQCH LRVVQCSDLG LDKVPKDLPP DTTLLDLQNN KITEIKDGDF KNLKNLHALI 1150       1160       1170       1180       1190       1200
LVNNKISKVS PGAFTPLVKL ERLYLSKNQL KELPEKMPKT LQELRAHENE ITKVRKVTFN
```

FIG. 17A

```
      1210       1220       1230       1240       1250       1260
GLNQMIVIEL GTNPLKSSGI ENGAFQGMKK LSYIRIADTN ITSIPQGLPP SLTELHLDGN 1270       1280       1290       1300       1310       1320
KISRVDAASL KGLNNLAKLG LSFNSISAVD NGSLANTPHL RELHLDNNKL TRVPGGLAEH 1330       1340       1350       1360       1370       1380
KYIQVVYLHN NNISVVGSSD FCPPGHNTKK ASYSGVSLFS NPVQYWEIQP STFRCVYVRS 1390       1400       1410       1420       1430       1440
AIQLGNYK*.  .......... .......... .......... .......... ..........
```

FIG. 17B

```
         10         20         30         40         50         60
QLSYGYDEKS TGGISVPGPM GPSGPRGLPG PPGAPGPQGF QGPPGEPGEP GASGPMGPRG 70         80         90        100        110        120
PPGPPGKNGD DGEAGKPGRP GERGPPGPQG ARGLPGTAGL PGMKGHRGFS GLDGAKGDAG 130        140        150        160        170        180
PAGPKGEPGS PGENGAPGQM GPRGLPGERG RPGAPGPAGA RGNDGATGAA GPPGPTGPAG 190        200        210        220        230        240
PPGFPGAVGA KGEAGPQGPR GSEGPQGVRG EPGPPGPAGA AGPAGNPGAD GQPGAKGANG 250        260        270        280        290        300
APGIAGAPGF PGARGPSGPQ GPGGPPGPKG NSGEPGAPGS KGDTGAKGEP GPVGVQGPPG 310        320        330        340        350        360
PAGEEGKRGA RGEPGPTGLP GPPGERGGPG SRGFPGADGV AGPKGPAGER GSPGPAGPKG 370        380        390        400        410        420
SPGEAGRPGE AGLPGAKGLT GSPGSPGPDG KTGPPGPAGQ DGRPGPPGPP GARGQAGVMG 430        440        450        460        470        480
FPGPKGAAGE PGKAGERGVP GPPGAVGPAG KDGEAGAQGP PGPAGPAGER GEQGPAGSPG 490        500        510        520        530        540
FQGLPGPAGP PGEAGKPGEQ GVPGDLGAPG PSGARGERGF PGERGVQGPP GPAGPRGANG 550        560        570        580        590        600
APGNDGAKGD AGAPGAPGSQ GAPGLQGMPG ERGAAGLPGP KGDRGDAGPK GADGSPGKDG 610        620        630        640        650        660
VRGLTGPIGP PGPAGAPGDK GESGPSGPAG PTGARGAPGD RGEPGPPGPA GFAGPPGADG 670        680        690        700        710        720
QPGAKGEPGD AGAKGDAGPP GPAGPAGPPG PIGNVGAPGA KGARGSAGPP GATGFPGAAG 730        740        750        760        770        780
RVGPPGPSGN AGPPGPPGPA GKEGGKGPRG ETGPAGRPGE VGPPGPPGPA GEKGSPGADG 790        800        810        820        830        840
PAGAPGTPGP QGIAGQRGVV GLPGQRGERG FPGLPGPSGE PGKQGPSGAS GERGPPGPMG 850        860        870        880        890        900
PPGLAGPPGE SGREGAPAAE GSPGRDGSPG AKGDRGETGP AGPPGAXGAX GAPGPVGPAG 910        920        930        940        950        960
KSGDRGETGP AGPAGPVGPA GARGPAGPQG PRGDKGETGE QGDRGIKGHR GFSGLQGPPG 970        980        990       1000       1010       1020
PPGSPGEQGP SGASGPAGPR GPPGSAGAPG KDGLNGLPGP IGPPGPRGRT GDAGPVGPPG 1030       1040       1050       1060       1070       1080
PPGPPGPPGP PSAGFDFSFL PQPPQEKAHD GGRYYRARSP KDLPPDTTLL DLQNNKITEI 1090       1100       1110       1120       1130       1140
KDGDFKNLKN LHALILVNNK ISKVSPG*..    ......... .........  .........
```

FIG. 18

```
                9          18         27         36         45         54
         CAG CTG TCT TAT GGC TAT GAT GAG AAA TCA ACC GGA GGA ATT TCC GTG CCT GGC CCC ATG 69         78         87         96        105        114
         GGT CCC TCT GGT CCT CGT GGT CTC CCT GGC CCC CCT GGT GCA CCT GGT CCC CAA GGC TTC 129        138        147        156        165        174
         CAA GGT CCC CCT GGT GAG CCT GGC GAG CCT GGA GCT TCA GGT CCC ATG GGT CCC CGA GGT 189        198        207        216        225        234
         CCC CCA GGT CCC CCT GGA AAG AAT GGA GAT GAT GGG GAA GCT GGA AAA CCT GGT CGT CCT 249        258        267        276        285        294
         GGT GAG CGT GGG CCT CCT GCG CCT CAG GGT GCT CGA GGA TTG CCC GGA ACA GCT GGC CTC 309        318        327        336        345        354
         CCT GGA ATG AAG GGA CAC AGA GGT TTC AGT GGT TTG GAT GGT GCC AAG GGA GAT GCT GGT 369        378        387        396        405        414
         CCT GCT GGT CCT AAG GGT GAG CCT CGC AGC CCT GGT GAA AAT GGA GCT CCT GGT CAG ATG 369        378        387        396        405        414
         CCT GCT GGT CCT AAG GGT GAG CCT CGC AGC CCT GGT GAA AAT GGA GCT CCT GGT CAG ATG 429        438        447        456        465        474
         GGC CCC CGT GGC CTG CCT GGT GAG AGA GGT CGC CCT GGA GCC CCT GGC CCT GCT GGT GCT 489        498        507        516        525        534
         CGT GGA AAT GAT GGT GCT ACT GGT GCT GCC GGG CCC CCT GGT CCC ACC GGC CCC GCT GGT 549        558        567        576        585        594
         CCT CCT GGC TTC CCT GGT GCT GTT GGT GCT AAG GGT GAA GCT GGT CCC CAA GGG CCC CGA 609        618        627        636        645        654
         GGC TCT GAA GGT CCC CAG GGT GTG CGT GGT GAG CCT GGC CCC CCT GGC CCT GCT GGT GCT 669        678        687        696        705        714
         GCT GGC CCT GCT GGA AAC CCT GGT GCT GAT GGA CAG CCT GGT GCT AAA GGT GCC AAT GGT 729        738        747        756        765        774
         GCT CCT GGT ATT GCT CGT GCT CCT GGC TTC CCT GGT GCC CGA GGC CCC TCT GGA CCC CAG 789        798        807        816        825        834
         GGC CCC GGC GGC CCT CCT GGT CCC AAG GGT AAC AGC GGT GAA CCT GGT GCT CCT GGC AGC 849        858        867        876        885        894
         AAA CGA GAC ACT GGT GCT AAG GGA GAG CCT GGC CCT GTT GGT GTT CAA GGA CCC CCT GGC 909        918        927        936        945        954
         CCT GCT GGA GAG CAA GGA AAG CGA GGA GCT CGA GGT GAA CCC GGA CCC ACT GGC CTG CCC 969        978        987        996       1005       1014
         GGA CCC CCT GGC GAG CGT GGT GGA CCT GGT AGC CGT GGT TTC CCT GGC GCA GAT GGT GTT 1029       1038       1047       1056       1065       1074
         GCT GGT CCC AAG GGT CCC GCT GGT GAA CGT GGT TCT CCT GGC CCC GCT GGC CCC AAA GGA 1089       1098       1107       1116       1125       1134
         TCT CCT CGT GAA GCT GGT CGT CCC GGT GAA GCT GGT CTG CCT GGT GCC AAG GGT CTG ACT
```

FIG. 19A

```
                1149        1158        1167        1176        1185        1194
        GGA AGC CCT GGC AGC CCT GGT CCT GAT GGC AAA ACT GGC CCC CCT GGT CCC GCC GGT CAA 1209        1218        1227        1236        1245        1254
        GAT GGT CGC CCC GGA CCC CCA GGC CCS CCT GGT GCC CGT GGT CAG GCT GGT GTG ATG GGA 1269        1278        1287        1296        1305        1314
        TTC CCT GGA CCT AAA GGT GCT GCT GGA GAG CCC GGC AAG GCT GGA GAG CGA GGT GTT CCC 1329        1338        1347        1356        1365        1374
        GGA CCC CCT CGC GCT GTC GGT CCT GCT GGC AAA GAT GGA GAG GCT GGA GCT CAG GGA CCC 1389        1398        1407        1416        1425        1434
        CCT GGC CCT GCT GGT CCC GCT GGC GAG AGA GGT GAA CAA GGC CCT GCT GGC TCC CCC GGA 1449        1458        1467        1476        1485        1494
        TTC CAG GGT CTC CCT GGT CCT GCT GGT CCT CCA GGT GAA GCA GGC AAA CCT GGT GAA CAG 1509        1518        1527        1536        1545        1554
        GGT GTT CCT GGA GAC CTT GGC GCC CCT GGC CCC TCT GGA GCA AGA GGC GAG AGA GGT TTC 1569        1578        1587        1596        1605        1614
        CCT GGC GAG CGT GGT GTG CAA GGT CCC CCT GGT CCT GCT GGA CCC CGA GGG GCC AAC GGT 1629        1638        1647        1656        1665        1674
        GCT CCC GGC AAC GAT GGT GCT AAG GGT GAT GCT GGT GCC CCT GGA GCT CCC GGT AGC CAG 1689        1698        1707        1716        1725        1734
        GGC GCC CCT GGC CTT CAG GGA ATG CCT GGT GAA CGT GGT GCA GCT GGT CTT CCA GGG CCT 1749        1758        1767        1776        1785        1794
        AAG GGT GAC AGA GGT GAT GCT GGT CCC AAA GGT GCT GAT GGC TCT CCT GGC AAA GAT GGC 1809        1818        1827        1836        1845        1854
        GTC CGT GGT CTG ACC GGC CCC ATT GGT CCT CCT GGC CCT GCT GGT GCC CCT GGT GAC AAG 1869        1878        1887        1896        1905        1914
        GGT GAA AGT GGT CCC AGC GGC CCT GCT GGT CCC ACT GGA GCT CGT GGT GCC CCC GGA GAC 1929        1938        1947        1956        1965        1974
        CGT GGT GAG CCT GGT CCC CCC GGC CCT GCT GGC TTT GCT GGC CCC CCT GGT GCT GAC GGC 1989        1998        2007        2016        2025        2034
        CAA CCT CGT GCT AAA GGC GAA CCT GGT GAT GCT GGT GCC AAA GGC GAT GCT GGT CCC CCT 2049        2058        2067        2076        2085        2094
        GGG CCT GCC GGA CCC GCT GGA CCC CCT GGC CCC ATT GGT AAT GTT GGT GCT CCT GGA GCC 2109        2118        2127        2136        2145        2154
        AAA GGT GCT CGC GGC AGC GCT GGT CCC CCT GGT GCT ACT GGT TTC CCT GGT GCT GCT GGC 2169        2178        2187        2196        2205        2214
        CGA GTC GGT CCT CCT GGC CCC TCT GGA AAT GCT GGA CCC CCT GGC CCT CCT GGT CCT GCT 2229        2238        2247        2256        2265        2274
        GGC AAA GAA GGC GGC AAA GGT CCC CGT GGT GAG ACT GGC CCT GCT GGA CGT CCT GGT GAA 2289        2298        2307        2316        2325        2334
        GTT GGT CCC CCT GGT CCC CCT GGC CCT GCT GGC GAG AAA GGA TCC CCT GGT GCT GAT GGT
```

*FIG. 19B*

```
                2349        2358        2367        2376        2385        2394
        CCT GCT GGT GCT CCT GGT ACT CCC GGG CCT CAA GGT ATT GCT GGA CAG CGT GGT GTG GTC
                2409        2418        2427        2436        2445        2454
        GGC CTG CCT GGT CAG AGA GGA GAG AGA GGC TTC CCT GGT CTT CCT GGC CCC TCT GGT GAA
                2469        2478        2487        2496        2505        2514
        CCT GGC AAA CAA GGT CCC TCT GGA GCA AGT GGT GAA CGT GGT CCC CCC GGT CCC ATG GGC
                2529        2538        2547        2556        2565        2574
        CCC CCT GGA TTG GCT GGA CCC CCT GGT GAA TCT GGA CGT GAG GGG GCT CCT GCT GCC GAA
                2589        2598        2607        2616        2625        2634
        GGT TCC CCT GGA CGA GAC GGT TCT CCT GGC GCC AAG GGT GAC CGT GGT GAG ACC GGC CCC
                2649        2658        2667        2676        2685        2694
        GCT GGA CCC CCT GGT GCT CCT GGT GCT CCT GGT GCC CCT GGC CCC GTT GGC CCT GCT GGC
                2709        2718        2727        2736        2745        2754
        AAG AGT GGT GAT CGT GGT GAG ACT GGT CCT GCT GGT CCC GCC GGT CCC GTC GGC CCC GCT
                2769        2778        2787        2796        2805        2814
        GGC GCC CGT GGC CCC GCC GGA CCC CAA GGC CCC CGT GGT GAC AAG GGT GAG ACA GGC GAA
                2829        2838        2847        2856        2865        2874
        CAG GGC GAC AGA GGC ATA AAG GGT CAC CGT GGC TTC TCT GGC CTC CAG GGT CCC CCT GGC
                2889        2898        2907        2916        2925        2934
        CCT CCT GGC TCT CCT GGT GAA CAA CGT CCC TCT GGA GCC TCT GGT CCT GCT GGT CCC CGA
                2949        2958        2967        2976        2985        2994
        GGT CCC CCT GGC TCT GCT GGT GCT CCT GGC AAA GAT GGA CTC AAC GGT CTC CCT GGC CCC
                3009        3018        3027        3036        3045        3054
        ATT GGG CCC CCT GGT CCT CGC GGT CGC ACT GGT GAT GCT GGT CCT GTT GGT CCC CCC GGC
                3069        3078        3087        3096        3105        3114
        CCT CCT GGA CCT CCT GGT CCC CCT GGT CCT CCC AGC GCT GGT TTC GAC TTC AGC TTC CTC
                3129        3138        3147        3156        3165        3174
        CCC CAG CCA CCT CAA GAG AAG GCT CAC GAT GGT GGC CGC TAC TAC CGG GCT AGA TCC GAT
                3189        3198        3207        3216        3225        3234
        GAG GCT TCT GGG ATA GGC CCA GAA GTT CCT GAT GAC CGC GAC TTC GAG CCC TCC CTA GGC
                3249        3258        3267        3276        3285        3294
        CCA GTG TGC CCC TTC CGC TGT CAA TGC CAT CTT CGA GTG GTC CAG TGT TCT GAT TTG GGT
                3309        3318        3327        3336        3345        3354
        CTG GAC AAA GTG CCA AAG GAT CTT CCC CCT GAC ACA ACT CTG CTA GAC CTG CAA AAC AAC
                3369        3378        3387        3396        3405        3414
        AAA ATA ACC GAA ATC AAA GAT GGA GAC TTT AAG AAC CTG AAG AAC CTT CAC GCA TTG ATT
                3429        3438        3447        3456        3465        3474
        CTT GTC AAC AAT AAA ATT AGC AAA GTT AGT CCT GGA GCA TTT ACA CCT TTG GTG AAG TTG
                3489        3498        3507        3516        3525        3534
        GAA CGA CTT TAT CTG TCC AAG AAT CAG CTG AAG GAA TTG CCA GAA AAA ATG CCC AAA ACT
```

*FIG. 19C*

```
          3549        3558        3567        3576        3585        3594
CTT CAG GAG CTG CGT GCC CAT GAG AAT GAG ATC ACC AAA GTG CGA AAA GTT ACT TTC AAT 3609        3618        3627        3636        3645        3654
GGA CTG AAC CAG ATG ATT GTC ATA GAA CTG GGC ACC AAT CCG CTG AAG AGC TCA GGA ATT 3669        3678        3687        3696        3705        3714
GAA AAT GGG GCT TTC CAG GGA ATG AAG AAG CTC TCC TAC ATC CGC ATT GCT GAT ACC AAT 3729        3738        3747        3756        3765        3774
ATC ACC AGC ATT CCT CAA GGT CTT CCT CCT TCC CTT ACG GAA TTA CAT CTT GAT GGC AAC 3789        3798        3807        3816        3825        3834
AAA ATC AGC AGA GTT GAT GCA GCT AGC CTG AAA GGA CTG AAT AAT TTG GCT AAG TTG GGA 3849        3858        3867        3876        3885        3894
TTG AGT TTC AAC AGC ATC TCT GCT GTT GAC AAT GGC TCT CTG GCC AAC ACG CCT CAT CTG 3909        3918        3927        3936        3945        3954
AGG GAG CTT CAC TTG GAC AAC AAC AAG CTT ACC AGA GTA CCT GGT GGG CTG GCA GAG CAT 3969        3978        3987        3996        4005        4014
AAG TAC ATC CAG GTT GTC TAC CTT CAT AAC AAC AAT ATC TCT GTA GTT GGA TCA AGT GAC 4029        4038        4047        4056        4065        4074
TTC TGC CCA CCT GGA CAC AAC ACC AAA AAG GCT TCT TAT TCG GGT GTG AGT CTT TTC AGC 4089        4098        4107        4116        4125        4134
AAC CCG GTC CAG TAC TGG GAG ATA CAG CCA TCC ACC TCC AGA TGT GTC TAC GTG CGC TCT 4149        4158        4167        4176        4185        4194
GCC ATT CAA CTC GGA AAC TAT AAG TAA ...  ...  ...  ...  ...  ...  ...  ...  ...
```

FIG. 19D

```
          10         20         30         40         50         60
gggaaggatt tccatttccC AGCTGTCTTA TGGCTATGAT GAGAAATCAA CCGGAGGAAT
          70         80         90        100        110        120
TTCCGTGCCT GGCCCCATGG GTCCCTCTGG TCCTCGTGGT CTCCCTGGCC CCCCTGGTGC
         130        140        150        160        170        180
ACCTGGTCCC CAAGGCTTCC AAGGTCCCCC TGGTGAGCCT GGCGAGCCTG GAGCTTCAGG
         190        200        210        220        230        240
TCCCATGGGT CCCCGAGGTC CCCCAGGTCC CCCTGGAAAG AATGGAGATG ATGGGGAAGC
         250        260        270        280        290        300
TGGAAAACCT GGTCGTCCTG GTGAGCGTGG GCCTCCTGGG CCTCAGGGTG CTCGAGGATT
         310        320        330        340        350        360
GCCCGGAACA GCTGGCCTCC CTGGAATGAA GGGACACAGA GGTTTCAGTG GTTTGGATGG
         370        380        390        400        410        420
TGCCAAGGGA GATGCTGGTC CTGCTGGTCC TAAGGGTGAG CCTGGCAGCC CTGGTGAAAA
         430        440        450        460        470        480
TGGAGCTCCT GGTCAGATGG GCCCCCGTGG CCTGCCTGGT GAGAGAGGTC GCCCTGGAGC
         490        500        510        520        530        540
CCCTGGCCCT GCTGGTGCTC GTGGAAATGA TGGTGCTACT GGTGCTGCCG GGCCCCCTGG
         550        560        570        580        590        600
TCCCACCGGC CCCGCTGGTC CTCCTGGCTT CCCTGGTGCT GTTGGTGCTA AGGGTGAAGC
         610        620        630        640        650        660
TGGTCCCCAA GGGCCCCGAG GCTCTGAAGG TCCCCAGGGT GTGCGTGGTG AGCCTGGCCC
         670        680        690        700        710        720
CCCTGGCCCT GCTGGTGCTG CTGGCCCTGC TGGAAACCCT GGTGCTGATG GACAGCCTGG
         730        740        750        760        770        780
TGCTAAAGGT GCCAATGGTG CTCCTGGTAT TGCTGGTGCT CCTGGCTTCC CTGGTGCCCG
         790        800        810        820        830        840
AGGCCCCTCT GGACCCCAGG GCCCCGGCGG CCCTCCTGGT CCCAAGGGTA ACAGCGGTGA
         850        860        870        880        890        900
ACCTGGTGCT CCTGGCAGCA AAGGAGACAC TGGTGCTAAG GGAGAGCCTG GCCCTGTTGG
         910        920        930        940        950        960
TGTTCAAGGA CCCCCTGGCC CTGCTGGAGA GGAAGGAAAG CGAGGAGCTC GAGGTGAACC
         970        980        990       1000       1010       1020
CGGACCCACT GGCCTGCCCG GACCCCCTGG CGAGCGTGGT GGACCTGGTA GCCGTGGTTT
        1030       1040       1050       1060       1070       1080
CCCTGGCGCA GATGGTGTTG CTGGTCCCAA GGGTCCCGCT GGTGAACGTG GTTCTCCTGG
        1090       1100       1110       1120       1130       1140
CCCCGCTGGC CCCAAAGGAT CTCCTGGTGA AGCTGGTCGT CCCGGTGAAG CTGGTCTGCC
        1150       1160       1170       1180       1190       1200
TGGTGCCAAG GGTCTGACTG GAAGCCCTGG CAGCCCTGGT CCTGATGGCA AAACTGGCCC
        1210       1220       1230       1240       1250       1260
CCCTGGTCCC GCCGGTCAAG ATGGTCGCCC CGGACCCCCA GGCCCACCTG GTGCCCGTGG
```

*FIG. 20A*

```
      1270       1280       1290       1300       1310       1320
TCAGGCTGGT GTGATGGGAT TCCCTGGACC TAAAGGTGCT GCTGGAGAGC CCGGCAAGGC 1330       1340       1350       1360       1370       1380
TGGAGAGCGA GGTGTTCCCG GACCCCCTGG CGCTGTCGGT CCTGCTGGCA AGATGGAGA 1390       1400       1410       1420       1430       1440
GGCTGGAGCT CAGGGACCCC CTGGCCCTGC TGGTCCCGCT GGCGAGAGAG GTGAACAAGG 1450       1460       1470       1480       1490       1500
CCCTGCTGGC TCCCCCGGAT TCCAGGGTCT CCCTGGTCCT GCTGGTCCTC CAGGTGAAGC 1510       1520       1530       1540       1550       1560
AGGCAAACCT GGTGAACAGG GTGTTCCTGG AGACCTTGGC GCCCCTGGCC CCTCTGGAGC 1570       1580       1590       1600       1610       1620
AAGAGGCGAG AGAGGTTTCC CTGGCGAGCG TGGTGTGCAA GGTCCCCCTG GTCCTGCTGG 1630       1640       1650       1660       1670       1680
ACCCCGAGGG GCCAACGGTG CTCCCGGCAA CGATGGTGCT AAGGGTGATG CTGGTGCCCC 1690       1700       1710       1720       1730       1740
TGGAGCTCCC GGTAGCCAGG GCGCCCCTGG CCTTCAGGGA ATGCCTGGTG AACGTGGTGC 1750       1760       1770       1780       1790       1800
AGCTGGTCTT CCAGGGCCTA AGGGTGACAG AGGTGATGCT GGTCCCAAAG GTGCTGATGG 1810       1820       1830       1840       1850       1860
CTCTCCTGGC AAAGATGGCG TCCGTGGTCT GACCGGCCCC ATTGGTCCTC CTGGCCCTGC 1870       1880       1890       1900       1910       1920
TGGTGCCCCT GGTGACAAGG GTGAAAGTGG TCCCAGCGGC CCTGCTGGTC CCACTGGAGC 1930       1940       1950       1960       1970       1980
TCGTGGTGCC CCCGGAGACC GTGGTGAGCC TGGTCCCCCC GGCCCTGCTG GCTTTGCTGG 1990       2000       2010       2020       2030       2040
CCCCCCTGGT GCTGACGGCC AACCTGGTGC TAAAGGCGAA CCTGGTGATG CTGGTGCCAA 2050       2060       2070       2080       2090       2100
AGGCGATGCT GGTCCCCCTG GGCCTGCCGG ACCCGCTGGA CCCCCTGGCC CCATTGGTAA 2110       2120       2130       2140       2150       2160
TGTTGGTGCT CCTGGAGCCA AAGGTGCTCG CGGCAGCGCT GGTCCCCCTG GTGCTACTGG 2170       2180       2190       2200       2210       2220
TTTCCCTGGT GCTGCTGGCC GAGTCGGTCC TCCTGGCCCC TCTGGAAATG CTGGACCCCC 2230       2240       2250       2260       2270       2280
TGGCCCTCCT GGTCCTGCTG GCAAAGAAGG CGGCAAAGGT CCCCGTGGTG AGACTGGCCC 2290       2300       2310       2320       2330       2340
TGCTGGACGT CCTGGTGAAG TTGGTCCCCC TGGTCCCCCT GGCCCTGCTG GCGAGAAAGG 2350       2360       2370       2380       2390       2400
ATCCCCTGGT GCTGATGGTC CTGCTGGTGC TCCTGGTACT CCCGGGCCTC AAGGTATTGC 2410       2420       2430       2440       2450       2460
TGGACAGCGT GGTGTGGTCG GCCTGCCTGG TCAGAGAGGA GAGAGAGGCT TCCCTGGTCT 2470       2480       2490       2500       2510       2520
TCCTGGCCCC TCTGGTGAAC CTGGCAAACA AGGTCCCTCT GGAGCAAGTG GTGAACGTGG
```

*FIG. 20B*

```
           2530       2540       2550       2560       2570       2580
      TCCCCCCGGT CCCATGGGCC CCCCTGGATT GGCTGGACCC CCTGGTGAAT CTGGACGTGA 2590       2600       2610       2620       2630       2640
      GGGGGCTCCT GCTGCCGAAG GTTCCCCTGG ACGAGACGGT TCTCCTGGCG CCAAGGGTGA 2650       2660       2670       2680       2690       2700
      CCGTGGTGAG ACCGGCCCCG CTGGACCCCC TGGTGCTCNT GGTGCTCNTG GTGCCCCTGG 2710       2720       2730       2740       2750       2760
      CCCCGTTGGC CCTGCTGGCA AGAGTGGTGA TCGTGGTGAG ACTGGTCCTG CTGGTCCCGC 2770       2780       2790       2800       2810       2820
      CGGTCCCGTC GGCCCCGCTG GCGCCCGTGG CCCCGCCGGA CCCCAAGGCC CCCGTGGTGA 2830       2840       2850       2860       2870       2880
      CAAGGGTGAG ACAGGCGAAC AGGGCGACAG AGGCATAAAG GGTCACCGTG GCTTCTCTGG 2890       2900       2910       2920       2930       2940
      CCTCCAGGGT CCCCCTGGCC CTCCTGGCTC TCCTGGTGAA CAAGGTCCCT CTGGAGCCTC 2950       2960       2970       2980       2990       3000
      TGGTCCTGCT GGTCCCCGAG GTCCCCCTGG CTCTGCTGGT GCTCCTGGCA AAGATGGACT 3010       3020       3030       3040       3050       3060
      CAACGGTCTC CCTGGCCCCA TTGGGCCCCC TGGTCCTCGC GGTCGCACTG GTGATGCTGG 3070       3080       3090       3100       3110       3120
      TCCTGTTGGT CCCCCCGGCC CTCCTGGACC TCCTGGTCCC CCTGGTCCTC CCAGCGCTGG 3130       3140       3150       3160       3170       3180
      TTTCGACTTC AGCTTCCTCC CCCAGCCACC TCAAGAGAAG GCTCACGATG GTGGCCGCTA 3190       3200       3210       3220       3230       3240
      CTACCGGGCT agatctCCAA AGGATCTTCC CCCTGACACA ACTCTGCTAG ACCTGCAAAA 3250       3260       3270       3280       3290       3300
      CAACAAAATA ACCGAAATCA AAGATGGAGA CTTTAAGAAC CTGAAGAACC TTCACGCATT 3310       3320       3330       3340       3350       3360
      GATTCTTGTC AACAATAAAA TTAGCAAAGT TAGTCCTGGA TAActgcag. ..........
```

*FIG. 20C*

MALE...ATC GAG GGA AGG ATT TCA GAA TTC GGA TCC TCT AGA GTC GAC CTG CAG GCA AGC TTG...LACZ

X m n 1    Eco RI   BamHI   Xba I   Sal I   Pst I   Hindi I I

*FIG. 22*

```
                9                18               27               36               45               54
5' CAG CTG TCT TAT GGC TAT GAT GAG AAA TCA ACC GGA GGA ATT TCC GTG CCT GGC
   Gln Leu Ser Tyr Gly Tyr Asp Glu Lys Ser Thr Gly Gly Ile Ser Val Pro Gly 63               72               81               90               99              108
   CCC ATG GGT CCC TCT GGT CCT CGT GGT CTC CCT GGC CCC CCT GGT GCA CCT GGT
   Pro Met Gly Pro Ser Gly Pro Arg Gly Leu Pro Gly Pro Pro Gly Ala Pro Gly 117              126              135              144              153              162
   CCC CAA GGC TTC CAA GGT CCC CCT GGT GAG CCT GGC GAG CCT GGA GCT TCA GGT
   Pro Gln Gly Phe Gln Gly Pro Pro Gly Glu Pro Gly Glu Pro Gly Ala Ser Gly 171              180              189              198              207              216
   CCC ATG GGT CCC CGA GGT CCC CCA GGT CCC CCT GGA AAG AAT GGA GAT GAT GGG
   Pro Met Gly Pro Arg Gly Pro Pro Gly Pro Pro Gly Lys Asn Gly Asp Asp Gly 225              234              243              252              261              270
   GAA GCT GGA AAA CCT GGT CGT CCT GGT GAG CGT GGG CCT CCT GGG CCT CAG GGT
   Glu Ala Gly Lys Pro Gly Arg Pro Gly Glu Arg Gly Pro Pro Gly Pro Gln Gly 279              288              297              306              315              324
   GCT CGA GGA TTG CCC GGA ACA GCT GGC CTC CCT GGA ATG AAG GGA CAC AGA GGT
   Ala Arg Gly Leu Pro Gly Thr Ala Gly Leu Pro Gly Met Lys Gly His Arg Gly 333              342              351              360              369              378
   TTC AGT GGT TTG GAT GGT GCC AAG GGA GAT GCT GGT CCT GCT GGT CCT AAG GGT
   Phe Ser Gly Leu Asp Gly Ala Lys Gly Asp Ala Gly Pro Ala Gly Pro Lys Gly 387              396              405              414              423              432
   GAG CCT GGC AGC CCT GGT GAA AAT GGA GCT CCT GGT CAG ATG GGC CCC CGT GGC
   Glu Pro Gly Ser Pro Gly Glu Asn Gly Ala Pro Gly Gln Met Gly Pro Arg Gly 441              450              459              468              477              486
   CTG CCT GGT GAG AGA GGT CGC CCT GGA GCC CCT GGC CCT GCT GGT GCT CGT GGA
   Leu Pro Gly Glu Arg Gly Arg Pro Gly Ala Pro Gly Pro Ala Gly Ala Arg Gly 495              504              513              522              531              540
   AAT GAT GGT GCT ACT GGT GCT GCC GGG CCC CCT GGT CCC ACC GGC CCC GCT GGT
   Asn Asp Gly Ala Thr Gly Ala Ala Gly Pro Pro Gly Pro Thr Gly Pro Ala Gly 549              558              567              576              585              594
   CCT CCT GGC TTC CCT GGT GCT GTT GGT GCT AAG GGT GAA GCT GGT CCC CAA GGG
   Pro Pro Gly Phe Pro Gly Ala Val Gly Ala Lys Gly Glu Ala Gly Pro Gln Gly 603              612              621              630              639              648
   CCC CGA GGC TCT GAA GGT CCC CAG GGT GTG CGT GGT GAG CCT GGC CCC CCT GGC
   Pro Arg Gly Ser Glu Gly Pro Gln Gly Val Arg Gly Glu Pro Gly Pro Pro Gly 657              666              675              684              693              702
   CCT GCT GGT GCT GCT GGC CCT GCT GGA AAC CCT GGT GCT GAT GGA CAG CCT GGT
   Pro Ala Gly Ala Ala Gly Pro Ala Gly Asn Pro Gly Ala Asp Gly Gln Pro Gly
```

*FIG. 27A*

```
      711           720           729           738           747           756
GCT AAA GGT GCC AAT GGT GCT CCT GGT ATT GCT GGT GCT CCT GGC TTC CCT GGT
Ala Lys Gly Ala Asn Gly Ala Pro Gly Ile Ala Gly Ala Pro Gly Phe Pro Gly 765           774           783           792           801           810
GCC CGA GGC CCC TCT GGA CCC CAG GGC CCC GGC GGC CCT CCT GGT CCC AAG GGT
Ala Arg Gly Pro Ser Gly Pro Gln Gly Pro Gly Gly Pro Pro Gly Pro Lys Gln 819           828           837           846           855           864
AAC AGC GGT GAA CCT GGT GCT CCT GGC AGC AAA GGA GAC ACT GGT GCT AAG GGA
Asn Ser Gly Glu Pro Gly Ala Pro Gly Ser Lys Gly Asp Thr Gly Ala Lys Gly 873           882           891           900           909           918
GAG CCT GGC CCT GTT GGT GTT CAA GGA CCC CCT GGC CCT GCT GGA GAG GAA GGA
Glu Pro Gly Pro Val Gly Val Gln Gly Pro Pro Gly Pro Ala Gly Glu Glu Gly 927           936           945           954           963           972
AAG CGA GGA GCT CGA GGT GAA CCC GGA CCC ACT GGC CTG CCC GGA CCC CCT GGC
Lys Arg Gly Ala Arg Gly Glu Pro Gly Pro Thr Gly Leu Pro Gly Pro Pro Gly 981           990           999          1008          1017          1026
GAG CGT GGT GGA CCT GGT AGC CGT GGT TTC CCT GGC GCA GAT GGT GTT GCT GGT
Glu Arg Gly Gly Pro Gly Ser Arg Gly Phe Pro Gly Ala Asp Gly Val Ala Gly 1035          1044          1053          1062          1071          1080
CCC AAG GGT CCC GCT GGT GAA CGT GGT TCT CCT GGC CCC GCT GGC CCC AAA GGA
Pro Lys Gly Pro Ala Gly Glu Arg Gly Ser Pro Gly Pro Ala Gly Pro Lys Gly 1089          1098          1107          1116          1125          1134
TCT CCT GGT GAA GCT GGT CGT CCC GGT GAA GCT GGT CTG CCT GGT GCC AAG GGT
Ser Pro Gly Glu Ala Gly Arg Pro Gly Glu Ala Gly Leu Pro Gly Ala Lys Gly 1143          1152          1161          1170          1179          1188
CTG ACT GGA AGC CCT GGC AGC CCT GGT CCT GAT GGC AAA ACT GGC CCC CCT GGT
Leu Thr Gly Ser Pro Gly Ser Pro Gly Pro Asp Gly Lys Thr Gly Pro Pro Gly 1197          1206          1215          1224          1233          1242
CCC GCC GGT CAA GAT GGT CGC CCC GGA CCC CCA GGC CCA CCT GGT GCC CGT GGT
Pro Ala Gly Gln Asp Gly Arg Pro Gly Pro Pro Gly Pro Pro Gly Ala Arg Gly 1251          1260          1269          1278          1287          1296
CAG GCT GGT GTG ATG GGA TTC CCT GGA CCT AAA GGT GCT GCT GGA GAG CCC GGC
Gln Ala Gly Val Met Gly Phe Pro Gly Pro Lys Gly Ala Ala Gly Glu Pro Gly 1305          1314          1323          1332          1341          1350
AAG GCT GGA GAG CGA GGT GTT CCC GGA CCC CCT GGC GCT GTC GGT CCT GCT GGC
Lys Ala Gly Glu Arg Gly Val Pro Gly Pro Pro Gly Ala Val Gly Pro Ala Gly
```

*FIG. 27B*

```
              1359        1368        1377        1386        1395        1404
    AAA GAT GGA GAG GCT GGA GCT CAG GGA CCC CCT GGC CCT GCT GGT CCC GCT GGC
    --- --- --- --- --- --- --- --- --- --- --- --- --- --- --- --- --- ---
    Lys Asp Gly Glu Ala Gyl Ala Gln Gly Pro Pro Gly Pro Ala Gly Pro Ala Gly 1413        1422        1431        1440        1449        1458
    GAG AGA GGT GAA CAA GGC CCT GCT GGC TCC CCC GGA TTC CAG GGT CTC CCT GGT
    --- --- --- --- --- --- --- --- --- --- --- --- --- --- --- --- --- ---
    Glu Arg Gly Glu Gln Gly Pro Ala Gly Ser Pro Gly Phe Gln Gly Leu Pro Gly 1467        1476        1485        1494        1503        1512
    CCT GCT GGT CCT CCA GGT GAA GCA GGC AAA CCT GGT GAA CAG GGT GTT CCT GGA
    --- --- --- --- --- --- --- --- --- --- --- --- --- --- --- --- --- ---
    Pro Ala Gly Pro Pro Gly Glu Ala Gly Lys Pro Gly Glu Gln Gly Val Pro Gly 1521        1530        1539        1548        1557        1566
    GAC CTT GGC GCC CCT GGC CCC TCT GGA GCA AGA GGC GAG AGA GGT TTC CCT GGC
    --- --- --- --- --- --- --- --- --- --- --- --- --- --- --- --- --- ---
    Asp Leu Gly Ala Pro Gly Pro Ser Gly Ala Arg Gly Glu Arg Gly Phe Pro Gly 1575        1584        1593        1602        1611        1620
    GAG CGT GGT GTG CAA GGT CCC CCT GGT CCT GCT GGA CCC CGA GGG GCC AAC GGT
    --- --- --- --- --- --- --- --- --- --- --- --- --- --- --- --- --- ---
    Glu Arg Gly Val Gln Gly Pro Pro Gly Pro Ala Gly Pro Arg Gly Ala Asm Gly 1629        1638        1647        1656        1665        1674
    GCT CCC GGC AAC GAT GGT GCT AAG GGT GAT GCT GGT GCC CCT GGA GCT CCC GGT
    --- --- --- --- --- --- --- --- --- --- --- --- --- --- --- --- --- ---
    Ala Pro Gly Asm Asp Gly Ala Lys Gly Asp Ala Gly Ala Pro Gly Ala Pro Gly 1683        1692        1701        1710        1719        1728
    AGC CAG GGC GCC CCT GGC CTT CAG GGA ATG CCT GGT GAA CGT GGT GCA GCT GGT
    --- --- --- --- --- --- --- --- --- --- --- --- --- --- --- --- --- ---
    Ser Gln Gly Ala Pro Gly Leu Gln Gly Met Pro Gly Glu Arg Gly Ala Ala Gly 1737        1746        1755        1764        1773        1782
    CTT CCA GGG CCT AAG GGT GAC AGA GGT GAT GCT GGT CCC AAA GGT GCT GAT GGC
    --- --- --- --- --- --- --- --- --- --- --- --- --- --- --- --- --- ---
    Leu Pro Gly Pro Lys Gly Asp Arg Gly Asp Ala Gly Pro Lys Gly Ala Asp Gly 1791        1800        1809        1818        1827        1836
    TCT CCT GGC AAA GAT GGC GTC CGT GGT CTG ACC GGC CCC ATT GGT CCT CCT GGC
    --- --- --- --- --- --- --- --- --- --- --- --- --- --- --- --- --- ---
    Ser Pro Gly Lys Asp Gly Val Arg Gly Leu Thr Gly Pro Ile Gly Pro Pro Gly 1845        1854        1863        1872        1881        1890
    CCT GCT GGT GCC CCT GGT GAC AAG GGT GAA AGT GGT CCC AGC GGC CCT GCT GGT
    --- --- --- --- --- --- --- --- --- --- --- --- --- --- --- --- --- ---
    Pro Ala Gly Ala Pro Gly Asp Lys Gly Glu Ser Gly Pro Ser Gly Pro Ala Gly 1899        1908        1917        1926        1935        1944
    CCC ACT GGA GCT CGT GGT GCC CCC GGA GAC CGT GGT GAG CCT GGT CCC CCC GGC
    --- --- --- --- --- --- --- --- --- --- --- --- --- --- --- --- --- ---
    Pro Thr Gly Ala Arg Gly Ala Pro gly Asp Arg Gly Glu Pro Gly Pro Pro Gly 1953        1962        1971        1980        1989        1998
    CCT GCT GGC TTT GCT GGC CCC CCT GGT GCT GAC GGC CAA CCT GGT GCT AAA GGC
    --- --- --- --- --- --- --- --- --- --- --- --- --- --- --- --- --- ---
    Pro Ala Gly Phe Ala Gly Pro Pro Gly Ala Asp Gly Gln Pro Gly Ala Lys Gly 2007        2016        2025        2034        2043        2052
    GAA CCT GGT GAT GCT GGT GCC AAA GGC GAT GCT GGT CCC CCT GGG CCT GCC GGA
    --- --- --- --- --- --- --- --- --- --- --- --- --- --- --- --- --- ---
    Gly Pro Gly Asp Ala Gly Ala Lys Gly Asp Ala Gly Pro Pro Gly Pro Ala Gly
```

*FIG. 27C*

```
     2061        2070        2079        2088        2097        2106
CCC GCT GGA CCC CCT GGC CCC ATT GGT AAT GTT GGT GCT CCT GGA GCC AAA GGT
Pro Ala Gly Pro Pro Gly Pro Ile Gly Asn Val Gly Ala Pro Gly Ala Lys Gly 2115        2124        2133        2142        2151        2160
GCT CGC GGC AGC GCT GGT CCC CCT GGT GCT ACT GGT TTC CCT GGT GCT GCT GGC
Ala Arg Gly Ser Ala Gly Pro Pro Gly Ala Thr Gly Phe Pro Gly Ala Ala Gly 2169        2178        2187        2196        2205        2214
CGA GTC GGT CCT CCT GGC CCC TCT GGA AAT GCT GGA CCC CCT GGC CCT CCT GGT
Arg Val Gly Pro Pro Gly Pro Ser Gly Asn Ala Gly Pro Pro Gly Pro Pro Gly 2223        2232        2241        2250        2259        2268
CCT GCT GGC AAA GAA GGC GGC AAA GGT CCC CGT GGT GAG ACT GGC CCT GCT GGA
Pro Ala Gly Lys Glu Gly Gly Lys Gly Pro Arg Gly Glu Thr Gly Pro Ala Gly 2277        2286        2295        2304        2313        2322
CGT CCT GGT GAA GTT GGT CCC CCT GGT CCC CCT GGC CCT GCT GGC GAG AAA GGA
Arg Pro Gly Glu Val Gly Pro Pro Gly Pro Pro Gly Pro Ala Gly Glu Lys Gly 2331        2340        2349        2358        2367        2376
TCC CCT GGT GCT GAT GGT CCT GCT GGT GCT CCT GGT ACT CCC GGG CCT CAA GGT
Ser Pro Gly Ala Asp Gly Pro Ala Gly Ala Pro Gly Thr Pro Gly Pro Gln Gly 2385        2394        2403        2412        2421        2430
ATT GCT GGA CAG CGT GGT GTG GTC GGC CTG CCT GGT CAG AGA GGA GAG AGA GGC
Ile Ala Gly Gln Arg Gly Val Val Gly Leu Pro Gly Gln Arg Gly Glu Arg Gly 2439        2448        2457        2466        2475        2484
TTC CCT GGT CTT CCT GGC CCC TCT GGT GAA CCT GGC AAA CAA GGT CCC TCT GGA
Phe Pro Gly Leu Pro Gly Pro Ser Gly Glu Pro Gly Lys Gln Gly Pro Ser Gly 2493        2502        2511        2520        2529        2538
GCA AGT GGT GAA CGT GGT CCC CCC GGT CCC ATG GGC CCC CCT GGA TTG GCT GGA
Ala Ser Gly Glu Arg Gly Pro Pro Gly Pro Met Gly Pro Pro Gly Leu Ala Gly 2547        2556        2565        2574        2583        2592
CCC CCT GGT GAA TCT GGA CGT GAG GGG GCT CCT GCT GCC GAA GGT TCC CCT GGA
Pro Pro Gly Glu Ser Gly Arg Glu Gly Ala Pro Ala Ala Glu Gly Ser Pro Gly 2601        2610        2619        2628        2637        2646
CGA GAC GGT TCT CCT GGC GCC AAG GGT GAC CGT GGT GAG ACC GGC CCC GCT GGA
Arg Asp Gly Ser Pro Gly Ala Lys Gly Asp Arg Gly Glu Thr Gly Pro Ala Gly 2655        2664        2673        2682        2691        2700
CCC CCT GGT GCT CCT GGT GCT CCT GGT GCC CCT GGC CCC GTT GGC CCT GCT GGC
Pro Pro Gly Ala Pro Gly Ala Pro Gly Ala Pro Gly Pro Val Gly Pro Ala Gly
```

*FIG. 27D*

```
     2709           2718           2727           2736           2745           2754
AAG AGT GGT GAT CGT GGT GAG ACT GGT CCT GCT GGT CCC GCC GGT CCC GTC GGC
--- --- --- --- --- --- --- --- --- --- --- --- --- --- --- --- --- ---
Lys Ser Gly Asp Arg Gly Glu Thr Gly Pro Ala Gly Pro Ala Gly Pro Val Gly 2763           2772           2781           2790           2799           2808
CCC GCT GGC GCC CGT GGC CCC GCC GGA CCC CAA GGC CCC CGT GGT GAC AAG GGT
--- --- --- --- --- --- --- --- --- --- --- --- --- --- --- --- --- ---
Pro Ala Gly Ala Arg Gly Pro Ala Gly Pro Gln Gly Pro Arg Gly Asp Lys Gly 2817           2826           2835           2844           2853           2862
GAG ACA GGC GAA CAG GGC GAC AGA GGC ATA AAG GGT CAC CGT GGC TTC TCT GGC
--- --- --- --- --- --- --- --- --- --- --- --- --- --- --- --- --- ---
Glu Thr Gly Glu Gln Gly Asp Arg Gly Ile Lys Gly His Arg Gly Phe Ser Gly 2871           2880           2889           2898           2907           2916
CTC CAG GGT CCC CCT GGC CCT CCT GGC TCT CCT GGT GAA CAA GGT CCC TCT GGA
--- --- --- --- --- --- --- --- --- --- --- --- --- --- --- --- --- ---
Leu Gln Gly Pro Pro Gly Pro Pro Gly Ser Pro Gly Glu Gln Gly Pro Ser Gly 2925           2934           2943           2952           2961           2970
GCC TCT GGT CCT GCT GGT CCC CGA GGT CCC CCT GGC TCT GCT GGT GCT CCT GGC
--- --- --- --- --- --- --- --- --- --- --- --- --- --- --- --- --- ---
Ala Ser Gly Pro Ala Gly Pro Arg Gly Pro Pro Gly Ser Ala Gly Ala Pro Gly 2979           2988           2997           3006           3015           3024
AAA GAT GGA CTC AAC GGT CTC CCT GGC CCC ATT GGG CCC CCT GGT CCT CGC GGT
--- --- --- --- --- --- --- --- --- --- --- --- --- --- --- --- --- ---
Lys Asp Gly Leu Asn Gly Leu Pro Gly Pro Ile Gly Pro Pro Gly Pro Arg Gly 3033           3042           3051           3060           3069           3078
CGC ACT GGT GAT GCT GGT CCT GTT GGT CCC CCC GGC CCT CCT GGA CCT CCT GGT
--- --- --- --- --- --- --- --- --- --- --- --- --- --- --- --- --- ---
Arg Thr Gly Asp Ala Gly Pro Val Gly Pro Pro Gly Pro Pro Gly Pro Pro Gly 3087           3096           3105           3114           3123           3132
CCC CCT GGT CCT CCC AGC GCT GGT TTC GAC TTC AGC TTC CTC CCC CAG CCA CCT
--- --- --- --- --- --- --- --- --- --- --- --- --- --- --- --- --- ---
Pro Pro Gly Pro Pro Ser Ala Gly Phe Asp Phe Ser Phe Leu Pro Gln Pro Pro 3141           3150           3159           3168
CAA GAG AAG GCT CAC GAT GGT GGC CGC TAC TAC CGG GCT 3'
--- --- --- --- --- --- --- --- --- --- --- --- ---
Gln Glu Lys Ala His Asp Gly Gly Arg Tyr Tyr Arg Ala
```

*FIG. 27E*

|  | HCol | ColECol |
|---|---|---|
| Proline |  |  |
| CCU | 139 | 11 |
| CCC | 93 | 12 |
| CCA | 6 | 27 |
| CCG | 0 | 189 |
| Glycine |  |  |
| GGU | 174 | 147 |
| GGC | 97 | 179 |
| GGA | 64 | 8 |
| GGG | 11 | 12 |

*FIG. 30*

```
                    9                18               27               36               45               54
5' CAG CTG AGC TAT GGC TAT GAT GAA AAA AGC ACC GGC GGC ATC AGC GTG CCG GGC
   Gln Leu Ser Tyr Gly Tyr Asp Glu Lys Ser Thr Gly Gly Ile Ser Val Pro Gly 63               72               81               90               99              108
   CCC ATG GGT CCG AGC GGC CCG CGT GGC CTG CCG GGC CCG CCA GGT GCG CCC GGT
   Pro Met Gly Pro Ser Gly Pro Arg Gly Leu Pro Gly Pro Pro Gly Ala Pro Gly 117              126              135              144              153              162
   CCG CAG GGC TTT CAG GGT CCG CCG GGC GAA CCG GGC GAA CCT GGT GCG AGC GGC
   Pro Gln Gly Phe Gln Gly Pro Pro Gly Glu Pro Gly Glu Pro Gly Ala Ser Gly 171              180              189              198              207              216
   CCG ATG GGC CCG CGC GGC CCG CCG GGT CCG CCA GGC AAA AAC GGC GAT GAT GGC
   Pro Met Gly Pro Arg Gly Pro Pro Gly Pro Pro Gly Lys Asn Gly Asp Asp Gly 225              234              243              252              261              270
   GAA GCG GGC AAA CCG GGA CGT CCG GGT GAA CGT GGC CCC CCG GGC CCG CAG GGC
   Glu Ala Gly Lys Pro Gly Arg Pro Gly Glu Arg Gly Pro Pro Gly Pro Gln Gly 279              288              297              306              315              324
   GCG CGC GGA CTG CCG GGT ACT GCG GGA CTG CCG GGC ATG AAA GGC CAC CGC GGT
   Ala Arg Gly Leu Pro Gly Thr Ala Gly Leu Pro Gly Met Lys Gly His Arg Gly 333              342              351              360              369              378
   TTC TCT GGT CTG GAT GGT GCC AAA GGA GAC GCG GGT CCG GCG GGT CCG AAA GGT
   Phe Ser Gly Leu Asp Gly Ala Lys Gly Asp Ala Gly Pro Ala Gly Pro Lys Gly 387              396              405              414              423              432
   GAG CCG GGC AGC CCG GGC GAA AAC GGC GCG CCG GGT CAG ATG GGC CCG CGT GGC
   Glu Pro Gly Ser Pro Gly Glu Asn Gly Ala Pro Gly Gln Met Gly Pro Arg Gly 441              450              459              468              477              486
   CTG CCT GGT GAA CGC GGT CGC CCG GGC GCC CCG GGC CCA GCT GGC GCA CGT GGC
   Leu Pro Gly Glu Arg Gly Arg Pro Gly Ala Pro Gly Pro Ala Gly Ala Arg Gly 495              504              513              522              531              540
   AAC GAT GGT GCG ACC GGT GCG GCC GGT CCA CCG GGC CCG ACG GGC CCG GCG GGT
   Asn Asp Gly Ala Thr Gly Ala Ala Gly Pro Pro Gly Pro Thr Gly Pro Ala Gly 549              558              567              576              585              594
   CCC CCG GGC TTT CCG GGT GCG GTG GGT GCG AAA GGC GAA GCA GGT CCG CAG GGG
   Pro Pro Gly Phe Pro Gly Ala Val Gly Ala Lys Gly Glu Ala Gly Pro Gln Gly 603              612              621              630              639              648
   CCG CGC GGG AGC GAG GGT CCT CAG GGC GTT CGT GGT GAA CCG GGC CCG CCG GGC
   Pro Arg Gly Ser Glu Gly Pro Gln Gly Val Arg Gly Glu Pro Gly Pro Pro Gly 657              666              675              684              693              702
   CCG GCG GGT GCG GCG GGC CCG GCT GGT AAC CCT GGC GCG GAC GGT CAG CCA GGT
   Pro Ala Gly Ala Ala Gly Pro Ala Gly Asn Pro Gly Ala Asp Gly Gln Pro Gly
```

*FIG. 39A*

```
         711           720           729           738           747           756
GCG AAA GGT GCC AAC GGC GCG CCG GGT ATT GCA GGT GCA CCG GGC TTC CCG GGT
Ala Lys Gly Ala Asn Gly Ala Pro Gly Ile Ala Gly Ala Pro Gly Phe Pro Gly 765           774           783           792           801           810
GCC CGC GGC CCG TCC GGC CCG CAG GGC CCG GGC GGC CCG CCC GGC CCG AAA GGG
Ala Arg Gly Pro Ser Gly Pro Gln Gly Pro Gly Gly Pro Pro Gly Pro Lys Gln 819           828           837           846           855           864
AAC AGC GGT GAA CCG GGT GCG CCG GGC AGC AAA GGC GAC ACC GGT GCG AAA GGT
Asn Ser Gly Glu Pro Gly Ala Pro Gly Ser Lys Gly Asp Thr Gly Ala Lys Gly 873           882           891           900           909           918
GAA CCG GGC CCA GTG GGT GTT CAA GGC CCG CCG GGC CCG GCG GGC GAG GAA GGC
Glu Pro Gly Pro Val Gly Val Gln Gly Pro Pro Gly Pro Ala Gly Glu Glu Gly 927           936           945           954           963           972
AAA CGC GGT GCT CGC GGT GAA CCG GGC CCG ACC GGC CTG CCT GGC CCG CCG GGA
Lys Arg Gly Ala Arg Gly Glu Pro Gly Pro Thr Gly Leu Pro Gly Pro Pro Gly 981           990           999          1008          1017          1026
GAA CGT GGT GGC CCG GGT AGC CGC GGT TTT CCG GGC GCG GAT GGT GTG GCG GGC
Glu Arg Gly Gly Pro Gly Ser Arg Gly Phe Pro Gly Ala Asp Gly Val Ala Gly 1035          1044          1053          1062          1071          1080
CCG AAA GGT CCG GCG GGT GAA CGT GGT AGC CCG GGC CCG GCG GGC CCA AAA GGC
Pro Lys Gly Pro Ala Gly Glu Arg Gly Ser Pro Gly Pro Ala Gly Pro Lys Gly 1089          1098          1107          1116          1125          1134
AGC CCG GGC GAG GCA GGA CGT CCG GGT GAA GCG GGT CTC CCG GGC GCC AAA GGT
Ser Pro Gly Glu Ala Gly Arg Pro Gly Glu Ala Gly Leu Pro Gly Ala Lys Gly 1143          1152          1161          1170          1179          1188
CTG ACC GGC TCT CCG GGC AGC CCG GGT CCG GAT GGC AAA ACG GGC CCG CCT GGT
Leu Thr Gly Ser Pro Gly Ser Pro Gly Pro Asp Gly Lys Thr Gly Pro Pro Gly 1197          1206          1215          1224          1233          1242
CCG GCC GGC CAG GAT GGT CGC CCG GGC CCG CCG GGC CCG CCG GGT GCC CGT GGT
Pro Ala Gly Gln Asp Gly Arg Pro Gly Pro Pro Gly Pro Pro Gly Ala Arg Gly 1251          1260          1269          1278          1287          1296
CAG GCG GGT GTC ATG GGC TTT CCA GGC CCC AAA GGT GCG GCG GGT GAA CCG GGC
Gln Ala Gly Val Met Gly Phe Pro Gly Pro Lys Gly Ala Ala Gly Glu Pro Gly 1305          1314          1323          1332          1341          1350
AAA GCG GGC GAA CGC GGT GTC CCG GGT CCG CCG GGC GCT GTC GGG CCG GCG GGC
Lys Ala Gly Glu Arg Gly Val Pro Gly Pro Pro Gly Ala Val Gly Pro Ala Gly
```

*FIG. 39B*

```
            1359        1368        1377        1386        1395        1404
AAA GAT GGC GAA GCG GGC GCG CAA GGC CCG CCG GGA CCA GCG GGT CCG GCG GGC
--- --- --- --- --- --- --- --- --- --- --- --- --- --- --- --- --- ---
Lys Asp Gly Glu Ala Gly Ala Gln Gly Pro Pro Gly Pro Ala Gly Pro Ala Gly 1413        1422        1431        1440        1449        1458
GAG CGC GGT GAA CAG GGC CCG GCA GGC AGC CCG GGT TTC CAG GGT CTG CCG GGC
--- --- --- --- --- --- --- --- --- --- --- --- --- --- --- --- --- ---
Glu Arg Gly Glu Gln Gly Pro Ala Gly Ser Pro Gly Phe Gln Gly Leu Pro Gly 1467        1476        1485        1494        1503        1512
CCT GCG GGT CCA CCG GGT GAA GCG GGC AAA CCG GGG GAA CAA GGT GTG CCG GGC
--- --- --- --- --- --- --- --- --- --- --- --- --- --- --- --- --- ---
Pro Ala Gly Pro Pro Gly Glu Ala Gly Lys Pro Gly Glu Gln Gly Val Pro Gly 1521        1530        1539        1548        1557        1566
GAC CTG GGC GCC CCA GGC CCG AGC GGC GCG CGC GGC GAA CGC GGT TTC CCG GGC
--- --- --- --- --- --- --- --- --- --- --- --- --- --- --- --- --- ---
Asp Leu Gly Ala Pro Gly Pro Ser Gly Ala Arg Gly Glu Arg Gly Phe Pro Gly 1575        1584        1593        1602        1611        1620
GAA CGT GGT GTG CAG GGC CCG CCC GGC CCG GCT GGT CCG CGC GGC GCC AAC GGC
--- --- --- --- --- --- --- --- --- --- --- --- --- --- --- --- --- ---
Glu Arg Gly Val Gln Gly Pro Pro Gly Pro Ala Gly Pro Arg Gly Ala Asn Gly 1629        1638        1647        1656        1665        1674
GCG CCG GGC AAC GAT GGT GCG AAA GGT GAT GCG GGT GCC CCA GGT GCG CCG GGC
--- --- --- --- --- --- --- --- --- --- --- --- --- --- --- --- --- ---
Ala Pro Gly Asn Asp Gly Ala Lys Gly Asp Ala Gly Ala Pro Gly Ala Pro Gly 1683        1692        1701        1710        1719        1728
AGC CAG GGC GCC CCG GGG CTG CAA GGC ATG CCG GGT GAA CGT GGT GCC GCG GGT
--- --- --- --- --- --- --- --- --- --- --- --- --- --- --- --- --- ---
Ser Gln Gly Ala Pro Gly Leu Gln Gly Met Pro Gly Glu Arg Gly Ala Ala Gly 1737        1746        1755        1764        1773        1782
CTA CCG GGT CCG AAA GGC GAC CGC GGT GAT GCG GGT CCA AAA GGT GCG GAT GGC
--- --- --- --- --- --- --- --- --- --- --- --- --- --- --- --- --- ---
Leu Pro Gly Pro Lys Gly Asp Arg Gly Asp Ala Gly Pro Lys Gly Ala Asp Gly 1791        1800        1809        1818        1827        1836
TCC CCT GGC AAA GAT GGC GTT CGT GGT CTG ACC GGC CCG ATC GGC CCG CCG GGC
--- --- --- --- --- --- --- --- --- --- --- --- --- --- --- --- --- ---
Ser Pro Gly Lys Asp Gly Val Arg Gly Leu Thr Gly Pro Ile Gly Pro Pro Gly 1845        1854        1863        1872        1881        1890
CCG GCA GGT GCC CCG GGT GAC AAA GGT GAA AGC GGT CCG AGC GGC CCA GCG GGC
--- --- --- --- --- --- --- --- --- --- --- --- --- --- --- --- --- ---
Pro Ala Gly Ala Pro Gly Asp Lys Gly Glu Ser Gly Pro Ser Gly Pro Ala Gly 1899        1908        1917        1926        1935        1944
CCC ACT GGT GCG CGT GGT GCC CCG GGC GAC CGT GGT GAA CCG GGT CCG CCG GGC
--- --- --- --- --- --- --- --- --- --- --- --- --- --- --- --- --- ---
Pro Thr Gly Ala Arg Gly Ala Pro Gly Asp Arg Gly Glu Pro Gly Pro Pro Gly 1953        1962        1971        1980        1989        1998
CCG GCG GGC TTT GCG GGC CCG CCA GCG GCT GAC GGC CAG CCG GGT GCG AAA GGC
--- --- --- --- --- --- --- --- --- --- --- --- --- --- --- --- --- ---
Pro Ala Gly Phe Ala Gly Pro Pro Ala Ala Asp Gly Gln Pro Gly Ala Lys Gly 2007        2016        2025        2034        2043        2052
GAA CCG GGG GAT GCG GGT GCC AAA GGC GAC GCG GGT CCG CCG GGC CCT GCC GGC
--- --- --- --- --- --- --- --- --- --- --- --- --- --- --- --- --- ---
Glu Pro Gly Asp Ala Gly Ala Lys Gly Asp Ala Gly Pro Pro Gly Pro Ala Gly
```

*FIG. 39C*

```
              2061           2070           2079           2088           2097           2106
CCG GCG GGC CCG CCA GGC CCG ATT GGC AAC GTG GGT GCG CCG GGT GCC AAA GGT
--- --- --- --- --- --- --- --- --- --- --- --- --- --- --- --- --- ---
Pro Ala Gly Pro Pro Gly Pro Ile Gly Asn Val Gly Ala Pro Gly Ala Lys Gly 2115           2124           2133           2142           2151           2160
GCG CGC GGC AGC GCT GGT CCG CCG GGC GCG ACC GGT TTC CCC GGT GCG GCG GGG
--- --- --- --- --- --- --- --- --- --- --- --- --- --- --- --- --- ---
Ala Arg Gly Ser Ala Gly Pro Pro Gly Ala Thr Gly Phe Pro Gly Ala Ala Gly 2169           2178           2187           2196           2205           2214
CGC GTG GGT CCG CCA GGC CCG AGC GGT AAC GCG GGC GCG CCG GGC CCG CCG GGC
--- --- --- --- --- --- --- --- --- --- --- --- --- --- --- --- --- ---
Arg Val Gly Pro Pro Gly Pro Ser Gly Asn Ala Gly Pro Pro Gly Pro Pro Gly 2223           2232           2241           2250           2259           2268
CCG GCG GGC AAA GAG GGC GGC AAA GGT CCG CGT GGT GAA ACC GGC CCT GCG GGA
--- --- --- --- --- --- --- --- --- --- --- --- --- --- --- --- --- ---
Pro Ala Gly Lys Glu Gly Gly Lys Gly Pro Arg Gly Glu Thr Gly Pro Ala Gly 2277           2286           2295           2304           2313           2322
CGT CCA GGT GAA GTG GGT CCG CCG GGC CCG CCG GGC CCG GCG GGC GAA AAA GGT
--- --- --- --- --- --- --- --- --- --- --- --- --- --- --- --- --- ---
Arg Pro Gly Glu Val Gly Pro Pro Gly Pro Pro Gly Pro Ala Gly Glu Lys Gly 2331           2340           2349           2358           2367           2376
AGC CCG GGT GCG GAT GGT CCC GCC GGT GCG CCA GGC ACG CCG GGT CCG CAA GGT
--- --- --- --- --- --- --- --- --- --- --- --- --- --- --- --- --- ---
Ser Pro Gly Ala Asp Gly Pro Ala Gly Ala Pro Gly Thr Pro Gly Pro Gln Gly 2385           2394           2403           2412           2421           2430
ATC GCT GGC CAG CGT GGT GTC GTC GGG CTG CCG GGT CAG CGC GGC GAA CGC GGC
--- --- --- --- --- --- --- --- --- --- --- --- --- --- --- --- --- ---
Ile Ala Gly Gln Arg Gly Val Val Gly Leu Pro Gly Gln Arg Gly Glu Arg Gly 2439           2448           2457           2466           2475           2484
TTT CCG GGT CTG CCG GGC CCG AGC GGT GAG CCG GGC AAA CAG GGT CCA TCT GGC
--- --- --- --- --- --- --- --- --- --- --- --- --- --- --- --- --- ---
Phe Pro Gly Leu Pro Gly Pro Ser Gly Glu Pro Gly Lys Gln Gly Pro Ser Gly 2493           2502           2511           2520           2529           2538
GCG AGC GGT GAA CGT GGC CCG CCG GGT CCC ATG GGC CCG CCG GGT CTG GCG GGC
--- --- --- --- --- --- --- --- --- --- --- --- --- --- --- --- --- ---
Ala Ser Gly Glu Arg Gly Pro Pro Gly Pro Met Gly Pro Pro Gly Leu Ala Gly 2547           2556           2565           2574           2583           2592
CCT CCG GGT GAA AGC GGT CGT GAA GGC GCG CCG GGT GCC GAA GGC AGC CCA GGC
--- --- --- --- --- --- --- --- --- --- --- --- --- --- --- --- --- ---
Pro Pro Gly Glu Ser Gly Arg Glu Gly Ala Pro Gly Ala Glu Gly Ser Pro Gly 2601           2610           2619           2628           2637           2646
CGC GAC GGT AGC CCG GGG GCC AAA GGG GAT CGT GGT GAA ACC GGC CCG GCG GGC
--- --- --- --- --- --- --- --- --- --- --- --- --- --- --- --- --- ---
Aeg Asp Gly Ser Pro Gly Ala Lys Gly Asp Arg Gly Glu Thr Gly Pro Ala Gly 2655           2664           2673           2682           2691           2700
CCC CCG GGT GCA CCG GGC GCG CCG GGT GCC CCA GGC CCG GTG GGC CCG GCG GGC
--- --- --- --- --- --- --- --- --- --- --- --- --- --- --- --- --- ---
Pro Pro Gly Ala Pro Gly Ala Pro Gly Ala Pro Gly Pro Val Gly Pro Ala Gly 2709           2718           2727           2736           2745           2754
AAA AGC GGT GAT CGT GGT GAG ACC GGT CCG GCG GGC CCG GCC GGT CCG GTG GGC
--- --- --- --- --- --- --- --- --- --- --- --- --- --- --- --- --- ---
Lys Ser Gly Asp Arg Gly Glu Thr Gly Pro Ala Gly Pro Ala Gly Pro Val Gly
```

*FIG. 39D*

```
     2763        2772        2781        2790        2799        2808
CCA GCG GGC GCC CGT GGC CCG GCC GGT CCG CAG GGC CCG CGG GGT GAC AAA GGT
--- --- --- --- --- --- --- --- --- --- --- --- --- --- --- --- --- ---
PRO ALA GLY ALA ARG GLY PRO ALA GLY PRO GLN GLY PRO ARG GLY ASP LYS GLY 2817        2826        2835        2844        2853        2862
GAA ACG GGC GAA CAG GGC GAC CGT GGC ATT AAA GGC CAC CGT GGC TTC AGC GGC
--- --- --- --- --- --- --- --- --- --- --- --- --- --- --- --- --- ---
GLU THR GLY GLU GLN GLY ASP ARG GLY ILE LYS GLY HIS ARG GLY PHE SER GLY 2871        2880        2889        2898        2907        2916
CTG CAG GGT CCA CCG GGC CCG CCG GGC AGT CCG GGT GAA CAG GGT CCG TCC GGA
--- --- --- --- --- --- --- --- --- --- --- --- --- --- --- --- --- ---
LEU GLN GLY PRO PRO GLY PRO PRO GLY SER PRO GLY GLU GLN GLY PRO SER GLY 2925        2934        2943        2952        2961        2970
GCC AGC GGG CCG GCG GGC CCA CGC GGT CCG CCG GGC AGC GCG GGT GCG CCG GGC
--- --- --- --- --- --- --- --- --- --- --- --- --- --- --- --- --- ---
ALA SER GLY PRO ALA GLY PRO ARG GLY PRO PRO GLY SER ALA GLY ALA PRO GLY 2979        2988        2997        3006        3015        3024
AAA GAC GGT CTG AAC GGT CTG CCG GGC CCG ATC GGC CCG CCG GGC CCA CGC GGC
--- --- --- --- --- --- --- --- --- --- --- --- --- --- --- --- --- ---
LYS ASP GLY LEU ASN GLY LEU PRO GLY PRO ILE GLY PRO PRO GLY PRO ARG GLY 3033        3042        3051        3060        3069        3078
CGC ACC GGT GAT GCG GGT CCG GTG GGT CCC CCG GGC CCG CCG GGC CCG CCA GGC
--- --- --- --- --- --- --- --- --- --- --- --- --- --- --- --- --- ---
ARG THR GLY ASP ALA GLY PRO VAL GLY PRO PRO GLY PRO PRO GLY PRO PRO GLY 3087        3096        3105        3114        3123        3132
CCG CCG GGT CCG CCG AGC GCG GGT TTC GAC TTC AGC TTC CTG CCG CAG CCG CCG
--- --- --- --- --- --- --- --- --- --- --- --- --- --- --- --- --- ---
PRO PRO GLY PRO PRO SER ALA GLY PHE ASP PHE SER PHE LEU PRO GLN PRO PRO 3141        3150        3159        3168
CAG GAG AAA GCG CAC GAC GGC GGT CGC TAC TAC CGT GCG 3'
--- --- --- --- --- --- --- --- --- --- --- --- ---
GLN GLU LYS ALA HIS ASP GLY GLY ARG TYR TYR ARG ALA
```

FIG. 39E

```
                    EcoRI start           Oligo N1-1                                                    BsrII stop    Hind III
5'-GGAATTCATGCAGCTGAGCTATGGCTATGATGAAAAAGCACCGGCGGCTGCCGGGGCCTGCCGGGGCCTGCCGGGGCCCGATGGGTCCGAGC-3'
                                      3'-GGCCCCGGGCTACCCAGGCTCGCCGGGGCTCGCACCGGACGGCCACCCGGCGGTCCAGCGGGCCAGCATTATTCGAACCC-5'
                                                                      Oligo N1-2

EcoRI  BsrII           Oligo N1-3                                                                    AatII stop   Hind III
5'-GGAATTCCGGGTCCGCCACGGCCTTTCACGGTCGCGCCGGCGAACCTGGTGCCAGCGGCGCCCGATGGCCCCGGCGCCCCGG-3'
                         3'-TACCCCGCCGCCGCCCCGGGCGCCGCCAGGCGGTCCGTTTTGCCGCTACTACCGCTTCGCCCGTTTGGCCCTGCCACCCATTATTCGAACCC-5'
                                                                      Oligo N1-4
```

FIG. 40

```
                9              18             27             36             45             54
5' CAG CTG AGC TAT GGC TAT GAT GAA AAA AGC ACC GGC GGC ATC AGC GTG CCG GGC
   Gln Leu Ser Tyr Gly Tyr Asp Glu Lys Ser Thr Gly Gly Ile Ser Val Pro Gly 63             72             81             90             99            108
   CCG ATG GGT CCG AGC GGC CCG CGT GGC CTG CCG GGC CCG CCA GGT GCG CCC GGT
   Pro Met Gly Pro Ser Gly Pro Arg Gly Leu Pro Gly Pro Pro Gly Ala Pro Gly

CCG
   Pro
```

FIG. 42

```
                9              18              27              36              45              54
5' CAG CTG AGC TAT GGC TAT GAT GAA AAA AGC ACC GGC GGC ATC AGC GTG CCG GGC
   Gln Leu Ser Tyr Gly Tyr Asp Glu Lys Ser Thr Gly Gly Ile Ser Val Pro Gly 63              72              81              90              99             108
   CCG ATG GGT CCG AGC GGC CCG CGT GGC CTG CCG GGC CCG CCA GGT GCG CCC GGT
   Pro Met Gly Pro Ser Gly Pro Arg Gly Leu Pro Gly Pro Pro Gly Ala Pro Gly 117             126             135             144             153             162
   CCG CAG GGC TTT CAG GGT CCG CCG GGC GAA CCG GGC GAA CCT GGT GCG AGC GGC
   Pro Gln Gly Phe Gln Gly Pro Pro Gly Glu Pro Gly Glu Pro Gly Ala Ser Gly 171             180             189             198             207             216
   CCG ATG GGC CCG CGC GGC CCG CCG GGT CCG CCA GGC AAA AAC GGC GAT GAT GGC
   Pro Met Gly Pro Arg Gly Pro Pro Gly Pro Pro Gly Lys Asn Gly Asp Asp Gly 225             234
   GAA GCG GGC AAA CCG GGA CGT CCG
   Glu Ala Gly Lys Pro Gly Arg Pro
```

*FIG. 44*

```
               9            18            27            36            45            54
5' CAG TAT GAT GGA AAA GGA GTT GGA CTT GGC CCT CGA CCA ATG GGC TTA ATG GGA
   --- --- --- --- --- --- --- --- --- --- --- --- --- --- --- --- --- ---
   Gln Tyr Asp Gly Lys Gly Val Gly Leu Gly Pro Gly Pro Met Gly Leu Met Gly 63            72            81            90            99           108
   CCT AGA GGC CCA CCT GGT GCA GCT GGA GCC CCA GGC CCT CAA GGT TTC CAA GGA
   --- --- --- --- --- --- --- --- --- --- --- --- --- --- --- --- --- ---
   Pro Arg Gly Pro Pro Gly Ala Ala Gly Ala Pro Gly Pro Gln Gly Phe Gln Gly 117           126           135           144           153           162
   CCT GCT GGT GAG CCT GGT GAA CCT GGT CAA ACT GGT CCT GCA GGT GCT CGT GGT
   --- --- --- --- --- --- --- --- --- --- --- --- --- --- --- --- --- ---
   Pro Ala Gly Glu Pro Gly Glu Pro Gly Gln Thr Gly Pro Ala Gly Ala Arg Gly 171           180           189           198           207           216
   CCA GCT GGC CCT CCT GGC AAG GCT GGT GAA GAT GGT CAC CCT GGA AAA CCC GGA
   --- --- --- --- --- --- --- --- --- --- --- --- --- --- --- --- --- ---
   Pro Ala Gly Pro Pro Gly Lys Ala Gly Glu Asp Gly His Pro Gly Lys Pro Gly 225           234           243           252           261           270
   CGA CCT GGT GAG AGA GGA GTT GTT GGA CCA CAG GGT GCT CGT GGT TTC CCT GGA
   --- --- --- --- --- --- --- --- --- --- --- --- --- --- --- --- --- ---
   Arg Pro Gly Glu Arg Gly Val Val Gly Pro Gln Gly Ala Arg Gly Phe Pro Gly 279           288           297           306           315           324
   ACT CCT GGA CTT CCT GGC TTC AAA GGC ATT AGG GGA CAC AAT GGT CTG GAT GGA
   --- --- --- --- --- --- --- --- --- --- --- --- --- --- --- --- --- ---
   Thr Pro Gly Leu Pro Gly Phe Lys Gly Ile Arg Gly His Asn Gly Leu Asp Gly 333           342           351           360           369           378
   TTG AAG GGA CAG CCC GGT GCT CCT GGT GTG AAG GGT GAA CCT GGT GCC CCT GGT
   --- --- --- --- --- --- --- --- --- --- --- --- --- --- --- --- --- ---
   Leu Lys Gly Gln Pro Gly Ala Pro Gly Val Lys Gly Glu Pro Gly Ala Pro Gly 387           396           405           414           423           432
   GAA AAT GGA ACT CCA GGT CAA ACA GGA GCC CGT GGG CTT CCT GGT GAG AGA GGA
   --- --- --- --- --- --- --- --- --- --- --- --- --- --- --- --- --- ---
   Glu Asn Gly Thr Pro Gly Gln Thr Gly Ala Arg Gly Leu Pro Gly Glu Arg Gly 441           450           459           468           477           486
   CGT GTT GGT GCC CCT GGC CCA GCT GGT GCC CGT GGC AGT GAT GGA AGT GTG GGT
   --- --- --- --- --- --- --- --- --- --- --- --- --- --- --- --- --- ---
   Arg Val Gly Ala Pro Gly Pro Ala Gly Ala Arg Gly Ser Asp Gly Ser Val Gly 495           504           513           522           531           540
   CCC GTG GGT CCT GCT GGT CCC ATT GGG TCT GCT GGC CCT CCA GGC TTC CCA GGT
   --- --- --- --- --- --- --- --- --- --- --- --- --- --- --- --- --- ---
   Pro Val Gly Pro Ala Gly Pro Ile Gly Ser Ala Gly Pro Pro Gly Phe Pro Gly 549           558           567           576           585           594
   GCC CCT GGC CCC AAG GGT GAA ATT GGA GCT GTT GGT AAC GCT GGT CCT GCT GGT
   --- --- --- --- --- --- --- --- --- --- --- --- --- --- --- --- --- ---
   Ala Pro Gly Pro Lys Gly Glu Ile Gly Ala Val Gly Asn Ala Gly Pro Ala Gly 603           612           621           630           639           648
   CCC GCC GGT CCC CGT GGT GAA GTG GGT CTT CCA GGC CTC TCC GGC CCC GTT GGA
   --- --- --- --- --- --- --- --- --- --- --- --- --- --- --- --- --- ---
   Pro Ala Gly Pro Arg Gly Glu Val Gly Leu Pro Gly Leu Ser Gly Pro Val Gly
```

*FIG. 49A*

|     | 657 |     |     | 666 |     |     | 675 |     |     | 684 |     |     | 693 |     |     | 702 |
|-----|-----|-----|-----|-----|-----|-----|-----|-----|-----|-----|-----|-----|-----|-----|-----|-----|
| CCT | CCT | GGT | AAT | CCT | GGA | GCA | AAC | GGC | CTT | ACT | GGT | GCC | AAG | GGT | GCT | GCT | GGC |
| Pro | Pro | Gly | Asn | Pro | Gly | Ala | Asn | Gly | Leu | Thr | Gly | Ala | Lys | Gly | Ala | Ala | Gly |

```
         711             720             729             738             747             756
CTT CCC GGC GTT GCT GGG GCT CCC GGC CTC CCT GGA CCC CGC GGT ATT CCT GGC
Leu Pro Gly Val Ala Gly Ala Pro Gly Leu Pro Gly Pro Arg Gly Ile Pro Gly 765             774             783             792             801             810
CCT GTT GGT GCT GCC GGT GCT ACT GGT GCC AGA GGA CTT GTT GGT GAG CCT GGT
Pro Val Gly Ala Ala Gly Ala Thr Gly Ala Arg Gly Leu Val Gly Glu Pro Gly 819             828             837             846             855             864
CCA GCT GGC TCC AAA GGA GAG AGC GGT AAC AAG GGT GAG CCC GGC TCT GCT GGG
Pro Ala Gly Ser Lys Gly Glu Ser Gly Asn Lys Gly Glu Pro Gly Ser Ala Gly 873             882             891             900             909             918
CCC CAA GGT CCT CCT GGT CCC AGT GGT GAA GAA GGA AAG AGA GGC CCT AAT GGG
Pro Gln Gly Pro Pro Gly Pro Ser Gly Glu Glu Gly Lys Arg Gly Pro Asn Gly 927             936             945             954             963             972
GAA GCT GGA TCT GCC GGC CCT CCA GGA CCT CCT GGG CTG AGA GGT AGT CCT GGT
Glu Ala Gly Ser Ala Gly Pro Pro Gly Pro Pro Gly Leu Arg Gly Ser Pro Gly 981             990             999             1008            1017            1026
TCT CGT GGT CTT CCT GGA GCT GAT GGC AGA GCT GGC GTC ATG GGC CCT CCT GGT
Ser Arg Gly Leu Pro Gly Ala Asp Gly Arg Ala Gly Val Met Gly Pro Pro Gly 1035            1044            1053            1062            1071            1080
AGT CGT GGT GCA AGT GGC CCT GCT GGA GTC CGA GGA CCT AAT GGA GAT GCT GGT
Ser Arg Gly Ala Ser Gly Pro Ala Gly Val Arg Gly Pro Asn Gly Asp Ala Gly 1089            1098            1107            1116            1125            1134
CGC CCT GGG GAG CCT GGT CTC ATG GGA CCC AGA GGT CTT CCT GGT TCC CCT GGA
Arg Pro Gly Glu Pro Gly Leu Met Gly Pro Arg Gly Leu Pro Gly Ser Pro Gly 1143            1152            1161            1170            1179            1188
AAT ATC GGC CCC GCT GGA AAA GAA GGT CCT GTC GGC CTC CCT GGC ATC GAC GGC
Asn Ile Gly Pro Ala Gly Lys Glu Gly Pro Val Gly Leu Pro Gly Ile Asp Gly 1197            1206            1215            1224            1233            1242
AGG CCT GGC CCA ATT GGC CCA GCT GGA GCA AGA GGA GAG CCT GGC AAC ATT GGA
Arg Pro Gly Pro Ile Gly Pro Ala Gly Ala Arg Gly Glu Pro Gly Asn Ile Gly 1251            1260            1269            1278            1287            1296
TTC CCT GGA CCC AAA GGC CCC ACT GGT GAT CCT GGC AAA AAC GGT GAT AAA GGT
Phe Pro Gly Pro Lys Gly Pro Thr Gly Asp Pro Gly Lys Asn Gly Asp Lys Gly 1305            1314            1323            1332            1341            1350
CAT GCT GGT CTT GCT GGT GCT CGG GGT GCT CCA GGT CCT GAT GGA AAC AAT GGT
His Ala Gly Leu Ala Gly Ala Arg Gly Ala Pro Gly Pro Asp Gly Asn Asn Gly
```

*FIG. 49B*

```
      1359            1368            1377            1386            1395            1404
GCT CAG GGA CCT CCT GGA CCA CAG GGT GTT CAA GGT GGA AAA GGT GAA CAG GGT
Ala Gln Gly Pro Pro Gly Pro Gln Gly Val Gln Gly Gly Lys Gly Glu Gln Gly 1413            1422            1431            1440            1449            1458
CCC GAT GGT CCT CCA GGC TTC CAG GGT CTG CCT GGC CCC TCA GGT CCC GCT GGT
Pro Asp Gly Pro Pro Gly Phe Gln Gly Leu Pro Gly Pro Ser Gly Pro Ala Gly 1467            1476            1485            1494            1503            1512
GAA GTT GGC AAA CCA GGA GAA AGG GGT CTC CAT GGT GAG TTT GGT CTC CCT GGT
Glu Val Gly Lys Pro Gly Glu Arg Gly Leu His Gly Glu Ohe Gly Leu Pro Gly 1521            1530            1539            1548            1557            1566
CCT GCT GGT CCA AGA GGG GAA CGC GGT CCC CCA GGT GAG AGT GGT GCT GCC GGT
Pro Ala Gly Pro Arg Gly Glu Arg Gly Pro Pro Gly Glu Ser Gly Ala Ala Gly 1575            1584            1593            1602            1611            1620
CCT ACT GGT CCT ATT GGA AGC CGA GGT CCT TCT GGA CCC CCA GGG CCT GAT GGA
Pro Thr Gly Pro Ile Gly Ser Arg Gly Pro Ser Gly Pro Pro Gly Pro Asp Gly 1629            1638            1647            1656            1665            1674
AAC AAG GGT GAA CCT GGT GTG GTT GGT GCT GTG GGC ACT GCT GGT CCA TCT GGT
Asn Lys Gly Glu Pro Gly Val Val Gly Ala Val Gly Thr Ala Gly Pro Ser Gly 1683            1692            1701            1710            1719            1728
CCT AGT GGA CTC CCA GGA GAG AGG GGT GCT GCT GGC ATA CCT GGA GGC AAG GGA
Pro Ser Gly Leu Pro Gly Glu Arg Gly Ala Ala Gly Ile Pro Gly Gly Lys Gly 1737            1746            1755            1764            1773            1782
GAA AAG GGT GAA CCT GGT CTC AGA GGT GAA ATT GGT AAC CCT GGC AGA GAT GGT
Glu Lys Gly Glu Pro Gly Leu Arg Gly Glu Ile Gly Asn Pro Gly Arg Asp Gly 1791            1800            1809            1818            1827            1836
GCT CGT GGT GCT CAT GGT GCT GTA GGT GCC CCT GGT CCT GCT GGA GCC ACA GGT
Ala Arg Gly Ala His Gly Ala Val Gly Ala Pro Gly Pro Ala Gly Ala Thr Gly 1845            1854            1863            1872            1881            1890
GAC CGG GGC GAA GCT GGG GCT GCT GGT CCT GCT GGT CCT GCT GGT CCT CGG GGA
Asp Arg Gly Glu Ala Gly Ala Ala Gly Pro Ala Gly Pro Ala Gly Pro Arg Gly 1899            1908            1917            1926            1935            1944
AGC CCT GGT GAA CGT GGC GAG GTC GGT CCT GCT GGC CCC AAC GGA TTT GCT GGT
Ser Pro Gly Glu Arg Gly Glu Val Gly Pro Ala Gly Pro Asn Gly Phe Ala Gly 1953            1962            1971            1980            1989            1998
CCG GCT GGT GCT GCT GGT CAA CCG GGT GCT AAA GGA GAA AGA GGA GCC AAA GGG
Pro Ala Gly Ala Ala Gly Gln Pro Gly Ala Lys Gly Glu Arg Gly Ala Lys Gly 2007            2016            2025            2034            2043            2052
CCT AAG GGT GAA AAC GGT GTT GTT GGT CCC ACA GGC CCC GTT GGA GCT GCT GGC
Pro Lys Gly Glu Asn Gly Val Val Gly Pro Thr Gly Pro Val Gly Ala Ala Gly
```

*FIG. 49C*

```
      2061        2070        2079        2088        2097        2106
CCN NNN GGT CCA AAT GGT CCC CCC GGT CCT GCT GGA AGT CGT GGT GAT GGA GGC
Pro Xxx Gly Pro Asn Gly Pro Pro Gly Pro Ala Gly Ser Arg Gly Asp Gly Gly 2115        2124        2133        2142        2151        2160
CCC CCT GGT ATG ACT GGT TTC CCT GGT GCT GCT GGA CGG ACT GGT CCC CCA GGA
Pro Pro Gly Met Thr Gly Phe Pro Gly Ala Ala Gly Arg Thr Gly Pro Pro Gly 2169        2178        2187        2196        2205        2214
CCC TCT GGT ATT TCT GGC CCT CCT GGT CCC CCT GGT CCT GCT GGG AAA GAA GGG
Pro Ser Gly Ile Ser Gly Pro Pro Gly Pro Pro Gly Pro Ala Gly Lys Glu Gly 2223        2232        2241        2250        2259        2268
CTT CGT GGA CCN CGA GGN GAC CAA GGA CCA GCA GGC CGA CCT GGA GAA GTA GGA
Leu Arg Gly Pro Arg Gly Asp Gln Gly Pro Ala Gly Arg Pro Gly Glu Val Gly 2277        2286        2295        2304        2313        2322
GCA CCG GGT CCC CCT GGC TTC GCT GGT GAG AAG GGT CCC TCT GGA GAG GCT GGT
Ala Pro Gly Pro Pro Gly Phe Ala Gly Glu Lys Gly Pro Ser Gly Glu Ala Gly 2331        2340        2349        2358        2367        2376
ACT GCT GGA CCT CCT GGC ACT CCA GGT CCT CAG GGT CTT CTT GGT GCT CCT GGT
Thr Ala Gly Pro Pro Gly Thr Pro Gly Pro Gln Gly Leu Leu Gly Ala Pro Gly 2385        2394        2403        2412        2421        2430
ATT CTG GGT CTC CCT GGC TCG AGA GGT GAA CGT GGT CTA CCT GGT GTT GCT GGT
Ile Leu Gly Leu Pro Gly Ser Arg Gly Glu Arg Gly Leu Pro Gly Val Ala Gly 2439        2448        2457        2466        2475        2484
GCT GTG CGT GAA CCT GGT CCT CTT GGC ATT GCC GGC CCT CCT GGG GCC CGT GGT
Ala Val Gly Glu Pro Gly Pro Leu Gly Ile Ala Gly Pro Pro Gly Ala Arg Gly 2493        2502        2511        2520        2529        2538
CCT CCT GGT GCT GTG GGT AGT CCT GGA GTC AAC GGT GCT CCT GGT GAA GCT GGT
Pro Pro Gly Ala Val Gly Ser Pro Gly Val Asn Gly Ala Pro Gly Glu Ala Gly 2547        2556        2565        2574        2583        2592
CGT GAT GGC AAC CCT GGG AAC GAT GGT CCC CCA GGT CGC GAT GGT CAA CCC GGA
Arg Asp Gly Asn Pro Gly Asn Asp Gly Pro Pro Gly Arg Asp Gly Gln Pro Gly 2601        2610        2619        2628        2637        2646
CAC AAG GGA GAG CGC GGT TAC CCT GGC AAT ATT GGT CCC GTT GGT GCT GCA GGT
His Lys Gly Glu Arg Gly Tyr Pro Gly Asn Ile Gly Pro Val Gly Ala Ala Gly 2655        2664        2673        2682        2691        2700
GCA CCT GGT CCT CAT GGC CCC GTG GGT CCT GCT GGC AAA CAT GGA AAC CGT GGT
Ala Pro Gly Pro His Gly Pro Val Gly Pro Ala Gly Lys His Gly Asn Arg Gly 2709        2718        2727        2736        2745        2754
GAA ACT GGT CCT TCT GGT CCT GTT GGT CCT GCT GGT GCT GTT GGC CCA AGA GGT
Glu Thr Gly Pro Ser Gly Pro Val Gly Pro Ala Gly Ala Val Gly Pro Arg Gly
```

*FIG. 49D*

```
      2763        2772        2781        2790        2799        2808
CCT AGT GGC CCA CAA GGC ATT CGT GGC GAT AAG GGA GAG CCC GGT GAA AAG GGG
--- --- --- --- --- --- --- --- --- --- --- --- --- --- --- --- --- ---
Pro Ser Gly Pro Gln Gly Ile Arg Gly Asp Lys Gly Glu Pro Gly Glu Lys Gly 2817        2826        2835        2844        2853        2862
CCC AGA GGT CTT CCT GGC TTC AAG GGA CAC AAT GGA TTG CAA GGT CTG CCT GGT
--- --- --- --- --- --- --- --- --- --- --- --- --- --- --- --- --- ---
Pro Arg Gly Leu Pro Gly Phe Lys Gly His Asn Gly Leu Gln Gly Leu Pro Gly 2871        2880        2889        2898        2907        2916
ATC GCT GGT CAC CAT GGT GAT CAA GGT GCT CCT GGC TCC GTG GGT CCT GCT GGT
--- --- --- --- --- --- --- --- --- --- --- --- --- --- --- --- --- ---
Ile Ala Gly His His Gly Asp Gln Gly Ala Pro Gly Ser Val Gly Pro Ala Gly 2925        2934        2943        2952        2961        2970
CCT AGG GGC CCT GCT GGT CCT TCT GGC CCT GCT GGA AAA GAT GGT CGC ACT GGA
--- --- --- --- --- --- --- --- --- --- --- --- --- --- --- --- --- ---
Pro Arg Gly Pro Ala Gly Pro Ser Gly Pro Ala Gly Lys Asp Gly Arg Thr Gly 2979        2988        2997        3006        3015        3024
CAT CCT GGT ACG GTT GGA CCT GCT GGC ATT CGA GGC CCT CAG GGT CAC CAA GGC
--- --- --- --- --- --- --- --- --- --- --- --- --- --- --- --- --- ---
His Pro Gly Thr Val Gly Pro Ala Gly Ile Arg Gly Pro Gln Gly His Gln Gly 3033        3042        3051        3060        3069        3078
CCT GCT GGC CCC CCT GGT CCC CCT GGC CCT CTT GGA CCT CTA GGT GTA AGC GGT
--- --- --- --- --- --- --- --- --- --- --- --- --- --- --- --- --- ---
Pro Ala Gly Pro Pro Gly Pro Pro Gly Pro Leu Gly Pro Leu Gly Val Ser Gly 3087        3096        3105        3114
GGT GGT TAT GAC TTT GGT TAC GAT GGA GAC TTC TAC AGG GCT 3'
--- --- --- --- --- --- --- --- --- --- --- --- --- ---
Gly Gly Tyr Asp Phe Gly Tyr Asp Gly Asp Phe Tyr Arg Ala
```

*FIG. 49E*

```
                    9              18              27              36              45              54
5' CAG TAC GAC GGT AAA GGC GTA GGC CTG GGT CCG GGT CCG ATG GGC CTG ATG GGT
   Gln Tyr Asp Gly Lys Gly Val Gly Leu Gly Pro Gly Pro Met Gly Leu Met Gly 63              72              81              90              99             108
   CCA CGT GGC CCA CCG GGT GCA GCA GGT GCG CCG GGT CCG CAG GGC TTC CAA GGT
   Pro Arg Gly Pro Pro Gly Ala Ala Gly Ala Pro Gly Pro Gln Gly Phe Gln Gly 117             126             135             144             153             162
   CCG GCG GGT GAA CCG GGC GAA CCG GGT CAG ACG GGT CCG GCG GGT GCT CGC GGT
   Pro Ala Gly Glu Pro Gly Glu Pro Gly Gln Thr Gly Pro Ala Gly Ala Arg Gly 171             180             189             198             207             216
   CCG GCT GGC CCA CCG GGC AAA GCT GGC GAA GAC GGT CAC CCG GGT AAG CCA GGC
   Pro Ala Gly Pro Pro Gly Lys Ala Gly Glu Asp Gly His Pro Gly Lys Pro Gly 225             234             243             252             261             270
   CGC CCG GGC GAA CGT GGC GTC GTG GGT CCG CAA GGT GCG CGT GGT TTC CCG GGC
   Arg Pro Gly Glu Arg Gly Val Val Gly Pro Gln Gly Ala Arg Gly Phe Pro Gly 279             288             297             306             315             324
   ACG CCG GGT CTG CCG GGT TTC AAA GGC ATT CGT GGT CAC AAC GGT CTG GAC GGT
   Thr Pro Gly Leu Pro Gly Phe Lys Gly Ile Arg Gly His Asn Gly Leu Asp Gly 333             342             351             360             369             378
   CTG AAA GGC CAA CCG GGT GCT CCG GGC GTC AAA GGC GAA CCG GGT GCC CCA GGC
   Leu Lys Gly Gln Pro Gly Ala Pro Gly Val Lys Gly Glu Pro Gly Ala Pro Gly 387             396             405             414             423             432
   GAA AAC GGT ACG CCG GGC CAG ACT GGT GCG CGT GGT CTG CCG GGT GAA CGC GGC
   Glu Asn Gly Thr Pro Gly Gln Thr Gly Ala Arg Gly Leu Pro Gly Glu Arg Gly 441             450             459             468             477             486
   CGT GTT GGC GCT CCG GGT CCG GCT GGC GCG CGT GGC AGC GAT GGC TCC GTC GGT
   Arg Val Gly Ala Pro Gly Pro Ala Gly Ala Arg Gly Ser Asp Gly Ser Val Gly 495             504             513             522             531             540
   CCG GTT GGC CCT GCG GGT CCG ATT GGT TCC GCT GGC CCT CCG GGT TTC CCG GGT
   Pro Val Gly Pro Ala Gly Pro Ile Gly Ser Ala Gly Pro Pro Gly Phe Pro Gly 549             558             567             576             585             594
   GCG CCG GGT CCG AAG GGT GAG ATC GGC GCG GTT GGC AAC GCA GGC CCG GCT GGT
   Ala Pro Gly Pro Lys Gly Glu Ile Gly Ala Val Gly Asn Ala Gly Pro Ala Gly 603             612             621             630             639             648
   CCA GCC GGC CCT CGT GGC GAA GTC GGT CTG CCG GGT CTG AGC GGT CCG GTA GGC
   Pro Ala Gly Pro Arg Gly Glu Val Gly Leu Pro Gly Leu Ser Gly Pro Val Gly
```

*FIG. 50A*

```
          657         666         675         684         693         702
CCA CCG GGT AAC CCG GGC GCA AAC GGC CTG ACG GGT GCA AAA GGT GCG GCT GGC
--- --- --- --- --- --- --- --- --- --- --- --- --- --- --- --- --- ---
Pro Pro Gly Asn Pro Gly Ala Asn Gly Leu Thr Gly Ala Lys Gly Ala Ala Gly 711         720         729         738         747         756
CTG CCG GGC GTT GCC GGT GCC CCG GGC CTG CCG GGT CCG CGC GGT ATT CCG GGT
--- --- --- --- --- --- --- --- --- --- --- --- --- --- --- --- --- ---
Leu Pro Gly Val Ala Gly Ala Pro Gly Leu Pro Gly Pro Arg Gly Ile Pro Gly 765         774         783         792         801         810
CCG GTA GGC GCA GCC GGT GCA ACT GGT GCC CGT GGC CTG GTT GGC GAA CCG GGT
--- --- --- --- --- --- --- --- --- --- --- --- --- --- --- --- --- ---
Pro Val Gly Ala Ala Gly Ala Thr Gly Ala Arg Gly Leu Val Gly Glu Pro Gly 819         828         837         846         855         864
CCG GCG GGT TCT AAA GGC GAA AGC GGT AAC AAA GGT GAG CCG GGT TCC GCG GGC
--- --- --- --- --- --- --- --- --- --- --- --- --- --- --- --- --- ---
Pro Ala Gly Ser Lys Gly Glu Ser Gly Asn Lys Gly Glu Pro Gly Ser Ala Gly 873         882         891         900         909         918
CCG CAG GGT CCG CCG GGT CCG AGC GGC GAA GAA GGT AAA CGT GGT CCG AAC GGC
--- --- --- --- --- --- --- --- --- --- --- --- --- --- --- --- --- ---
Pro Gln Gly Pro Pro Gly Pro Ser Gly Glu Glu Gly Lys Arg Gly Pro Asn Gly 927         936         945         954         963         972
GAG GCT GGT TCC GCA GGC CCT CCG GGT CCG CCG GGT CTG CGT GGC AGC CCG GGT
--- --- --- --- --- --- --- --- --- --- --- --- --- --- --- --- --- ---
Glu Ala Gly Ser Ala Gly Pro Pro Gly Pro Pro Gly Leu Arg Gly Ser Pro Gly 981         990         999        1008        1017        1026
AGC CGT GGC CTG CCG GGC GCG GAC GGC CGT GCG GGC GTG ATG GGT CCG CCG GGT
--- --- --- --- --- --- --- --- --- --- --- --- --- --- --- --- --- ---
Ser Arg Gly Leu Pro Gly Ala Asp Gly Arg Ala Gly Val Met Gly Pro Pro Gly 1035        1044        1053        1062        1071        1080
TCC CGT GGT GCC TCT GGT CCG GCT GGT GTC CGT GGT CCG AAT GGC GAC GCG GGC
--- --- --- --- --- --- --- --- --- --- --- --- --- --- --- --- --- ---
Ser Arg Gly Ala Ser Gly Pro Ala Gly Val Arg Gly Pro Asn Gly Asp Ala Gly 1089        1098        1107        1116        1125        1134
CGT CCG GGT GAA CCG GGC CTG ATG GGT CCG CGT GGC CTG CCG GGT AGC CCG GGT
--- --- --- --- --- --- --- --- --- --- --- --- --- --- --- --- --- ---
Arg Pro Gly Glu Pro Gly Leu Met Gly Pro Arg Gly Leu Pro Gly Ser Pro Gly 1143        1152        1161        1170        1179        1188
GAT CGT GGC GAA GCT GGT GCA GCG GGT CCG GCG GGT CCG GCC GGC CCT CGC GGT
--- --- --- --- --- --- --- --- --- --- --- --- --- --- --- --- --- ---
Asn Ile Gly Pro Ala Gly Lys Glu Gly Pro Val Gly Leu Pro Gly Ile Asp Gly 1197        1206        1215        1224        1233        1242
AAC ATT GGT CCG GCG GGT AAG GAG GGT CCG GTA GGT CTG CCG GGT ATT GAT GGT
--- --- --- --- --- --- --- --- --- --- --- --- --- --- --- --- --- ---
Arg Pro Gly Pro Ile Gly Pro Ala Gly Ala Arg Gly Glu Pro Gly Asn Ile Gly 1251        1260        1269        1278        1287        1296
TTT CCG GGT CCG AAG GGT CCG ACG GGC GAC CCG GGC AAG AAC GGT GAT AAA GGC
--- --- --- --- --- --- --- --- --- --- --- --- --- --- --- --- --- ---
Phe Pro Gly Pro Lys Gly Pro Thr Gly Asp Pro Gly Lys Asn Gly Asp Lys Gly 1305        1314        1323        1332        1341        1350
CAT GCA GGT CTG GCA GGT GCC CGT GGT GCA CCG GGT CCG GAT GGT AAC AAT GGT
--- --- --- --- --- --- --- --- --- --- --- --- --- --- --- --- --- ---
His Ala Gly Leu Ala Gly Ala Arg Gly Ala Pro Gly Pro Asp Gly Asn Asn Gly
```

*FIG. 50B*

```
     1359        1368        1377        1386        1395        1404
GCG CAG GGT CCG CCG GGT CCG CAG GGC GTA CAG GGT GGC AAA GGT GAA CAG GGT
--- --- --- --- --- --- --- --- --- --- --- --- --- --- --- --- --- ---
Ala Gln Gly Pro Pro Gly Pro Gln Gly Val Gln Gly Gly Lys Gly Glu Gln Gly 1413        1422        1431        1440        1449        1458
CCG GCA GGC CCA CCG GGC TTC CAG GGT CTG CCG GGT CCG AGC GGC CCG GCT GGT
--- --- --- --- --- --- --- --- --- --- --- --- --- --- --- --- --- ---
Pro Ala Gly Pro Pro Gly Phe Gln Gly Leu Pro Gly Pro Ser Gly Pro Ala Gly 1467        1476        1485        1494        1503        1512
GAA GTG GGC AAA CCG GGC GAA CGT GGC CTC CAT GGC GAG TTT GGC CTG CCG GGT
--- --- --- --- --- --- --- --- --- --- --- --- --- --- --- --- --- ---
Glu Val Gly Lys Pro Gly Glu Arg Gly Leu His Gly Glu Ohe Gly Leu Pro Gly 1521        1530        1539        1548        1557        1566
CCG GCC GGT CCG CGT GGT GAG CGC GGC CCT CCG GGC GAA TCC GGC GCG GCA GGT
--- --- --- --- --- --- --- --- --- --- --- --- --- --- --- --- --- ---
Pro Ala Gly Pro Arg Gly Glu Arg Gly Pro Pro Gly Glu Ser Gly Ala Ala Gly 1575        1584        1593        1602        1611        1620
CCG ACC GGC CCG ATT GGT TCC CGT GGT CCG AGC GGC CCA CCG GGT CCG GAC GGC
--- --- --- --- --- --- --- --- --- --- --- --- --- --- --- --- --- ---
Pro Thr Gly Pro Ile Gly Ser Arg Gly Pro Ser Gly Pro Pro Gly Pro Asp Gly 1629        1638        1647        1656        1665        1674
AAC AAA GGC GAG CCG GGT GTT GTT GGT GCT GTT GGT ACC GCC GGC CCG TCT GGT
--- --- --- --- --- --- --- --- --- --- --- --- --- --- --- --- --- ---
Asn Lys Gly Glu Pro Gly Val Val Gly Ala Val Gly Thr Ala Gly Pro Ser Gly 1683        1692        1701        1710        1719        1728
CCG AGC GGT CTG CCG GGC GAA CGC GGT GCC GCT GGT ATT CCG GGC GGC AAA GGT
--- --- --- --- --- --- --- --- --- --- --- --- --- --- --- --- --- ---
Pro Ser Gly Leu Pro Gly Glu Arg Gly Ala Ala Gly Ile Pro Gly Gly Lys Gly 1737        1746        1755        1764        1773        1782
GAA AAA GGT GAA CCG GGT CTG CGC GGT GAG ATT GGC AAC CCG GGC CGT GAC GGT
--- --- --- --- --- --- --- --- --- --- --- --- --- --- --- --- --- ---
Glu Lys Gly Glu Pro Gly Leu Arg Gly Glu Ile Gly Asn Pro Gly Arg Asp Gly 1791        1800        1809        1818        1827        1836
GCT CGC GGT GCA CAC GGC GCG GTT GGC GCA CCG GGT CCG GCA GGC GCG ACT GGT
--- --- --- --- --- --- --- --- --- --- --- --- --- --- --- --- --- ---
Ala Arg Gly Ala His Gly Ala Val Gly Ala Pro Gly Pro Ala Gly Ala Thr Gly 1845        1854        1863        1872        1881        1890
GAT CGT GGC GAA GCT GGT GCA GCG GGT CCG GCG GGT CCG GCC GGC CCT CGC GGT
--- --- --- --- --- --- --- --- --- --- --- --- --- --- --- --- --- ---
Asp Arg Gly Glu Ala Gly Ala Ala Gly Pro Ala Gly Pro Ala Gly Pro Arg Gly 1899        1908        1917        1926        1935        1944
TCC CCG GGC GAA CGC GGC GAA GTC GGC CCG GCT GGC CCG AAT GGC TTT GCT GGC
--- --- --- --- --- --- --- --- --- --- --- --- --- --- --- --- --- ---
Ser Pro Gly Glu Arg Gly Glu Val Gly Pro Ala Gly Pro Asn Gly Phe Ala Gly 1953        1962        1971        1980        1989        1998
CCA GCG GGC GCT GCG GGC CAA CCG GGT GCG AAA GGT GAG CGC GGT GCC AAA GGC
--- --- --- --- --- --- --- --- --- --- --- --- --- --- --- --- --- ---
Pro Ala Gly Ala Ala Gly Gln Pro Gly Ala Lys Gly Glu Arg Gly Ala Lys Gly 2007        2016        2025        2034        2043        2052
CCG AAA GGT GAA AAT GGT GTA GTT GGT CCG ACG GGT CCG GTT GGT GCG GCT GGT
--- --- --- --- --- --- --- --- --- --- --- --- --- --- --- --- --- ---
Pro Lys Gly Glu Asn Gly Val Val Gly Pro Thr Gly Pro Val Gly Ala Ala Gly
```

*FIG. 50C*

```
      2061        2070        2079        2088        2097        2106
CCG GCT GGC CCG AAT GGT CCG CCG GGT CCG GCA GGC AGC CGT GGC GAT GGT GGC
Pro Ala Gly Pro Asn Gly Pro Pro Gly Pro Ala Gly Ser Arg Gly Asp Gly Gly 2115        2124        2133        2142        2151        2160
CCA CCG GGC ATG ACC GGT TTC CCT GGC GCG GCC GGT CGC ACC GGC CCG CCG GGT
Pro Pro Gly Met Thr Gly Phe Pro Gly Ala Ala Gly Arg Thr Gly Pro Pro Gly 2169        2178        2187        2196        2205        2214
CCG TCT GGC ATT TCT GGC CCA CCG GGT CCG CCG GGT CCG GCG GGC AAA GAA GGT
Pro Ser Gly Ile Ser Gly Pro Pro Gly Pro Pro Gly Pro Ala Gly Lys Glu Gly 2223        2232        2241        2250        2259        2268
CTG CGT GGC CCA CGC GGC GAC CAG GGT CCG GTG GGC CGT ACC GGC GAA GTC GGT
Leu Arg Gly Pro Arg Gly Asp Gln Gly Pro Val Gly Arg Thr Gly Glu Val Gly 2277        2286        2295        2304        2313        2322
GCT GTT GGC CCT CCG GGC TTT GCG GGT GAG AAA GGT CCG AGC GGT GAA GCT GGC
Ala Val Gly Pro Pro Gly Phe Ala Gly Glu Lys Gly Pro Ser Gly Glu Ala Gly 2331        2340        2349        2358        2367        2376
ACC GCA GGC CCG CCG GGT ACG CCG GGT CCG CAA GGT CTG CTG GGT GCT CCG GGT
Thr Ala Gly Pro Pro Gly Thr Pro Gly Pro Gln Gly Leu Leu Gly Ala Pro Gly 2385        2394        2403        2412        2421        2430
ATC CTG GGC CTG CCG GGC TCC CGT GGC GAA CGC GGT CTG CCG GGC GTT GCA GGC
Ile Leu Gly Leu Pro Gly Ser Arg Gly Glu Arg Gly Leu Pro Gly Val Ala Gly 2439        2448        2457        2466        2475        2484
GCT GTA GGC GAA CCG GGT CCG CTG GGT ATC GCG GGT CCG CCG GGT GCG CGT GGT
Ala Val Gly Glu Pro Gly Pro Leu Gly Ile Ala Gly Pro Pro Gly Ala Arg Gly 2493        2502        2511        2520        2529        2538
CCG CCG GGT GCC GTG GGC TCT CCG GGT GTT AAC GGC GCC CCT GGT GAA GCG GGC
Pro Pro Gly Ala Val Gly Ser Pro Gly Val Asn Gly Ala Pro Gly Glu Ala Gly 2547        2556        2565        2574        2583        2592
CGC GAC GGC AAT CCG GGC AAC GAT GGT CCG CCG GGT CGT GAT GGT CAG CCG GGT
Arg Asp Gly Asn Pro Gly Asn Asp Gly Pro Pro Gly Arg Asp Gly Gln Pro Gly 2601        2610        2619        2628        2637        2646
CAC AAA GGT GAG CGT GGC TAC CCG GGT AAC ATC GGT CCG GTT GGT GCG GCC GGC
His Lys Gly Glu Arg Gly Tyr Pro Gly Asn Ile Gly Pro Val Gly Ala Ala Gly 2655        2664        2673        2682        2691        2700
GCT CCG GGT CCG CAC GGT CCG GTA GGC CCA GCC GGC AAA CAC GGT AAC CGT GGT
Ala Pro Gly Pro His Gly Pro Val Gly Pro Ala Gly Lys His Gly Asn Arg Gly 2709        2718        2727        2736        2745        2754
GAA ACG GGT CCG TCC GGT CCG GTA GGT CCG GCG GGT GCT GTT GGT CCA CGC GGC
Glu Thr Gly Pro Ser Gly Pro Val Gly Pro Ala Gly Ala Val Gly Pro Arg Gly
```

*FIG. 50D*

```
              2763              2772              2781              2790              2799              2808
CCG TCC GGC CCG CAG GGT ATT CGC GGT GAC AAA GGC GAA CCG GGC GAA AAA GGT
--- --- --- --- --- --- --- --- --- --- --- --- --- --- --- --- --- ---
Pro Ser Gly Pro Gln Gly Ile Arg Gly Asp Lys Gly Glu Pro Gly Glu Lys Gly 2817              2826              2835              2844              2853              2862
CCG CGT GGT CTG CCG GGC CTT AAG GGC CAC AAC GGT CTG CAA GGT CTG CCG GGT
--- --- --- --- --- --- --- --- --- --- --- --- --- --- --- --- --- ---
Pro Arg Gly Leu Pro Gly Leu Lys Gly His Asn Gly Leu Gln Gly Leu Pro Gly 2871              2880              2889              2898              2907              2916
ATC GCG GGT CAC CAC GGT GAT CAG GGT GCT CCG GGT TCC GTT GGT CCG GCC GGT
--- --- --- --- --- --- --- --- --- --- --- --- --- --- --- --- --- ---
Ile Ala Gly His His Gly Asp Gln Gly Ala Pro Gly Ser Val Gly Pro Ala Gly 2925              2934              2943              2952              2961              2970
CCG CGT GGC CCG GCT GGT CCG TCT GGT CCG GCC GGT AAA GAC GGC CGT ACG GGC
--- --- --- --- --- --- --- --- --- --- --- --- --- --- --- --- --- ---
Pro Arg Gly Pro Ala Gly Pro Ser Gly Pro Ala Gly Lys Asp Gly Arg Thr Gly 2979              2988              2997              3006              3015              3024
CAC CCG GGT ACG GTG GGT CCG GCC GGC ATT CGC GGT CCG CAA GGT CAC CAG GGT
--- --- --- --- --- --- --- --- --- --- --- --- --- --- --- --- --- ---
His Pro Gly Thr Val Gly Pro Ala Gly Ile Arg Gly Pro Gln Gly His Gln Gly 3033              3042              3051              3060              3069              3078
CCG GCG GGT CCG CCG GGT CCG CCG GGT CCG CCG GGT CCG CCG GGT GTT AGC GGT
--- --- --- --- --- --- --- --- --- --- --- --- --- --- --- --- --- ---
Pro Ala Gly Pro Pro Gly Pro Pro Gly Pro Pro Gly Pro Pro Gly Val Ser Gly 3087              3096              3105              3114
GGC GGT TAT GAT TTT GGT TAT GAC GGT GAT TTC TAT CGT GCG 3'
--- --- --- --- --- --- --- --- --- --- --- --- --- ---
Gly Gly Tyr Asp Phe Gly Tyr Asp Gly Asp Phe Tyr Arg Ala
```

*FIG. 50E*

```
                 EcoRI start            Oligo N1-1(α2)                                              BsrFI stop        Hind III
5'-GGAATTCATGCAGTATGATGGCAAAGGCGTCGGCCTCGGCCTCGCCCGGCCCCGGGCCCAATGGGCCTCATGGGCCCCGGCGGGCCCA-3'
                        3'-CCGGGCGCCGCGGGTGGCCCACGTCGACCGGGTGTCCGGGCGTTCCAAAGGTCCCGGGACGGCCAATTATTCGAACCC-5'
                                                             Oligo N1-2 (α2)

EcoRI   BsrFI        Oligo N1-3(α2)                                                            stop   Hind III
5'-GGAATTCGCCGGTGAGCCGGGTGAACCGGGCCAAACGGGCTCGGCCAGGTCCACGTGGTCCAGGTCACGTGGTCCAGGGCCCCGCCTGGCAAGGCG-3'
                        3'-CCGGGCGGACCGTTCCGCCCACTTCTACCGGTGGACCGTTTGGCCCGGCGGCCCACTCCGACCGCCATCCACATTATTCGAACCC-5'
                                                             Oligo N1-4 (α2)
```

FIG. 51

```
              9           18          27          36          45          54
5' CAG TAT GAT GGC AAA GGC GTC GGC CTC GGC CCG GGC CCA ATG GGC CTC ATG GGC
   --- --- --- --- --- --- --- --- --- --- --- --- --- --- --- --- --- ---
   Gln Tyr Asp Gly Lys Gly Val Gly Leu Gly Pro Gly Pro Met Gly Leu Met Gly 63          72          81          90          99         108
   CCG CGC GGC CCA CCG GGT GCA GCT GGC GCC CCA GGC CCG CAA GGT TTC CAG GGC
   --- --- --- --- --- --- --- --- --- --- --- --- --- --- --- --- --- ---
   Pro Arg Gly Pro Pro Gly Ala Ala Gly Ala Pro Gly Pro Gln Gly Phe Gln Gly 117         126         135         144         153         162
   CCT GCC GGT GAG CCG GGT GAA CCG GGC CAA ACG GGT CCG GCA GGT GCA CGT GGT
   --- --- --- --- --- --- --- --- --- --- --- --- --- --- --- --- --- ---
   Pro Ala Gly Glu Pro Gly Glu Pro Gly Gln Thr Gly Pro Ala Gly Ala Arg Gly 171         180         189         198         207         216
   CCA GCG GGC CCG CCT GGC AAG GCG GGT GAA GAT GGC CAC CCT GGC AAA CCG GGC
   --- --- --- --- --- --- --- --- --- --- --- --- --- --- --- --- --- ---
   Pro Ala Gly Pro Pro Gly Lys Ala Gly Glu Asp Gly His Pro Gly Lys Pro Gly 225         234
   CGC CCG GGT GAG CGT GGC GTA GTG
   --- --- --- --- --- --- --- ---
   Arg Pro Gly Glu Arg Gly Val Val
```

FIG. 54

```
                    9              18             27             36             45             54
5' ATG GGG CTC GCT GGC CCA CCG GGC GAA CCG GGT CCG CCA GGC CCG AAA GGT CCG
   --- --- --- --- --- --- --- --- --- --- --- --- --- --- --- --- --- ---
    M   G   L   A   G   P   P   G   E   P   G   P   P   G   P   K   G   P
                   63             72             81             90             99            108
   CGT GGC GAT AGC GGG CTC GCT GGC CCA CCG GGC GAA CCG GGT CCG CCA GGC CCG
   --- --- --- --- --- --- --- --- --- --- --- --- --- --- --- --- --- ---
    R   G   D   S   G   L   A   G   P   P   G   E   P   G   P   P   G   P
                  117            126            135            144            153            162
   AAA GGT CCG CGT GGC GAT AGC GGG CTC GCT GGC CCA CCG GGC GAA CCG GGT CCG
   --- --- --- --- --- --- --- --- --- --- --- --- --- --- --- --- --- ---
    K   G   P   R   G   D   S   G   L   A   G   P   P   G   E   P   G   P
                  171            180            189            198            207            216
   CCA GGC CCG AAA GGT CCG CGT GGC GAT AGC GGG CTC GCT GGC CCA CCG GGC GAA
   --- --- --- --- --- --- --- --- --- --- --- --- --- --- --- --- --- ---
    P   G   P   K   G   P   R   G   D   S   G   L   A   G   P   P   G   E
                  225            234            243            252            261            270
   CCG GGT CCG CCA GGC CCG AAA GGT CCG CGT GGC GAT AGC GGG CTC CCG GGC GAT
   --- --- --- --- --- --- --- --- --- --- --- --- --- --- --- --- --- ---
    P   G   P   P   G   P   K   G   P   R   G   D   S   G   L   P   G   D

TCC TAA 3'
   --- ---
    S   *
```

FIG. 61

Gene for 219 amino acid C-terminal fragment of Type I (α1) human collagen with optimized E. coli codon usage fused to gene for glutathione S-transferase.

Gene for 207 amino acid C-terminal fragment of Type I (α2) human collagen with optimized E. coli codon usage fused to gene for glutathione S-transferase.

Protein Sequence of the First 13 amino acids of D4-α1. Predicted From the DNA Sequence:

H$_2$N-Gly-Pro-Pro-Gly-Leu-Ala-Gly-Pro-Pro-Gly-Glu-Ser-Gly

Experimentally-Determined Protein Sequence of the First 13 amino acids of D4-α1:

H$_2$N-Gly-Hyp-Hyp-Gly-Leu-Ala-Gly-Hyp-Hyp-Gly-Glu-Ser-Gly

*FIG. 69*

```
              9           18          27          36          45          54
ATG GGC CCG CCG CGT CTG GCG GGC CCT CCG GGT GAA AGC GGT CGT GAA GGC GCG CCG GGT 69          78          87          96         105         114
GCC GAA GGC AGC CCA GGC CGC GAC GGT AGC CCG CGG GCC AAA GGG GAT CGT GGT GAA ACC 129         138         147         156         165         174
GGC CCG GCG GGC CCC CCG GGT GCA CCG GGC GCG CCG GGT GCC CCA GGC CCG GTG GGC CCG 189         198         207         216         225         234
GCG GGC AAA AGC GGT GAT CGT GGT GAG ACC GGT CCG GCG GGC CCG GCC GGT CCG GTG GGC 249         258         267         276         285         294
CCA GCG GGC GCC CGT GGC CCG GCC GGT CCG CAG GGC CCG CGG GGT GAC AAA GGT GAA ACG 309         318         327         336         345         354
GGC GAA CAG GGC GAC CGT GGC ATT AAA GGC CAC CGT GGC TTC AGC GGC CTG CAG GGT CCA 369         378         387         396         405         414
CCG GGC CCG CCG GGC AGT CCG GGT GAA CAG GGT CCG TCC GGA GCC AGC GGG CCG GCG GGC 429         438         447         456         465         474
CCA CGC GGT CCG CCG GGC AGC GCG GGC GCG CCG GGC AAA GAC GGT CTG AAC GGT CTG CCG 489         498         507         516         525         534
GGC CCG ATC GGC CCG CCG GGC CCA CGC GGC CGC ACC GGT GAT GCG GGT CCG GTG GGT CCC 549         558         567         576         585         594
CCG GGC CCG CCG GGC CCG CCA GGC CCG CCG GGA CCG CCG AGC GCG GGT TTC GAC TTC AGC 609         618         627         636         645         654
TTC CTG CCG CAG CCG CCG CAG GAG AAA GCG CAC GAC GGC GGT CGC TAC TAC CGT GCG TAA 669         678         687         696         705         714
... ... ... ... ... ... ... ... ... ... ... ... ... ... ... ... ... ... ... ...
```

*FIG. 71*

|  | 10 | 20 | 30 | 40 | 50 | 60 |
|---|---|---|---|---|---|---|
|  | MGPPGLAGPP | GESGREGAPG | AEGSPGRDGS | PGAKGDRGET | GPAGPPGAPG | APGAPGPVGP |
|  | 70 | 80 | 90 | 100 | 110 | 120 |
|  | AGKSGDRGET | GPAGPAGPVG | PAGARGPAGP | QGPRGDKGET | GEQGDRGIKG | HRGFSGLQGP |
|  | 130 | 140 | 150 | 160 | 170 | 180 |
|  | PGPPGSPCEQ | GPSGASGPAG | PRGPPGSAGA | PGKDGLNGLP | GPIGPPGPRG | RTGDAGPVGP |
|  | 190 | 200 | 210 | 220 | 230 | 240 |
|  | PGPPGPPGPP | GPPSAGFDFS | FLPQPPQEKA | HDGGRYYRA* | .......... | .......... |

FIG. 72

```
ATGGGCTCTCCGGGTGTTAACGGCGCCCCTGGTGAAGCGGGCCGCGACGGCAATCCGGG
CAACGATGGTCCGCCGGGTCGTGATGGTCAGCCGGGTCACAAAGGTGAGCGTGGCTACC
CGGGTAACATCGGTCCGGTTGGTGCGGCCGGCGCTCCGGGTCCGCACGGTCCGGTAGGC
CCAGCCGGCAAACACGGTAACCGTGGTGAAACGGGTCCGTCCGGTCCGGTAGGTCCGGC
GGGTGCTGTTGGTCCACGCGGCCCGTCCGGCCCGCAGGGTATTCGCGGTGACAAAGGCG
AACCGGGCGAAAAAGGTCCGCGTGGTCTGCCGGGCCTTAAGGGCCACAACGGTCTGCAA
GGTCTGCCGGGTATCGCGGGTCACCACGGTGATCAGGGTGCTCCGGGTTCCGTTGGTCCG
GCCGGTCCGCGTGGCCCGGCTGGTCCGTCTGGTCCGGCCGGTAAAGACGGCCGTACGGG
CCACCCGGGTACGGTGGGTCCGGCCGGCATTCGCGGTCCGCAAGGTCACCAGGGTCCGG
CGGGTCCGCCGGGTCCGCCGGGTCCGCCGGGTCCGCCGGGTGTTAGCGGTGGCGGTTAT
GATTTGGTTATGACGGTGATTTCTATCGTGCGTAA
```

FIG. 79

MGPPGLAGPPGESGREGAPGAEGSPGRDGSPGAKGDRGETGPAGPPGAPGAPGAPGPVGPA
GKSGDRGETGPAGPAGPVGPAGARGPAGPQGPRGDKGETGEQGDRGIKGHRGFSGLQGPPG
PPGSPGEQGPSGASGPAGPRGPPGSAGAPGKDGLNGLPGPIGPPGPRGRTGDAGPVGPPG
PPGPPGPPSAGFDFSFLPQPPQEKAHDGGRYYRA

FIG. 80

Oligo N4-1

5'GGAATTCTCCCATGGGCCCGCCGGGTCTGGCGGGCCCTCCGGGTGAAAGCGGTCGTGA
AGGCGCGCCGGGTGCCGAAGGCAGCCCAGGCCGCGAC

Oligo N4-2

3'CTTCCGTCGGGTCCGGCGCTGCCATCGGGCCCCCGGTTTCCCCTAGCACCACTTTGGCC
GGGCCGCCCGGGGGGCCCACGTGGCATTATTCGAACCC

Oligo N4-3

5'GGAATTCGGTGCACCGGGCGCGCCGGGTGCCCCAGGCCCGGTGGGCCCGGCGGGCAAA
AGCGGTGATCGTGGCGAGACCGGTCCGGCGGGC

Oligo N4-4

3'CTCTGGCCAGGCCGCCCGGGCCGGCCAGGCCACCCGGGTCGCCCGCGGGCACCGGGCC
GGCCAGGCGTCCCGGGCGCCATTATTCGAACCC

FIG. 81

NUCLEIC ACID ENCODING EXTRACELLULAR MATRIX PROTEIN OR FRAGMENT THEREOF

CROSS REFERENCE TO RELATED APPLICATIONS

This application is a Continuation of U.S. application Ser. No. 09/169,768, filed on Oct. 9, 1998, now U.S. Pat. No. 6,492,508, which is a Continuation-In-Part of U.S. application Ser. No. 08/655,086, filed Jun. 3, 1996, now U.S. Pat. No. 5,821,089, the entire contents of which are hereby incorporated by reference.

BACKGROUND

1. Technical Field

Engineered polypeptides and chimeric polypeptides having incorporated amino acids which enhance or otherwise modify properties of such polypeptides.

2. Description of Related Art

Genetic engineering allows polypeptide production to be transferred from one organism to another. In doing so, a portion of the production apparatus indigenous to an original host is transplanted into a recipient. Frequently, the original host has evolved certain unique processing pathways in association with polypeptide production which are not contained in or transferred to the recipient For example, it is well known that mammalian cells incorporate a complex set of post-translational enzyme systems which impart unique characteristics to protein products of the systems. When a gene encoding a protein normally produced by mammalian cells is transferred into a bacterial or yeast cell, the protein may not be subjected to such post translational modification and the protein may not function as originally intended.

Normally, the process of polypeptide or protein synthesis in living cells involves transcription of DNA into RNA and translation of RNA into protein. Three forms of RNA are involved in protein synthesis: messenger RNA (MRNA) carries genetic information to ribosomes made of ribosomal RNA (rRNA) while transfer RNA (tRNA) links to free amino acids in the cell pool. Amino acid/tRNA complexes line up next to codons of mRNA, with actual recognition and binding being mediated by tRNA. Cells can contain up to twenty amino acids which are combined and incorporated in sequences of varying permutations into proteins. Each amino acid is distinguished from the other nineteen amino acids and charged to tRNA by enzymes known as aminoacyl-tRNA synthetases. As a general rule, amino acid/tRNA complexes are quite specific and normally only a molecule with an exact stereochemical configuration is acted upon by a particular aminoacyl-tRNA synthetase.

In many living cells some amino acids are taken up from the surrounding environment and some are synthesized within the cell from precursors, which in turn have been assimilated from outside the cell. In certain instances, a cell is auxotrophic, i.e., it requires a specific growth substance beyond the minimum required for normal metabolism and reproduction which it must obtain from the surrounding environment. Some auxotrophs depend upon the external environment to supply certain amino acids. This feature allows certain amino acid analogs to be incorporated into proteins produced by auxotrophs by taking advantage of relatively rare exceptions to the above rule regarding stereochemical specificity of aminoacyl-tRNA synthetases. For example, proline is such an exception, i.e., the amino acid activating enzymes responsible for the synthesis of prolyl-tRNA complex are not as specific as others. As a consequence certain proline analogs have been incorporated into bacterial, plant, and animal cell systems. See Tan et al., Proline Analogues Inhibit Human Skin Fibroblast Growth and Collagen Production in Culture, Journal of Investigative Dermatology, 80:261–267(1983).

A method of incorporating unnatural amino acids into proteins is described, e.g., in Noren et al., A General Method For Site-Specific Incorporation of Unnatural Amino Acids Into Proteins, Science, Vol. 244, pp. 182–188 (1989) wherein chemically acylated suppressor tRNA is used to insert an amino acid in response to a stop codon substituted for the codon encoding residue of interest. See also, Dougherty et al., Synthesis of a Genetically Engineered Repetitive Polypeptide Containing Periodic Selenomethionine Residues, Macromolecules, Vol. 26, No. 7, pp. 1779–1781 (1993), which describes subjecting an *E. coli* methionine auxotroph to selenomethionine containing medium and postulates on the basis of experimental data that selenomethionine may completely replace methionine in all proteins produced by the cell.

cis-Hydroxy-L-proline has been used to study its effects on collagen by incorporation into eukaryotic cells such as cultured normal skin fibroblasts (see Tan et al., supra) and tendon cells from chick embryos (see e.g., Uitto et al., Procollagen Polypeptides Containing cis 4-Hydroxy-L-proline are Overglycosylated and Secreted as Nonhelical Pro-γ-Chains, Archives of Biochemistry and Biophysics, 185:1:214–221(1978)). However, investigators found that trans4-hydroxyproline would not link with proline specific tRNA of prokaryotic *E. coli*. See Papas et al., Analysis of the Amino Acid Binding to the Proline Transfer Ribonucleic Acid Synthetase of *Escherichia coli*, Journal of Biological Chemistry, 245:7:1588–1595(1970). Another unsuccessful attempt to incorporate trans-4-hydroxyproline into prokaryotes is described in Deming et al., In Vitro Incorporation of Proline Analogs into Artificial Proteins, Poly. Mater. Sci. Engin. Proceed., Vol. 71, p. 673–674 (1994). Deming et al. report surveying the potential for incorporation of certain proline analogs, i.e., L-azetidine-2-carboxylic acid, L-γ-thiaproline, 3,4-dehydroproline and L-trans4-hydroxyproline into artificial proteins expressed in *E. coli* cells. Only L-azetidine-2-carboxylic acid, L-γ-thiaproline and 3,4 dehydroproline are reported as being incorporated into proteins in *E. coli* cells in vivo.

Extracellular matrix proteins ("EMPs") are found in spaces around or near cells of multicellular organisms and are typically fibrous proteins of two functional types: mainly structural, e.g., collagen and elastin, and mainly adhesive, e.g., fibronectin and laminin. Collagens are a family of fibrous proteins typically secreted by connective tissue cells. Twenty distinct collagen chains have been identified which assemble to form a total of about ten different collagen molecules. A general discussion of collagen is provided by Alberts, et al., The Cell, Garland Publishing, pp. 802–823 (1989), incorporated herein by reference. Other fibrous or filamentous proteins include Type I IF proteins, e.g., keratins; Type II IF proteins, e.g., vimentin, desmin and glial fibrillary acidic protein; Type III IF proteins, e.g., neurofilament proteins; and Type IV IF proteins, e.g., nuclear laminins.

Type I collagen is the most abundant form of the fibrillar, interstitial collagens and is the main component of the extracellular matrix. Collagen monomers consist of about 1000 amino acid residues in a repeating array of Gly-X-Y triplets. Approximately 35% of the X and Y positions are occupied by proline and trans 4-hydroxyproline. Collagen monomers associate into triple helices which consist of one α2 and two α1 chains. The triple helices associate into fibrils which are oriented into tight bundles. The bundles of collagen fibrils are further organized to form the scaffold for extracellular matrix.

In mammalian cells, post-translational modification of collagen contributes to its ultimate chemical and physical properties and includes proteolytic digestion of pro-regions, hydroxylation of lysine and proline, and glycosylation of hydroxylated lysine. The proteolytic digestion of collagen involves the cleavage of pro regions from the N and C termini. It is known that hydroxylation of proline is essential for the mechanical properties of collagen. Collagen with low levels of 4-hydroxyproline has poor mechanical properties, as highlighted by the sequelae associated with scurvy. 4-hydroxyproline adds stability to the triple helix through hydrogen bonding and through restricting rotation about C—N bonds in the polypeptide backbone. In the absence of a stable structure, naturally occurring cellular enzymes contribute to degrading the collagen polypeptide.

The structural attributes of Type I collagen along with its generally perceived biocompatability make it a desirable surgical implant material. Collagen is purified from bovine skin or tendon and used to fashion a variety of medical devices including hemostats, implantable gels, drug delivery vehicles and bone substitutes. However, when implanted into humans bovine collagen can cause acute and delayed immune responses.

As a consequence, researchers have attempted to produce human recombinant collagen with all of its structural attributes in commercial quantities through genetic engineering. Unfortunately, production of collagen by commercial mass producers of protein such as E. coli has not been successful. A major problem is the extensive post-translational modification of collagen by enzymes not present in E. coli. Failure of E. coli cells to provide proline hydroxylation of unhydroxylated collagen proline prevents manufacture of structurally sound collagen in commercial quantities.

Another problem in attempting to use E. coli to produce human collagen is that E. coli prefer particular codons in the production of polypeptides. Although the genetic code is identical in both prokaryotic and eukaryotic organisms, the particular codon (of the several possible for most amino acids) that is most commonly utilized can vary widely between prokaryotes and eukaryotes. See, Wada, K.-N., Y. Wada, F. Ishibashi, T. Gojobori and T. Ikemura. Nucleic Acids Res. 20, Supplement: 2111–2118, 1992. Efficient expression of heterologous (e.g. mammalian) genes in prokaryotes such as E. coli can be adversely affected by the presence in the gene of codons infrequently used in E. coli and expression levels of the heterologous protein often rise when rare codons are replaced by more common ones. See, e.g., Williams, D. P., D. Regier, D. Akiyoshi, F. Genbauffe and J. R. Murphy. Nucleic Acids Res. 16: 10453–10467, 1988 and Höög, J.-O., H. v. Bahr-Lindström, H. Jörnvall and A. Holmgren. Gene. 43: 13–21, 1986. This phenomenon is thought to be related, at least in part, to the observation that a low frequency of occurrence of a particular codon correlates with a low cellular level of the transfer RNA for that codon. See, Ikemura, T. J. Mol. Biol. 158: 573–597, 1982 and Ikemura, T. J. Mol. Biol. 146: 1–21, 1981. Thus, the cellular tRNA level may limit the rate of translation of the codon and therefore influence the overall translation rate of the full-length protein. See, Ikemura, T. J. Mol. Biol. 146: 1–21, 1981; Bonekamp, F. and F. K. Jensen. Nucleic Acids Res. 16: 3013–3024, 1988; Misra, R. and P. Reeves, Eur. J. Biochem. 152: 151–155, 1985; and Post, L. E., G. D. Strycharz, M. Nomura, H. Lewis and P. P. Lewis. Proc. Natl. Acad. Sci. U.S.A. 76: 1697–1701, 1979. In support of this hypothesis is the observation that the genes for abundant E. coli proteins generally exhibit bias towards commonly used codons that represent highly abundant tRNAs. See, Ikemura, T. J. Mol. Biol. 146: 1–21, 1981; Bonekamp, F. and F. K. Jensen. Nucleic Acids Res.16: 3013–3024, 1988; Misra, R. and P. Reeves, Eur. J. Biochem. 152: 151–155, 1985; and Post, L. E., G. D. Strycharz, M. Nomura, H. Lewis and P. P. Lewis. Proc. Natl. Acad. Sci. U.S.A. 76: 1697–1701, 1979. In addition to codon frequency, the codon context (i.e. the surrounding nucleotides) can also affect expression.

Although it would appear that substituting preferred codons for rare codons could be expected to increase expression of heterologous proteins in host organisms, such is not the case. Indeed, "it has not been possible to formulate general and unambiguous rules to predict whether the content of low-usage codons in a specific gene might adversely affect the efficiency of its expression in E. coli." See page 524 of S. C. Makrides (1996), Strategies for Achieving High-Level Expression of Genes in Escherichia coli. Microbiological Reviews 60, 512–538. For example, in one case, various gene fusions between yeast a factor and somatomedin C were made that differed only in coding sequence. In these experiments, no correlation was found between codon bias and expression levels in E. coli; Ernst, J. F. and Kawashima, E. (1988), J. Biotechnology, 7, 1–10. In another instance, it was shown that despite the higher frequency of optimal codons in a synthetic β-globin gene compared to the native sequence, no difference was found in the protein expression from these two constructs when they were placed behind the T7 promoter. Heman et al. (1992), Biochemistry, 31, 8619–8628. Conversely, there are many examples of proteins with a relatively high percentage of rare codons that are well expressed in E. coli. A table listing some of these examples and a general discussion can be found in Makoff, A. J. et al. (1989), Nucleic Acids Research, 17, 10191–10202. In one case, introduction of non-optimal, rare arginine codons at the 3' end of a gene actually increased the yield of expressed protein. Gursky, Y. G. and Beabealashvilli, R. Sh. (1994), Gene 148, 15–21.

Failure to provide post-translational modifications such as hydroxylation of proline and the presence in human collagen of rare codons for E. coli may be contributing to the difficulties encountered in the expression of human collagen genes in E. coli.

SUMMARY

A method of incorporating an amino acid analog into a polypeptide produced by a cell is provided which includes providing a cell selected from the group consisting of prokaryotic cell and eukaryotic cell, providing growth media containing at least one amino acid analog selected from the group consisting of trans-4-hydroxyproline, 3-hydroxyproline, cis-4-fluoro-L-proline and combinations thereof and contacting the cell with the growth media wherein the at least one amino acid analog is assimilated into the cell and incorporated into at least one polypeptide.

Also provided is a method of substituting an amino acid analog of an amino acid in a polypeptide produced by a cell selected from the group consisting of prokaryotic cell and eukaryotic cell, which includes providing a cell selected from the group consisting of prokaryotic cell and eukaryotic cell, providing growth media containing at least one amino acid analog selected from the group consisting of trans-4- hydroxyproline, 3-hydroxyproline, cis4-fluoro-L-proline and combinations thereof and contacting the cell with the growth media wherein the at least one amino acid analog is assimilated into the cell and incorporated as a substitution for at least one naturally occurring amino acid in at least one polypeptide.

A method of controlling the amount of an amino acid analog incorporated into a polypeptide is also provided which includes providing at least a first cell selected from the group consisting of prokaryotic cell and eukaryotic cell, providing a first growth media containing a first predetermined amount of at least one amino acid analog selected from the group consisting of trans-4-hydroxyproline, 3-hydroxyproline, cis-4-fluoro-L-proline and combinations thereof and contacting the first cell with the first growth media wherein a first amount of amino acid analog is assimilated into the first cell and incorporated into at least one polypeptide. At least a second cell selected from the group consisting of prokaryotic cell and eukaryotic cell, is also provided along with a second growth media containing a second predetermined amount of an amino acid analog selected from the group consisting of trans4-hydroxyproline, 3-hydroxyproline, cis4-fluoro-L-proline and combinations thereof and the at least second cell is contacted with the second growth media wherein a second amount of amino acid analog is assimilated into the second cell and incorporated into at least one polypeptide.

Also provided is a method of increasing stability of a recombinant polypeptide produced by a cell which includes providing a cell selected from the group consisting of prokaryotic cell and eukaryotic cell, and providing growth media containing an amino acid analog selected from the group consisting of trans4-hydroxyproline, 3-hydroxyproline, cis4-fluoro-L-proline and combinations thereof and contacting the cell with the growth media wherein the amino acid analog is assimilated into the cell and incorporated into a recombinant polypeptide, thereby stabilizing the polypeptide.

A method of increasing uptake of an amino acid analog into a cell and causing formation of an amino acid analog/tRNA complex is also provided which includes providing a cell selected from the group consisting of prokaryotic cell and eukaryotic cell, providing hypertonic growth media containing amino acid analog selected from the group consisting of trans-4-hydroxyproline, 3-hydroxyproline, cis4-fluoro-L-proline and combinations thereof and contacting the cell with the hypertonic growth media wherein the amino acid analog is assimilated into the cell and incorporated into an amino acid analog/tRNA complex. In any of the other above methods, a hypertonic growth media can optionally be incorporated to increase uptake of an amino-acid analog into a cell.

A composition is provided which includes a cell selected from the group consisting of prokaryotic cell and eukaryotic cell, and hypertonic media including an amino acid analog selected from the group consisting of trans4-hydroxyproline, 3-hydroxyproline, cis-4-fluoro-L-proline and combinations thereof.

Also provided is a method of producing an Extracellular Matrix Protein (EMP) or a fragment thereof capable of providing a self-aggregate in a cell which does not ordinarily hydroxylate proline which includes providing a nucleic acid sequence encoding the EMP or fragment thereof which has been optimized for expression in the cell by substitution of codons preferred by the cell for naturally occurring codons not preferred by the cell, incorporating the nucleic acid sequence into the cell, providing hypertonic growth media containing at least one amino acid selected from the group consisting of trans-4-hydroxyproline and 3-hydroxyproline, and contacting the cell with the growth media wherein the at least one amino acid is assimilated into the cell and incorporated into the EMP or fragment thereof.

Nucleic acid encoding a chimeric protein is provided which includes a domain from a physiologically active peptide and a domain from an extracellular matrix protein (EMP) which is capable of providing a self-aggregate. The nucleic acid may be inserted into a cloning vector which can then be incorporated into a cell.

Also provided is a chimeric protein including a domain from a physiologically active peptide and a domain from an extracellular matrix protein (EMP) which is capable of providing a self aggregate.

Also provided is human collagen produced by a prokaryotic cell, the human collagen being capable of providing a self aggregate.

Also provided is nucleic acid encoding a human Extracellular Matrix Protein (EMP) wherein the codon usage in the nucleic acid sequence reflects preferred codon usage in a prokaryotic cell.

BRIEF DESCRIPTION OF THE DRAWINGS

FIGS. 3A and 3B depict a DNA sequence encoding human Type 1 ($\alpha_1$) collagen (SEQ. ID. NO. 1).

FIG. 5 depicts a DNA sequence encoding a fragment of human Type 1 ($\alpha_1$) collagen (SEQ. ID. NO. 2).

FIG. 7 depicts a DNA sequence encoding a collagen-like peptide wherein the region coding for gene collagen-like peptide is underlined (SEQ. ID. NO. 3).

FIG. 8 depicts an amino acid sequence of a collagen-like peptide (SEQ. ID. NO. 4).

FIG. 10 depicts a DNA sequence encoding mature bone morphogenic protein (SEQ. ID. NO. 5).

FIG. 13 depicts a collagen I ($\alpha$1)/BMP-2B chimeric amino acid sequence (SEQ. ID. NO. 6).

FIG. 14A–14C depicts a collagen I ($\alpha$1)/BMP-2B chirneric nucleotide sequence (SEQ. ID. NO. 7).

FIG. 15 depicts a collagen I ($\alpha$1)/TGF-$\beta_1$amino acid sequence (SEQ. ID. NO. 8).

FIG. 16A–16C depict a collagen I ($\alpha$1), TGF-$\beta_1$ nucleotide sequence (SEQ. ID. NO. 9). Lower case lettering indicates non-coding sequence.

FIGS. 17A–17B depict a collagen I ($\alpha$1)/decorin amino acid sequence (SEQ. ID. NO. 10).

FIG. 18 depicts a collagen I ($\alpha$1)/decorin peptide amino acid sequence (SEQ. ID. NO. 11).

FIGS. 19A–19D depict a collagen I (α1)/decorin nucleotide sequence (SEQ. ID. NO. 12).

FIGS. 20A–20C depict a collagen/decorin peptide nucleotide sequence (SEQ. ID. NO. 13). Lower case lettering indicates non-coding sequence.

FIG. 22 depicts a polylinker cloning site contained in the pMal cloning vector of FIG. 21 (SEQ. ID. NO. 14).

FIG. 27A–27E depicts a human collagen Type I ($α_1$) nucleotide sequence (SEQ. ID. NO. 15) and corresponding amino acid sequence (SEQ. ID. NO. 16).

FIG. 30 is a Table depicting occurrence of four proline and four glycine codons in the human Collagen Type I ($α_1$) gene with optimized codon usage (ColECol).

FIGS. 39A–39E depict the nucleotide (SEQ. ID. NO. 19) and amino acid (SEQ. ID. NO. 20) sequence of HuCol$^{Ec}$, the helical region of human Type I ($α_1$) collagen plus 17 amino terminal extra-helical amino acids and 26 carboxy terminal extra-helical amino acids with codon usage optimized for *E. coli*.

FIG. 40 depicts sequence and restriction maps of synthetic oligos used to reconstruct the first 243 base pairs of the human Type I ($α_1$) collagen gene with optimized *E. coli* codon usage. The synthetic oligos are labelled N1-1 (SEQ. ID. NO. 21), N1-2 (SEQ. ID. NO. 22), N1-3 (SEQ. ID. NO. 23) and N1-4 (SEQ. ID. NO. 24).

FIG. 42 depicts the nucleotide (SEQ. ID. NO. 25) and amino acid (SEQ. ID. NO. 26) sequence of a fragment of human collagen Type I ($α_1$) gene with optimized *E. coli* codon usage encoded by plasmid pBSN1-1.

FIG. 44 depicts the nucleotide (SEQ. ID. NO. 27) and amino acid (SEQ. ID. NO. 28) sequence of a fragment of human collagen Type I ($α_1$) gene with optimized *E. coli* codon usage encoded by plasmid pBSN1-2.

FIGS. 49A–49E depict the nucleotide (SEQ. ID. NO. 29) and amino acid (SEQ. ID. NO. 30) sequence of a helical region of human Type I ($α_2$) collagen plus 11 amino terminal extra-helical amino acids and 12 carboxy terminal extrahelical amino acids.

FIGS. 50A–50E depict the nucleotide (SEQ. ID. NO. 31) and amino acid (SEQ. ID. NO. 32) sequence of HuCol($α_2$)$^{Ec}$, the helical region of human Type I ($α_2$) collagen plus 11 amino terminal extra-helical amino acids and 12 carboxy terminal extra-helical amino acids with codon usage optimized for *E. coli*.

FIG. 51 depicts sequence and restriction maps of synthetic oligos used to reconstruct the first 240 base pairs of human Type I ($α_2$) collagen gene with optimized *E. coil* codon usage. The synthetic oligos are labelled N1-1 (α2) (SEQ. ID. NO. 33), N1-2 (α2) (SEQ. ID. NO. 34), N1-3 (α2) (SEQ. ID. NO. 35) and N1-4 (α2) (SEQ. ID. NO. 36).

FIG. 54 depicts the nucleotide (SEQ. ID. NO. 37) and amino acid (SEQ. ID. NO. 38) sequence of a fragment of human collagen Type I ($α_2$) gene with optimized *E. coli* codon usage encoded by plasmid pBSN1-2($α_2$).

FIG. 61 depicts the nucleotide (SEQ. ID. NO. 39) and amino acid (SEQ. ID. NO. 40) sequence of collagen mimetic 4.

FIG. 69 depicts the predicted amino acid sequence from the DNA sequence of the first 13 amino acid acids of protein D4-α1 (SEQ. ID. NO. 41) and the amino acid sequence as experimentally determined (SEQ. ID NO. 42).

FIG. 71 depicts the nucleotide sequence of a 657 nucleotide human collagen Type I (α1)3' fragment with optimized E. coli codon usage designated D4 (SEQ. ID. NO. 43).

FIG. 72 depicts the amino acid sequence of a 219 amino acid C-terminal fragment of human collagen Type I (α1) designed D4 (SEQ. ID. NO. 44).

FIG. 79 depicts the nucleotide sequence of a 627 nucleotide human collagen Type I (α2) 3' fragment with optimized E. coli codon usage (SEQ. ID. NO.45).

FIG. 80 depicts the amino acid sequence of a 209 amino acid C-terminal fragment of human collagen Type I (α2) (SEQ. ID. NO. 46).

FIG. 81 depicts the sequence of synthetic oligos used to reconstruct the first 282 base pairs of the gene for the carboxy terminal 219 amino acids of human Type I (α1) collagen with optimized E. coli codon usage designated N4-1 (SEQ. ID. NO. 47), N4-2 (SEQ. ID. NO. 48), N4-3 (SEQ. ID. NO. 49) and N4-4 4 (SEQ. ID. NO. 50).

DETAILED DESCRIPTION OF PREFERRED EMBODIMENTS

Prokaryotic cells and eukaryotic cells can unexpectedly be made to assimilate and incorporate trans-4-hydroxyproline into proteins contrary to both Papas et al. and Deming et al., supra. Such assimilation and incorporation is especially useful when the structure and function of a polypeptide depends on post translational hydroxylation of proline not provided by the native protein production system of a recombinant host. Thus, prokaryotic bacteria such as E. coli and eukaryotic cells such as Saccharomyces cerevisiae, Saccharomyces carlsbergensis and Schizosaccharomyces pombe that ordinarily do not hydroxylate proline and additional eukaryotes such as insect cells including lepidopteran cell lines including Spodoptera frugiperda, Trichoplasia ni, Heliothis virescens, Bombyx mori infected with a baculovirus; CHO cells, COS cells and NIH 3T3 cells which fail to adequately produce certain polypeptides whose structure and function depend on such hydroxylation can be made to produce polypeptides having hydroxylated prolines. Incorporation includes adding trans-4-hydroxyproline to a polypeptide, for example, by first changing an amino acid to proline, creating a new proline position that can in turn be substituted with trans-4-hydroxyproline or substituting a naturally occurring proline in a polypeptide with trans-4-hydroxyproline as well.

The process of producing recombinant polypeptides in mass producing organisms is well known. Replicable expression vectors such as plasmids, viruses, cosrnids and artificial chromosomes are commonly used to transport genes encoding desired proteins from one host to another. It is contemplated that any known method of cloning a gene, ligating the gene into an expression vector and transforming a host cell with such expression vector can be used in furtherance of the present disclosure.

Not only is incorporation of trans-4-hydroxyproline into polypeptides which depend upon trans-4-hydroxyproline for chemical and physical properties useful in production systems which do not have the appropriate systems for converting proline to trans-4-hydroxyproline, but useful as well in studying the structure and function of polypeptides which do not normally contain trans-4-hydroxyproline. It is contemplated that the following amino acid analogs may also be incorporated in accordance with the present disclosure: trans-4 hydroxyproline, 3-hydroxyproline, cis-4-fluoro-L-proline and combinations thereof (hereinafter referred to as the "amino acid analogs"). Use of prokaryotes and eukaryotes is desirable since they allow relatively inexpensive mass production of such polypeptides. It is contemplated that the amino acid analogs can be incorporated into any desired polypeptide. In a preferred embodiment the prokaryotic cells and eukaryotic cells are starved for proline by decreasing or eliminating the amount of proline in growth media prior to addition of an amino acid analog herein.

Figure 1:
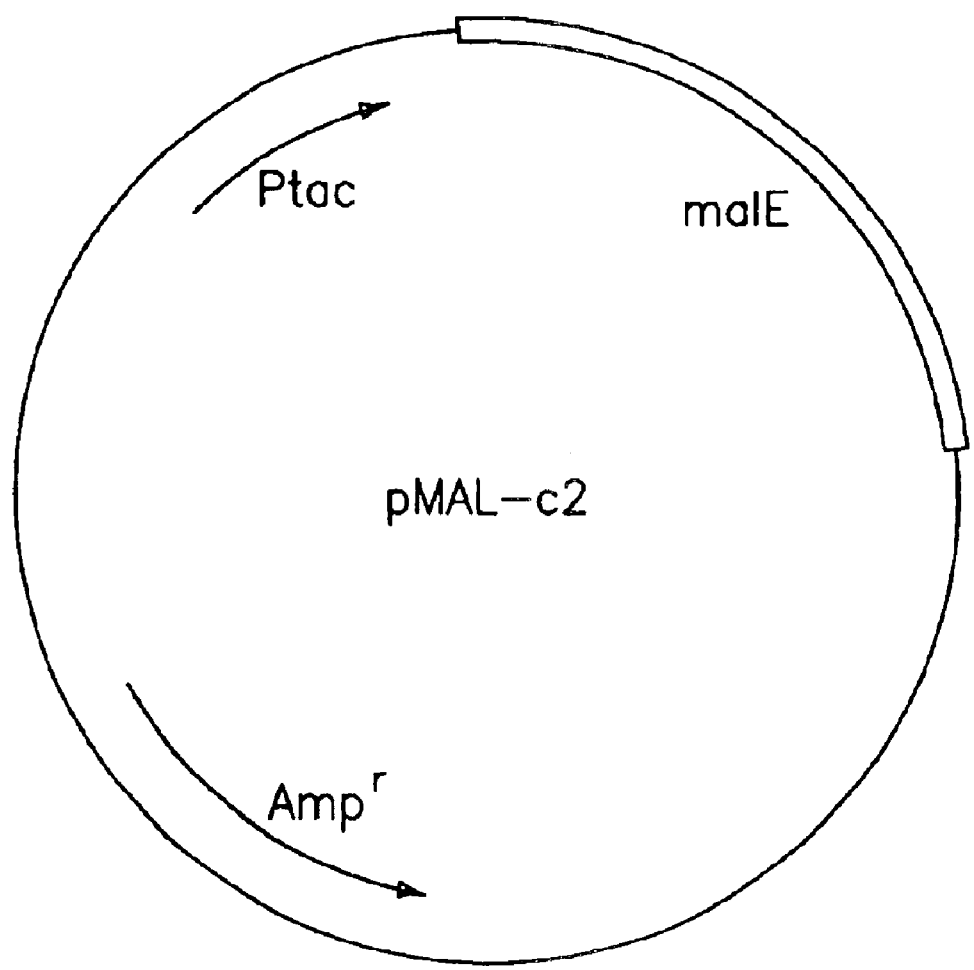
FIG. 1 is a plasmid map illustrating pMAL-c2.

Expression vectors containing the gene for maltose binding protein (MBP), e.g., see FIG. 1 illustrating plasmid pMAL-c2, commercially available from New England BioLabs, are transformed into prokaryotes such as E. coli proline auxotrophs or eukaryotes such as S. cerevisiae auxotrophs which depend upon externally supplied proline for protein synthesis and anabolism. Other preferred expression vectors for use in prokaryotes are commercially available plasmids which include pKK-223 (Pharmacia), pTRC (Invitrogen), pGEX (Pharnacia), pET (Novagen) and pQE (Quiagen). It should be understood that any suitable expression vector may be utilized by those with skill in the art.

Figure 2:
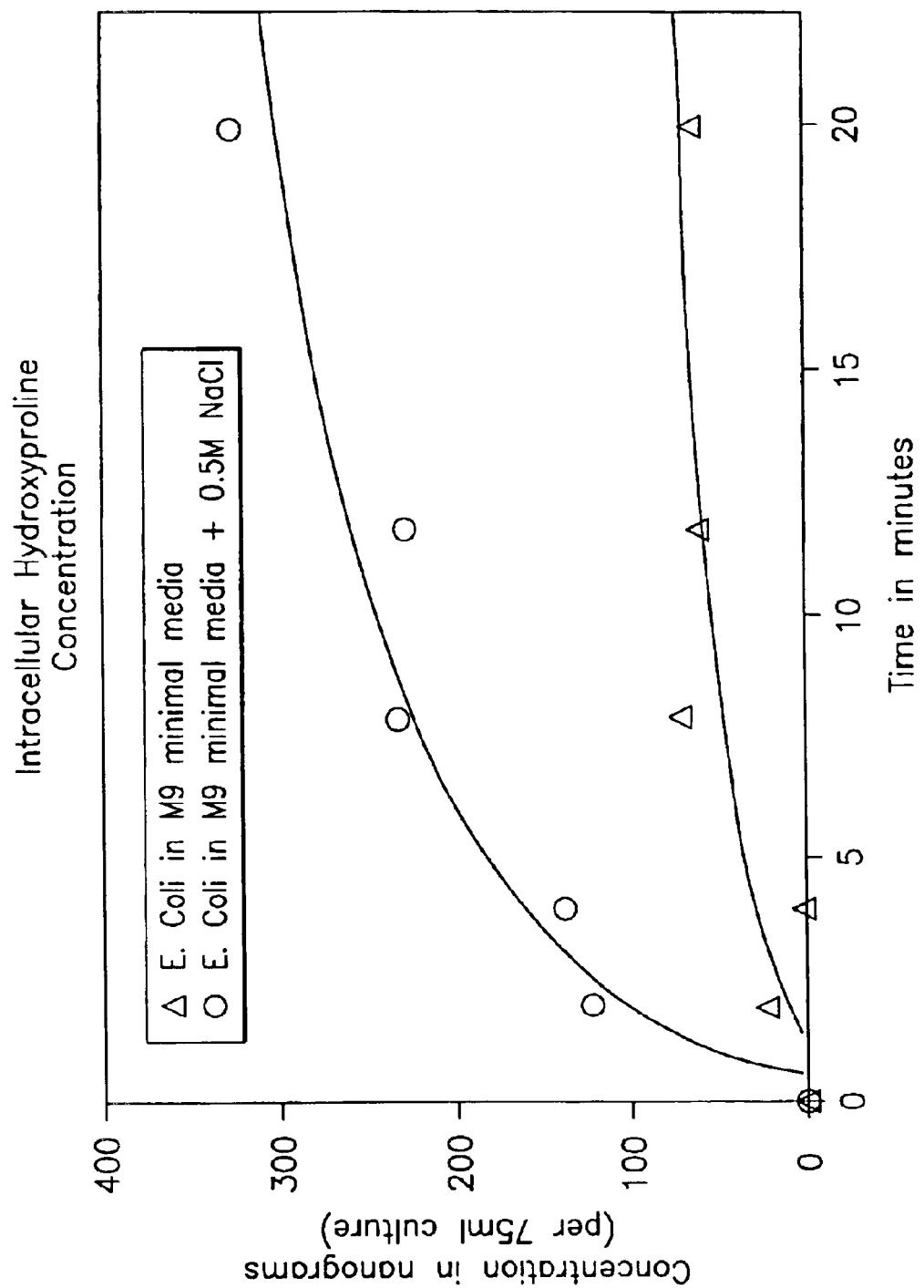
FIG. 2 is a graphical representation of the concentration of intracellular hydroxyproline based upon concentration of trans4-hydroxyproline in growth culture over time.

Substitution of the amino acid analogs for proline in protein synthesis occurs since prolyl tRNA synthetase is sufficiently promiscuous to allow misacylation of proline tRNA with any one of the amino acid analogs. A sufficient quantity, i.e., typically ranging from about 0.001 M to about 1.0 M, but more preferably from about 0.005M to about 0.5M of the amino acid analog(s) is added to the growth medium for the tansforned cells to compete with proline in cellular uptake. After sufficient time, generally from about 30 minutes to about 24 hours or more, the amino acid analog(s) is assimilated by the cell and incorporated into protein synthetic pathways. As can be seen from FIGS. 2 and 2A, intracellular concentration of trans-4-hydroxyproline increases by increasing the concentration of sodium chloride in the growth media. In a preferred embodiment the prokaryotic cells and/or eukaryotic cells are starved for proline by decreasing or eliminating the amount of proline in growth media prior to addition of an amino acid analog herein.

Figure 4:
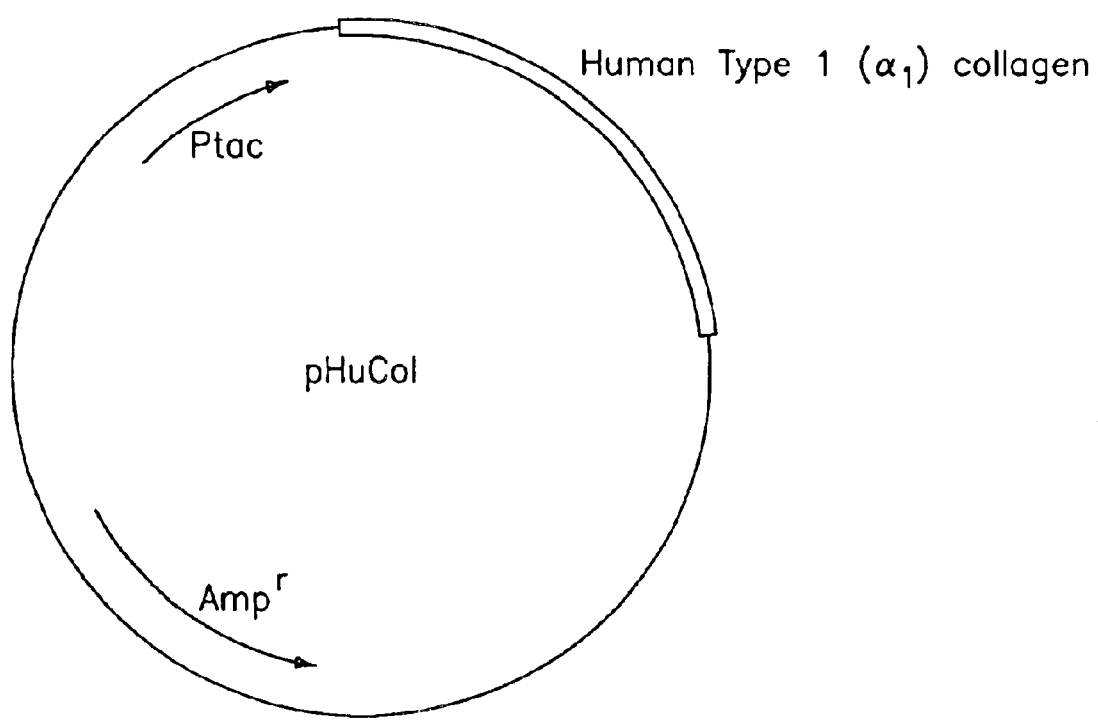
FIG. 4 is a plasmid map illustrating pHuCol.

Expression vectors containing the gene for human Type 1 ($\alpha$1) collagen (DNA sequence illustrated in FIGS. 3 and 3A; plasmid map illustrated in FIG. 4) are transformed into prokaryotic or eukaryotic proline auxotrophs which depend upon externally supplied proline for protein synthesis and anabolism. As above, substitution of the amino acid analog (s) occurs since prolyl tRNA synthetase is sufficiently promiscuous to allow misacylation of proline tRNA with the amino acid analog(s). The quantity of amino acid analog(s) in media given above is again applicable.

Figure 6:
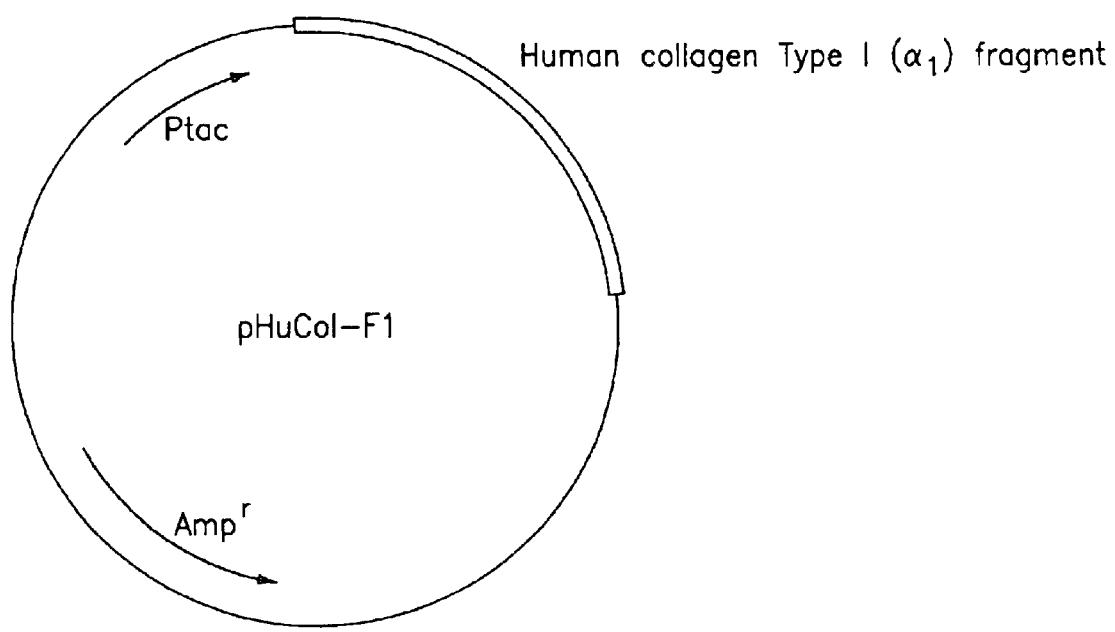
FIG. 6 is a plasmid map illustrating pHuCol-Fl.
Figure 9:
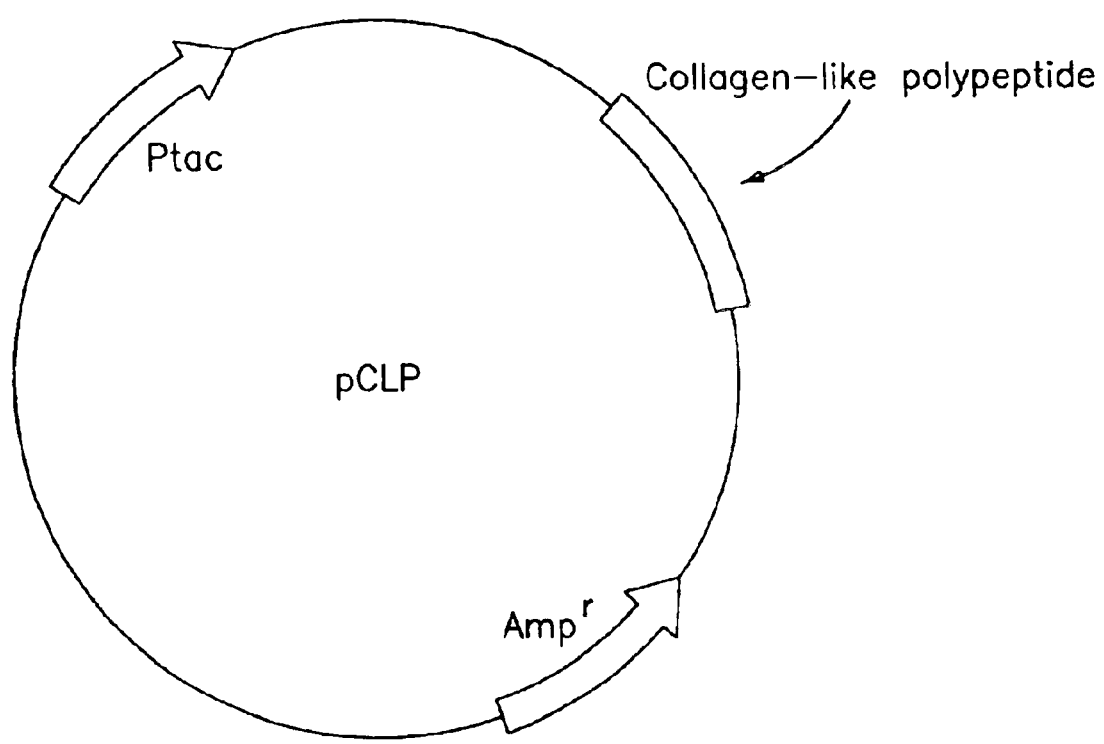
FIG. 9 is a plasmid map illustrating pCLP.

Expression vectors containing DNA encoding fragments of human Type 1 ($\alpha$1) collagen (e.g., DNA sequence illustrated in FIG. 5 and plasmid map illustrated in FIG. 6) are transformed into prokaryotic or eukaryotic auxotrophs as above. Likewise, expression vectors containing DNA encoding collagen-like polypeptide (e.g., DNA sequence illustrated in FIG. 7, amino acid sequence illustration in FIG. 8 and plasmid map illustrated in FIG. 9) can be used to transform prokaryotic or eukaryotic auxotrophs as above. Collagen-like peptides are those which contain at least partial homology with collagen and exhibit similar chemical and physical characteristics to collagen. Thus, collagen-like peptides consist, e.g., of repeating arrays of Gly-X-Y triplets in which about 35% of the X and Y positions are occupied by proline and 4-hydroxyproline. Collagen-like peptides are interchangeably referred to herein as collagen-like proteins, collagen-like polypeptides, collagen mimetic polypeptides and collagen mimetic. Certain preferred collagen fragments and collagen-like peptides in accordance herewith are capable of assembling into an extracellular matrix. In both collagen fragments and collagen-like peptides as described above, substitution with amino acid analog(s) occurs since prolyl tRNA synthetase is sufficiently promiscuous to allow misacylation of proline tRNA with one or more of the amino acid analog(s). The quantity of amino acid analog(s) given above is again applicable.

Figure 11:
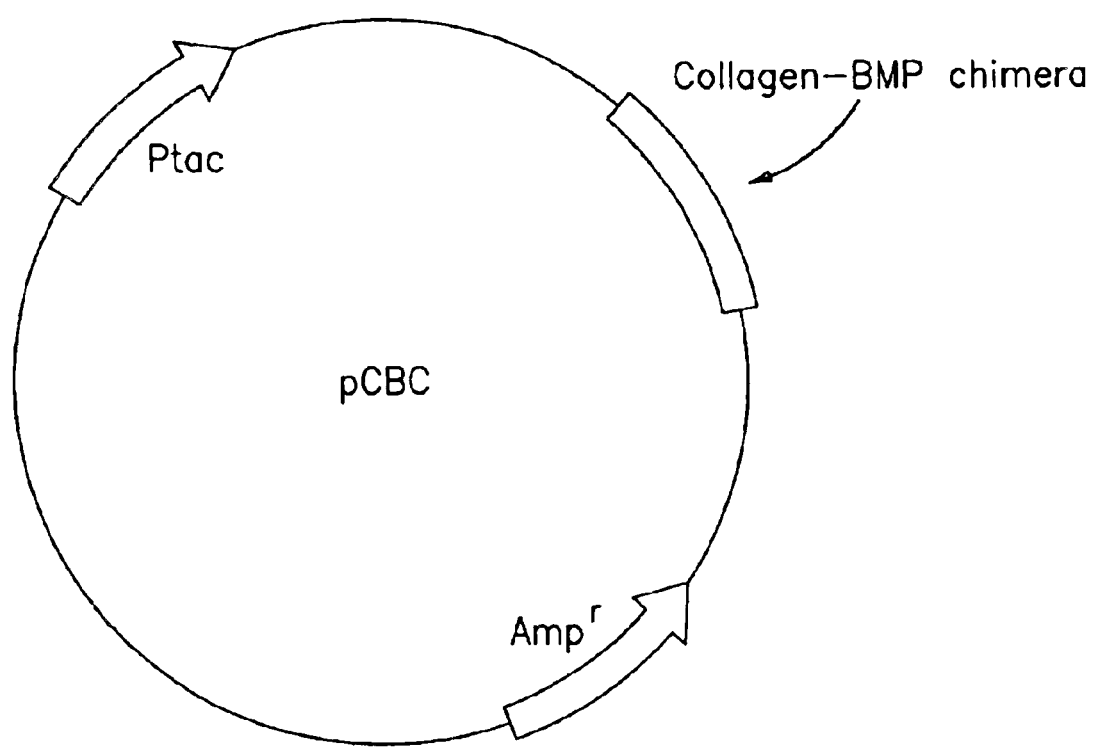
FIG. 11 is a plasmid map illustrating pCBC.

It is contemplated that any polypeptide having an extracellular matrix protein domain such as a collagen, collagen fragment or collagen-like peptide domain can be made to incorporate amino acid analog(s) in accordance with the disclosure herein. Such polypeptides include collagen, a collagen fragment or collagen-like peptide domain and a domain having a region incorporating one or more physiologically active agents such as glycoproteins, proteins, peptides and proteoglycans. As used herein, physiologically active agents exert control over or modify existing physiologic functions in living things. Physiologically active agents include hormones, growth factors, enzymes, ligands and receptors. Many active domains of physiologically active agents have been defined and isolated. It is contemplated that polypeptides having a collagen, collagen fragment or collagen-like peptide domain can also have a domain incorporating one or more physiologically active domains which are active fragments of such physiologically active agents. As used herein, physiologically active agent is meant to include entire peptides, polypeptides, proteins, glycoproteins, proteoglycans and active fragments of any of them. Thus, chimeric proteins are made to incorporate amino acid analog(s) by transforming a prokaryotic proline auxotroph or a eukaryotic proline auxotroph with an appropriate expression vector and contacting the transformed auxotroph with growth media containing at least one of the amino acid analogs. For example, a chimeric collagen/bone morphogenic protein (BMP) construct or various chireric collagen/growth factor constructs are useful in accordance herein. Such growth factors are well-known and include insulin-like growth factor, transforming growth factor, platelet derived growth factor and the like. FIG. 10 illustrates DNA of BMP which can be fused to the 3' terminus of DNA encoding collagen, DNA encoding a collagen fragment or DNA encoding a collagen-like peptide. FIG. 11 illustrates a map of plasmid pCBC containing a collagen/BMP construct. In a preferred embodiment, proteins having a collagen, collagen fragment or collagen-like peptide domain assemble or aggregate to form an extracellular matrix which can be used as a surgical implant. The property of self-aggregation as used herein includes-the ability to form an aggregate with the same or similar molecules or to form an aggregate with different molecules that share the property of aggregation to form, e.g., a double or triple helix. An example of such aggregation is the structure of assembled collagen matrices.

Indeed, chimeric polypeptides which may also be referred to herein as chimeric proteins provide an integrated combination of a therapeutically active domain from a physiologically active agent and one or more EMP moieties. The EMP domain provides an integral vehicle for delivery of the therapeutically active moiety to a target site. The two domains are linked covalently by one or more peptide bonds contained in a linker region. As used herein, integrated or integral means characteristics which result from the covalent association of one or more domains of the chimeric proteins. The therapeutically active moieties disclosed herein arc typically made of amino acids linked to form peptides, polypeptides, proteins, glycoproteins or proteoglycans. As used herein, peptide encompasses polypeptides and proteins.

The inherent characteristics of EMPs are ideal for use as a vehicle for the therapeutic moiety. One such characteristic is the ability of the EMPs to form the self-aggregate. Examples of suitable EMPs are collagen, elastin, fibronectin, fibrinogen and fibrin. Fibrillar collagens (Type I, II and III) assemble into ordered polymers and often aggregate into larger bundles. Type IV collagen assembles into sheetlike meshworks. Elastin molecules form filaments and sheets in which the elastin molecules are highly cross-linked to one another to provide good elasticity and high tensile strength. The cross-linked, random-coiled structure of the fiber network allows it to stretch and recoil like a rubber band. Fibronectin is a large fibril forming glycoprotein, which, in one of its forms, consists of highly insoluble fibrils cross-linked to each other by disulfide bonds. Fibrin is an insoluble protein formed from fibrinogen by the proteolytic activity of thrombin during the normal clotting of blood.

The molecular and macromolecular morphology of the above EMPs defines networks or matrices to provide substratum or scaffolding in integral covalent association with the therapeutically active moiety. The networks or matrices formed by the EMP domain provide an environment particularly well suited for ingrowth of autologous cells involved in growth, repair and replacement of existing tissue. The integral therapeutically active moieties covalently bound within the networks or matrices provide maximum exposure of the active agents to their targets to elicit a desired response.

Implants formed of or from the present chimeric proteins provide sustained release activity in or at a desired locus or target site. Since it is linked to an EMP domain, the therapeutically active domain of the present chimeric protein is not free to separately diffuse or otherwise be transported away from the vehicle which carries it, absent cleavage of peptide bonds. Consequently, chimeric proteins herein provide an effective anchor for therapeutic activity which allows the activity to be confined to a target location for a prolonged duration. Because the supply of therapeutically active agent does not have to be replenished as often when compared to non-sustained release dosage forms, smaller amounts of therapeutically active agent may be used over the course of therapy. Consequently, certain advantages provided by the present chimeric proteins are a decrease or elimination of local and systemic side effects, less potentiation or reduction in therapeutic activity with chronic use, and minimization of drug accumulation in body tissue with chronic dosing.

Use of recombinant technology allows manufacturing of non-immunogenic chimeric proteins. The DNA encoding both the therapeutically active moiety and the EMP moiety should preferably be derived from the same species as the patient being treated to avoid an immunogenic reaction. For example, if the patient is human, the therapeutically active moiety as well as the EMP moiety is preferably derived from human DNA.

Osteogenic/EMP chimeric proteins provide biodegradable and biocompatible agents for inducing bone formation at a desired site. As stated above, in one embodiment, a BMP moiety is covalently linked with an EMP to form chimeric protein. The BMP moiety induces osteogenesis and the extracellular matrix protein moiety provides an integral substratum or scaffolding for the BMP moiety and cells which are involved in reconstruction and growth. Compositions containing the BMP/EMP chimeric protein provide effective sustained release delivery of the BMP moiety to desired target sites. The method of manufacturing such an osteogenic agent is efficient because the need for extra time consuming steps as purifying EMP and then admixing it with the purified BMP are eliminated. An added advantage of the BMP/EMP chimeric protein results from the stability created by the covalent bond between BMP and the EMP, i.e., the BMP portion is not free to separately diffuse away from the EMP, thus providing a more stable therapeutic agent.

Bone morphogenic proteins are class identified as BMP-1 through BMP-9. A preferred osteogenic protein for use in human patients is human BMP-2B. A BMP-2B/collagen IA chimeric protein is illustrated in FIG. 13 (SEQ. ID. NO. 6). The protein sequence illustrated in FIG. 15 (SEQ. ID. NO. 8) includes a collagen helical domain depicted at amino acids 1–1057 and a mature form of BMP-2B at amino acids 1060–1169. The physical properties of the chimeric protein are dominated in part by the EMP component. In the case of a collagen moiety, a concentrated solution of chimeric protein will have a gelatinous consistency that allows easy handling by the medical practitioner. The EMP moiety acts as a sequestering agent to prevent rapid desorption of the BMP moiety from the desired site and to provide sustained release of BMP activity. As a result, the BMP moiety remains at the desired site and provides sustained release of BMP activity at the desired site for a period of time necessary to effectively induce bone formation. The EMP moiety also provides a matrix which allows a patient's autologous cells, e.g., chondrocytes and the like, which are normally involved in osteogenesis to collect therein and form an autologous network for new tissue growth. The gelatinous consistency of the chimeric protein also provides a useful and convenient therapeutic manner for immobilizing active BMP on a suitable vehicle or implant for delivering the BMP moiety to a site where bone growth is desired.

The BMP moiety and the EMP moiety are optionally linked together by linker sequences of amino acids. Examples of linker sequences used are illustrated within the sequence depicted in FIGS. 14A–14C (SEQ. ID. NO. 7), 16A–16C (SEQ. ID. NO. 9), 19A–19C (SEQ. ID. NO. 12) and 20A–20C (SEQ. ID. NO. 13), and are described in more detail below. Linker sequences may be chosen based on particular properties which they impart to the chimeric protein. For example, amino acid sequences such as Ile-Glu-Gly-Arg and Leu-Val-Pro-Arg are cleaved by factor XA and thrombin enzymes, respectively. Incorporating sequences which are cleaved by proteolytic enzymes into chimeric proteins herein provides cleavage at the linker site upon exposure to the appropriate enzyme and separation of the two domains into separate entities. It is contemplated that numerous linker sequences can be incorporated into any of the chimeric proteins.

In another embodiment, a chimeric DNA construct includes a gene encoding an osteogenic protein or a fragment thereof linked to gene encoding an EMP or a fragment thereof The gene sequence for various BMPs are known, see, e.g., U.S. Pat. Nos. 4,294,753, 4,761,471, 5,106,748, 5,187,076, 5,141,905, 5,108,922, 5,116,738 and 5,168,050, each incorporated herein by reference. A BMP-2B gene for use herein is synthesized by ligating oligonucleotides encoding a BMP protein. The oligonucleotides encoding BMP-2B are synthesized using an automated DNA synthesizer (Beckmen Oligo-1000). In preferred embodiment, the nucleotide sequence encoding the BMP is maximized for expression in $E.\ coli$. This is accomplished by using $E.\ coli$ utilization tables to translate the sequence of amino acids of the BMP into codons that are utilized most often by $E.\ coli$. Alternatively, native DNA encoding BMP isolated from mammals including humans may be purified and used.

The BMP gene and the DNA sequence encoding an extracellular matrix protein are cloned by standard genetic engineering methods as described in Sambrook et al., Molecular Cloning: A Laboratory Manual, Cold Spring Harbor 1989, hereby incorporated by reference.

The DNA sequence corresponding to the helical and telepeptide region of collagen l(α1) is cloned from a human fibroblast cell line. Two sets of polymerase chain reactions are carried out using cDNA prepared by standard methods from AG02261A cells. The first pair of PCR primers include a 5' primer bearing an XmnI linker sequence and a 3' primer bearing the BsmI site at nucleotide number 1722. The resulting PCR product consists of sequence from position 1 to 1722. The second pair of primers includes the BsmI site at 1722 and a linker sequence at the 3' end bearing a BglII site. The resulting PCR product consists of sequence from position 1722 to 3196. The complete sequence is assembled by standard cloning techniques. The two PCR products are ligated together at the BsmI site, and the combined clone is inserted into any vector with XmnI-BglII sites such as pMAL-c2 vector.

To clone the BMP-2B gene, total cellular RNA is isolated from human osteosarcoma cells (U-2OS) by the method described by Robert E. Farrel Jr. (Academic Press, CA, 1993 pp. 68–69) (herein incorporated by reference). The integrity of the RNA is verified by spectrophotometric analysis and electrophoresis through agarose gels. Typical yields of total RNA are 50 µg from a 100mm confluent tissue culture dish. The RNA is used to generate cDNA by reverse transcription using the Superscript pre-amplification system by Gibco BRL. The cDNA is used as template for PCR amplification using upstream and downstream primers specific for BMP-2B (GenBank HUMBMP2B accession #M22490). The resulting PCR product consists of BMP-2B sequence from position 1289–1619. The PCR product is resolved by electrophoresis through agarose gels, purified with gene clean (BIO 101) and ligated into pMal-c2 vector (New England Biolabs). The domain of human collagen I($\alpha$1) chain is cloned in a similar manner. However, the total cellular RNA is isolated from a human fibroblast cell line (AG02261A human skin fibroblasts).

A chimeric BMP/EMP DNA construct is obtained by ligating a synthetic BMP gene to a DNA sequence encoding an EMP such as collagen, fibrinogen, fibrin, fibronectin, elastin or laminin. However, chimeric polypeptides herein are not limited to these particular proteins. FIGS. 14A–14C (SEQ. ID. NO. 7) illustrate a DNA construct which encodes a BMP-2B/collagen I($\alpha$1) chimeric protein. The coding sequence for an EMP may be ligated upstream and/or downstream and in-frame with a coding sequence for the BMP. The DNA encoding an EMP may be a portion of the gene or an entire EMP gene. Furthermore, two different EMPs may be ligated upstream and downstream from the BMP.

The BMP-2B/collagen I($\alpha$1) chimeric protein illustrated in FIGS. 14A–14C includes an XmnI linker sequence at base pairs (bp) 1–19, a collagen domain (bp 20–3190), a BglII/BamHI linker sequence (bp 3191–3196), a mature form of BMP2b (bp 3197–3529) and a HindIII linker sequence (bp 3530–3535).

Any combination of growth factor and matrix protein sequences are contemplated including repeating units, or multiple arrays of each segment in any order.

Incorporation of fragments of both matrix and growth factor proteins is also contemplated. For example, in the case of collagen, only the helical domain may be included. Other matrix proteins have defined domains, such as laminin, which has EGF-like domains. In these cases, specific functionalities can be chosen to achieve desired effects. Moreover, it may be useful to combine domains from disparate matrix proteins, such as the helical region of collagen and the cell attachment regions of fibronectin. In the case of growth factors, specific segments have been shown to be removed from the mature protein by post translational processing. Chimeric proteins can be designed to include only the mature biologically active region. For example, in the case of BMP-2B only the final 110 amino acids are found in the active protein.

In another embodiment, a transforming growth factor (TGF) moiety is covalently linked with an EMP to form a chimeric protein. The TGF moiety increases efficacy of the body's normal soft tissue repair response and also induces osteogenesis. Consequently, TGF/EMP chimeric proteins may be used for either or both functions. One of the fundamental properties of the TGF-$\beta$s is their ability to turn on various activities that result in the synthesis of new connective tissue. See, Piez and Sporn eds., Transforming Growth Factor-$\beta$s Chemistry, Biology and Therapeutics, Annals of the New York Academy of Sciences, Vol. 593, (1990). TGF-$\beta$ is known to exist in at least five different isoforms. The DNA sequence for Human TGF-$\beta_1$, is known and has been cloned. See Derynck et al., Human Transforming Growth Factor-Beta cDNA Sequence and Expression in Tumour Cell Lines, Nature, Vol.316, pp. 701–705 (1985), herein incorporated by reference. TGF-$\beta_2$ has been isolated from bovine bone, human glioblastoma cells and porcine platelets. TGF-$B_3$ has also been cloned. See ten Dijke, et al., Identification of a New Member of the Transforming Growth Factor-$\beta$ Gene Family, Proc. Natl. Acad. Sci. (USA), Vol.85, pp. 4715–4719 (1988) herein incorporated by reference.

A TGF-$\beta$/EMP chimeric protein incorporates the known activities of TGF-$\beta$s and provides integral scaffolding or substratum of the EMP as described above to yield a composition which further provides sustained release focal delivery at target sites.

The TGF-$\beta$ moiety and the EMP moiety are optionally linked together by linker sequences of amino acids. Linker sequences may be chosen based upon particular properties which they impart to the chimeric protein. For example, amino acid sequences such as Ile-Glu-Glyn-Arg and Leu-Val-Pro-Arg are cleaved by Factor XA and Thrombin enzymes, respectively. Incorporating sequences which are cleaved by proteolytic enzymes into the chimeric protein provides cleavage at the linker site upon exposure to the appropriate enzyme and separation of the domains into separate entities. FIG. 15 depicts an amino acid sequence for a TGF-$\beta_1$/collagen IA chimeric protein (SEQ. ID. NO. 8). The illustrated amino acid sequence includes the collagen domain (1–1057) and a mature form of TGF-$\beta_1$ (1060–1171).

A chimeric DNA construct includes a gene encoding TGF-$\beta_1$ or a fragment thereof, or a gene encoding TGF-$\beta_2$ or a fragment thereof, or a gene encoding TGF-$\beta_3$ or a fragment thereof, ligated to a DNA sequence encoding an EMP protein such as collagen (I–IV), fibrin, fibrinogen, fibronectin, elastin or laminin. A preferred chimeric DNA construct combines DNA encoding TGF-$\beta_1$, a DNA linker sequence, and DNA encoding collagen IA. A chimeric DNA construct containing TGF-$\beta_1$, gene and a collagen I($\alpha$1) gene is shown in FIGS. 16A–16C (SEQ. ID. NO. 9). The illustrated construct includes an XmnI linker sequence (bp 1–19), DNA encoding a collagen domain (bp 20–3190), a BglII linker sequence (bp 3191–3196), DNA encoding a mature form of TGF-$\beta_1$, (3197–3535), and an XbaI linker sequence (bp 3536–3541).

The coding sequence for EMP may be ligated upstream and/or downstream and in-frame with a coding sequence for the TGF$\beta$. The DNA encoding the extracellular matrix protein may encode a portion of a fragment of the EMP or may encode the entire EMP. Likewise, the DNA encoding the TGF-β may be one or more fragments thereof or the entire gene. Furthermore, two or more different TGF-βs or two or more different EMPs may be ligated upstream or downstream of alternate moieties.

In yet another embodiment, a dermatan sulfate proteoglycan moiety, also known as decorin or proteoglycan II, is covalently linked with an EMP to form a chimeric protein. Decorin is known to bind to type I collagen and thus affect fibril formation, and to inhibit the cell attachment-promoting activity of collagen and fibrinogen by binding to such molecules near their cell binding sites. Chimeric proteins which contain a decorin moiety act to reduce scarring of healing tissue. The primary structure of the core protein of decorin has been deduced from cloned cDNA. See Krusius et al., Primary Structure of an Extracellular Matrix Proteoglycan Core Protein-Deduced from Cloned cDNA, Proc. Natl. Acad. Sci. (USA), Vol. 83, pp. 7683–7687 (1986) incorporated herein by reference.

A decorin/EMP chimeric protein incorporates the known activities of decorin and provides integral scaffolding or substratum of the EMP as described above to yield a composition which allows sustained release focal delivery to target sites. FIGS. 17A–17B illustrate a decorin/collagen IA chimeric protein (SEQ. ID. NO. 10) in which the collagen domain includes amino acids 1–1057 and the decorin mature protein incudes amino acids 1060–1388. FIG. 18 illustrates a decorin peptide/colagen IA chimeric protein (SEQ. ID. NO. 11) in which the collagen helical domain includes amino acids 1–1057 and the decorin peptide fragment includes amino acids 1060–1107. The decorin peptide fragment is composed of P46 to G93 of the mature form of decorin.

Further provided is a chimeric DNA construct which includes a gene encoding decorin or one or more fragments thereof, optionally ligated via a DNA linker sequence to a DNA sequence encoding an EMP such as collagen (I–IV), fibrin, fibrinogen, fibronectin, elastin or laminin. A preferred chimeric DNA construct combines DNA encoding decorin, a DNA linker sequence, and DNA encoding collagen I(α1). A chimeric DNA construct containing a decorin gene and a collagen I(α1) gene is shown in FIGS. 19A–19D (SEQ. ID. NO. 12). The illustrated construct includes an XmnI linker sequence (bp 1–19), DNA encoding a collagen domain (bp 20–3190), a BglII linker sequence (bp 3191–3196), DNA encoding a mature form of decorin (bp 3197–4186) and a PstI linker sequence. A chimeric DNA construct containing a decorin peptide gene and a collagen I(α1) gene is shown in FIGS. 20A–20C (SEQ. ID. NO. 13). The illustrated construct includes an XmnI linker sequence (bp 1–19), DNA encoding a collagen domain (bp 20–3190), a BglII linker sequence (bp 3191–3196), DNA encoding a peptide fragment of decorin (bp 3197–3343), and a PstI linker sequence (bp 3344–3349).

The coding sequence for an EMP may be ligated upstream and/or downstream and in-frame with a coding sequence for decorin. The DNA encoding the EMP may encode a portion or fragment of the EMP or may encode the entire EMP. Likewise, the DNA encoding decorin may be a fragment thereof or the entire gene. Furthermore, two or more different EMPs may be ligated upstream and/or downstream from the DNA encoding decorin moiety.

Figure 21:
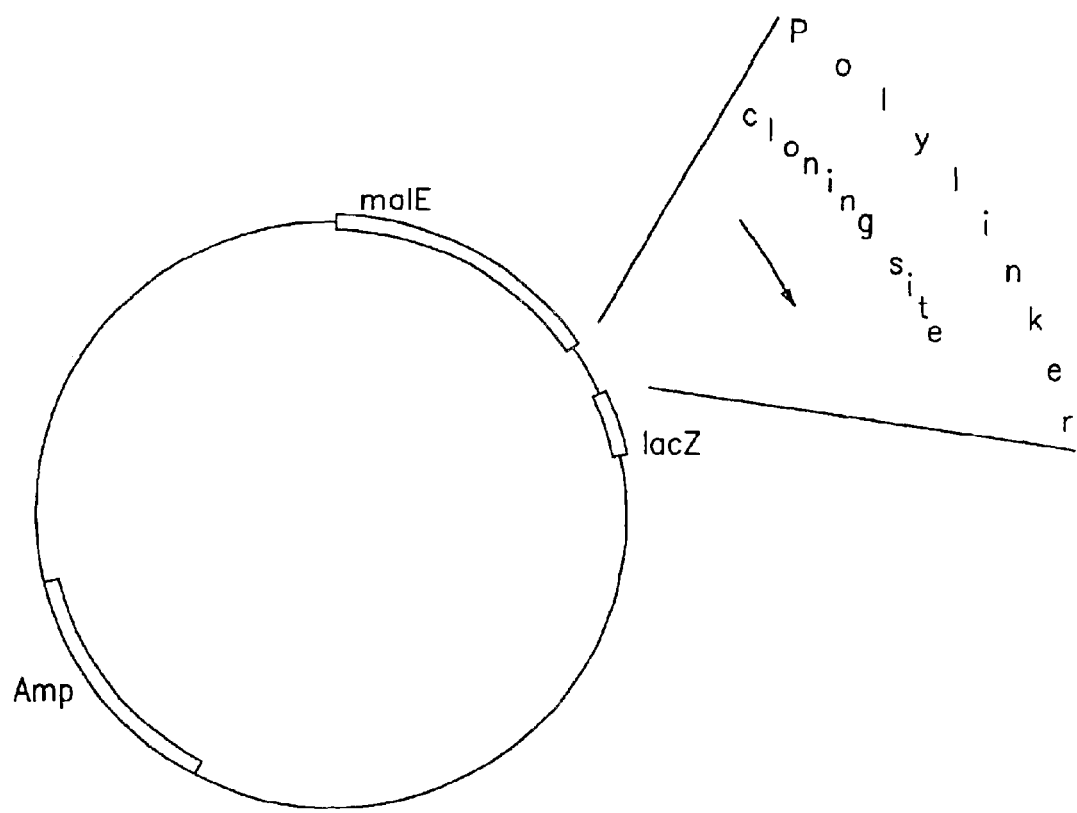
FIG. 21 depicts a pMal cloning vector and polylinker cloning site.

Any of the above described chimeric DNA constructs may be incorporated into a suitable cloning vector. FIG. 21 depicts a pMal cloning vector containing a polylinker cloning site. Examples of cloning vectors are the plasmids pMal-p2 and pMal-c2 (commercially available from New England Biolabs). The desired chimeric DNA construct is incorporated into a polylinker sequence of the plasmid which contains certain useful restriction endonuclease sites which are depicted in FIG. 22 (SEQ. ID. NO. 14). The pMal-p2 polylinker sequence has XmnI, EcoRI, BamHI, HindIII, XbaI, SalI and PstI restriction endonuclease sites which are depicted in FIG. 22. The polylinker sequence is digested with an appropriate restriction endonuclease and the chimeric construct is incorporated into the cloning vector by ligating it to the DNA sequences of the plasmid. The chimeric DNA construct may be joined to the plasmid by digesting the ends of the DNA construct and the plasmid with the same restriction endonuclease to generate "sticky ends" having 5' phosphate and 3' hydroxyl groups which allow the DNA construct to anneal to the cloning vector. Gaps between the inserted DNA construct and the plasmid are then sealed with DNA ligase. Other techniques for incorporating the DNA construct into plasmid DNA include blunt end ligation, poly(dA.dT) tailing techniques, and the use of chemically synthesized linkers. An alternative method for introducing the chimeric DNA construct into a cloning vector is to incorporate the DNA encoding the extracellular matrix protein into a cloning vector already containing a gene encoding a therapeutically active moiety.

The cloning sites in the above-identified polylinker site allow the cDNA for the collagen I(α1)/BMP-2B chimeric protein illustrated in FIGS. 14A–14C (SEQ. ID. NO. 7) to be inserted between the XmnI and the HindIII sites. The cDNA encoding the collagen I(α1)TGF-β$_1$, protein illustrated in FIGS. 16A–16C (SEQ. ID. NO. 9) is inserted between the XmnI and the XbaI sites. The cDNA encoding the collagen l(α1)/decorin protein illustrated in FIGS. 19A–19D (SEQ. ID. NO. 12) inserted between the XmnI and the PstI sites. The cDNA encoding the collagen I(α1)/decorin peptide illustrated in FIGS. 20A–20C (SEQ. ID. NO. 13) is inserted between the XmnI and PstI sites.

Plasmids containing the chimeric DNA construct are identified by standard techniques such as gel electrophoresis. Procedures and materials for preparation of recombinant vectors, transfornation of host cells with the vectors, and host cell expression of polypeptides are described in Sambrook et al., Molecular Cloning: A Laboratory Manual, supra. Generally, prokaryotic or eukaryotic host cells may be transformed with the recombinant DNA plasmids. Transformed host cells may be located through phenotypic selection genes of the cloning vector which provide resistance to a particular antibiotic when the host cells are grown in a culture medium containing that antibiotic.

Transformed host cells are isolated and cultured to promote expression of the chirneric protein The chimeric protein may then be isolated from the culture medium and purified by various methods such as dialysis, density gradient centrifugation, liquid column chromatography, isoelectric precipitation, solvent fractionation, and electrophoresis. However, purification of the chimeric protein by affinity chromatography is preferred whereby the chimeric protein is purified by ligating it to a binding protein and contacting it with a ligand or substrate to which the binding protein has a specific affinity.

In order to obtain more effective expression of mammalian or human eukaryotic genes in bacteria (prokaryotes), the mammalian or human gene may be placed under the control of a bacterial promoter. A protein fusion and purification system is employed to obtain the chimeric protein.

Figure 23:
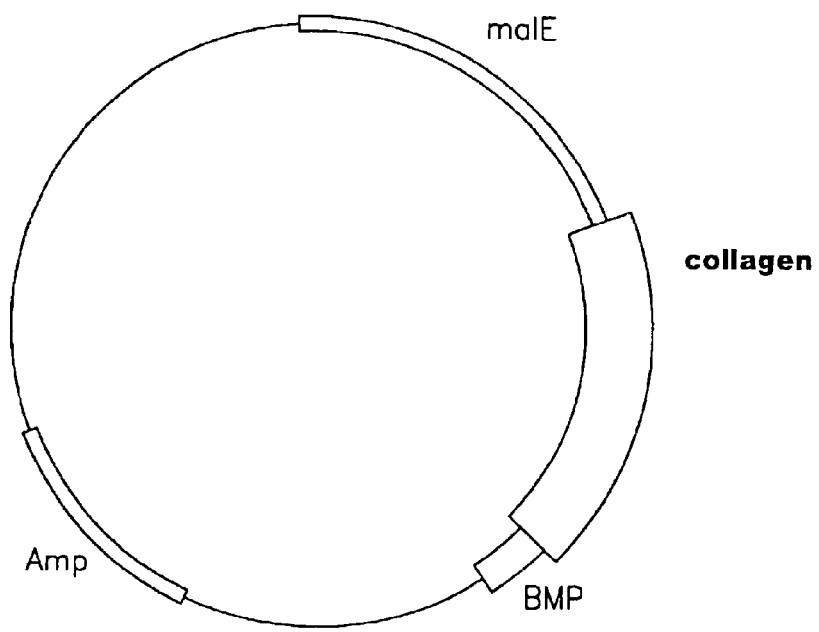
FIG. 23 depicts a pMal cloning vector containing a BMP/collagen nucleotide chimeric constuct.
Figure 24:
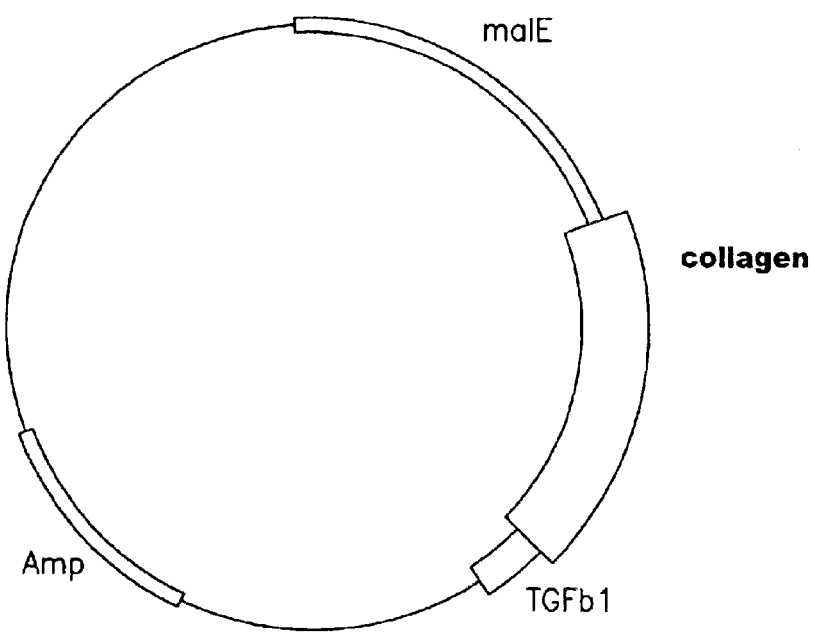
FIG. 24 depicts a pMal cloning vector containing a TGF-$β_1$/collagen nucleotide chimeric construct.
Figure 25:
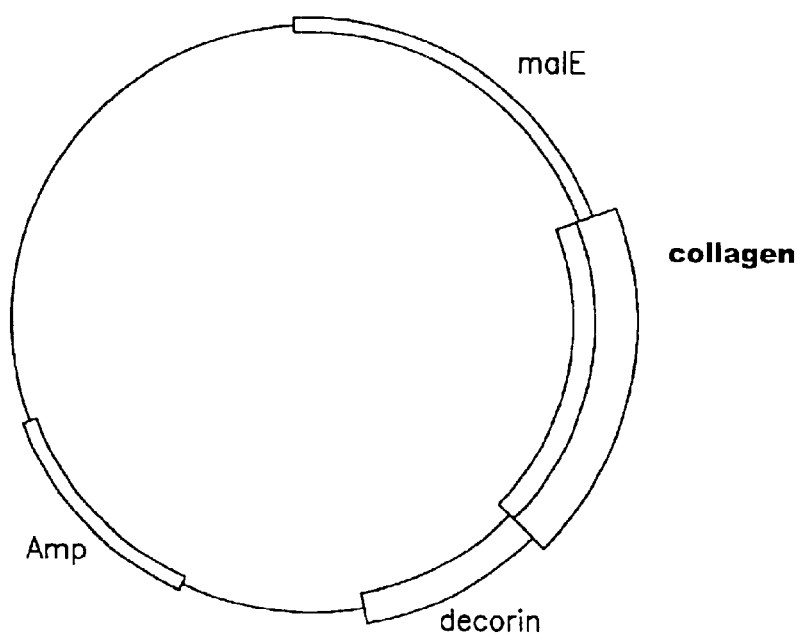
FIG. 25 depicts a pMal cloning vector containing a decorin/collagen nucleotide chimeric construct.
Figure 26:
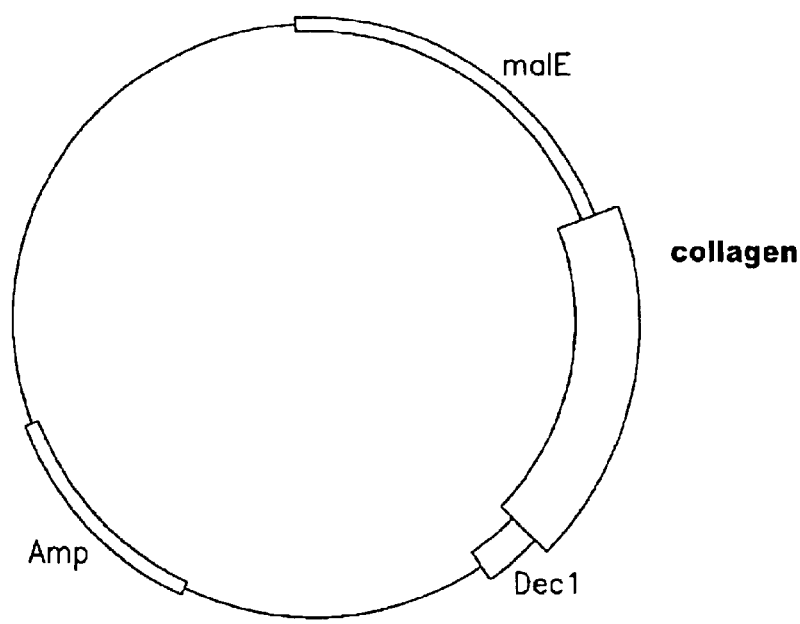
FIG. 26 depicts a pMal cloning vector containing a decorin peptide/collagen nucleotide chimeric construct.

Preferably, any of the above-described chimeric DNA constructs is cloned into a pMal vector at a site in the vector's polylinker sequence. As a result, the chimeric DNA construct is operably fused with the malE gene of the pMal vector. The malE gene encodes maltose binding protein (MBP). FIG. 23 depicts a pMal cloning vector containing a BMP/collagen DNA construct. A spacer sequence coding for 10 asparagine residues is located between the malE sequence and the polylinker sequence. This spacer sequence insulates MBP from the protein of interest. FIGS. 24, 25 and 26 depict pMal cloning vectors containing DNA encoding collagen chimeras with TGF-$\beta_1$, decorin and a decorin peptide, respectively. The pMal vector containing any of the chimeric DNA constructs fused to the malE gene is transformed into E. coli.

The E. coli is cultured in a medium which induces the bacteria to produce the maltose-binding protein fused to the chimeric protein. This technique utilizes the $P_{tac}$ promoter of the pMal vector. The MBP contains a 26 amino acid N-terminal signal sequence which directs the MBP-chimeric protein through the E. coli cytoplasmic membrane. The protein can then be purified from the periplasm. Alternatively, the pMal-c2 cloning vector can be used with this protein fusion and purification system. The pMal-c2 vector contains an exact deletion of the malE signal sequence which results in cytoplasmic expression of the fusion protein. A crude cell extract containing the fusion protein is prepared and poured over a column of amylose resin. Since MBP has an affinity for the amylose it binds to the resin. Alternatively, the column can include any substrate for which MBP has a specific affinity. Unwanted proteins present in the crude extract are washed through the column. The MBP fused to the chimeric protein is eluted from the column with a neutral buffer containing maltose or other dilute solution of a desorbing agent for displacing the hybrid polypeptide. The purified MBP-chimeric protein is cleaved with a protease such as factor Xa protease to cleave the MBP from the chimeric protein. The pMal-p2 plasmid has a sequence encoding the recognition site for protease factor Xa which cleaves after the amino acid sequence Isoleucine-Glutamic acid-Glycine-Arginine of the polylinker sequence.

The chimeric protein is then separated from the cleaved MlBP by passing the mixture over an amylose column. An alternative method for separating the MBP from the chimeric protein is by ion exchange chromatography. This system yields up to 100 mg of MBP-chimeric protein per liter of culture. See Riggs, P., in Ausebel, F. M., Kingston, R. E., Moore, D. D., Seidman, J. G., Smith, J. A., Struhl, K. (eds.) Current Protocols in Molecular Biology, Supplement 19 (16.6.1–16.6.10) (1990) Green Associates/Wiley Interscience, New York, New England Biolabs (cat #800-65S 9pMALc2) pMal protein fusion and purification system hereby incorporated herein by reference. (See also European Patent No. 286 239 herein incorporated by reference which discloses a similar method for production and purification of a protein such as collagen.)

Other protein fusion and purification systems may be employed to produce chimeric proteins. Prokaryotes such as E. coli are the preferred host cells for expression of the chimeric protein. However, systems which utilize eukaryote host cell lines are also acceptable such as yeast, human, mouse, rat, hamster, monkey, amphibian, insect, algae, and plant cell lines. For example, HeLa (human epithelial), 3T3 (mouse fibroblast), CHO (Chinese hamster ovary), and SP 2 (mouse plasma cell) are acceptable cell lines. The particular host cells that are chosen should be compatible with the particular cloning vector that is chosen.

Another acceptable protein expression system is the Baculovirus Expression System manufactured by Invitrogen of San Diego, Calif. Baculoviruses form prominent crystal occlusions within the nuclei of cells they infect. Each crystal occlusion consists of numerous virus particles enveloped in a protein called polyhedrin. In the baculovirus expression system, the native gene encoding polyhedrin is substituted with a DNA construct encoding a protein or peptide having a desired activity. The virus then produces large amounts of protein encoded by the foreign DNA construct. The preferred cloning vector for use with this system is pBlueBac III (obtained from Invitrogen of San Diego, Calif.). The baculovirus system utilizes the Autograph californica multiple nuclear polyhidrosis virus (ACMNPV) regulated polyhedrin promoter to drive expression of foreign genes. The chimeric gene, i.e., the DNA construct encoding the chimeric protein, is inserted into the pBlueBac III vector immediately downstream from the baculovirus polyhedrin promoter.

The pBlueBac III transfer vector contains a B-galactosidase reporter gene which allows for identification of recombinant virus. The B-galactosidase gene is driven by the baculovirus ETL promoter ($P_{ETL}$) which is positioned in opposite orientation to the polyhedrin promoter ($P_{pH}$) and the multiple cloning site of the vector. Therefore, recombinant virus coexpresses B-galactosidase and the chimeric gene.

Spodoptera frugiperda (Sf9) insect cells are then cotransfected with wild type viral DNA and the pBlueBac III vector containing the chimeric gene. Recombination sequences in the pBlueBac III vector direct the vector's integration into the genome of the wild type baculovirus. Homologous recombination occurs resulting in replacement of the native polyhedrin gene of the baculovirus with the DNA construct encoding the chimeric protein. Wild type baculovirus which do not contain foreign DNA express the polyhedrin protein in the nuclei of the infected insect cells. However, the recombinants do not produce polyhedrin protein and do not produce viral occlusions. Instead, the recombinants produce the chimeric protein.

Alternative insect host cells for use with this expression system are Sf21 cell line derived from Spodoptera frugiperda and High Five cell lines derived from Trichoplusia ni.

Other acceptable cloning vectors include phages, cosmids or artificial chromosomes. For example, bacteriophage lambda is a useful cloning vector. This phage can accept pieces of foreign DNA up to about 20,000 base pairs in length. The lambda phage genome is a linear double stranded DNA molecule with single stranded complementary (cohesive) ends which can hybridize with each other when inside an infected host cell. The lambda DNA is cut with a restriction endonuclease and the foreign DNA, e.g. the DNA to be cloned, is ligated to the phage DNA fragments. The resulting recombinant molecule is then packaged into infective phage particles. Host cells are infected with the phage particles containing the recombinant DNA. The phage DNA replicates in the host cell to produce many copies of the desired DNA sequence.

Cosmids are hybrid plasmid/bacteriophage vectors which can be used to clone DNA fragments of about 40,000 base pairs. Cosmids are plasmids which have one or more DNA sequences called "cos" sites derived from bacteriophage lambda for packaging lambda DNA into infective phage particles. Two cosmids are ligated to the DNA to be cloned. The resulting molecule is packaged into infective lambda phage particles and transfected into bacteria host cells.

When the cosmids are inside the host cell they behave like plasmids and multiply under the control of a plasmid origin of replication. The origin of replication is a sequence of DNA which allows a plasmid to multiply within a host cell.

Yeast artificial chromosome vectors are similar to plasmids but allow for the incorporation of much larger DNA sequences of about 400,000 base pairs. The yeast artificial chromosomes contain sequences for replication in yeast. The yeast artificial chromosome containing the DNA to be cloned is transformed into yeast cells where it replicates thereby producing many copies of the desired DNA sequence. Where phage, cosmids, or yeast artificial chromosomes are employed as cloning vectors, expression of the chimeric protein may be obtained by culturing host cells that have been transfected or transformed with the cloning vector in a suitable culture medium.

Chimeric proteins disclosed herein are intended for use in treating mamals or other animals. The therapeutically active moieties described above, e.g., osteogenic agents such as BMPs, TGFs, decorin, and/or fragments of each of them, are all to be considered as being or having been derived from physiologically active agents for purposes of this description. The chimeric proteins and DNA constructs which incorporate a domain derived from one or more cellular physiologically active agents can be used for in vivo therapeutic treatment, in vitro research or for diagnostic purposes in general.

When used in vivo, formulations containing the present chimeric proteins may be placed in direct contact with viable tissue, including bone, to induce or enhance growth, repair and/or replacement of such tissue. This may be accomplished by applying a chimeric protein directly to a target site during surgery. It is contemplated that minimally invasive techniques such as endoscopy are to be used to apply a chimeric protein to a desired location. Formulations containing the chimeric proteins disclosed herein may consist solely of one or more chimeric proteins or may also incorporate one or more pharmaceutically acceptable adjuvants.

In an alternate embodiment, any of the above-described chimeric proteins may be contacted with, adhered to, or otherwise incorporated into an implant such as a drug delivery device or a prosthetic device. Chimeric proteins may be microencapsulated or macroencapsulated by liposomes or other membrane forming materials such as alginic acid derivatives prior to implantation and then implanted in the form of a pouchlike implant. The chimeric protein may be microencapsulated in structures in the form of spheres, aggregates of core material embedded in a continuum of wall material or capillary designs. Microencapsulation techniques are well known in the art and are described in the Encyclopedia of Polymer Science and Engineering, Vol. 9, pp. 724 et seq. (1980) hereby incorporated herein by reference.

Chimeric proteins may also be coated on or incorporated into medically useful materials such as meshes, pads, felts, dressings or prosthetic devices such as rods, pins, bone plates, artificial joints, artificial limbs or bone augmentation implants. The implants may, in part, be made of biocompatible materials such as glass, metal, ceramic, calcium phosphate or calcium carbonate based materials. Implants having biocompatible biomaterials are well known in the art and are all suitable for use herein. Implant biomaterials derived from natural sources such as protein fibers, polysaccharides, and treated naturally derived tissues are described in the Encyclopedia of Polymer Science and Engineering, Vol. 2, pp. 267 et seq. (1989) hereby incorporated herein by reference. Synthetic biocompatible polymers are well known in the art and are also suitable implant materials. Examples of suitable synthetic polymers include urethanes, olefins, terephthalates, acrylates, polyesters and the like. Other acceptable implant materials are biodegradable hydrogels or aggregations of closely packed particles such as polymethylmethacrylate beads with a polymerized hydroxyethyl methacrylate coating. See the Encyclopedia of Polymer Science and Engineering, Vol. 2, pp. 267 et seq. (1989) hereby incorporated herein by reference.

The chimeric protein herein provides a useful way for immobilizing or coating a physiologically active agent on a pharmaceutically acceptable vehicle to deliver the physiologically active agent to desired sites in viable tissue. Suitable vehicles include those made of bioabsorbable polymers, biocompatible nonabsorbable polymers, lactoner putty and plaster of Paris. Examples of suitable bioabsorbable and biocompatible polyrners include homopolymers, copolymers and blends of hydroxyacids such as lactide and glycolide, other absorbable polymers which may be used alone or in combination with hydroxyacids including dioxanones, carbonates such as trimethylene carbonate, lactones such as caprolactone, polyoxyalkylenes, and oxylates. See the Encyclopedia of Polymer Science and Engineering, Vol. 2, pp. 230 et seq. (1989) hereby incorporated herein by reference.

These vehicles may be in the form of beads, particles, putty, coatings or film vehicles. Diffusional systems in which a core of chimeric protein is surrounded by a porous membrane layer are other acceptable vehicles.

Figure 2A:
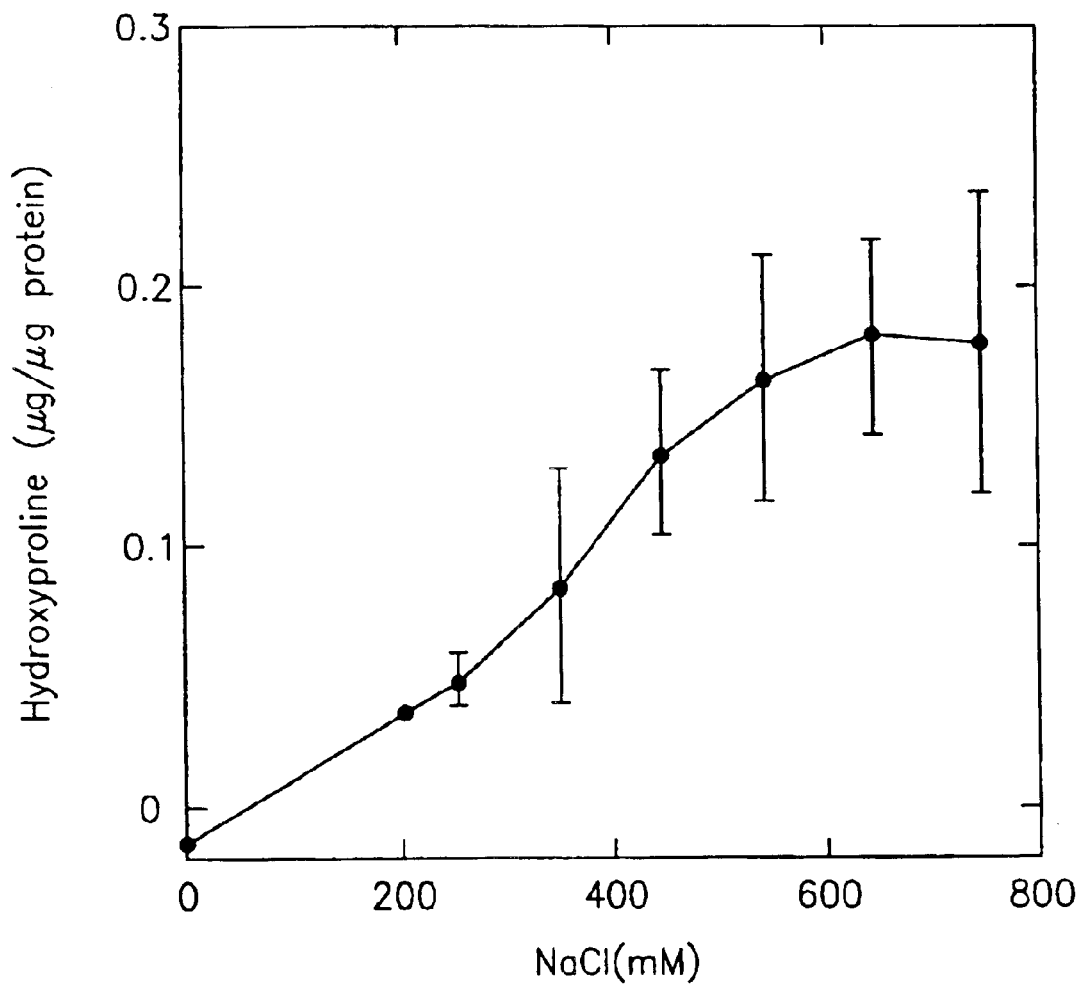
FIG. 2A is a graphical representation of the concentration of intracellular hydroxyproline as a function of sodium chloride concentration.
Figure 12:
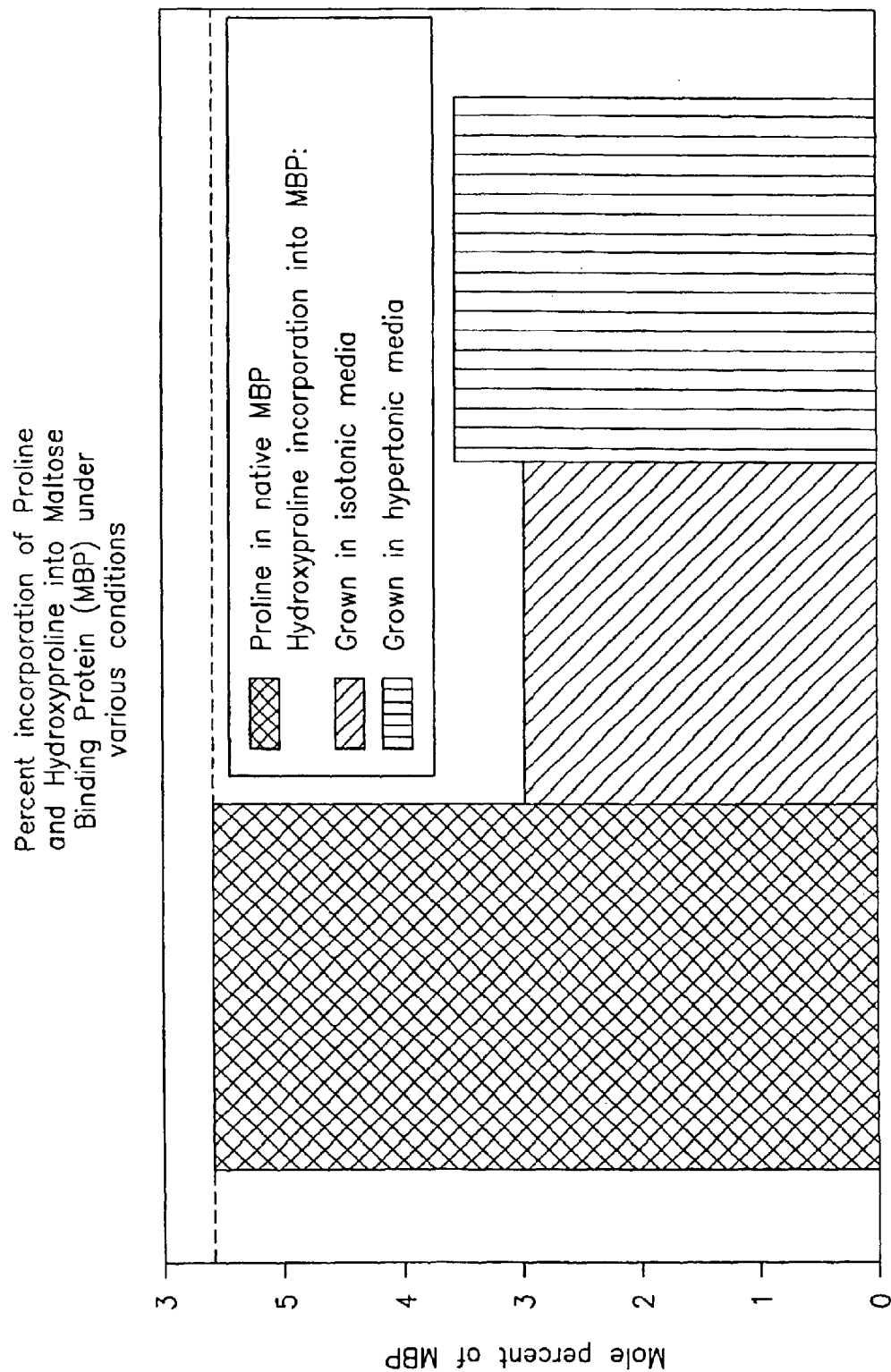
FIG. 12 is a graphical representation of the percent incorporation of proline and trans-4-hydroxyproline into maltose binding protein under various conditions.

In another aspect, the amount of amino acid analog(s) transport into a target cell can be regulated by controlling the tonicity of the growth media A hypertonic growth media increases uptake of trans-4-hydroxyproline into $E.$ $coli$ as illustrated in FIG. 2A. All known methods of increasing osmolality of growth media are appropriate for use herein including addition of salts such as sodium chloride, KCl, $MgCl_2$ and the like, and sugars such as sucrose, glucose, maltose, etc. and polymers such as polyethylene glycol (PEG), dextran, cellulose, etc. and amino acids such as glycine. Increasing the osmolality of growth media results in greater intracellular concentration of amino acid analog(s) and a higher degree of complexation of amino acid analog(s) to tRNA. As a consequence, proteins produced by the cell achieve a higher degree of incorporation of amino acid analogs. FIG. 12 illustrates percentage of incorporation of proline and hydroxyproline into MBP under isotonic and hypertonic media conditions in comparison to proline in native MBP. Thus, manipulating osmolality, in addition to adjusting concentration of amino acid analog(s) in growth media allows a dual-faceted approach to regulating their uptake into prokaryotic cells and eukaryotic cells as described above and consequent incorporation into target polypeptides.

Any growth media can be used herein including commercially available growth media such as M9 minimal medium (available from Gibco Life Technologies, Inc.), LB medium, NZCYM medium, terrific broth, SOB medium and others that are well known in the art.

Collagen from different tissues can contain different amounts of trans-4-hydroxyproline. For example, tissues that require greater strength such as bone contain a higher number of trans-4-hydroxyproline residues than collagen in tissues requiring less strength, e.g., skin. The present system provides a method of adjusting the amount of trans 4-hydroxyproline in collagen, collagen fragments, collagen-like peptides, and chimeric peptides having a collagen domain, collagen fragment domain or collagen-like peptide domain fused to a physiologically active domain, since by increasing or decreasing the concentration of trans-4-hydroxyproline in growth media, the amount of trans-4-hydroxyproline incorporated into such polypeptides is increased or decreased accordingly. The collagen, collagen fragments, collagen-like peptides and above-chimeric peptides can be expressed with predetermined levels of trans-4-hydroxyproline. In this manner physical characteristics of an extracellular matrix can be adjusted based upon requirements of end use. Without wishing to be bound by any particular theory, it is believed that incorporation of trans-4-hydroxyproline into the EMP moieties herein provides a basis for self aggregation as described herein.

In another aspect, the combination of incorporation of trans-4-hydroxyproline into collagen and fragments thereof using hyperosmotic media and genes which have been altered such that codon usage more closely reflects that found in E. coli, but retaining the amino acid sequence found in native human collagen, surprisingly resulted in production by E. coli of human collagen and fragments thereof which were capable of self aggregation.

The human collagen Type I ($\alpha_1$) gene sequence (FIG. 27A–27E) (SEQ. ID. NO. 15) contains a large number of glycine and proline codons (347 glycine and 240 proline codons) arranged in a highly repetitive manner. Table I below is a codon frequency tabulation for the human Type 1 ($\alpha_1$) collagen gene. Of particular note is that the GGA glycine codon occurs 64 times and the CCC codon for proline occurs 93 times. Both of these codons are considered to be rare codons in E. coli. See, Sharp, P. M. and W.-H. Li. Nucleic Acids Res. 14: 7737–7749, 1986. These, and similar considerations for other human collagen genes are shown herein to account for the difficulty in expressing human collagen genes in E. coli.

TABLE 1

| Codon | Count | % age |
|---|---|---|
| TTT-Phe | 1 | 0.09 |
| TTC-Phe | 14 | 1.32 |
| TTA-Leu | 0 | 0.00 |
| TTG-Leu | 3 | 0.28 |
| CTT-Leu | 4 | 0.37 |
| CTC-Leu | 7 | 0.66 |
| CTA-Leu | 0 | 0.00 |
| CTG-Leu | 7 | 0.66 |
| ATT-Ile | 6 | 0.56 |
| ATC-Ile | 0 | 0.00 |
| ATA-Ile | 1 | 0.09 |
| ATG-Met | 7 | 0.66 |
| GTT-Val | 10 | 0.94 |
| GTC-Val | 5 | 0.47 |
| GTA-Val | 0 | 0.00 |
| GTG-Val | 5 | 0.47 |
| TCT-Ser | 18 | 1.70 |
| TCC-Ser | 4 | 0.37 |
| TCA-Ser | 2 | 0.18 |
| TCG-Ser | 0 | 0.00 |
| CCT-Pro | 141 | 13.33 |
| CCC-Pro | 93 | 8.79 |
| CCA-Pro | 6 | 0.56 |
| CCG-Pro | 0 | 0.00 |
| ACT-Thr | 11 | 1.04 |
| ACC-Thr | 4 | 0.37 |
| ACA-Thr | 2 | 0.18 |
| ACG-Thr | 0 | 0.00 |
| GCT-Ala | 93 | 8.79 |
| GCC-Ala | 24 | 2.27 |
| GCA-Ala | 6 | 0.56 |

TABLE 1-continued

| Codon | Count | % age |
|---|---|---|
| GCG-Ala | 0 | 0.00 |
| TAT-Tyr | 2 | 0.18 |
| TAC-Tyr | 2 | 0.18 |
| TAA-*** | 0 | 0.00 |
| TAG-*** | 0 | 0.00 |
| CAT-His | 0 | 0.00 |
| CAC-His | 3 | 0.28 |
| CAA-Gln | 13 | 1.22 |
| CAG-Gln | 17 | 1.60 |
| AAT-Asn | 6 | 0.56 |
| AAC-Asn | 5 | 0.47 |
| AAA-Lys | 19 | 1.79 |
| AAG-Lys | 19 | 1.79 |
| GAT-Asp | 23 | 2.17 |
| GAC-Asp | 11 | 1.04 |
| GAA-Glu | 24 | 2.27 |
| GAG-Glu | 25 | 2.36 |
| TGT-Cys | 0 | 0.00 |
| TGC-Cys | 0 | 0.00 |
| TGA-*** | 0 | 0.00 |
| TGG-Trp | 0 | 0.00 |
| CGT-Arg | 26 | 2.45 |
| CGC-Arg | 6 | 0.56 |
| CGA-Arg | 11 | 1.04 |
| CGG-Arg | 1 | 0.09 |
| AGT-Ser | 4 | 0.37 |
| AGC-Ser | 11 | 1.04 |
| AGA-Arg | 9 | 0.85 |
| AGG-Arg | 0 | 0.00 |
| GGT-Gly | 174 | 16.46 |
| GGC-Gly | 97 | 9.17 |
| GGA-Gly | 64 | 6.05 |
| GGG-Gly | 11 | 1.04 |

Figure 28:
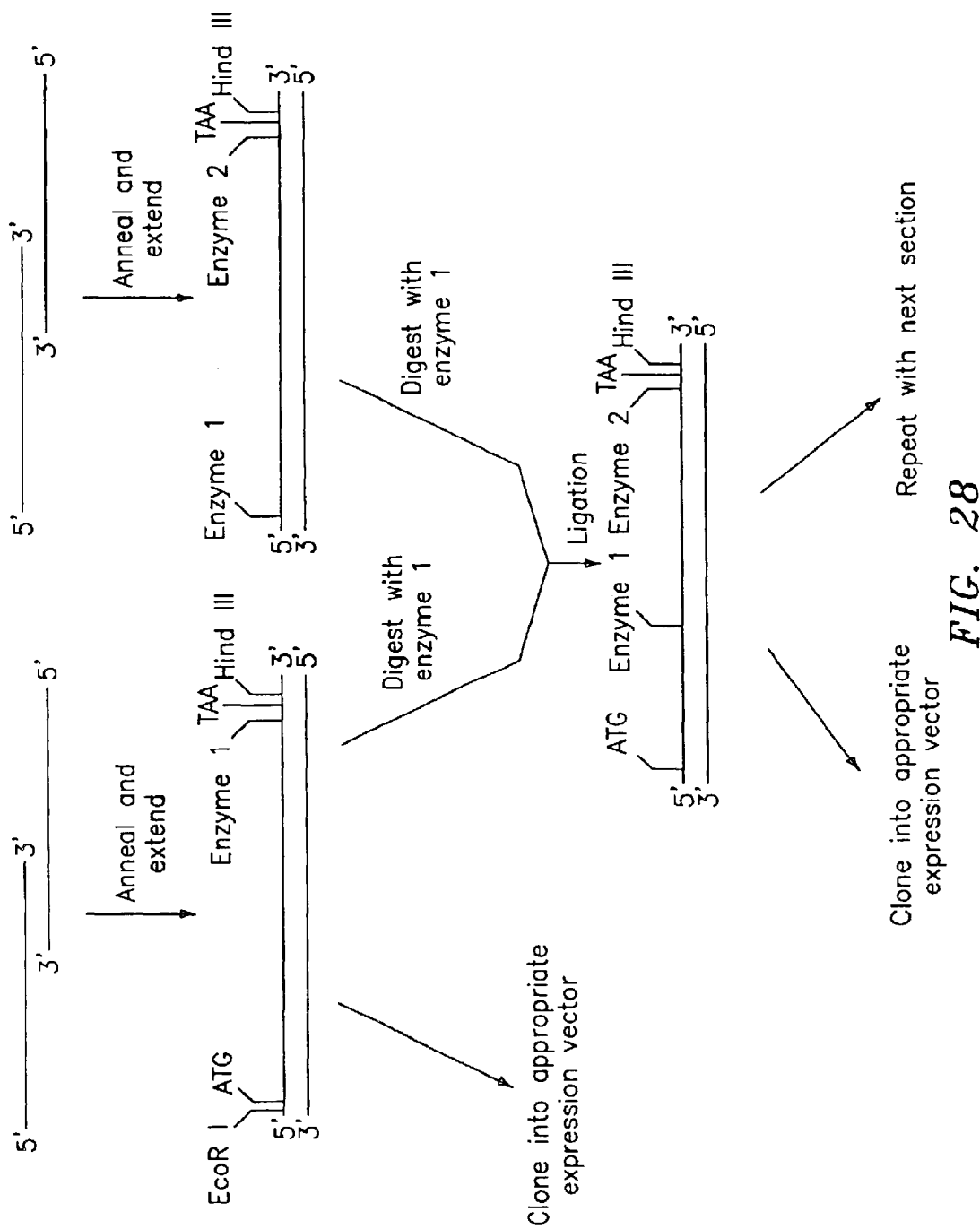
FIG. 28 is a schematic diagram of the construction of the human collagen gene from synthetic oligonucleotides.

In a first step, the sequence of the heterologous collagen gene is changed to reflect the codon bias in E. coli as given in codon usage tables (e.g. Ausubel et al., (1995) Current Protocols in Molecular Biology, John Wiley & Sons, New York, N.Y.; Wada et al., 1992, supra). Rare E. coli codons (See, Sharp, P. M. and W.-H. Li. Nucleic Acids Res. 14: 7737–7749, 1986) are avoided. Second, unique restriction enzyme sites are chosen that are located approximately every 120–150 base pairs in the sequence. In certain cases this entails altering the nucleotide sequence but does not change the amino acid sequence. Third, oligos of approximately 80 nucleotides are synthesized such that when two such oligos are annealed together and extended with a DNA polymerase they reconstruct a approximately 120–150 base pair section of the gene (FIG. 28). The section of the gene encoding the very amino terminal portion of the protein has an initiating methionine (ATG) codon at the 5' end and a unique restriction site followed by a stop (TAAT) signal at the 3' end. The remaining sections have unique restriction sites at the 5' end and unique restriction sites followed by a TAAT stop signal the 3' end. The gene is assembled by sequential addition of each section to the preceding 5' section. In this manner, each successively larger section can be independently constructed and expressed. FIG. 28 is a schematic representation of the construction of the human collagen gene starting from synthetic oligos.

Figure 29:
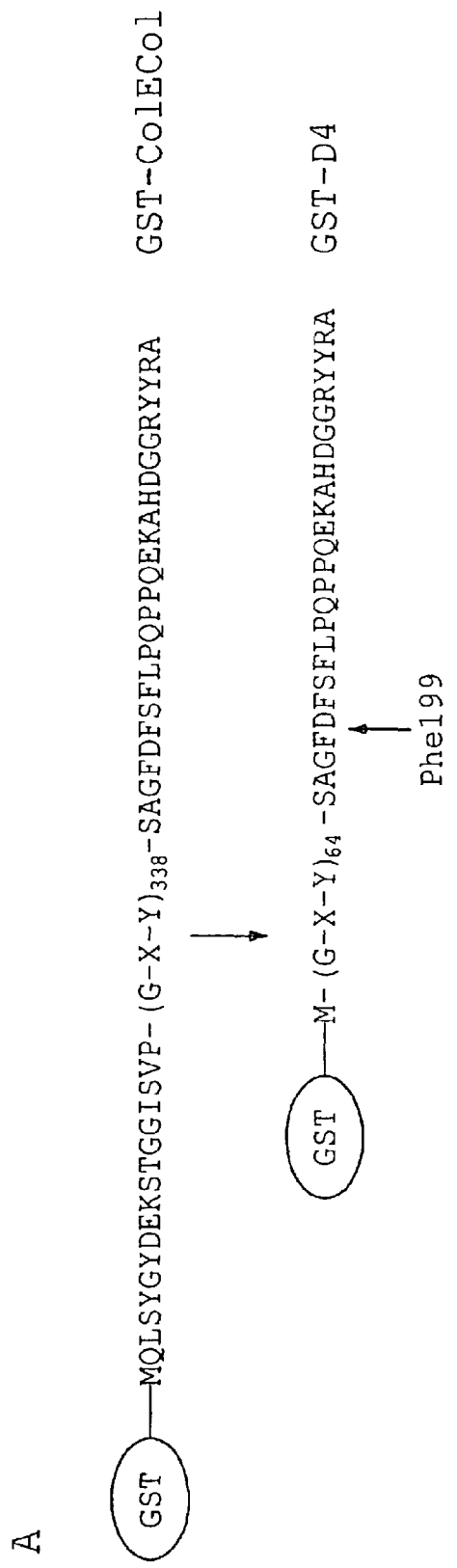
FIG. 29 is a schematic depiction of the amino acid sequence of chimeric proteins GST-ColECol (SEQ. ID. NO. 17) and GST-D4 (SEQ. ID. NO. 18).
Figure 31:
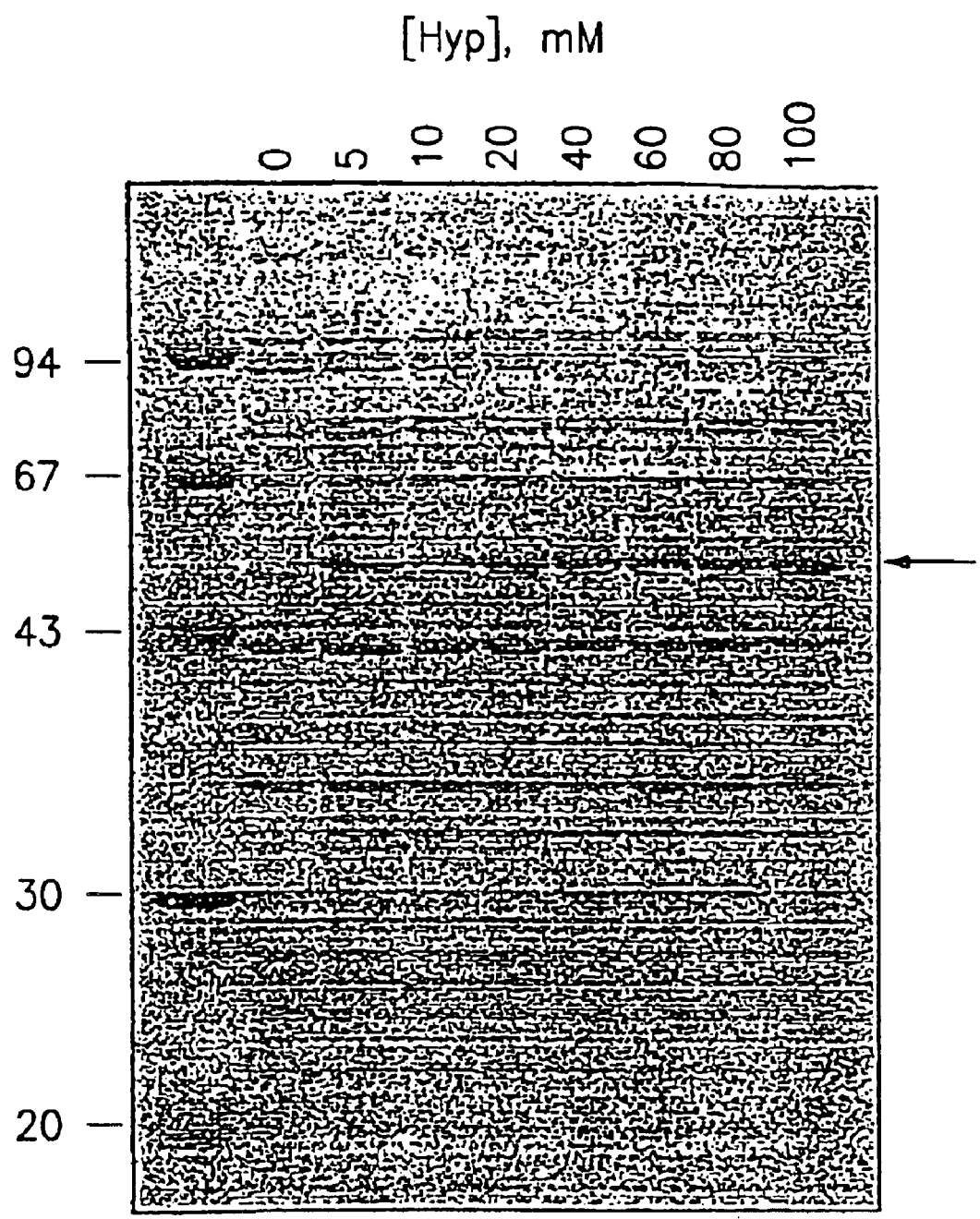
FIG. 31 depicts a gel reflecting expression and dependence of expression of GST-D4 on hydroxyproline.

A fragment of the human Type I α1 collagen chain fused to the C-terminus of glutathione S-transferase (GST-D4, FIG. 29) (SEQ. ID. NO. 18) was prepared and tested for expression in E. coli strain JM109 (F-) under conditions of hyperosmotic shock. The collagen fragment included the C-terminal 193 amino acids of the triple helical region and the 26 amino acid C-terminal telopeptide. FIG. 29 is a schematic of the amino acid sequence of the GST-ColECol (SEQ. ID. NO. 17) and GST-D4 (SEQ. ID. NO. 18) fusion proteins. ColECol comprises the 17 amino acid N-terminal telopeptide, 338 Gly-X-Y repeating tripeptides, and the 26 amino acid C-terminal telopeptide. There is a unique methionine at the junction of GST and D4, followed by 64 Gly-X-Y repeats, and the 26 amino acid telopeptide. The residue (Phe199) in the C-terminal telopeptide of D4 where pepsin cleaves is indicated. The gene was synthesized for the collagen fragment from synthetic oligonucleotides designed to reflect optimal E. coli usage. FIG. 30 is a table depicting occurrence of the four proline and four glycine codons in the human Type I α1 gene (HCol) and the Type I α1 gene with optimized E. coli codon usage (ColECol). Usage of the remaining codons in ColECol was also optimized for E. coil expression according to Wada et al., supra. Protein GST-D4 was efficiently expressed in JM109 (F-) in minimal media lacking proline but supplemented with Hyp and NaCl (See FIGS. 31 and 32). Expression was dependent on induction with isopropyl-1-thio-β-galactopyranoside (IPTG), Irans-4-hydroxyproline and NaCl. At a fixed NaCl concentration of 500 mM, expression was minimal at trans-4-hydroxyproline concentrations below −20 mM while the expression level plateaued at trans-4-hydroxyproline concentrations above 40 mM. See FIG. 31 which depicts a gel showing expression and dependence of expression of GST-D4 on hydroxyproline. The concentration of hydroxyproline is indicated above each lane. Osmolyte (NaCl) was added at 500 mM in each culture and each was induced with 1.5 mM IPTG. The arrow marks the position of GST-D4. Likewise, at a fixed trans-4-hydroxyproline concentration of 40 mM, NaCl concentrations below 300 mM resulted in little protein accumulation and expression decreased above 700–800 MM NaCl. See FIG. 32 which depicts a gel showing expression of GST-D4 in hyperosmotic media Lanes 2 and 3 are uninduced and induced samples, respectively, each without added osmolyte. The identity and quantity of osmolyte is indicated above each of the other lanes. Trans-4-Hydroxyproline was added at 4mM in each culture and all cultures except that in lane 1 were induced with 1.5 mM IPTG. The arrow marks the position of GST-D4.

Figure 32:
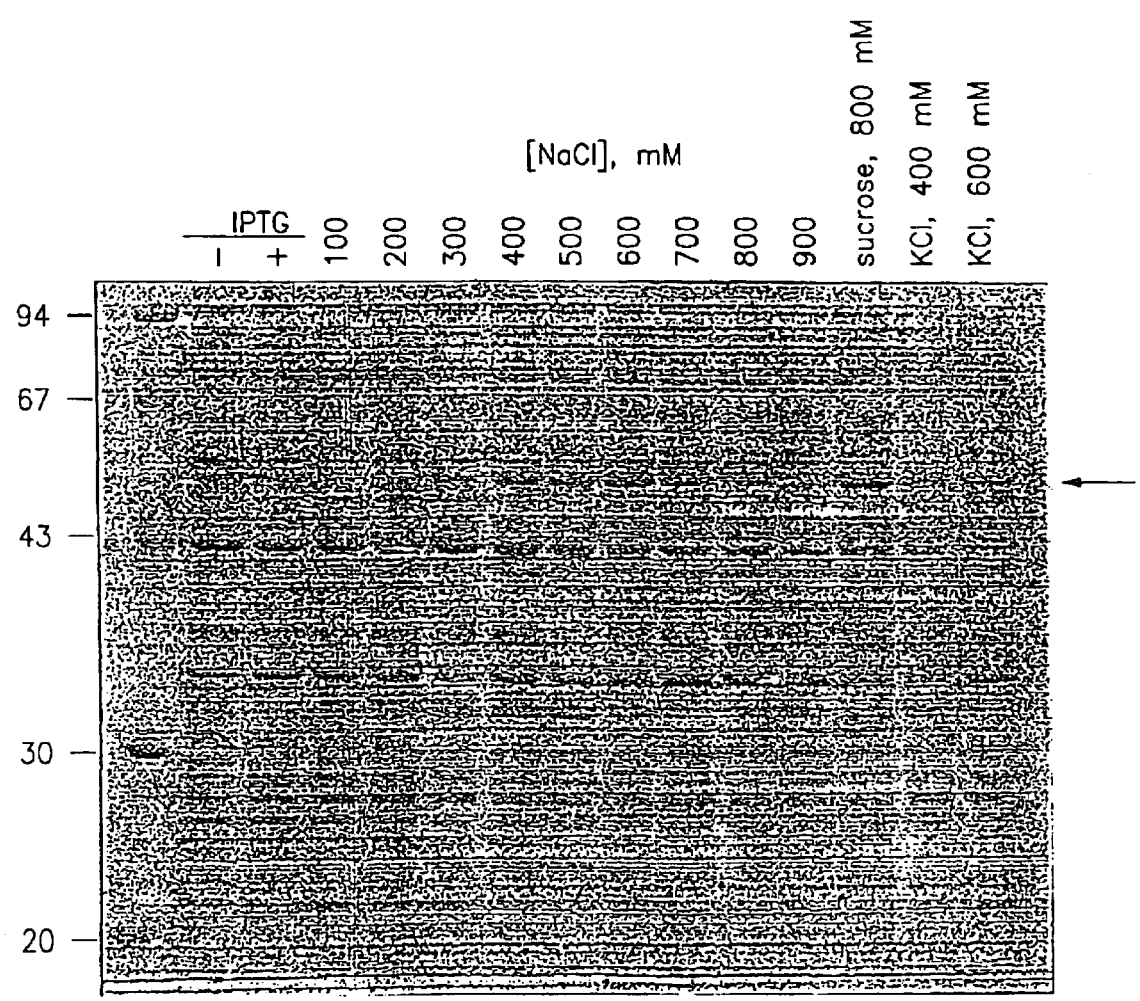
FIG. 32 depicts a gel showing expression of GST-D4 in hypertonic media.

Either sucrose or KCI can be substituted for NaCl as the osmolyte (See FIG. 32). Thus, the osmotic shock-mediated intracellular accumulation of trans-4-hydroxyproline was a critical determinant of expression rather than the precise chemical identity of the osmolyte. Despite the large number of prolines (66) in GST-D4, its size (46 kDA), and non-optimal growth conditions, it was expressed at ~10% of the total cellular protein. Expressed proteins of less than full-length indicative of aborted transcription, translation, or mRNA instability were not detected.

The gene for protein D4 contains 52 proline codons. In the expression experiments reflected in FIGS. 31 and 32, it was expected that trans-4-hydroxyproline would be inserted at each of these codons resulting in a protein where trans-4-hydroxyproline had been substituted for all prolines. To confirm this, GST-D4 was cleaved with BrCN in 0.1 N HCl at methionines within GST and at the unique methionine at the N-terminal end of D4, and D4 purified by reverse phase HPLC. Crude GST-D4 was dissolved in 0.1 M HCl in a round bottom flask with stirring. Following addition of a 2–10 fold molar excess of clear, crystalline BrCN, the flask was evacuated and filled with nitrogen. Cleavage was allowed to proceed for 24 hours, at which time the solvent was removed in vacuo. The residue was dissolved in 0.1% trifluoroacetic acid (TFA) and purified by reverse-phase HPLC using a Vydac C4 RP-HPLC column (10×250 mm, 5μ, 300 Å) on a BioCad Sprint system (perceptive Biosystems, Framingham, Mass.). D4 was eluted with a gradient of 15 to 40% acetonitrile/0.1% TFA over a 45 min. period. D4 eluted as a single peak at 26% acetonitrile/0.1% TFA Standard BrCN cleavage conditions (70% formic acid) resulted in extensive formylation of D4, presumably at the hydroxyl groups of the trans-4-hydroxyproline residues. Formylation of BrCN/formic acid-cleaved proteins had been noted before (Beavis et al., Anal. Chem., 62, 1836 (1990)). Amino acid analysis was carried out on a Beckman ion exchange instrument with post-column derivatization. N-terminal sequencing was performed on an Applied Biosystems sequencer equipped with an on-line HLPC system. Electrospray mass spectra were obtained with a VG Biotech BIO-Q quadropole analyzer by M-Scan, Inc. (West Chester, Pa.). For CD thermal melts, the temperature was raised in 0.5° C. increments from 4° C. to 85° C. with a four minute equilibration between steps. Data were recorded at 221.5 nm. The thermal transition was calculated using the program ThermoDyne (MORE). The electrospray mass spectroscopy of this protein gave a single molecular ion corresponding to a mass of 20,807 Da This mass is within 0.05% of that expected for D4 if it contains 100% trans-4-hydroxyproline in lieu of proline. Proline was not detected in amino acid analysis of purified D4, again consistent with complete substitution of trans-4-hydroxyproline for proline. To confirm further that trans-4-hydroxyproline substitution had only occurred at proline codons, the N-termninal 13 amino acids of D4 was sequenced as above. The first 13 codons of D4 specify the protein sequence $H_2$N-Gly-Pro-Pro-Gly-Leu-Ala-Gly-Pro-Pro-Gly-Glu-Ser-Gly (SEQ. ID. NO. 41). The sequence found was $H_2$N-Gly-Hyp-Hyp-Gly-Leu-Ala-Gly-Hyp-Hyp-Gly-Glu-Ser-Gly (SEQ. ID. NO. 42), see FIG. 69. Taken together, these results indicate that trans-4-hydroxyproline (Hyp) was inserted only at proline codons and that the fidelity of the E. coli translational machinery was not otherwise altered by either the high intracellular concentration or trans-4-hydroxyproline or hyperosmotic culture conditions.

Figure 33:
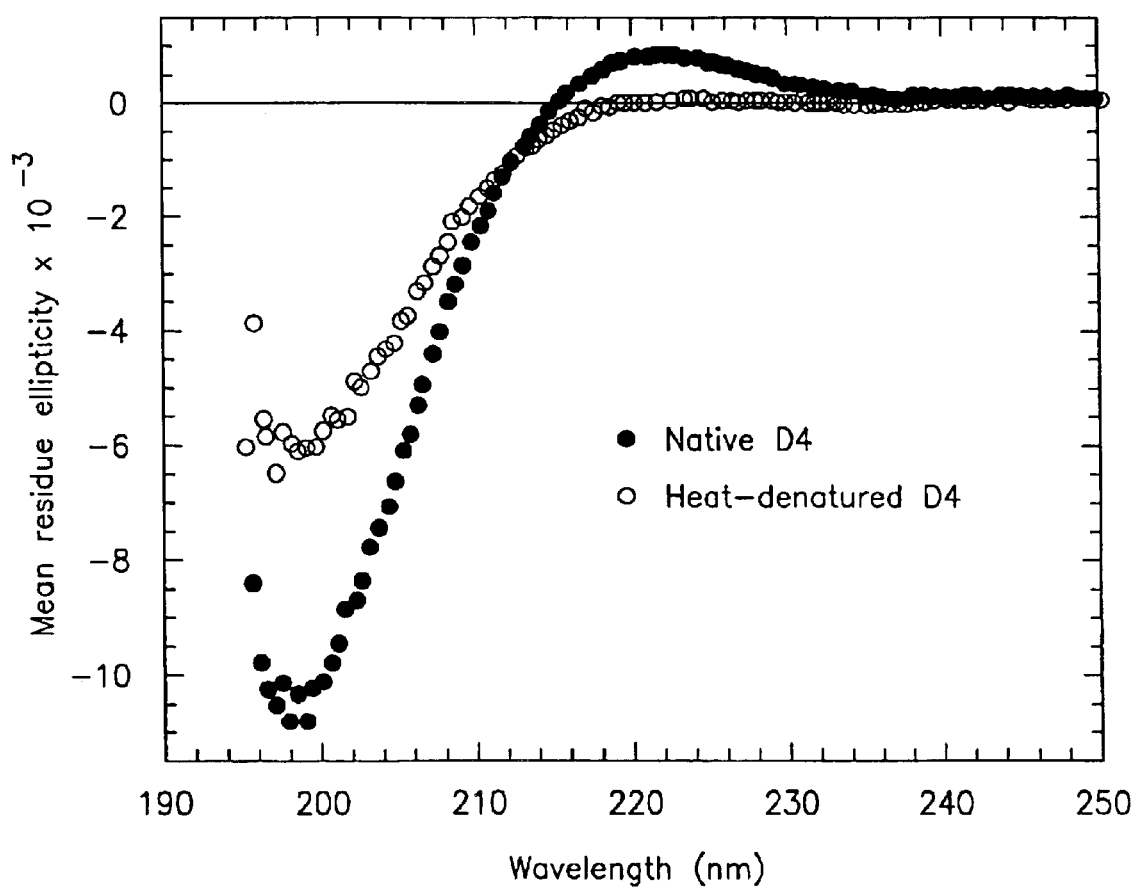
FIG. 33 is a graph showing circular dichroism spectra of native and denatured D4 in neutral phosphate buffer.

To determine whether D4, containing trans-4-hydroxyproline in both the X and Y positions, forms homotrimeric helices and to compare stability to native collagen, the following was noted: In neutral pH phosphate buffer, D4 exhibits a circular dichroism (CD) spectrum characteristic of a triple helix (See FIG. 33 and Bhatnagar et al., Circular Dichroism and the Conformational Analysis of Biomolecules, G. D. Fasman, Ed. Plenum Press, New York, (1996 p. 183). FIG. 33 illustrates circular dichroism spectra of native and heat-denatured D4 in neutral phosphate buffer. HPLC-purified D4 was dissolved in 0.1M sodium phosphate, pH 7.0, to a final concentration of 1 mg/mL ($E^{280}$=3628 $M^{-1}.cm^{-1}$). The solution was incubated at 4° C. for two days to allow triple helices to form prior to analysis. Spectra were obtained on an Aviv model 62DS spectropolarimeter (Yale University, Molecular Biophysics and Biochemistry Department). A 1 mm path length quartz suprasil fluorimeter cell was used. Following a 10 min. incubation period at 4° C., standard wavelength spectra were recorded from 260 to 190 nm using 10 sec acquisition times and 0.5 nm scan steps. This spectrum is characterized by a negative ellipticity at 198 nm and a positive ellipticity at 221 nm. The magnitudes of both of these absorbances was greater in neutral pH buffer compared to acidic conditions. Comparable dependence of stability on pH has been noted for collagen-like triple helices. See, e.g., Venugopal et al., Biochemistry, 33, 7948 (1994). Heating at 85° C. for five minutes prior to obtaining the CD spectrum decreased the magnitude of the absorbance at 198 nm and abolished the absorbance at 221 mn (FIG. 33). This behavior is also typical of the triple helical structure of collagen. See, R. S. Bhatnagar et al., *Circular Dichroism and the Conformational Analysis of biomolecules* G. D. Fasman, Ed., supra. A thermal melt profile of D4 conducted as above in phosphate buffer gave a melting temperature of about 29° C. A fragment of the C-terminal region of the bovine Type I α1 collagen chain comparable in length to D4 forms homotrimeric helices with a melting temperature of 26° C. (See, A. Rossi, et al., *Biochemistry* 35, 6048 (1996)).

Figure 34:
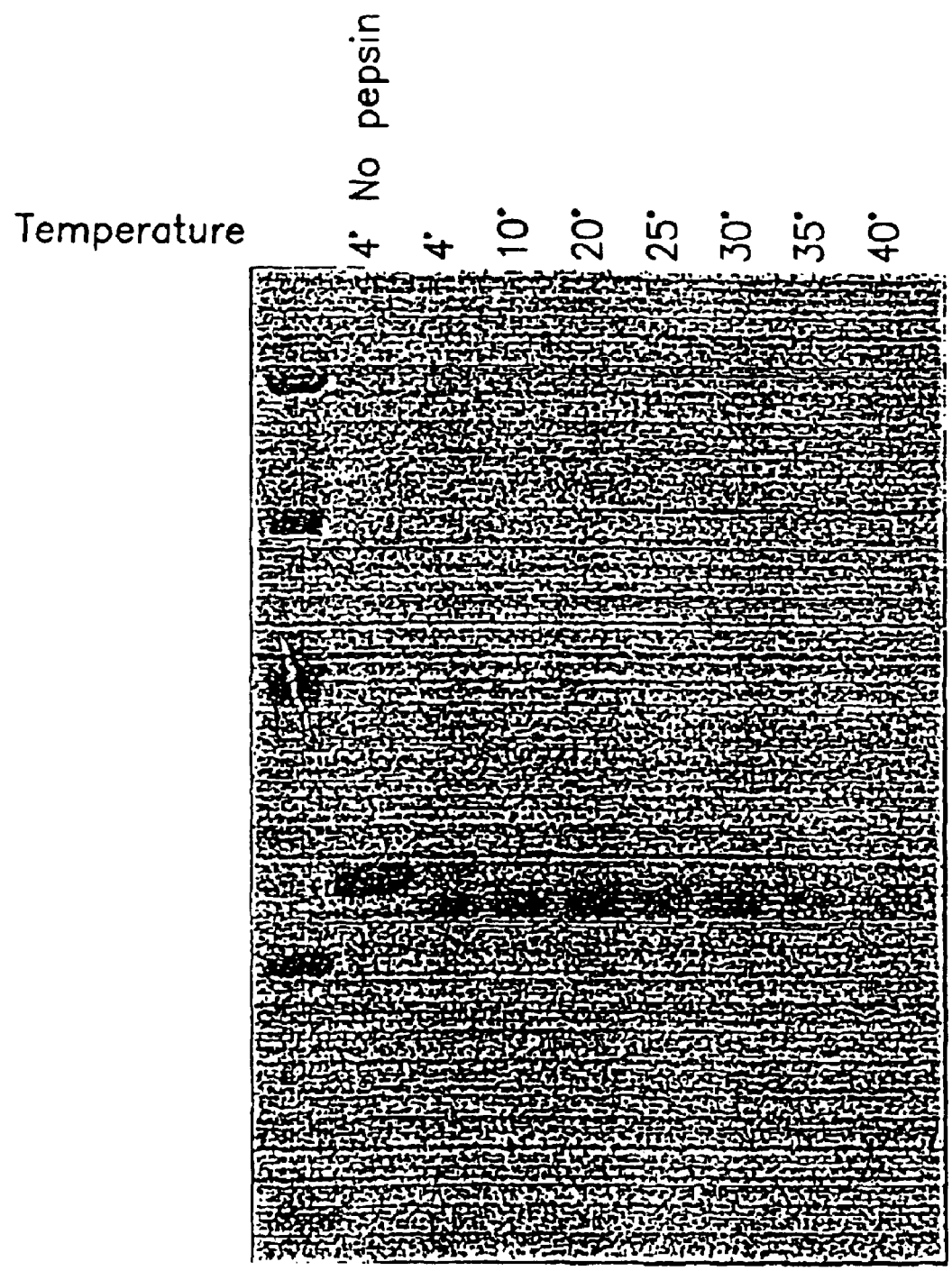
FIG. 34 depicts a gel representing digestion of D4 with bovine pepsin.

Resistance to pepsin digestion is a second commonly used indication of triple helical structure. At 4° C., the majority of D4 is digested rapidly by pepsin to a protein of slightly lower molecular weight. FIG. 34 is a gel illustrating the result of digestion of D4 with bovine pepsin. Purified D4 was dissolved in 0.1 M sodium phosphate, pH 7.0, to 1.6 µg/µl and incubated at 4° C. for 7 days. Aliquots (10 µl) were placed into 1.5 ml centrifuge tubes and adjusted with water and 1 M acetic acid solutions to 25 µl final volume and 200 mM final acetic acid concentration. Each tube was then incubated for 20 min. at the indicated temperature and pepsin (0.5 µl of a 0.25 µg/µl solution) was added to each tube and digestion allowed to proceed for 45 minutes. Following digestion, samples were quenched with loading buffer and analyzed by SDS-PAGE. However, the initial pepsin cleavage product is resistant to further digestion up to ~30° C. Amino terminal sequencing as above of the initial pepsin cleavage product showed that the N-terminus was identical to that of full-length D4. Mass spectral analysis as above of the digestion product gave a parent ion with a molecular weight consistent with cleavage in the C-terminal telopeptide on the N-terminal side of Phe119 (See FIG. 29) suggesting that this portion of the protein is either globular or of ill-defined structure and rapidly cleaved by pepsin while the triple helical region is resistant to digestion. Thus, despite global trans-4-hydroxyproline for proline substitution in both the X and Y positions, D4 formed triple helices of stability similar to comparably sized fragments of bovine collagen containing Hyp at the normal percentage and only in the Y position.

Figure 35:
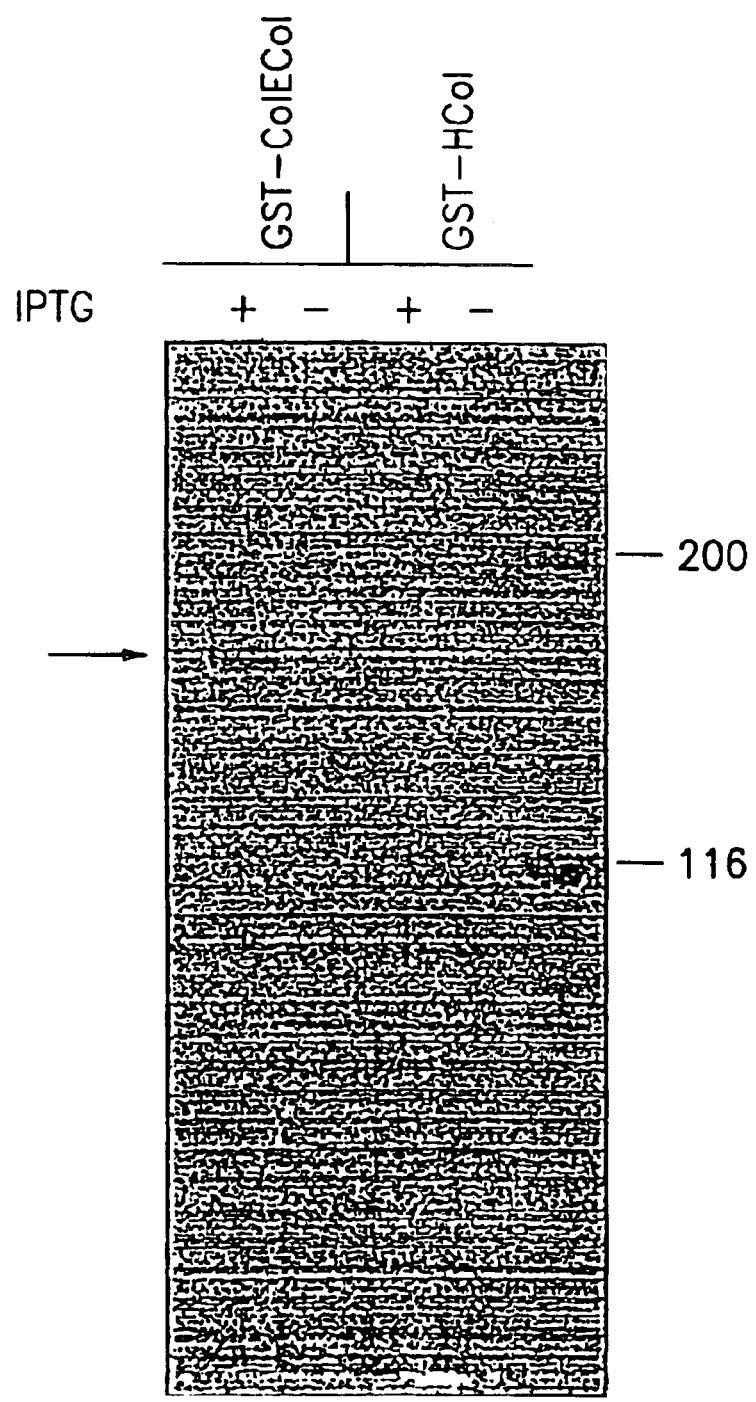
FIG. 35 depicts a gel representing expression of GST-H Col and GST-ColECol under specified conditions.

The full-length human Type I α1 collagen chain, although more than four times the size of D4, also expressed as a N-terminal fusion with GST (GST-ColECol, FIG. 29) in JM109(F-) in Hyp/NaCl media FIG. 35 is a gel depicting expression of GST-HCol and GST-ColECol. Trans-4-hydroxyproline was added at 40 mM and NaCl at 500 mM. Expression was induced with 1.5 mM IPTG. The arrow marks the position of GST-ColECol. In the procedures resulting in the gels shown in FIGS. 31, 32 and 35, five ml cultures of JM109 (F-) harboring the expression plasmid in LB media containing 100 µg/ml ampicillin were grown overnight. Cultures were centrifuged and the cell pellets washed twice with five ml of M9/Amp media (See, J. Sambrook, E. F. Fritsch, T. Maniatis, *Molecular Cloning: A Laboratory Manual.* (Cold Spring Harbor Laboratory, Cold Spring Harbor, N.Y., 1989)) supplemented with 0.5% glucose and 100 µg/ml of all amino acids except glycine and alanine which were at 200 µg/ml and containing no proline. The cells were finally resuspended in five ml of the above media. Following incubation at 37° C. for 30 min., hydroxyproline, osmolyte, or IPTG were added as indicated. After four hours, aliquots of the cultures were analyzed by SDS-PAGE.

Like D4, the gene for protein ColECol was constructed from synthetic oligonucleotides designed to mimic codon usage in highly-expressed *E. coli* genes. In contrast to GST-ColECol, expression from a GST-human Type I α1 gene fusion (pHCol) identical to GST-ColECol in coded amino acid sequence but containing the human codon distribution could not be detected in Coomassie blue-stained SDS-PAGE gels of total cell lysates of induced JM109 (F-)/pHCol cultures (FIG. 35). The gene for the Type I α1 collagen polypeptide was cloned by polymerase chain reaction of the gene from MRNA isolated from human foreskin cells (HS27, ATCC 1634) with primers designed from the published gene sequence (GenBank Z74615). The 5' primer added a flanking EcoR I recognition site and the 3' primer a flanking Hind III recognition site. The gene was cloned into the EcoR I/Hind III site of plasmid pBSKS⁺ (Stratagene, La Jolla, Calif.), four mutations corrected using the ExSite mutagenesis kit (Stratagene, La Jolla, Calif.), the sequence confirmed by dideoxy sequencing, and finally the EcoR I/Xho I fragment subcloned into plasmid pGEX-4T.1 (Pharmacia, Piscataway, N.J.). The GST-HCol gene is expression-competent because a protein of the same molecular weight as GST-ColECol is detected when immunoblots of total cell lysates are probed with an anti-Type I collagen antibody. Thus, sequence or structural differences between the genes for ColECol and HCol are critical determinants of expression efficiency in *E. coli*. This is likely due to the codon distribution in these genes and ultimately to differences in tRNA isoacceptor levels in *E. coli* compared to humans. GST-ColECol, GST-D4, and GST-HCol do not accumulate in hyperosmotic shock media when proline is substituted for hydroxyproline or in rich media. A possible explanation is that the trans-4-hydroxyproline-containing proteins may be resistant to degradation because they fold into a protease-resistant triple helix while the proline-containing proteins do not adopt this structure. The large number of codons non-optimal for *E. coli* found in the human gene and the instability of proline-containing collagen in *E. coli* may, in part, explain why expression of human collagen in *E. coli* has not been previously reported.

As discussed above, collagen mimetic polypeptides, i.e., engineered polypeptides having certain compositional and structural traits in common with collagen are also provided herein. Such collagen mimetic polypeptides may also be made to incorporate amino acid analogs as described above. GST-CM4 consists of glutathione S-transferase fused to 30 repeats of a Gly-X-Y sequence. The Gly-X-Y repeating section mimics the Gly-X-Y repeating unit of human collagen and is referred to as collagen mimetic 4 or CM4 herein. Thus, the hydroxyproline-incorporating technology was also demonstrated to work with a protein and DNA sequence analogous to that found in human collagen. Amino acid analysis of purified CM4 protein express in *E. coli* strain JM109 (F-) under hydroxyproline-incorporating conditions compared to analysis of the same protein expressed under proline-incorporating conditions, demonstrates that the techniques herein result in essentially complete substitution of hydroxyproline for proline. The amino acid analysis was performed on CM4 protein that had been cleaved from and purified away from GST. This removes any possible ambiguities associated with the fusion protein.

Expression in media containing at least about 200 mM NaCl is preferable to accumulate significant amount of protein containing hydroxyproline. A concentration of about 400–500 mM NaCl appears to be optimal. Either KCl, sucrose or combinations thereof may be used in substitution of or with NaCl. However, expression in media without an added osmolyte (i.e. under conditions that more closely mimic those of Deming et al., In Vivo Incorporation of Proline Analogs into Artificial Protein, Poly. Mater. Sci. Engin. Proceed., supra.) did not result in significant expression of hydroxyproline-containing proteins in JM109 (F-).

Figure 36:
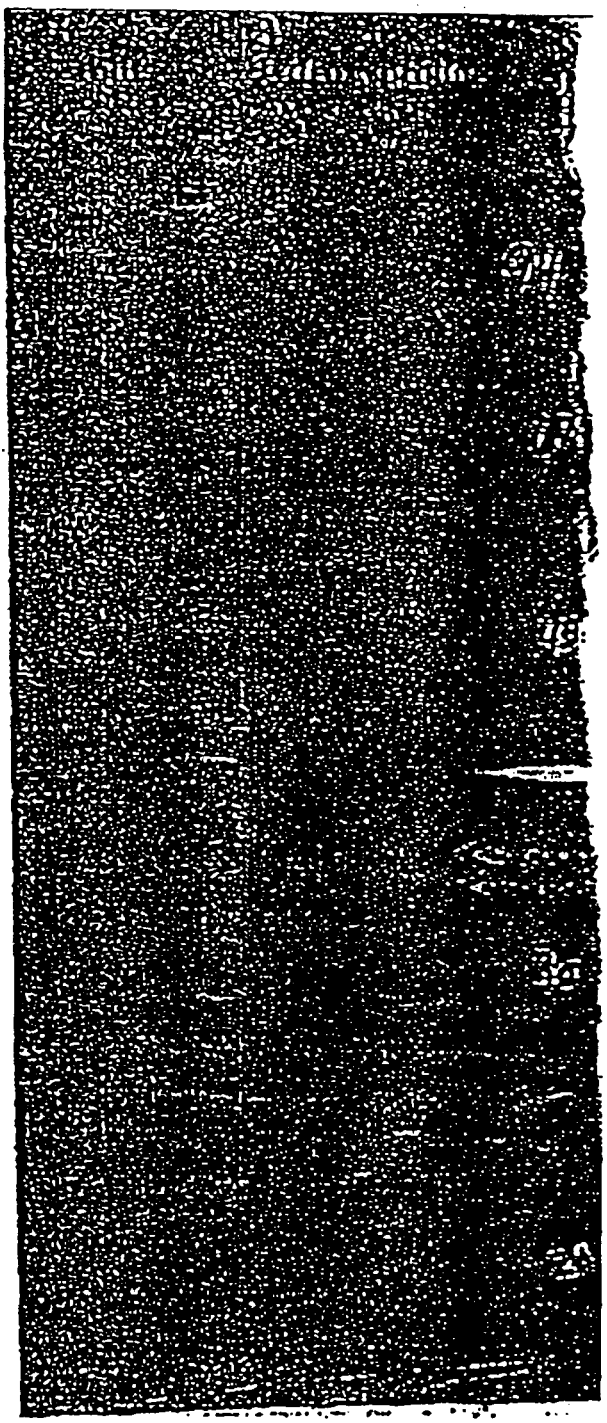
FIG. 36 depicts a gel representing expression of GST-CM4 in media with or without NaCl and either proline or hydroxyproline.
Figure 37:
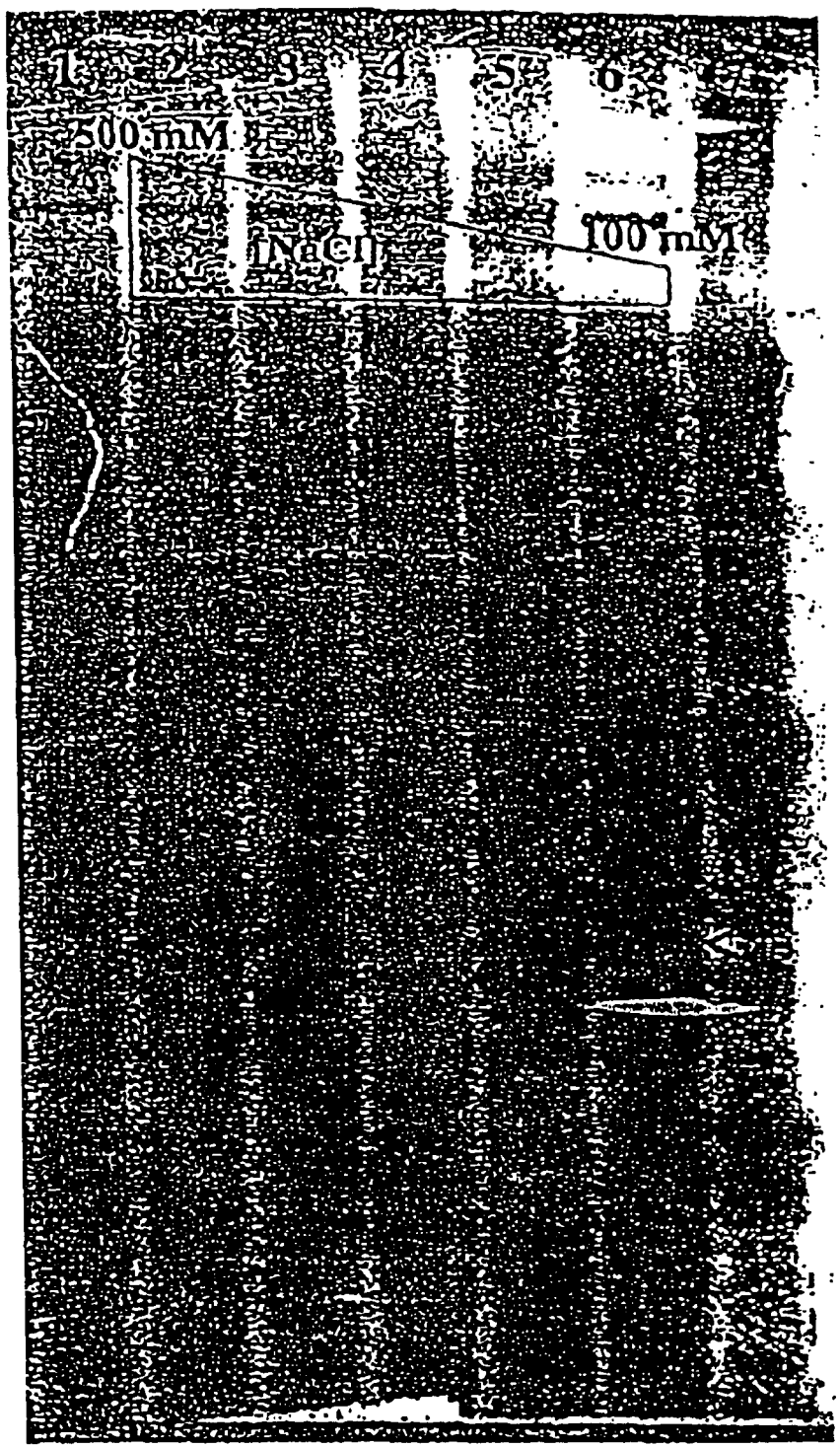
FIG. 37 depicts a gel of six hour post induction samples of GST-CM4 expressed in *E. coli* with varying concentrations of NaCl.
Figure 38:
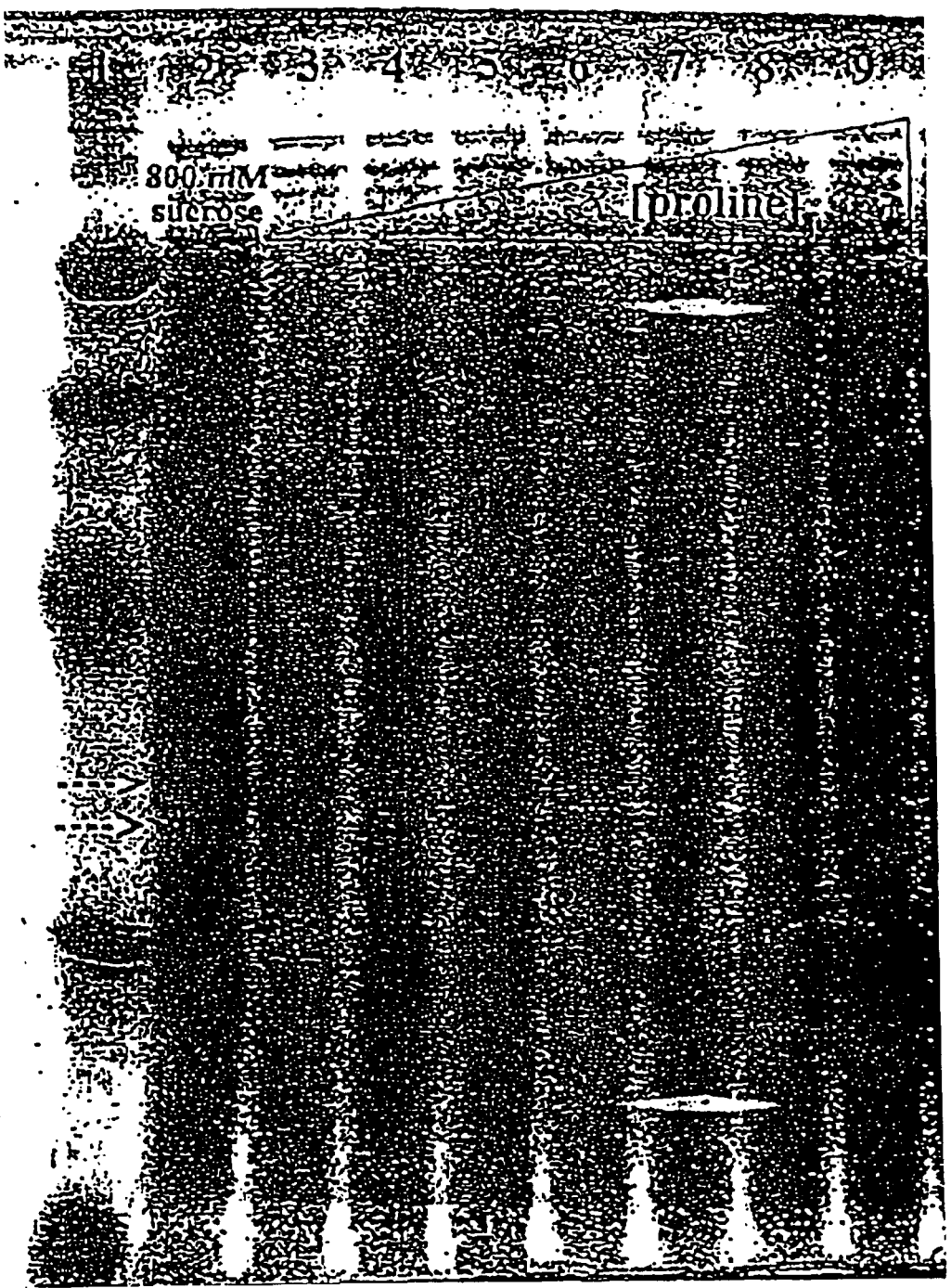
FIG. 38 depicts a gel of 4 hour post induction samples of GST-CM4 expressed in *E. coli* with constant amounts of hydroxyproline and varying amounts of proline.

This is illustrated in FIG. 36 which is a scan of a SDS-PAGE gel showing the expression of GST-CM4 in media with or without 500 mM NaCl and containing either proline or hydroxyproline. The SDS-PAGE gel reflects 5 hour post-induction samples of GST-CM4 expressed in JM109 (F-). Equivalent amounts, based on OD600 nm, of each culture were loaded in each lane. Gels were stained with Coomasie Blue, destained, and scanned on a PDI 420 oe scanner. Lane 1: 2.5 mM proline/0 mM NaCl. Lane 2: 2.5 mM proline/500 mM NaCl. Lane 3: 80 mM hydroxyproline/0 mM NaCl. Lane 4: 80 mM hydroxyproline/500 mM NaCl. Lane 5: Molecular weight markers. The lower arrow indicates the migration position of proline-containing GST-CM4 in lanes 1 and 2. The upper arrow indicates the migration position of hydroxyproline-containing GST-CM4 in lanes 3 and 4. Note that GST-CM4 expressed in the presence of hydroxyproline runs at a higher apparent molecular weight (compare lanes 1 and 4). This is expected since hydroxyproline is of greater molecular weight than proline. If all the prolines in GST-CM4 are substituted with hydroxyproline, the increase in molecular weight is 671 Da (+2%). Note also that protein expressed in the presence of proline accumulates in cultures irrespective of the NaCl concentration (compare lanes 1 and 2). In contrast, significant expression in the presence of hydroxyproline only occurs in the culture containing 500 mM NaCl (compare lanes 3 and 4). FIG. 37 further illustrates the dependence of expression on NaCl concentration by showing that significant expression of GST-CM4 occurs only at NaCl concentration greater than 200 mM. The SDS-PAGE gel reflects 6 hour post-induction samples of GST-CM4 expressed in JM109 (F-) with varying concentrations of NaCl. All cultures contained 80 mM hydroxyproline. Lane 1: 500 mM NaCl, not induced. Lanes 2–6: 500 mM, 400 mM, 300 mM, 200 mM, and 100 mM NaCl, respectively. All induced with 1.5 mM IPTG. Lane 7: Molecular weight markers. The arrow indicates the migration position of hydroxyproline-containing GST-CM4. FIG. 38 is a scan of an SDS-PAGE gel of expression of GST-CM4 in either 400 mM NaCl or 800 mM sucrose. The SDS-PAGE gel reflects 4 hour post-induction samples of GST-CM4 expressed in JM109 (F-). All cultures contained 80 mM hydroxyproline and all, except that electrophoresed in lane 2, contained 400 mM NaCl. Lane 2 demonstrates expression in sucrose in lieu of NaCl. Lane 1: Molecular weight markers. Lane 2: 800 mM sucrose (no NaCl). Lanes 3–9: 0 mM, 0.025 mM, 0.1 mM, 0.4 mM, 0.8 mM, 1.25 mM, 2.5 mM proline, respectively. The upper arrow indicates the migration position of hydroxyproline-containing GST-CM4 and the lower arrow indicates the migration position of proline-containing GST-CM4. Expression is apparent in both cases (compare lanes 2 and 3).

If expression of GST-CM4, as described in Example 17 below, is performed in varying ratios of hydroxyproline and proline the expressed protein appears to contain varying amounts of hydroxyproline. Thus, if only hydroxyproline is present during expression, a single expressed protein of the expected molecular weight is evident on a SDS-PAGE gel (FIG. 38, lane 3). If greater than approximately 1 mM proline is present, again a single expressed protein is evident, but at a lower apparent molecular weight, as expected for the protein containing only proline (FIG. 38, lanes 7–9). If lesser amount of proline are used during expression, species of apparent molecular weight intermediate between these extremes are evident. This phenomenon, evident as a "smear" or "ladder" of proteins running between the two molecular weight extremes on an SDS-PAGE gel, is illustrated in lanes 3–9 of FIG. 38. Lanes 3–9 on this gel are proteins from expression in a fixed concentration of 80 mM hydroxyproline and 400 mM NaCl. However, in moving from lane 3 to 9 the proline concentration increases from none (lane 3) to 2.5 mM (lane 9) and expression shifts from a protein of higher molecular weight (hydroxyproline-containing GST-CM4) to lower molecular weight (proline-containing GST-CM4). At proline concentrations of 0.025 mM and 0.1 mM, species of intermediate molecular weight are apparent (lanes 4 and 5). This clearly demonstrates that the percent incorporation of hydroxyproline in an expressed protein can be controlled by expression in varying ratios of analogue to amino acid.

Proline starvation prior to hydroxyproline incorporation is an important technique used herein. It insures that no residual proline is present during expression to compete with hydroxyproline. This enables essentially 100% substitution with the analogue. As shown in FIG. 38, starvation conditions allow expression under precisely controlled ratios of proline and hydroxyproline. The amount of hydroxyproline vs. proline incorporated into the recombinant protein can therefore be controlled. Thus, particular properties of the recombinant protein that depend upon the relative amount of analogue incorporated can be tailored by the present methodology to produce polypeptides with unique and beneficial properties.

Human collagen, collagen fragments, collagen-like peptides (collagen mimetics) and the above chimeric polypeptides produced by recombinant processes have distinct advantages over collagen and its derivatives obtained from non-human aninals. Since the human gene is used, the collagen will not act as a xenograft in the context of a medical implant Moreover, unlike naturally occurring collagen, the extent of proline hydroxylation can be predetermined. This unprecedented degree of control permits detailed investigation of the contribution of trans-4-hydroxyproline to triple helix stabilization, fibril formation and biological activity. In addition, design of medical implants based upon the desired strength of collagen fibrils is enabled.

The following examples are included for purposes of illustration and are not to be construed as limitations herein.

EXAMPLE 1

Trans-membrane Transport

A 5 mL culture of *E. coli* strain DH5α (supE44 ΔlacU169 (φ80lacZ ΔM15) hsdR17 recA1 endA1 gryA96 thi-1 relA1) containing a plasmid conferring resistance to ampicillin (pMAL-c2, FIG. 1) was grown in Luria Broth to confluency (~16 hours from inoculation). These cells were used to inoculate a 1 L shaker flask containing 500 mL of M9 minimal medium (M9 salts, 2% glucose, 0.01 mg/mL thiamine, 100 µg/mL ampicillin supplemented with all amino acids at 20 µg/mL) which was grown to an $AU_{600}$ of 1.0 (18–20 hours). The culture was divided in half and the cells harvested by centrifugation. The cells from one culture, were resuspended in 250 mL M9 media and those from the other in 250 mL of M9 media containing 0.5M NaCl. The cultures were equilibrated in an air shaker for 20 minutes at 37° C. (225 rpm) and divided into ten 25 mL aliquots. The cultures were returned to the shaker and 125 µl of 1 M hydroxyproline in distilled $H_2O$ was added to each tube. At 2, 4, 8, 12, and 20 minutes, 4 culture tubes (2 isotonic, 2 hypertonic) were vacuum filtered onto 1 µm polycarbonate filters that were immediately placed into 2 mL microfuge tubes containing 1.2 mL of 0.2M NaOH/2% SDS in distilled H₂O. After overnight lysis, the filters were carefully removed from the tubes, and the supernatant buffer was assayed for hydroxyproline according to the method of Grant, Journal of Clinical Pathology, 17:685 (1964). The intracellular concentration of trans-4-hydroxyproline versus time is illustrated graphically in FIG. 2.

EXAMPLE 2

Effects of Salt Concentration on Transmembrane Transport

To determine the effects of salt concentration on transmembrane transport, an approach similar to Example 1 was taken. A 5 mL culture of E. coli strain DH5 α1 (supE44 ΔlacU169 (φ80lacZ ΔM15) hsdR17 recA1 ental gyrA96 thi-1 relA1) containing a plasmid conferring resistance to ampicillin (pMAL-c2, FIG. 1) was grown in Luria Broth to confluency (~16 hours from inoculation). These cells were used to inoculate a 1 L shaker flask containing 500 mL of M9 minimal medium (M9 salts, 2% glucose, 0.01 mg/mL thiamine, 100 μg/mL ampicillin supplemented with all amino acids at 20 μg/mL) that was then grown to an $AU_{600}$ of 0.6. The culture was divided into three equal parts, the cells in each collected by centrifugation and resuspended in 150 mL M9 media, 150 mL M9 media containing 0.5M NaCl, and 150 mL M9 media containing 1.0 M NaCl, respectively. The cultures were equilibrated for 20 minutes on a shaker at 37° C. (225 rpm) and then divided into six 25 mL aliquots. The cultures were returned to the shaker and 125 μL of 1 M hydroxyproline in distilled H₂O was added to each tube. At 5 and 15 minutes, 9 culture tubes (3 isotonic, 3×0.5M NaCl, and 3×1.0M NaCl) were vacuum filtered onto 1 μm polycarbonate filters that were immediately placed into 2 mL microfuge tubes containing 1.2 mL of 0.2M NaOH/2% SDS in distilled H₂O. After overnight lysis, the filters were removed from the tubes and the supernatant buffer assayed for hydroxyproline according to the method of Grant, supra.

EXAMPLE 2A

Effects of Salt Concentration on Transmembrane Transport

Figure 48:
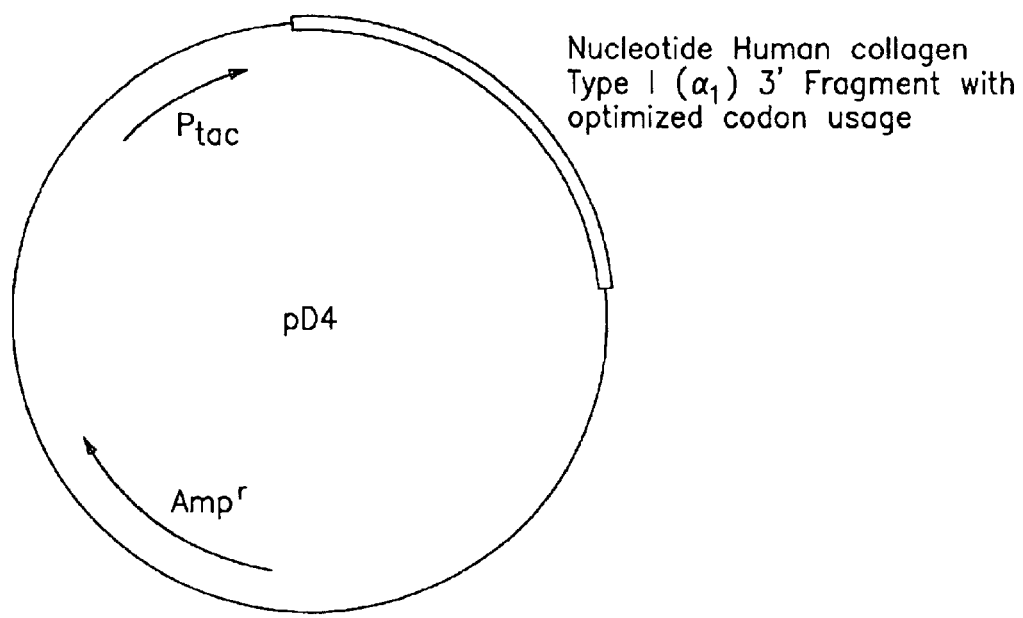
FIG. 48 depicts a plasmid map of pD4 containing a 657 nucleotide human collagen Type I ($α_1$) 3' fragment with optimized *E. coli* codon usage.

To determine the effects of salt concentration on transmembrane transport, an approach similar to Example 1 was taken. A saturated culture of JM109 (F-) harboring plasmid pD4 (FIG. 48) growing in Luria Broth (LB) containing 100 μg/ml ampicillin (Amp) was used to inoculate 20 ml cultures of LB/Amp to an OD at 600 nm of 0.1 AU. The cultures were grown with shaking at 37° C. to an OD 600 nm between 0.7 and 1.0 AU. Cells were collected by centrifugation and washed with 10 ml of M9 media. Each cell pellet was resuspended in 20 ml of M9/Amp media supplemented with 0.5% glucose and 100 μg/ml of all of the amino acids except proline. Cultures were grown at 37° C. for 30 min. to deplete endogenous proline. After out-growth, NaCl was added to the indicated concentration, Hyp was added to 40 mM, and IPTG to 1.5 mM. After 3 hours at 37° C., cells from three 5 ml aliquots of each culture were collected separately on polycarbonate filters and washed twice with five ml of M9 media containing 0.5% glucose and the appropriate concentration of NaCl. Cells were lysed in 1 ml of 70% ethanol by vortexing for 30 min. at room temperature. Cell lysis supernatants were taken to dryness, resuspended in 100 μl of 2.5 N NaOH, and assayed for Hyp by the method of Neurnan and Logan, R. E. Neuman and M. A. Logan, Journal of Biological Chernistry, 184:299 (1950). Total protein was determined with the BCA kit (Pierce, Rockford II) after cell lysis by three sonication/freeze-thaw cycles. The data are the mean ± standard error of three separate experirnents. The intracellular concentration of trans-4-hydroxyproline versus NaCl concentration is illustrated graphically in FIG. 2A.

EXAMPLE 3

Determination Of Proline Starvation Conditions in E. coli

Proline auxotrophic E. coli strain NM519 (pro⁻) including plasmid pMAL-c2 which confers ampicillin resistance was grown in M9 minimal medium (M9 salts, 2% glucose, 0.01 mg/ML thiamine, 100 μg mL ampicillin supplemented with all amino acids at 20 μg/mL except proline which was supplemented at 12.5 mg/L) to a constant $AU_{600}$ of 0.53 AU (17 hours post-inoculation). Hydroxyproline was added to 0.08M and hydroxyproline-dependent growth was demonstrated by the increase in the $OD_{600}$ to 0.61 AU over a one hour period.

EXAMPLE 4

Hydroxyproline Incorporation Into Protein in E. coli Under Proline Starvation Conditions Plasmid pMAL-c2 (commercially available from New England Biolabs) containing DNA encoding for maltose-binding protein (MBP) was used to transform proline auxotrophic E. coli strain NM519 (pro⁻). Two 1 L cultures of transformed NM519 (pro⁻) in M9 minimal medium (M9 salts, 2% glucose, 0.01 mg/mL thiamine, 100 μg/mL ampicillin supplemented with all amino acids at 20 μg/mL except proline which was supplemented at 12.5 mg/L) were grown to an $AU_{600}$ Of 0.53 (~17 hours post-inoculation). The cells were harvested by centrifugation, the media in one culture was replaced with an equal volume of M9 media containing 0.08M hydroxyproline and the media in the second culture was replaced with an equal volume of M9 media containing 0.8M hydroxyproline and 0.5M NaCl. After a one hour equilibration, the cultures were induced with 1 mM isopropyl-β-D-thiogalactopyranoside. After growing for an additional 3.25 hours, cells were harvested by centrifugation, resuspended in 10 mL of 10 mM Tris-HCl (pH 8), 1 mM EDTA, 100 mM NaCl (TEN buffer), and lysed by freezing and sonication. MBP was purified by passing the lysates over 4 mL amylose resin spin columns, washing the columns with 10 mL of TEN buffer, followed by elution of bound MBP with 2 mL of TEN buffer containing 10 mM maltose. Eluted samples were sealed in ampules under nitrogen with an equal volume of concentrated HCl (11.7 M) and hydrolysed for 12 hours at 120° C. After clarification with activated charcoal, hydroxyproline content in the samples was determined by HPLC and the method of Grant, supra. The percent incorporation of trans-4-hydroxyproline compared to proline into MBP is shown graphically in FIG. 12.

EXAMPLE 5

Hydroxyproline Incorporation Into Protein in S. cerevisiae via Integrating Vectors Under Proline Starvation Conditions The procedure described in Example 4 above is performed in yeast using an integrating vector which disrupts the proline biosynthetic pathway. A gene encoding human Type 1 (α₁) collagen is inserted into a unique shuttle vector behind the inducible GAL10 promoter. This promoter/gene cassette is flanked by a 5' and 3' terminal sequence derived from a *S. cerevisiae* proline synthetase gene. The plasmid is linearized by restriction digestion in both the 5' and 3' terminal regions and used to transform a proline-prototrophic *S. cerevisiae* strain. The transformation mixture is plated onto selectable media and transformants are selected. By homologous recombination and gene disruption, the construct simultaneously forms a stable integration and converts the *S. cerevisiae* strain into a proline auxotroph. A single transfotmant is selected and grown at 30° C. in YPD media to an $OD_{600}$ of 2 AU. The culture is centrifuged and the cells resuspended in yeast dropout media supplemented with all amino acids except proline and grown to a constant $OD_{600}$ indicating proline starvation conditions. 0.08M L-hydroxyproline and 2% (w/v) galactose is then added. Cultures are grown for an additional 6–48 hours. Cells are harvested by centrifugation (5000 rpm, 10 minutes) and lysed by mechanical disruption. Hydroxyproline-containing human Type 1 ($\alpha_1$) collagen is purified by ammonium sulfate fractionation and column chromatography.

EXAMPLE 6

Hydroxyproline Incorporation Into Protein in *S. cerevisiae* via Non-Integrating Vectors Under Proline Starvation Conditions The procedure described above in Example 4 is performed in a yeast proline auxotroph using a non-integrating vector. A gene encoding human Type 1 ($\alpha_1$) collagen is inserted behind the inducible GAL10 promoter in the YEp24 shuttle vector that contains the selectable $Ura^+$ marker. The resulting plasmid is transformed into proline auxotrophic *S. cerevisiae* by spheroplast transformation. The transformation mixture is plated on selectable media and transformants are selected. A single transformant is grown at 30° C. in YPD media to an $OD_{600}$ of 2 AU. The culture is centrifuged and the cells resuspended in yeast dropout media supplemented with all amino acids except proline and grown to a constant $OD_{600}$ indicating proline starvation conditions. 0.08M L-hydroxyproline and 2% (w/v) galactose is then added. Cultures are grown for an additional 6–48 hours. Cells are harvested by centrifugation (5000 rpm, 10 minutes) and lysed by mechanical disruption. Hydroxyproline-containing human Type 1 ($\alpha_1$) collagen is purified by ammonium sulfate fractionation and column chromatography.

EXAMPLE 7

Hydroxyproline Incorporation Into Protein in a Baculovirus Expression System

A gene encoding human Type 1 ($\alpha_1$) collagen is inserted into the pBacPAK8 baculovirus expression vector behind the AcMNPV polyhedron promoter. This construct is co-transfected into SF9 cells along with linearized AcMNPV DNA by standard calcium phosphate co-precipitation. Transfectants are cultured for 4 days at 27° C. in TNM-FH media supplemented with 10% FBS. The media is harvested and recombinant virus particles are isolated by a plaque assay. Recombinant virus is used to infect 1 liter of SF9 cells growing in Grace's media minus proline supplemented with 10% FBS and 0.08M hydroxyproline. After growth at 27° C. for 2–10 days, cells are harvested by centrifugation and lysed by mechanical disruption. Hdroxyproline-containing human Type 1 ($\alpha_1$) collagen is purified by ammonium sulfate fractionation and column chromatography.

EXAMPLE 8

Hydroxyproline Incorporation Into Human Collagen Protein in *Escherichia coli* Under Proline Starvation Conditions A plasmid (pHuCol, FIG. 4) encoding the gene sequence of human Type I ($\alpha_1$) collagen (FIGS. 3A and 3B) (SEQ. ID. NO. 1) placed behind the isopropyl-$\beta$-D-thiogalactopyranoside (IPTG)-inducible tac promotor and also encoding $\beta$-lactamase is transformed into *Escherichia coli* proline auxotrophic strain NM519 (pro⁻) by standard heat shock transformation. Transformation cultures are plated on Luria Broth (LB) containing 100 µg/ml ampicillin and after overnight growth a single ampicillin-resistant colony is used to inoculate 5 ml of LB containing 100 µg/ml ampicillin. After growth for 10–16 hours with shaking (225 rpm) at 37° C., this culture is used to inoculate 1 L of M9 minimal medium (M9 salts, 2% glucose, 0.01 mg/mL thiamine, 100 µg/ML ampicillin, supplemented with all amino acids at 20 µg/mL except proline which is supplemented at 12.5 mg/L) in a 1.5 L shaker flask. After growth at 37° C., 225 rpm, for 15–20 hours post-inoculation, the optical density at 600 nm is constant at approximately 0.5 OD/mL. The cells are harvested by centrifugation (5000 rpm, 5 minutes), the media decanted, and the cells resuspended in 1 L of M9 minimal media containing 100 µg/mL ampicillin, 0.08M L-hydroxyproline, and 0.5M NaCl. Following growth for 1 hour at 37° C., 225 rpm, IPTG is added to 1 mM and the cultures allowed to grow for an additional 5–15 hours. Cells are harvested by centrifugation (5000 rpm, 10 minutes) and lysed by mechanical disruption. Hydroxyproline-containing collagen is purified by ammonium sulfate fractionation and column chromatography.

EXAMPLE 9

Hydroxyproline Incorporation Into Fragments of Human Collagen Protein in *Escherichia coli* Under Proline Starvation Conditions A plasmid (pHuCol-FI, FIG. 6) encoding the gene sequence of the first 80 amino acids of human Type 1 ($\alpha_1$) collagen (FIG. 5) (SEQ. ID. NO. 2) placed behind the isopropyl-$\beta$-D-thiogalactopyranoside (IPTG)-inducible tac promotor and also encoding $\beta$-lactamase is transformed into *Escherichia coli* proline auxotrophic strain NM519 (pro⁻) by standard heat shock transformation. Transformation cultures are plated on Luria Broth (LB) containing 100 µg/mL ampicillin and after overnight growth a single ampicillin-resistant colony is used to inoculate 5 mL of LB containing 100 µg/mL ampicillin. After growth for 10–16 hours with shaking (225 rpm) at 37° C., this culture is used to inoculate 1 L of M9 minimal medium (M9 salts, 2% glucose, 0.01 mg/mL thiamine, 100 µg/mL ampicillin, supplemented with all amino acids at 20 µg/mL except proline which is supplemented at 12.5 mg/L) in a 1.5 L shaker flask. After growth at 37° C., 225 rpm, for 15–20 hours post-inoculation, the optical density at 600 nm is constant at approximately 0.5 OD/mL. The cells are harvested by centrifugation (5000 rpm, 5 minutes), the media decanted, and the cells resuspended in 1 L of M9 minimal media containing 100 µg/mL ampicillin, 0.08M L-hydroxyproline, and 0.5M NaCl. Following growth for 1 hour at 37° C., 225 rpm, IPTG is added to 1 mM and the cultures allowed to grow for an additional 5–15 hours. Cells are harvested by centrifugation (5000 rpm, 10 minutes) and lysed by mechanical disruption. The hydroxyproline-containing collagen fragment is purified by ammonium sulfate fractionation and column chromatography.

EXAMPLE 10

Construction and Expression in E. coli of the Hunan Collagen Type 1 ($\alpha_1$) Gene with Optimized E. coli Codon Usage A. Construction of the gene:

The nucleotide sequence of the helical region of human collagen Type I ($\alpha_1$) gene flanked by 17 amino acids of the amino terminal extra-helical and 26 amino acids of the C-terminal extra-helical region is shown in FIG. 27 (SEQ. ID. NO. 15). A tabulation of the codon frequency of this gene is given in Table I. The gene sequence shown in FIG. 27 was first changed to reflect E. coli codon bias. An initiating methionine was inserted at the 5' end of the gene and a TAAT stop sequence at the 3' end. Unique restriction sites were identified or created approximately every 150 base pairs. The resulting gene (HuCol$^{EC}$, FIG. 39A–39E) (SEQ. ID. NO. 20) has the codon usage given in Table II as shown below. Other sequences that approximate E. coli codon bias are also acceptable.

TABLE II

| Codon | Count | % age |
|---|---|---|
| TTT-Phe | 6 | 0.56 |
| TTC-Phe | 9 | 0.85 |
| TTA-Leu | 0 | 0.00 |
| TTG-Leu | 0 | 0.00 |
| CTT-Leu | 0 | 0.00 |
| CTC-Leu | 1 | 0.08 |
| CTA-Leu | 1 | 0.08 |
| CTG-Leu | 19 | 1.79 |
| ATT-Ile | 3 | 0.28 |
| ATC-Ile | 4 | 0.37 |
| ATA-Ile | 0 | 0.00 |
| ATG-Met | 8 | 0.75 |
| GTT-Val | 3 | 0.28 |
| GTC-Val | 5 | 0.47 |
| GTA-Val | 0 | 0.00 |
| GTG-Val | 12 | 1.13 |
| TCT-Ser | 3 | 0.28 |
| TCC-Ser | 3 | 0.28 |
| TCA-Ser | 0 | 0.00 |
| TCG-Ser | 0 | 0.00 |
| CCT-Pro | 13 | 1.22 |
| CCC-Pro | 12 | 1.13 |
| CCA-Pro | 29 | 2.74 |
| CCG-Pro | 186 | 17.58 |
| ACT-Thr | 2 | 0.18 |
| ACC-Thr | 11 | 1.03 |
| ACA-Thr | 0 | 0.00 |
| ACG-Thr | 4 | 0.37 |
| GCT-Ala | 10 | 0.94 |
| GCC-Ala | 24 | 2.26 |
| GCA-Ala | 8 | 0.75 |
| GCG-Ala | 80 | 7.56 |
| TAT-Tyr | 2 | 0.18 |
| TAC-Tyr | 2 | 0.18 |
| TAA-*** | 0 | 0.00 |
| TAG-*** | 0 | 0.00 |
| CAT-His | 0 | 0.00 |
| CAC-His | 3 | 0.28 |
| CAA-Gln | 5 | 0.47 |
| CAG-Gln | 25 | 2.36 |
| AAT-Asn | 0 | 0.00 |
| AAC-Asn | 11 | 1.03 |
| AAA-Lys | 38 | 3.59 |
| AAG-Lys | 0 | 0.00 |
| GAT-Asp | 20 | 1.69 |
| GAC-Asp | 14 | 1.32 |
| GAA-Glu | 40 | 3.78 |
| GAG-Glu | 9 | 0.85 |
| TGT-Cys | 0 | 0.00 |
| TGC-Cys | 0 | 0.00 |
| TGA-*** | 0 | 0.00 |
| TGG-Trp | 0 | 0.00 |
| CGT-Arg | 26 | 2.45 |
| CGC-Arg | 26 | 2.45 |
| CGA-Arg | 0 | 0.00 |
| CGG-Arg | 1 | 0.09 |
| AGT-Ser | 1 | 0.09 |
| AGC-Ser | 32 | 3.02 |
| AGA-Arg | 0 | 0.00 |
| AGG-Arg | 0 | 0.00 |
| GGT-Gly | 148 | 13.98 |
| GGC-Gly | 178 | 16.82 |
| GGA-Gly | 9 | 0.85 |
| GGG-Gly | 32 | 1.13 |

Oligos of approximately 80 nucleotides were synthesized on a Beckman Oligo 1000 DNA synthesizer, cleaved and deprotected with aqueous NH$_4$OH, and purified by electrophoresis in 7M urea/12% polyacrylamide gels. Each set of oligos was designed to have an EcoR I restriction enzyme site at the 5' end, a unique restriction site near the 3' end, followed by the TAAT stop sequence and a Hind III restriction enzyme site at the very 3' end. The first four oligos, comprising the first 81 amino acids of the human collagen Type I ($\alpha_1$) gene, are given in FIG. 40 which shows the sequence and restriction maps of synthetic oligos used to construct the first 243 base pairs of the human Type I ($\alpha_1$) collagen gene with optimized E. coli codon usage. Oligos N1-1 (SEQ. ID. NO. 21) and N1-2 (SEQ. ID. NO. 22) were designed to insert an initiating methionine (ATG) codon at the 5' end of the gene.

Figure 41:
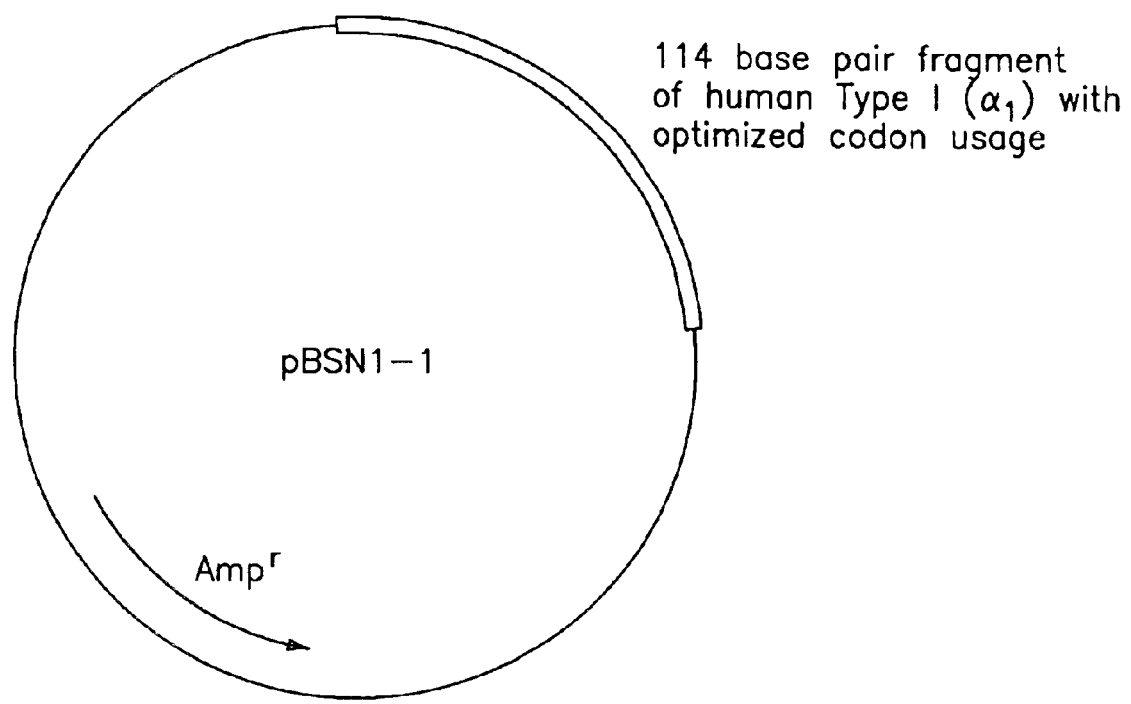
FIG. 41 depicts a plasmid map of pBSN1-1 containing a 1-1 base pair fragment of human collagen Type I ($α_1$) with optimized *E. coli* codon usage.

In one instance, oligos N1-1 and N1-2 (1 µg each) were annealed in 20 µL of T7 DNA polymerase buffer (40 mM Tris.HCl (pH 8.0), 5 mM MgCl$_2$, 5 mM dithiothreitol, 50 mM NaCl, 0.05 mg/mL bovine serum albumin) by heating at 90° C. for 5 minutes followed by slow cooling to room temperature. After brief centrifugation at 14,000 rpm, 10 units of T7 DNA polymerase and 2 µL of a solution of all four dNTPs (dATP, dGTP, dCTP, dTTP, 2.5 mM each) were added to the annealed oligos. Extension reactions were incubated at 37° C. for 30 minutes and then heated at 70° C. for 10 minutes. After cooling to room temperature, Hind III buffer (5 µL of 10×concentration), 20 µL of H$_2$O, and 10 units of Hind III restriction enzyme were added and the tubes incubated at 37° C. for 10 hours. Hind III buffer (2 µL of 10×concentration), 13.5 µL of 0.5M Tris.HCl (pH 7.5), 1.8 µL of 1% Triton X100, 5.6 µL of H$_2$O, and 20 U of EcoR I were added to each tube and incubation continued for 2 hours at 37° C. D gests were extracted once with an equal volume of phenol, once with phenol/chloroform/isoamyl alcohol, and once with chloroform/isoamyl alcohol. After ethanol precipitation, the pellet was resuspended in 10 µL of TE buffer (10 mM Tris.HCl (pH 8.0), 1 mM EDTA). Resuspended pellet (4 µL) was ligated overnight at 16° C. with agarose gel-purified EcoRI/Hind III digested pBSKS+ vector (1 µg) using T4 DNA ligase (100 units). One half of the transformation mixture was transformed by heat shock into DH5α cells and 100 µL of the 1.0 mL transformation mixture was plated on Luria Broth (LB) agar plates containing 70 µg/mL ampicillin. Plates were incubated overnight at 37° C. Ampicillin resistant colonies (6–12) were picked and grown overnight in LB media containing 70 mg/mL ampicillin. Plasmid DNA was isolated from each culture by Wizard Minipreps (Promega Corporation, Madison Wis.) and screened for the presence of the approximately 120 base pair insert by digestion with EcoR I and Hind III and running the digestion products on agarose electrophoresis gels. Clones with inserts were confirmed by standard dideoxy termination DNA sequencing. The correct clone was named pBSN1-1 (FIG. 41) and the collagen fragment has the nucleic acid sequence given in FIG. 42 (SEQ. ID. NO. 25).

Figure 43:
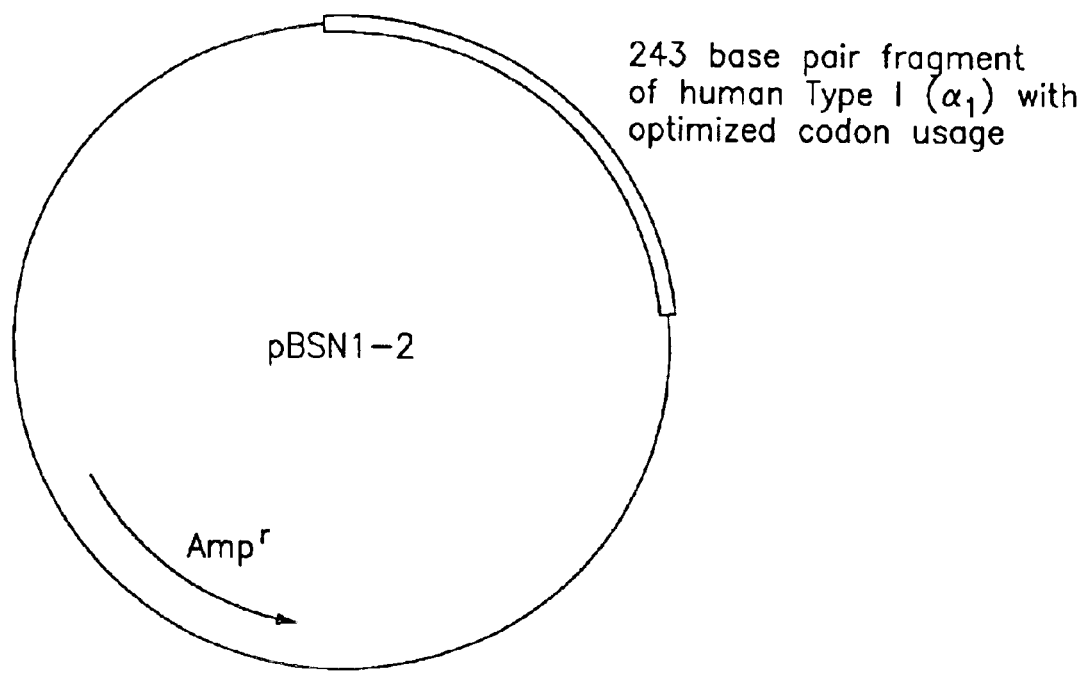
FIG. 43 depicts a plasmid map of pBSN1-2 containing a 243 base pair fragment of human collagen Type I ($α_1$) with optimized *E. coli* codon usage.

Oligos N1-3 (SEQ. ID. NO. 23) and N1-4 (SEQ. ID. NO. 24) (FIG. 40) were synthesized, purified, annealed, extended, and cloned into pBSKS+ following the same procedure given above for oligos N1-1 and N1-2. The resulting plasmid was named pBSN1-2A. To clone together the sections of the collagen gene from pBSN1-1 and pBSN1-2A, plasmid pBSN1-1 (1 μg) was digested for 2 hours at 37° C. with Rsr II and Hind III. The digested vector was purified by agarose gel electrophoresis. Plasmid pBSN1-2A (3 μg) was digested for 2 hours at 37° C. with Rsr II and Hind III and the insert purified by agarose gel electrophoresis. Rsr II/Hind III-digested pBSN1-1 was ligated with this insert overnight at 16° C. with T4 DNA ligase. One half of the ligation mixture was transformed into DH5α cells and ⅒ of the transformation mixture was plated on LB agar plates containing 70 μg/mL ampicillin. After overnight incubation at 37° C., ampicillin-resistant clones were picked and screened for the presence of insert DNA as described above. Clones were confirmed by dideoxy termination sequencing. The correct clone was named pBSN1-2 (FIG. 43) and the collagen fragment has the sequence given in FIG. 44.

In similar manner, the remainder of the collagen gene is constructed such that the final DNA sequence is that given in FIG. 39A–39E (SEQ. ID. NO. 19). B) Expression of the gene in *E. coli:*

Figure 45:
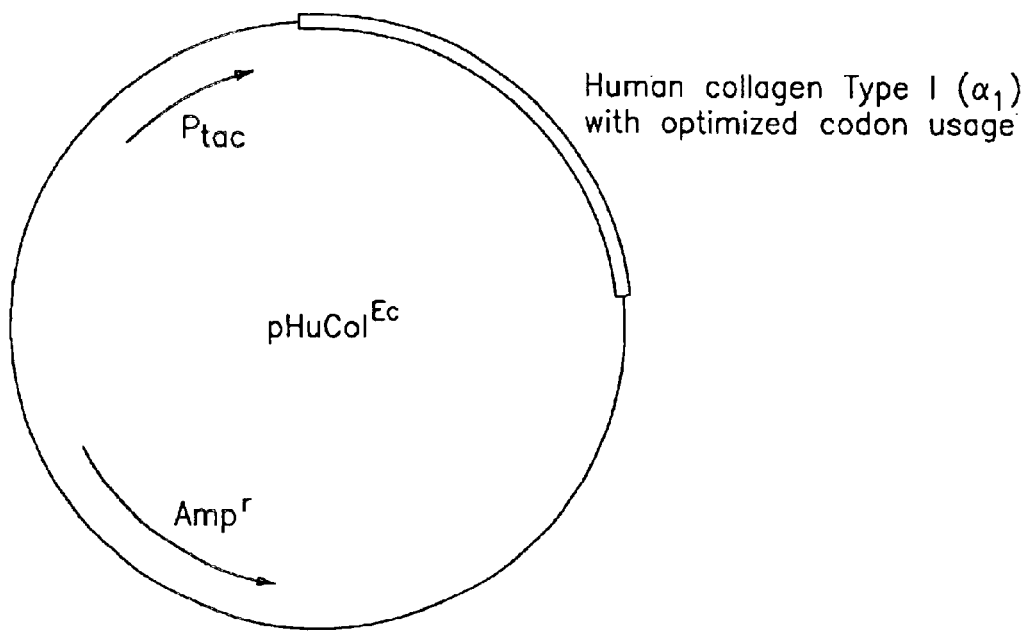
FIG. 45 depicts a plasmid map of pHuCol$^{Ec}$ containing human collagen Type I ($α_1$) with optimized *E. coli* codon usage.

Following construction of the entire human collagen Type I ($\alpha_1$) gene with codon usage optimized for *E. coli*, the cloned gene is expressed in *E coli*. A plasmid (pHuCol$^{Ec}$, FIG. 45) encoding the entire synthetic collagen gene (FIG. 39A–39E) placed behind the isopropyl-β-D-thiogalactopyranoside (IPTG)-inducible tac promotor and also encoding β-lactamase is transformed into *Escherichia coli* strain DH5α (supE44 ΔlacU169 (φ80lacZ ΔM15) hsdR17 recA1 endA1 gyrA96 thi-1 relA1) by standard heat shock transformation. Transformation cultures are plated on Luria Broth (LB) containing 100 μg/mL ampicillin and after overnight growth a single ampicillin-resistant colony is used to inoculate 10 mL of LB containing 100 μg/mL ampicillin. After growth for 10–16 hours with shaking (225 rpm) at 37° C., this culture is used to inoculate 1 L of LB containing 100 μg/mL ampicillin in a 1.5 L shaker flask. After growth at 37° C., 225 rpm, for 2 hours post-inoculation, the optical density at 600 nm is approximately 0.5 OD/mL. IPTG is added to 1 mM and the culture allowed to grow for an additional 5–10 hours. Cells are harvested by centrifugation (5000 rpm, 10 minutes) and lysed by mechanical disruption. Recombinant human collagen is purified by ammonium sulfate fractionation and column chromatography. The yield is typically 15–25 mg/L of culture.

EXAMPLE 11

Figure 46:
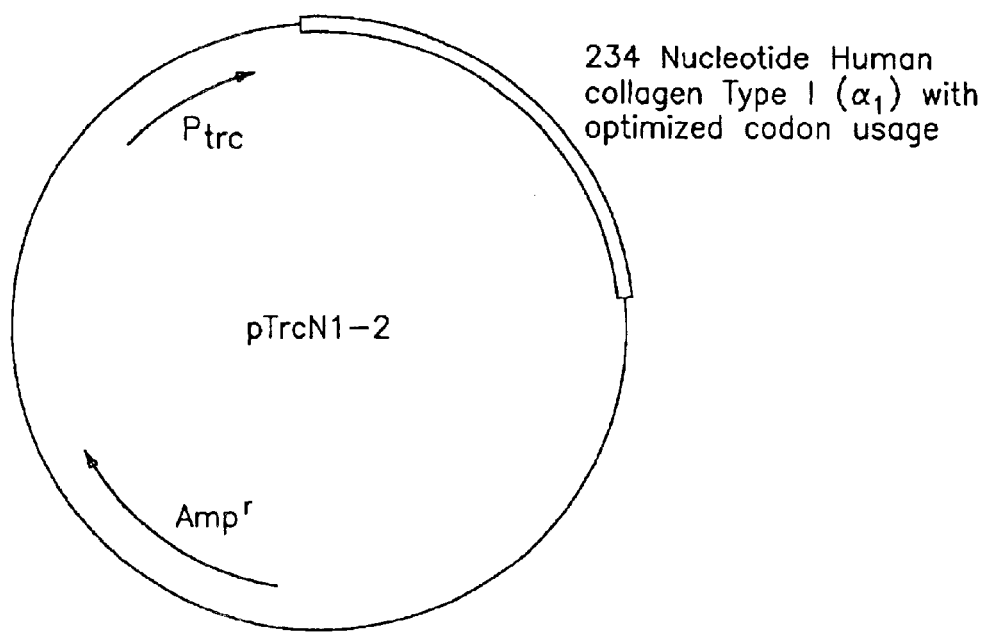
FIG. 46 depicts a plasmid map of pTrc N1-2 containing a 234 nucleotide human collagen Type I ($α_1$) fragment with optimized *E. coli* codon usage.

Expression in *E. coli* of an 81 Amino Acid Fragment of Human Collagen Type I(α1) with Optimized *E. coli* Codon Usage A plasmid (pTrcN1-2, FIG. 46) encoding the gene sequence of the first 81 amino acids of human Type I($\alpha_1$) collagen with optimized *E. coli* codon usage cloned in fusion with a 6 histidine tag at the 5' end of the gene and placed behind the isopropyl-β-D-thiogalactopyranoside (IPTG)-inducible trc promotor and also encoding β-lactamase was constructed by subcloning the EcoR I/Hind III insert from pBSN1-2 into the EcoR I/Hind III site of plasmid pTrcB (Invitrogen, San Diego, Calif.). Plasmid pTrcN1-2 was transformed into *Escherichia coli* strain DH5α (supE44ΔlacU169 (φ80lacIZ ΔM15) hsdR17 recA1 endA1 gyrA96 thi-1 relA1) by standard heat shock transformation. Transformation cultures were plated on Luria Broth (LB) containing 100 μg/mL ampicillin and after overnight growth a single ampicillin-resistant colony was used to inoculate 5 mL of LB containing 100 μg/mL ampicillin. After growth for 10–16 hours with shaking (225 rpm) at 37° C., this culture was used to inoculate 50 mL of LB containing 100 μg/mL ampicillin in a 250 mL shaker flask. After growth at 37° C., 225 rpm, for 2 hours post-inoculation, the optical density at 600 nm was approximately 0.5 OD/mL. IPTG was added to 1 mM and the culture allowed to grow for an additional 5–10 hours. Cells were harvested by centrifugation (5000 rpm, 10 minutes) and stored at −200° C. The 6 histidine tag-collagen fragment fusion was purified on nickel resin columns. Cell pellets were resuspended in 10 mL of 6M guanidine hydrochloride/20 mM sodium phosphate/500 mM NaCl (pH 7.8) and bound in two 5 mL batches to the nickel resin. Columns were washed two times with 4 mL of binding buffer (8M urea/20 mM sodium phosphate/500 mM NaCl (pH 7.8)), two times with wash buffer 1 (8M urea/20 mM sodium phosphate/500 mM NaCl (pH 6.0)), and two times with wash buffer 2 (8 m urea/20 mM sodium phosphate/500 mM NaCl (pH 5.3). The 6 histidine tag-collagen fragment fusion was eluted from the column with 5 mL of elution buffer (8M urea/20 mM sodium phosphate/500 mM NaCl (pH 4.0) in 1 mL fractions. Fractions were assessed for protein by gel electrophoresis and fusion-containing fractions were concentrated and stored at −20° C. The yield was typically 15–25 mg/L of culture.

The collagen is cleaved from the 6 histidine tag with enterokinase. Fusion-containing fractions are dialyzed against cleavage buffer (50 mM Tris-HCl, pH 8.0/5 mM CaC$_{12}$). After addition of enterokinase at 1 μg enzyme for each 100 μg fusion, the solution is incubated at 37° C. for 4–10 hours. Progress of the cleavage is monitored by gel electrophoresis. The cleaved 6 histidine tag may be separated from the collagen fragment by passage over a nickel resin column as outlined above.

EXAMPLE 12

Figure 47:
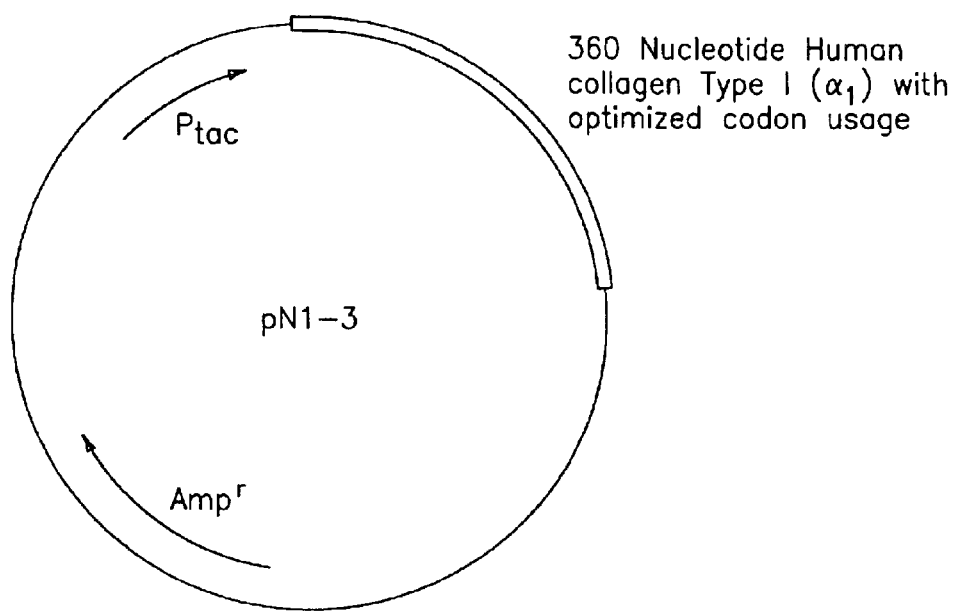
FIG. 47 depicts a plasmid map of pN1-3 containing a 360 nucleotide human collagen Type I ($α_1$) fragment with optimized *E. coli* codon usage.

Expression in *E. coli* of Fragments of Human Collagen Type I ($\alpha_1$) with Optimized *E. coli* Codon Usage A plasmid (pN1-3, FIG. 47) encoding the gene for the amino terminal 120 amino acids of human collagen Type I ($\alpha_1$) with optimized *E. coli* codon usage placed behind the isopropyl-β-D-thiogalactopyranoside (IPTG)-inducible tac promotor and also encoding β-lactamase is transformed into *Escherichia coli* strain DH5α (sup E44 ΔlacU169 (φ80lacZ ΔM15) hsdR17 recA1 endA1 gyrA96 thi-1 relA1) by standard heat shock transformation. Transformation cultures are plated on Luria Broth (LB) containing 100 μg/mL ampicillin and after overnight growth a single ampicillin-resistant colony is used to inoculate 10 mL of LB containing 100 μg/mL ampicillin. After growth for 10–16 hours with shaking (225 rpm) at 37° C., this culture is used to inoculate 1 L of LB containing 100 μg/mL ampicillin in a 1.5 L shaker flask. After growth at 37° C., 225 rpm, for 2 hours post-inoculation, the optical density at 600 nm is approximately 0.5 OD/mL. IPTG is added to 1 mM and the culture allowed to grow for an additional 5–10 hours. Cells are harvested by centrifugation (5000 rpm, 10 minutes) and lysed by mechanical disruption. Recombinant human collagen is purified by ammonium sulfate fractionation and column chromatography. The yield is typically 15–25 mg/L of culture.

EXAMPLE 13

Expression in *E. coli* of a C-terminal Fragment of Human Collagen Type I ($\alpha_1$) with Optimized *E. coli* Codon Usage A plasmid (pD4, FIG. 48) encoding the gene for the carboxy terminal 219 amino acids of human collagen Type I ($\alpha_1$) with optimized *E. coli* codon usage placed behind the isopropyl-$\beta$-D-thiogalactopyranoside (IPTG)-inducible tac promotor and also encoding $\beta$-lactamase is transformed into *Escherichia coli* strain DH5$\alpha$ (sup E44 $\Delta$lacU169 ($\phi$80lacZ $\Delta$M15) hsdR17 recA1 endA1 gyrA96 thi-1 relA1) by standard heat shock transformation. Transformation cultures are plated on Luria Broth (LB) containing 100 $\mu$g/mL ampicillin and after overnight growth a single ampicillin-resistant colony is used to inoculate 10 mL of LB containing 100 $\mu$g/mL ampicillin. After growth for 10–16 hours with shaking (225 rpm) at 37° C., this culture is used to inoculate 1 L of LB containing 100 $\mu$g/mL ampicillin in a 1.5 L shaker flask. After growth at 37° C., 225 rpm, for 2 hours post-inoculation, the optical density at 600 nm is approximately 0.5 OD/mL. IPTG is added to 1 mM and the culture allowed to grow for an additional 5–10 hours. Cells are harvested by centrifugation (5000 rmp, 10 minutes) and lysed by mechanical disruption. Recombinant human collagen fragment is purified by ammonium sulfate fractionation and column chromatography. The yield is typically 15–25 mg/L of culture.

EXAMPLE 14

Construction and Expression in *E. coli* of the Human Collagen Type 1 ($\alpha$2) Gene with Optimized *E. coli* Codon Usage A) Construction of the Gene:

The nucleotide sequence of the helical region of human collagen Type I ($\alpha_2$) gene flanked by 11 amino acids of the amino terminal extra-helical and 12 amino acids of the C-terniinal extra-helical region is shown in FIGS. 49A–49E (SEQ. ID. NO. 29). A tabulation of the codon frequency of this gene is given in Table III below. The gene sequence shown in FIGS. 49A–49E was first changed to reflect *E. coli* codon bias. An initiating methionine was inserted at the 5' end of the gene and a TAAT stop sequence at the 3' end. Unique restriction sites are identified or created approximately every 150 base pairs. The resulting gene (HuCol($\alpha_2$))$^{Ec}$, FIGS. 50A–50E) (SEQ. ID. NO. 31) has the codon usage given in Table IV below. Other sequences that approximate *E. coli* codon bias are also acceptable.

TABLE III

| Codon | Count | % age |
|---|---|---|
| TTT-Phe | 3 | 0.28 |
| TTC-Phe | 10 | 0.96 |
| TTA-Leu | 1 | 0.09 |
| TTG-Leu | 2 | 0.19 |
| CTT-Leu | 16 | 1.54 |
| CTC-Leu | 9 | 0.86 |
| CTA-Leu | 2 | 0.19 |
| CTG-Leu | 5 | 0.48 |

TABLE III-continued

| Codon | Count | % age |
|---|---|---|
| ATT-Ile | 14 | 1.35 |
| ATC-Ile | 3 | 0.28 |
| ATA-Ile | 1 | 0.09 |
| ATG-Met | 5 | 0.48 |
| GTT-Val | 20 | 1.93 |
| GTC-Val | 5 | 0.48 |
| GTA-Val | 3 | 0.28 |
| GTG-Val | 10 | 0.96 |
| TCT-Ser | 11 | 1.06 |
| TCC-Ser | 4 | 0.38 |
| TCA-Ser | 1 | 0.09 |
| TCG-Ser | 1 | 0.09 |
| CCT-Pro | 125 | 12.06 |
| CCC-Pro | 42 | 4.05 |
| CCA-Pro | 30 | 2.89 |
| CCG-Pro | 3 | 0.28 |
| ACT-Thr | 14 | 1.35 |
| ACC-Thr | 0 | 0.00 |
| ACA-Thr | 3 | 0.28 |
| ACG-Thr | 1 | 0.09 |
| GCT-Ala | 82 | 7.91 |
| GCC-Ala | 17 | 1.64 |
| GCA-Ala | 9 | 0.86 |
| GCG-Ala | 0 | 0.00 |
| TAT-Tyr | 2 | 0.19 |
| TAC-Tyr | 3 | 0.28 |
| TAA-*** | 0 | 0.00 |
| TAG-*** | 0 | 0.00 |
| CAT-His | 7 | 0.67 |
| CAC-His | 6 | 0.57 |
| CAA-Gln | 13 | 1.25 |
| CAG-Gln | 9 | 0.86 |
| AAT-Asn | 10 | 0.96 |
| AAC-Asn | 14 | 1.35 |
| AAA-Lys | 15 | 1.44 |
| AAG-Lys | 16 | 1.54 |
| GAT-Asp | 20 | 1.93 |
| GAC-Asp | 5 | 0.43 |
| GAA-Glu | 29 | 2.79 |
| GAG-Glu | 16 | 1.54 |
| TGT-Cys | 0 | 0.00 |
| TGC-Cys | 0 | 0.00 |
| TGA-*** | 0 | 0.00 |
| TGG-Trp | 0 | 0.00 |
| CGT-Arg | 17 | 1.64 |
| CGC-Arg | 6 | 0.57 |
| CGA-Arg | 6 | 0.57 |
| CGG-Arg | 4 | 0.38 |
| AGT-Ser | 11 | 1.06 |
| AGC-Ser | 4 | 0.39 |
| AGA-Arg | 16 | 1.54 |
| AGG-Arg | 6 | 0.57 |
| GGT-Gly | 179 | 17.27 |
| GGC-Gly | 74 | 7.14 |
| GGA-Gly | 80 | 7.72 |
| GGG-Gly | 16 | 1.54 |

TABLE IV

| Codon | Count | % age |
|---|---|---|
| TTT-Phe | 5 | 0.48 |
| TTC-Phe | 7 | 0.67 |
| TTA-Leu | 0 | 0.00 |
| TTG-Leu | 0 | 0.00 |
| CTT-Leu | 1 | 0.09 |
| CTC-Leu | 1 | 0.09 |
| CTA-Leu | 0 | 0.00 |
| CTG-Leu | 32 | 3.07 |
| ATT-Ile | 11 | 1.06 |
| ATC-Ile | 7 | 0.67 |
| ATA-Ile | 0 | 0.00 |
| ATG-Met | 6 | 0.57 |
| GTT-Val | 18 | 1.72 |

TABLE IV-continued

| Codon | Count | % age |
|---|---|---|
| GTC-Val | 7 | 0.67 |
| GTA-Val | 9 | 0.85 |
| GTG-Val | 6 | 0.57 |
| TCT-Ser | 7 | 0.67 |
| TCC-Ser | 12 | 1.15 |
| TCA-Ser | 0 | 0.00 |
| TCG-Ser | 0 | 0.00 |
| CCT-Pro | 10 | 0.96 |
| CCC-Pro | 0 | 0.00 |
| CCA-Pro | 15 | 1.44 |
| CCG-Pro | 177 | 17.00 |
| ACT-Thr | 3 | 0.28 |
| ACC-Thr | 6 | 0.57 |
| ACA-Thr | 0 | 0.00 |
| ACG-Thr | 10 | 0.96 |
| GCT-Ala | 30 | 2.88 |
| GCC-Ala | 21 | 2.01 |
| GCA-Ala | 20 | 1.92 |
| GCG-Ala | 38 | 3.66 |
| TAT-Tyr | 3 | 0.28 |
| TAC-Tyr | 2 | 0.19 |
| TAA-*** | 0 | 0.00 |
| TAG-*** | 0 | 0.00 |
| CAT-His | 2 | 0.19 |
| CAC-His | 11 | 1.05 |
| CAA-Gln | 7 | 0.67 |
| CAG-Gln | 15 | 1.44 |
| AAT-Asn | 6 | 0.57 |
| AAC-Asn | 18 | 1.72 |
| AAA-Lys | 25 | 2.40 |
| AAG-Lys | 6 | 0.57 |
| GAT-Asp | 11 | 1.05 |
| GAC-Asp | 13 | 1.24 |
| GAA-Glu | 33 | 3.17 |
| GAG-Glu | 12 | 1.15 |
| TGT-Cys | 0 | 0.00 |
| TGC-Cys | 0 | 0.00 |
| TGA-*** | 0 | 0.00 |
| TGG-Trp | 0 | 0.00 |
| CGT-Arg | 37 | 3.55 |
| CGC-Arg | 18 | 1.72 |
| CGA-Arg | 0 | 0.00 |
| CGG-Arg | 0 | 0.00 |
| AGT-Ser | 0 | 0.00 |
| AGC-Ser | 13 | 1.24 |
| AGA-Arg | 0 | 0.00 |
| AGG-Arg | 0 | 0.00 |
| GGT-Gly | 209 | 20.07 |
| GGC-Gly | 141 | 13.54 |
| GGA-Gly | 0 | 0.00 |
| GGG-Gly | 0 | 0.00 |

Oligos of approximately 80 nucleotides are synthesized on a Beckman Oligo 1000 DNA synthesizer, cleaved and deprotected with aqueous NH$_4$OH, and purified by electrophoresis in 7M urea/12% polyacrylamide gels. Each set of oligos is designed to have an EcoR I restriction enzyme site at the 5' end, a unique restriction site near the 3' end, followed by the TAAT stop sequence and a Hind III restriction enzyme site at the very 3' end. Oligos N1-1($\alpha_2$) and N1-2($\alpha_2$) are designed to insert an initiating methionine (ATG) codon at the 5' end of the gene.

Figure 52:
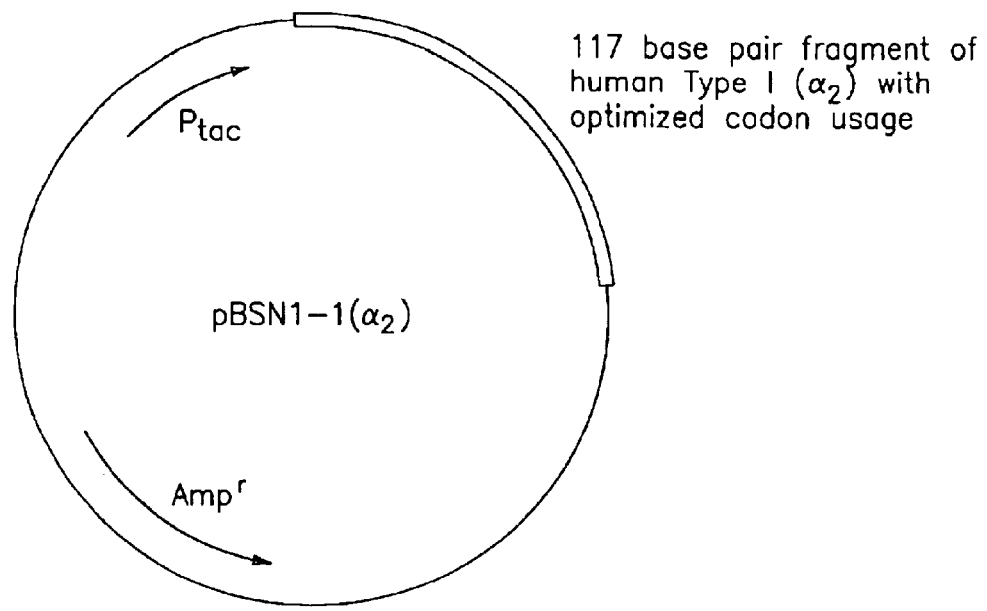
FIG. 52 depicts a plasmid map of pBSN1-1 ($α_2$) containing a 117 base pair fragment of human collagen Type I ($α_2$) with optimized *E. coli* codon usage.

In one instance, oligos N1-1($\alpha_2$) and N1-2($\alpha_2$) (1 µg each) (FIG. 51 depicts sequence and restriction maps of synthetic oligos used to construct the first 240 base pairs of human Type 1 ($\alpha_2$) collagen gene with optimized E. coli codon usage) are annealed in 20 µL of T7 DNA polymerase buffer (40 mM Tris.HCl (pH 8.0), 5 mM MgCl$_2$, 5 mM dithiothreitol, 50 mM NaCl, 0.05 mg/mL bovine serum albumin) by heating at 90° C. for 5 minutes followed by slow cooling to room temperature. After brief centrifugation at 14,000 rpm, 10 units of T7 DNA polymerase and 2 µL of a solution of all four dNTPs (dATP, dGTP, dCTP, dTTP, 2.5 mM each) are added to the annealed oligos. Extension reactions are incubated at 37° C. for 30 minutes and then heated at 70° C. for 10 minutes. After cooling to room temperature, Hind III buffer (5 µL of 10× concentration), 20 µL of H$_2$O, and 10 units of Hind III restriction enzyme are added and the tubes incubated at 37° C. for 10–16 hours. Hind III buffer (2 µL of 10× concentration), 13.5 µL of 0.5 Tris.HCl (pH 7.5), 1.8 µL of 1% Triton X100, 5.6 µL of H$_2$O, and 20 U of EcoR I are added to each tube and incubation continued for 2 hours at 37° C. Digests are extracted once with an equal volume of phenol once with phenol/chloroform/isoamyl alcohol, and once with chloroform/isoamyl alcohol. After ethanol precipitation, the pellet is resuspended in 10 µL of TE buffer (10 mM Tris.HCl (pH 8.0), 1 mM EDTA). Resuspended pellet (4 µL) is ligated overnight at 16° C. with agarose gel-purified EcoRI/Hind III digested pBSKS$^+$ vector (1 µg) using T4 DNA ligase (100 units). One half of the transformation mixture is transformed by heat shock into DH5α cells and 100 µL of the 1.0 mL transformation mixture is plated on Luria Broth (LB) agar plates containing 70 µg/mL ampicillin. Plates are incubated overnight at 37° C. Ampicillin resistant colonies (6–12) are picked and grown overnight in LB media containing 70 µg/mL ampicillin. Plasmid DNA is isolated from each culture by Wizard Minipreps (Promega Corporation, Madison, Wis.) and screened for the presence of the approximately 120 base pair insert by digestion with EcoR I and Hind III and running the digestion products on agarose electrophotesis gels. Clones with inserts are confirmed by standard dideoxy termination DNA sequencing. The correct clone is named pBSN1-1 ($\alpha_2$) FIG. 52).

Figure 53:
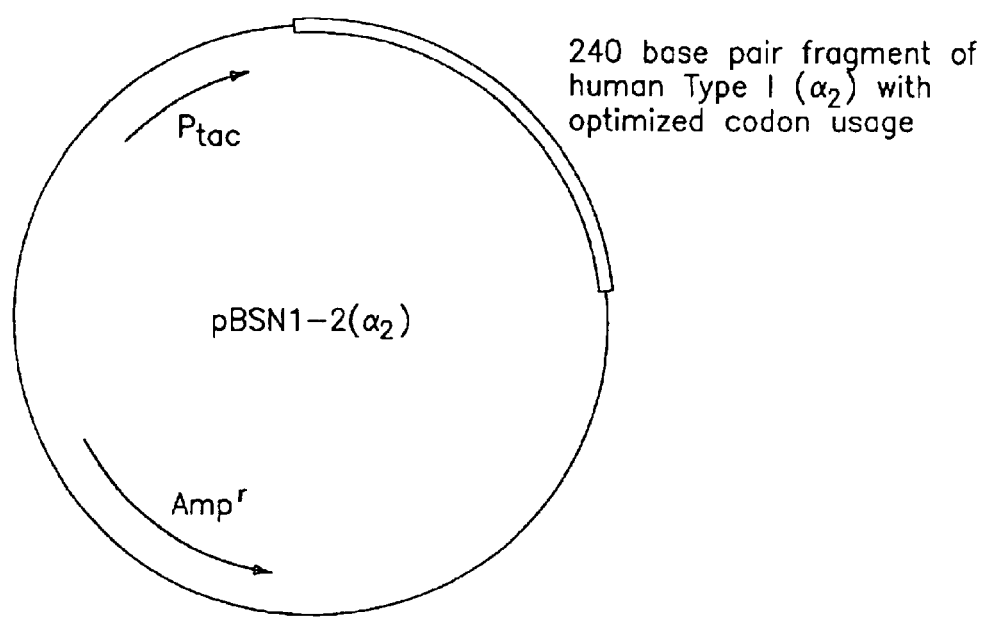
FIG. 53 depicts a plasmid map of pBSN1-2 ($α_2$) containing a 240 base pair fragment of human collagen Type I ($α_2$) with optimized *E. coli* codon usage.

Oligos N1-3($\alpha_2$) and N1-4($\alpha_2$) are synthesized, purified, annealed, extended, and cloned into pBSKS$^+$ following the same procedure given above for oligos N1-1($\alpha$2) and N1-2 ($\alpha_2$). The resulting plasmid is named pBSN1-2A. To clone together the sections of the collagen gene from pBSN1-1 ($\alpha_2$) (1 µg) is digested for 2 hours at 37° C. with BsrF I and Hind III. The digested vector is purified by agarose gel electrophoresis. Plasmid pBSn1-2($\alpha_2$) (3 µg) is digested for 2 hours at 37° C. with BsrF I and Hind III and the insert purified by agarose gel electrophoresis. BsrF I/Hind III-digested pBSN1-1 is ligated with this insert overnight at 16° C. with T4 DNA ligase. One half of the ligation mixture is transformed into DH5α cells and 1/10 of the transformation mixture is plated on LB agar plates containing 70 µg/mL ampicillin. After overnight incubation at 37° C., ampicillin-resistant clones are picked and screened for the presence of insert DNA as described above. Clones are confirmed by dideoxy termination sequencing. The correct clone is name pBSN1-2($\alpha_2$) (FIG. 53) and the collagen fragment has the sequence given in FIG. 54 (SEQ. ID. NO. 37).

In a similar manner, the remainder of the collagen gene is constructed such that the final DNA sequence is that given in FIGS. 50A–50E (SEQ. ID. NO. 31).

Figure 55:
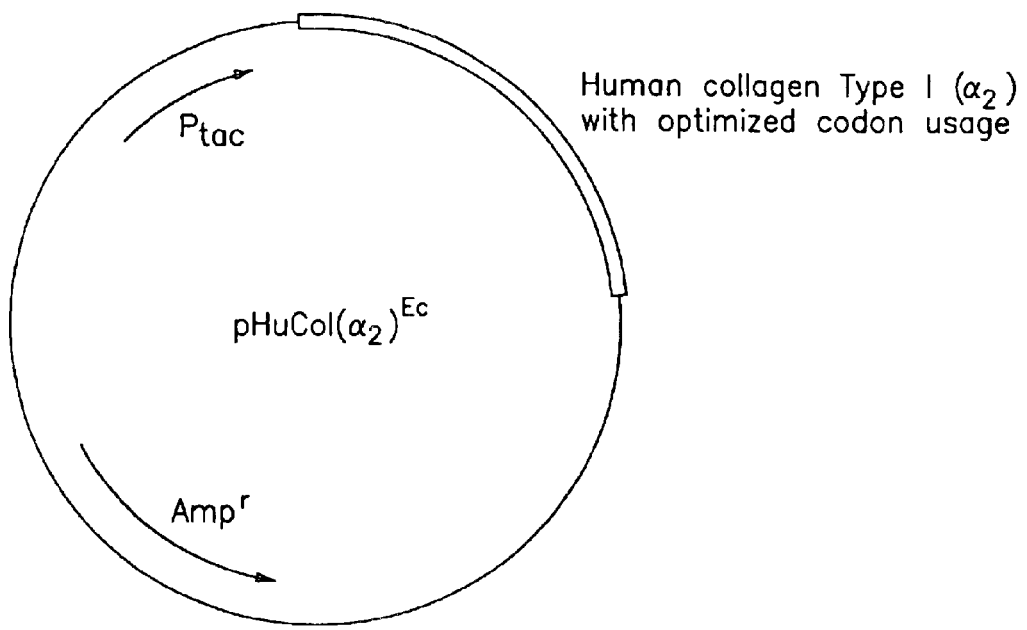
FIG. 55 depicts a plasmid map of pHuCol($α_2$)$^{Ec}$ containing the entire human collagen Type I ($α_2$) gene with optimized *E. coli* codon usage.

B) Expression of the Gene in E. coli:

Following construction of the entire human collagen Type I ($\alpha$2) gene with codon usage optimized for E. coli, the cloned gene is expressed in E. coli. A plasmid (pHuCol($\alpha_2$)$^{Ec}$, FIG. 55) encoding the entire synthetic collagen gene (FIGS. 50A–50E) placed behind the isopropyl-β-D-thiogalactopyranoside (IPTG)-inducible tac promotor and also encoding β-lactamase is transformed into Escherichia coli strain DH5α (supE44 ΔlacU169 (φ80lacZ ΔM15) hsdR17 recA1 endA1 gyrA96 thi-1 relA1) by standard heat shock transformation. Transformation cultures are plated on Luria Broth (LB) containing 100 µg/mL ampicillin and after overnight growth a single ampicillin-resistant colony is used to inoculate 10 mL of LB containing 100 μg/mL ampicillin and after overnight growth a single ampicillin-resistant colony is used to inoculate 10 mL of LB containing 100 μg/mL ampicillin. After growth for 10–16 hours with shaking (225 rpm) at 37° C., this culture is used to inoculate 1 L of LB containing 100 μg/mL ampicillin in a 1.5 L shaker flask. After growth at 37° C., 225 rpm, for 2 hours post-inoculation, the optical density at 600 nm is approximately 0.5 OD/mL. IPTG is added to 1 mM and the culture allowed to grow for an additional 5–10 hours. Cells are harvested by centrifugation (5000 rpm, 10 minutes) and lysed by mechanical disruption. Recombinant human collagen is purified by ammonium sulfate fractionation and column chromatography. The yield is typically 15–25 mg/L of culture.

EXAMPLE 14A

Alternative Construction and Expression in *E. coli* of the Human Collagen Type 1 (α2) Gene with Optimized *E. coli* Codon Usage A) Construction of the Gene:

The nucleotide sequence of the helical region of human collagen Type 1 (α2) gene flanked by 11 amino acids of the amino terminal extra-helical and 12 amino acids of the C-termiinal extra-helical region is shown in FIGS. 49A–49E (SEQ. ID. NO. 29). A tabulation of the codon frequency of this gene is given in Table III. The gene sequence shown in FIGS. 49A–49E was first changed to reflect *E. coli* codon bias. An initiating methionine was inserted at the 5' end of the gene and a TAAT stop sequence at the 3' end. Unique restriction sites were identified or created at appropriate locations in the gene (approximately every 150 base pairs). The resulting gene (HuCol(α2)$^{Ec}$, FIGS. 50A–50E) (SEQ. ID. NO. 31) has the codon usage given in Table IV. Other sequences that approximate *E. coli* codon bias are also acceptable.

Oligonucleotides were synthesized on a Beckman Oligo 1000 DNA synthesizer, cleaved and deprotected with aqueous NH$_4$OH, and purified by electrophoresis in 7M urea/12% polyacrylarnide gels. Purified oligos (32.5 pmol) were dissolved in 20 μL of ligation buffer (Boehringer Mannheim, Cat. No. 1635 379) and annealed by heating to 95° C. followed by slow cooling to 20° C. over 45 minutes. The annealed oligonucleotides were ligated for 5 minutes at room temperature with digested vector (1 μg) using T4 DNA ligase (5 units). One half of the transformation mixture was transformed by heat shock into DH5α cells and 100 μL of the 1 mL transformation mixture plated on Luria Broth (LB) agar plates containing 70 μg/mL ampicillin. Plates were incubated overnight at 37° C. Ampicillin resistant colonies (6–12) were picked and grown overnight in LB media containing 7 μg/mL ampicillin. Plasmid DNA was isolated from each culture by QIAprep Miniprep (Qiagen, Valencia, Calif.) and screened for the presence of insert by digestion with flanking restriction enzymes and running the digestion products on agarose electrophoresis gels. Clones with inserts were confirmed by standard dideoxy termination DNA sequencing. To clone together the sections of the collagen gene, and insert covering a flanking portion of the gene was ligated into vector containing the neighboring gene portion. Inserts were isolated from plasmids and vectors were cut by double digestion for 2 hours at 37° C. with the appropriate restriction enzymes. The digested vector and insert were purified by agarose gel electrophoresis. Insert and vector were ligated for 5 minutes at room temperature following the procedure in the Rapid DNA Ligation Kit (Boehringer Mannheim). One half of the ligation mixture is transformed into DH5α cells and ⅒ of the transformation mixture was plated on LB agar plates containing 70 μg/mL ampicillin. After overnight incubation at 37° C., ampicillin-resistant clones were picked and screened for the presence of insert DNA as described above. Clones were confirmed by dideoxy termination sequencing.

In a similar manner, the remainder of the collagen gene was constructed such that the final DNA sequence is that given in FIGS. 50A–50E (SEQ. ID. NO. 31).

B) Expression of the Gene in *E. coli*:

Following construction of the entire human collagen Type 1 (α2) gene with codon usage optimized for *E. coli*, the cloned gene is expressed in *E. coli*. A plasmid (pHuCol) (α2)$^{Ec}$, FIG. 55) encoding the entire collagen gene (FIGS. 50A–50E) placed behind the isopropyl-β-D-thiogalactopyranoside (IPTG)-inducible tac promoter and also encoding β-lactamase is transformed into *Escherichia coli* strain DH5α (supE44 ΔlacU169 (φ80lacZ ΔM15) hsdR17 recA1 endA1 gyrA96 thi-1 relA1) by standard heat shock transformation. Transformation cultures are plated on Luria Broth (LB) containing 100 μg/mL ampicillin and after overnight growth a single ampicillin-resistant colony is used to inoculate 10 mL of LB containing 100 μg/mL ampicillin. After growth for 10–16 hours with shaking (225 rpm) at 37° C., this culture is used to inoculate 1 L of LB containing 100 μg/mL ampicillin in a 1.5 L shaker flask. After growth at 37° C., 225 rpm, for 2 hours post-inoculation, the optical density at 600 nm is approximately 0.5 OD/mL. IPTG is added to 1 mM and the culture allowed to grow for an additional 5–10 hours. Cells are harvested by centrifugation (5000 rpm, 10 minutes) and lysed by mechanical disruption. Recombinant human collagen is purified by ammonium sulfate fractionation and column chromatograph. The yield is typically 15–25 mg/L of culture.

EXAMPLE 15

Figure 56:
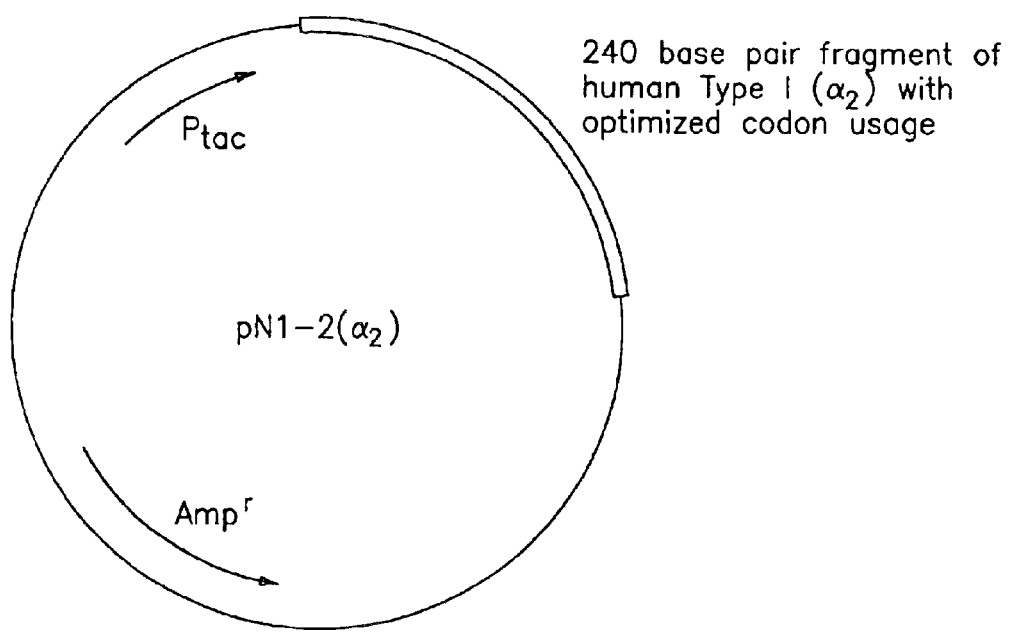
FIG. 56 depicts a plasmid map of pN1-2 ($α_2$) containing a 240 base pair frament of human collagen Type I ($α_2$) with optimized *E. coli* codon usage.

Expression in *E. coli* of Fragments of Human Collagen Type I (α$_2$) with Optimized *E. coli* Codon Usage A plasmid (pN1-2, FIG. 56) encoding the gene for the amino terminal 80 amino acids of human collagen Type I (α$_2$) (SEQ. ID. NO. 31, FIG. 54) with optimized *E. coil* codon usage placed behind the isopropyl-β-D-thiogalactopyranoside (IPTG)-inducible tac promotor and also encoding β-lactamase is transformed into *Escherichia coli* strain DH5α (supE44 ΔlacU169 (φ80lacZ ΔM15) hsdR17 recA1 endA1 gyrA96 thi-1 relA1) by standard heat shock transformation. Transformation cultures are plated on Luria Broth (LB) containing 100 μg/mL ampicillin and after overnight growth a single ampicillin-resistant colony is used to inoculate 10 mL of LB containing 100 μg/mL ampicillin. After growth for 10–16 hours with shaking (225 rpm) at 37° C., this culture is used to inoculate 1 L of LB containing 100 μg/mL ampicillin in a 1.5 L shaker flask. After growth at 37° C., 225 rpm, for 2 hours post-inoculation, the optical density at 600 nm is approximately 0.5 OD/mL. IPTG is added to 1 mM and the culture allowed to grow for an additional 5–10 hours. Cells arc harvested by centrifugation (5000 rpm, 10 minutes) and lysed by mechanical disruption. Recombinant human collagen is purified by ammonium sulfate fractionation and column chromatography. The yield is typically 15–25 mg/L of culture.

EXAMPLE 16

Figure 57:
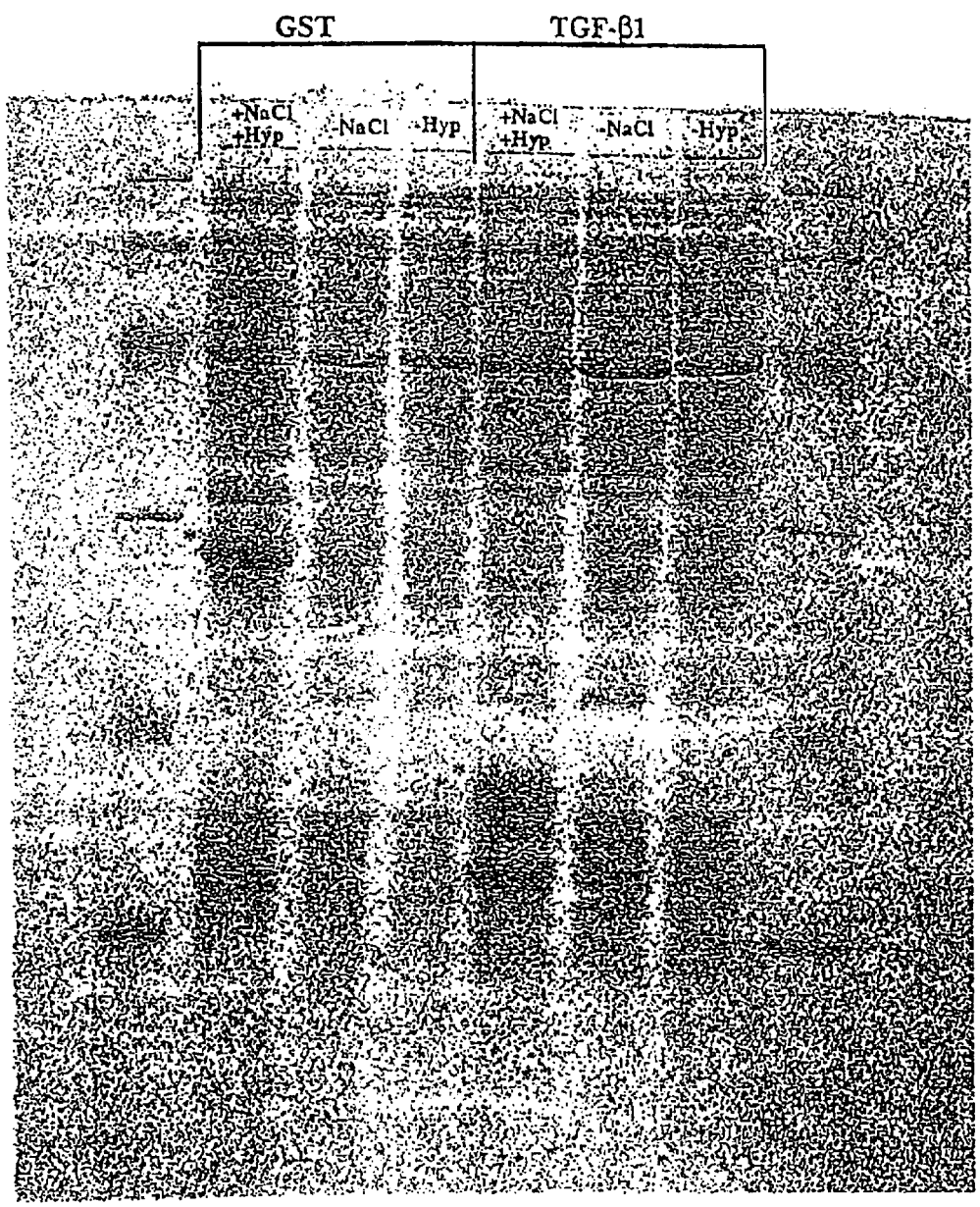
FIG. 57 depicts a gel reflecting expression of GST and TGF-β1 under specified conditions.
Figure 58:
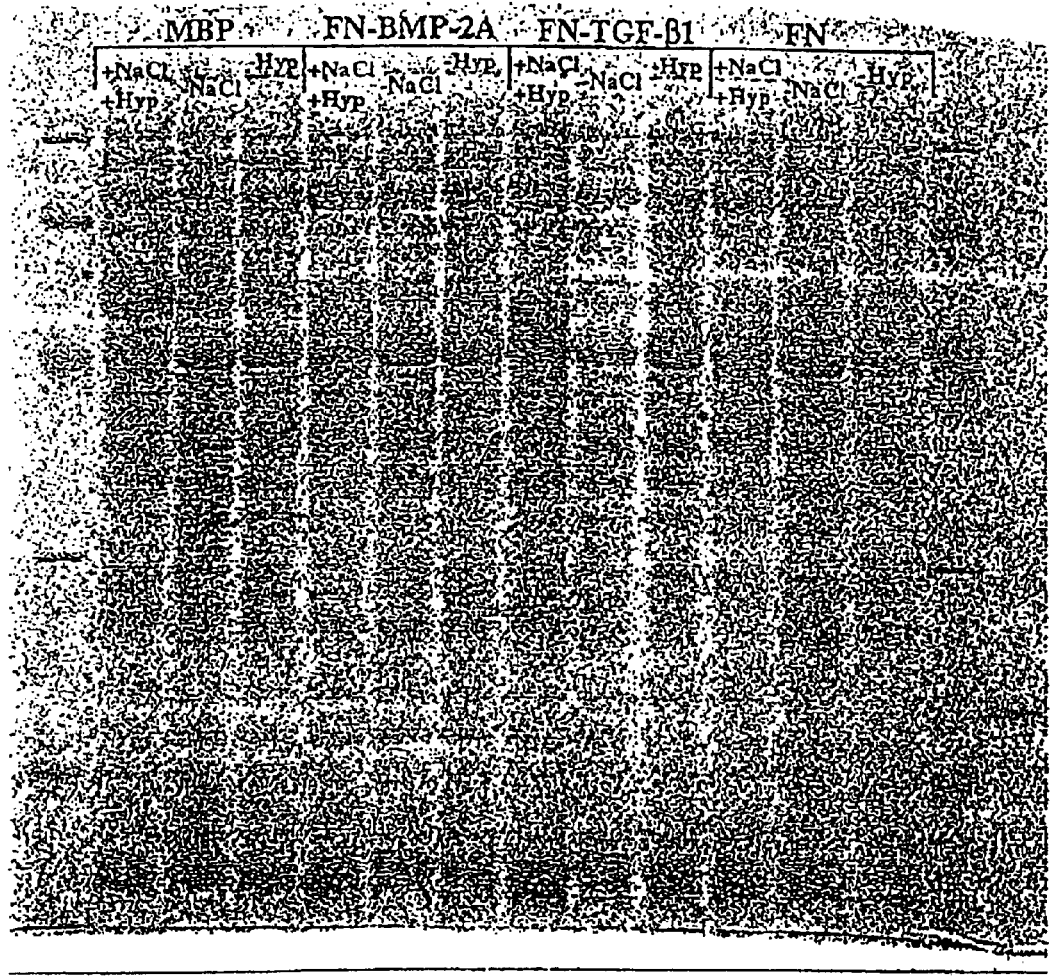
FIG. 58 depicts a gel reflecting expression of MBP, FN-BMP-2A, FN-TGF-β1 and FN under specified conditions.
Figure 73:
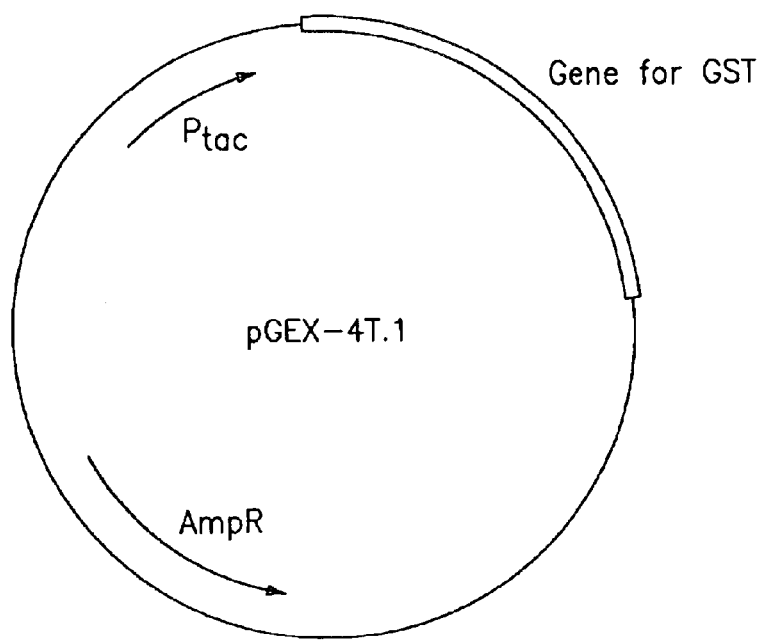
FIG. 73 is a plasmid map illustrating pGEX-4T.1 containing the gene for glutatione S-transferase.
Figure 74:
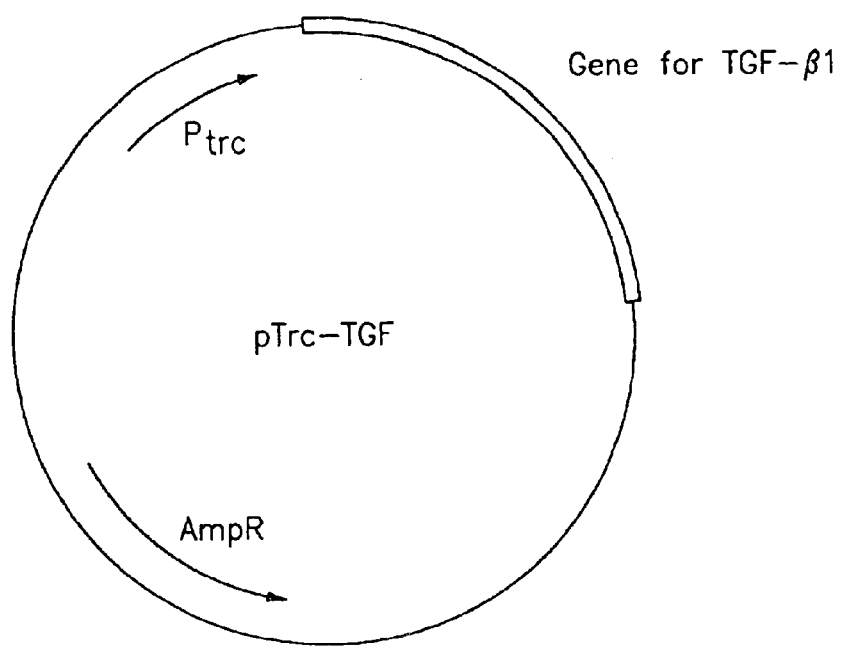
FIG. 74 is a plasmid map illustrating pTrc-TGF containing the gene for the mature human TGF-β1 polypeptide.
Figure 75:
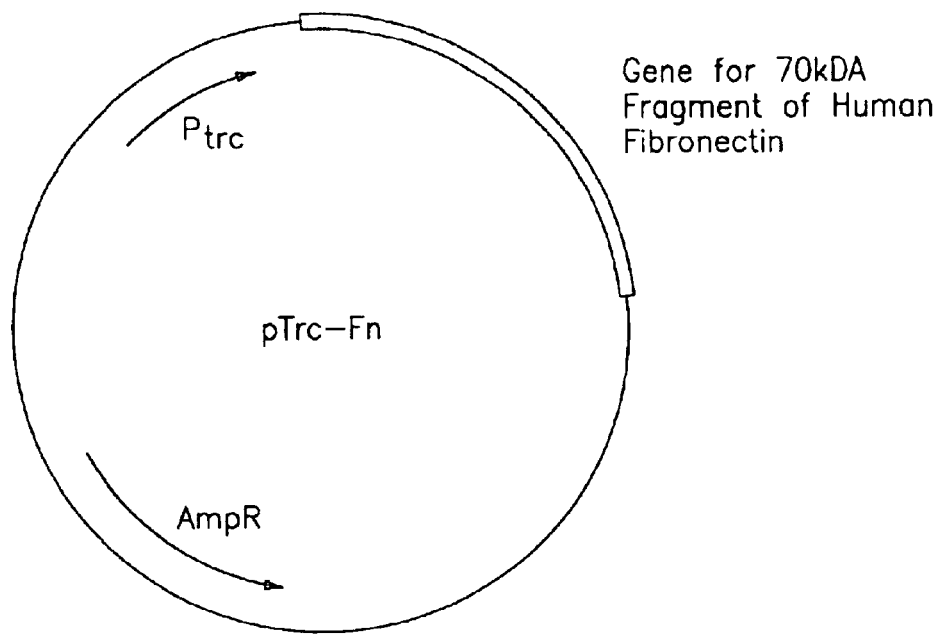
FIG. 75 is a plasmid map illustrating pTrc-Fn containing the gene for a 70 kDa fragment of human fibronectin.
Figure 76:
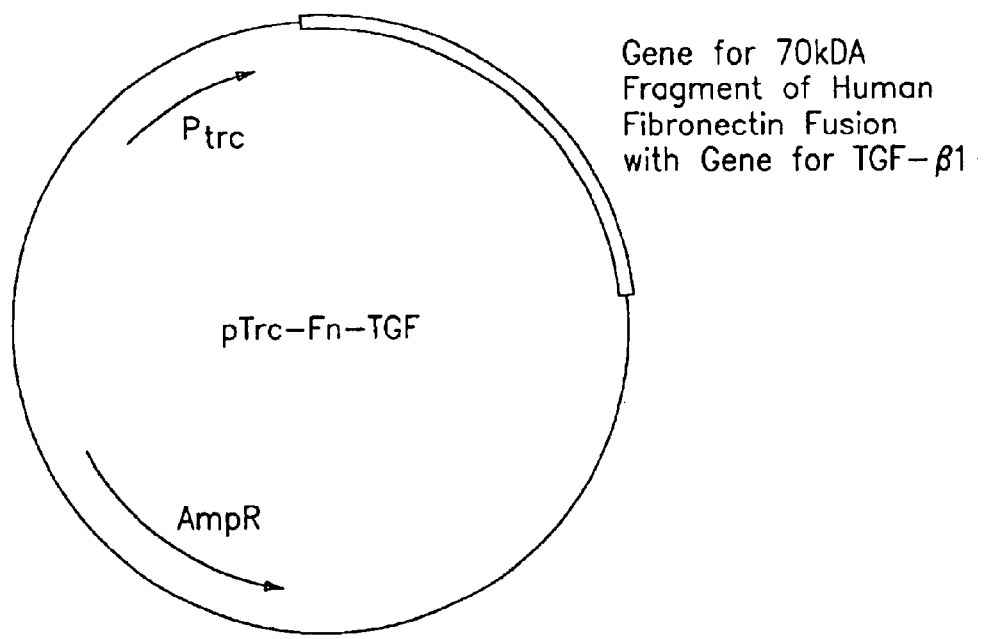
FIG. 76 is a plasmid map illustrating pTrc-Fn-TGF containing the gene for a fusion protein of a 70 kDA fragment of human fibronectin and the mature human TGF-β1 polypeptide.
Figure 77:
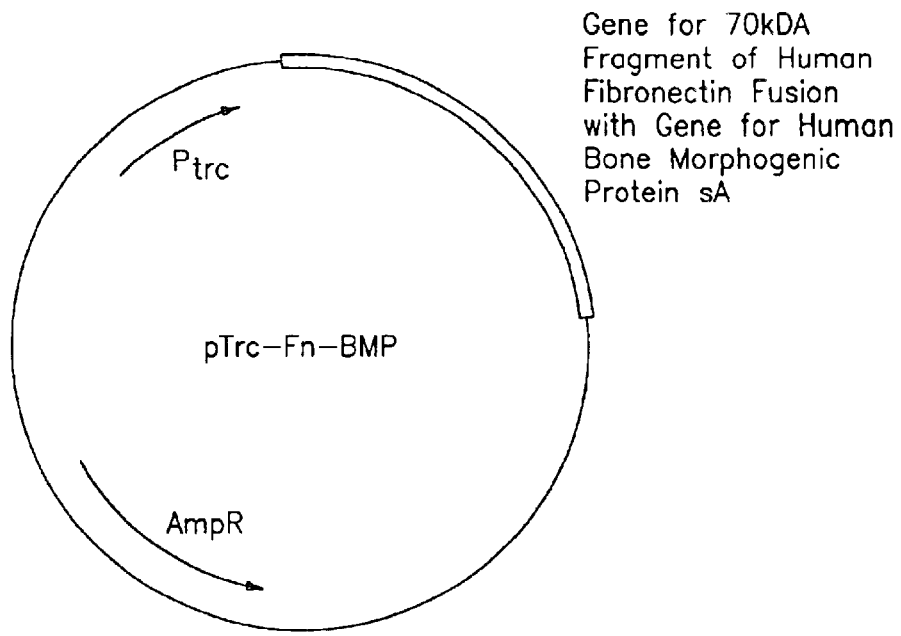
FIG. 77 is a plasmid map illustrating pTrc-Fn-BMP containing the gene for a fusion protein of a 70 kDa fragment of human fibronectin and human bone morphogenic protein 2A.
Figure 78:
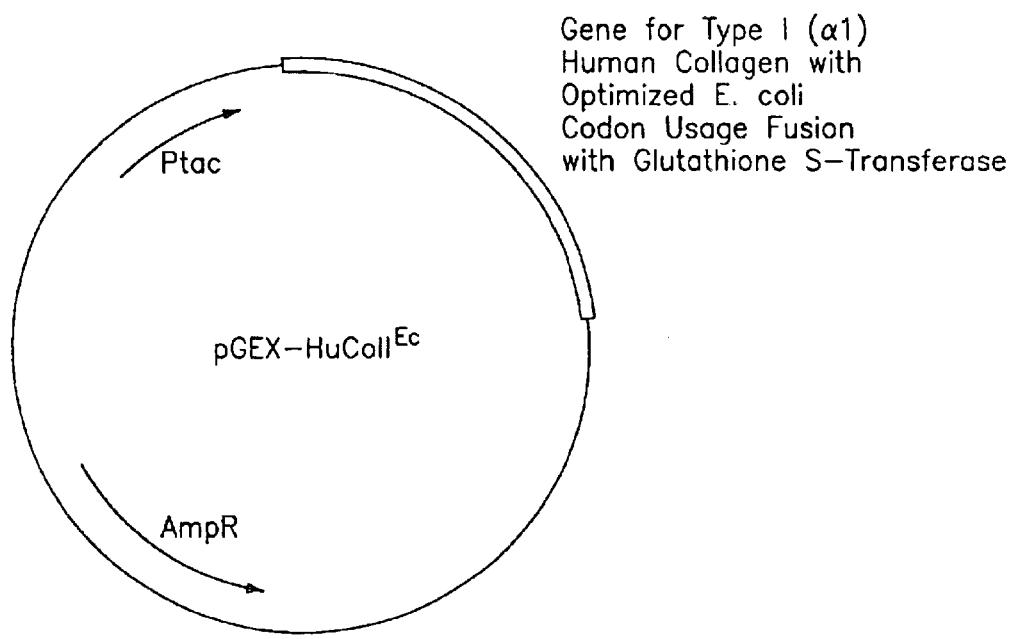
FIG. 78 is a plasmid map illustrating pGEX-HuColl$^{Ec}$ containing the gene for a fusion between glutathione S-transferase and Type I (α1) human collagen with optimized E. coli codon usage.

Hydroxyproline Incorporation Into Proteins In *E. coli* Under Proline Starvation Conditions Seven plasmids, pGEX-4T.1 (FIG. 73), pTrc-TGF (FIG. 74), pMal-C2 (FIG. 1), pTrc-FN (FIG. 75), pTrc-FN-TGF (FIG. 76), pTrc-FN-Bmp (FIG. 77) and pGEX-HuColl$^{Ec}$, each separately containing genes encoding the following proteins: glutathione S-transferase (GST), the mature human TGF-β1 polypeptide (TGF-β1), mannose-binding protein (MBP), a 70 kDA fragment of human fibronectin (FN), a fusion of FN and TGF-β1 (FN-TGF-β1), a fusion of FN and human bone morphogenic protein 2A (FN-BMP-2A), and a fusion of GST and collagen (GST-Coll), were used individually to transform proline auxotrophic E. coli strain JM109 (F-). Transformation cultures were plated on LB agar containing 100 μg/ml ampicillin. After overnight incubation at 37° C., a single colony from a fresh transformation plate was used to inoculate 5 ml of LB media containing 400 mg ampicillin. After overnight growth at 37° C., this culture was centrifuged, the supernatant discarded, and the cell pellet washed twice with 5 ml of M9 medium (1× M9 salts, 0.5% glucose, 1 mM MgCl$_2$, 0.01% thiamine, 200 μg/ml glycine, 200 μg/ml alanine, 100 μg/ml of the other anino acids except proline, and 400 μg/ml ampicillin). The cells were finally resuspended in 5 ml of M9 medium. After incubation with shaking at 37° C. for 30 minutes, trans-4-hydroxyproline was added to 40 mM, NaCl to 0.5 M, and isopropyl-B-D-thiogalactopyyranoside to 1.5 mM. In certain cultures one of these additions was not made, as indicated in the labels for the lanes of the gels. After addition, incubation with shaking at 37° C. was continued. After 4 hours, the cultures were centrifuged, the supernatants discarded, and the cell pellets resuspended in SDS-PAGE sample buffer (300 mM Tris (pH6.8)/0.5% SDS/10% glycerol/0.4M β-mercapthoethanol/0.2% bromophenol blue) to 15 OD600 nm AU/ml, placed in boiling water bath for five minutes, and electrophoresed in denaturing polyacrylaminde gels. Proteins in the gels were visualized by staining with Coomassie Blue R250. The results of the gels are depicted in scans shown in FIGS. 57–59. The scans relating to GST, TGF-β1, MBP, FN, FN-TGF-β1, and FN-BMP-2A (FIGS. 57 and 58) show three lanes relating to each peptide, i.e., one lane indicating +NaCl/+Hyp wherein NaCl (hyperosmotic) and trans-4-hydroxyproline are present; one lane indicating –NaCl wherein trans-4-hydroxyproline is present but NaCl is not; and one lane indicating –Hyp which is +NaCl but absent trans-4-hydroxyproline. Asterisks on the scans mark protein bands which correspond to the expressed target protein. The instances in which target protein was expressed all involve +NaCl in connection with +Hyp thus demonstrating +NaCl and +Hyp dependence.

Figure 59:
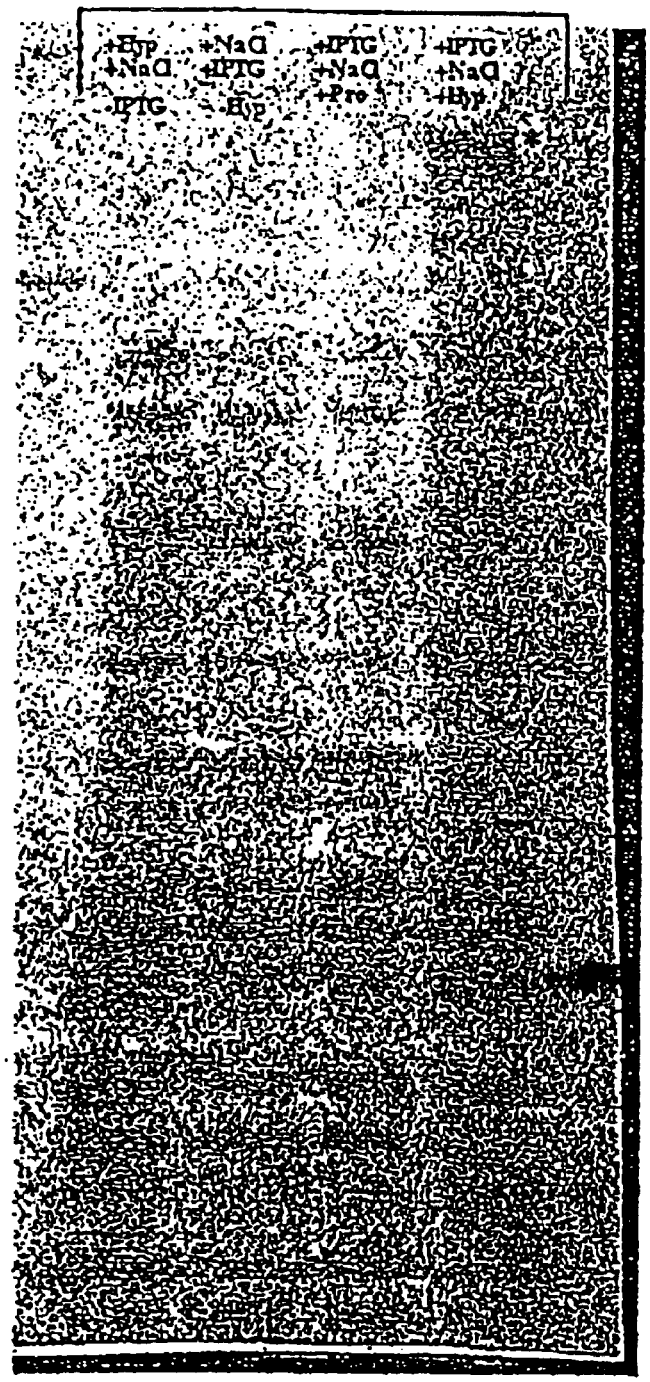
FIG. 59 depicts a gel showing expression of GST-ColI under specified conditions.

The scan shown in FIG. 59 relating to GST-collagen shows four lanes relating to GSTColl, i.e., one lane indicating +Hyp/+NaCl/–IPTG wherein trans-4-hydroxyproline and NaCl are present but IPTG (the protein expression inducer) is not and since there is no inducer, there is no target protein band; one lane indicating +NaCl/+IPTG/–Hyp wherein NaCl and IPTG are present but trans-4-hydroxyproline is not and, since trans-4-hydroxyproline is not present no target protein band is evident; one lane indicating +NaCl/+Pro/+IPTG wherein NaCl, proline and IPTG are present, but since the target protein is not stable when it contains proline, there is no target protein band; and one lane designated +IPTG/+NaCl/+Hyp wherein IPTG, NaCl and trans-4-hydroxyproline are present and since the protein is stabilized by the presence of trans-4-hydroxyproline an asterisk marked protein band is evident.

EXAMPLE 17

Hydroxyproline Incorporation into a Collagen-like Peptide in E. coli.

Figure 60:
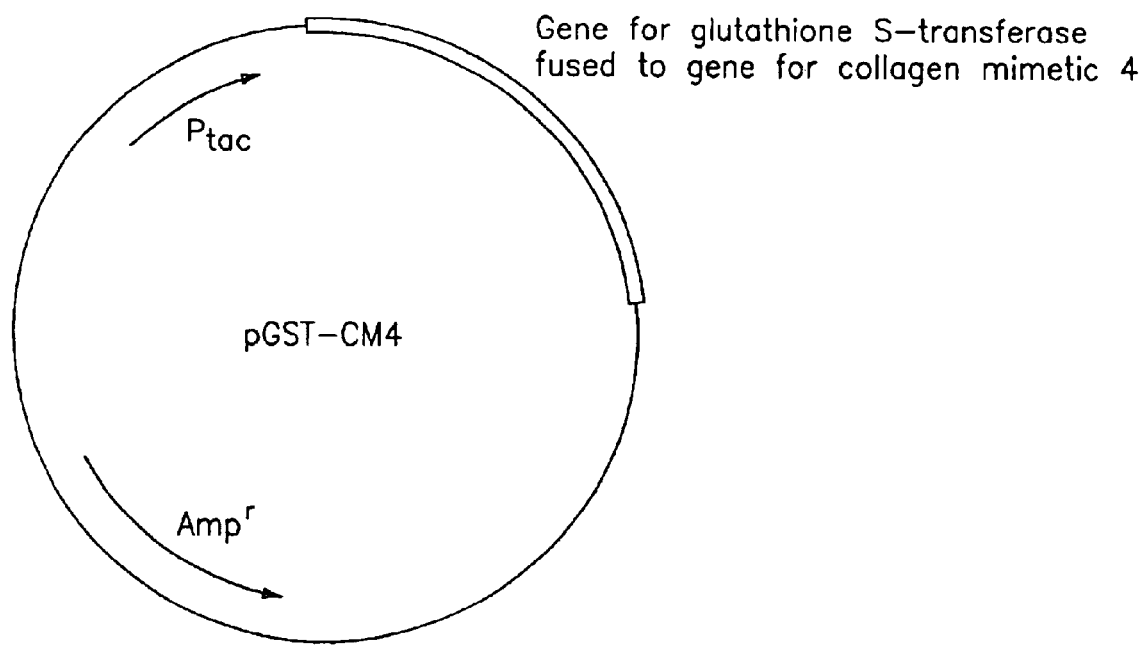
FIG. 60 depicts a plasmid map of pGST-CM4 containing the gene for glutathione S-transferase fused to the gene for collagen mimetic 4.

A plasmid (pGST-CM4, FIG. 60) containing the gene for collagen mimetic 4 (CM4, FIG. 61) (SEQ. ID. NO. 39) genetically linked to the 3' end of the gene for S. japonicum glutathione S-transferase was used to transform by electroporation proline auxotrophic E. coli strain JM109 (F-). Transformation cultures were plated on LB agar containing 100 μg/ml ampicillin. After overnight incubation at 37° C., a single colony from a fresh transformation plate was used to inoculate 5 ml of LB media containing 100 μg/ml ampicillin. After overnight growth at 37° C., 500 μl of this culture was centrifuged, the supernatent discarded, and the cell pellet washed once with 500 μl of M9 medium (1× M9 salts, 0.5% glucose, 1 mM MgCl$_2$, 0.01% thiamine, 200 μg/ml glycine, 200 μg/ml alanine, 100 μg/ml of the other amino acids except proline, and 400 μg/ml ampicillin). The cells were finally suspended in 5 ml of M9 medium containing 10 μm/ml proline and 2 ml of this was used to inoculate 30 ml of M9 medium containing 10 μg/ml proline. After incubation with shaking at 37° C. for 8 hours, the culture was centrifuged and the cell pellet washed once with M9 medium containing 5 μg/ml proline. The pellet was resuspended in 15 ml of M9 medium containing 5 μg/ml of proline and this culture was used to inoculate 1 L of M9 medium containing 5 μg/ml of proline. This culture was grown for 18 hours at 37° C. to proline starvation. At this time, the culture was centrifuged, the cells washed once with M9 medium (with no proline), and the cells resuspended in 1 L of M9 medium containing 80 mM hydroxyproline, 0.5M NaCl, and 1.5 mM isopropyl-β-D-thiogalactopyranoside. Incubation was continued at 37° C. with shaking for 22 hours. The cultures were centrifuged and the cell pellets stored at –20° C. until processed further.

EXAMPLE 18

Proline Incorporation into a Collagen-like Peptide in E. coli

A plasmid (pGST-CM4, FIG. 60) containing the gene for collagen mimetic 4 (CM4, FIG. 61) (SEQ. ID. NO. 39) genetically linked to the 3' end of the gene for S. japonicum glutathione S-transferase was used to transform by electroporation proline auxotrophic E. coli strain JM109 (F-). Transformation cultures were plated on LB agar containing 100 μg/ml ampicillin. After overnight incubation at 37° C., a single colony from a fresh transformation plate was used to inoculate 5 ml of LB media containing 100 μg/ml ampicillin. After overnight growth at 37° C., 500 μl of this culture was centrifuged, the supernatant discarded, and the cell pellet washed once with 500 μl of M9 medium (1× M9 salts, 0.5% glucose, 1 mM MgCl$_2$, 0.01% thiamine, 200 μg/ml glycine, 200 μg/ml alanine, 100 μg/ml of the other amino acids except proline, and 400 μg/mL ampicillin). The cells were finally resuspended in 5 ml of M9 medium containing 10 μg/ml proline and 2 ml of this was used to inoculate 30 ml of M9 medium containing 10 μg/ml proline. This culture was incubated with shaling at 37° C. for 8 hours. The culture was centrifuged and the cell pellet washed once with M9 medium containing 5 μg/ml proline. The pellet was resuspended in 15 ml of M9 medium containing 5 μg/ml of proline and this culture was used to inoculate 1 L of M9 medium containing 5 μg/ml of proline. This culture was grown for 18 hours at 37° C. to proline starvation. At this time, the culture was centrifuged, the cells washed once with M9 medium (with no proline), and finally the cells were resuspended in 1 L of M9 medium containing 2.5 mM proline, 0.5 M NaCl, and 1.5 mM isopropyl-p-β-thiogalactopyranoside. Incubation was continued at 37° C. with shaking for 22 hours. The cultures were then centrifuged and the cell pellets stored at –20° C. until processed further.

EXAMPLE 19

Purification of Hydroxyproline-contaiig Collagen-like Peptide from *E. coli*

Figure 62B:
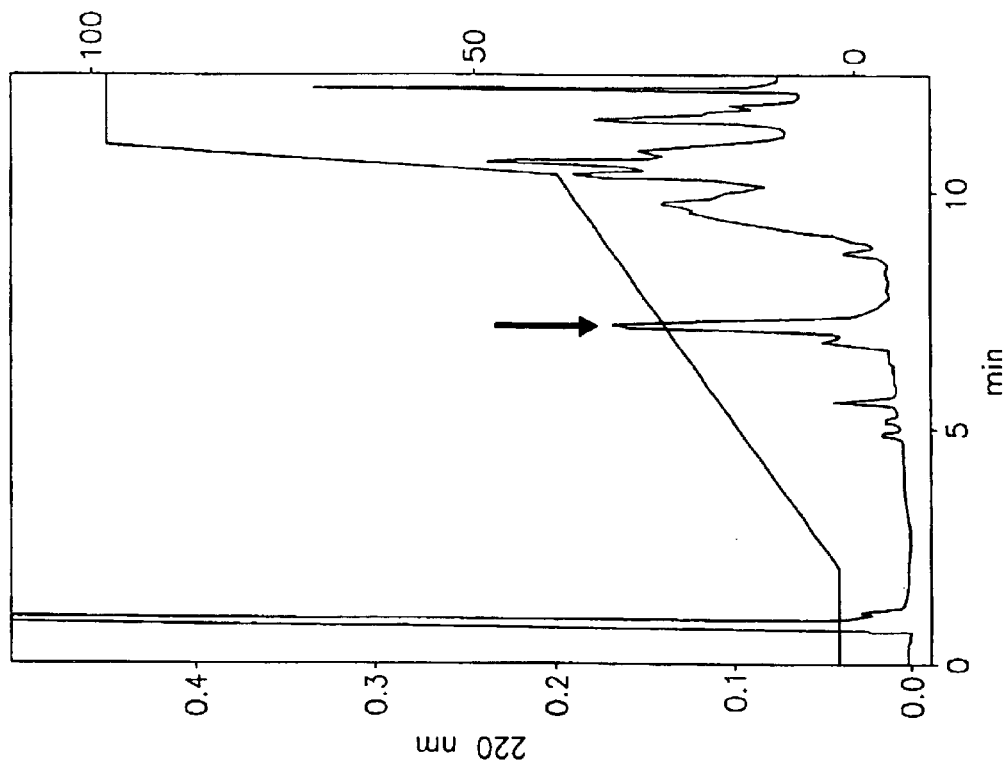
FIG. 62B depicts a chromatogram of the elution of proline-containing collagen mimetic 4 from a Poros RP2 column. The arrow indicates the peak containing proline containing collagen mimetic 4.
Figure 62A:
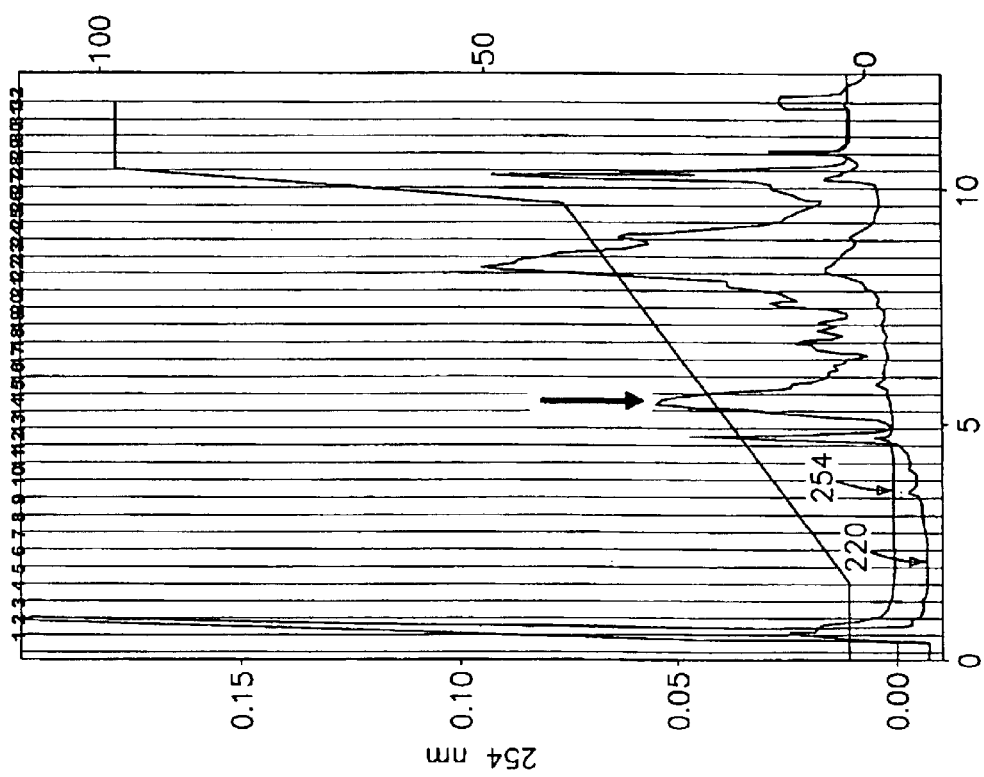
FIG. 62A depicts a chromatogram of the elution of hydroxyproline containing collagen mimetic 4 from a Poros RP2 column. The arrow indicates the peak containing hydroxyproline containing collagen mimetic 4.

The cell pellet from a 1 L fermentation culture prepared as described in Example 17 above, was resuspended in 20 ml of Dulbecco's phosphate buffered saline (pH 7.1) (PBS) containing 1 mM EDTA, 100 μM PMSF, 0.5 μg/ml E64, and 0.7 μg/ml pepstatin (resuspension buffer). The cells were lysed by twice passing through a French press. Following lysis, the suspension was centrifuged for 30 minutes at 30,000×g. The supernatant was discarded and the pellet washed once with 5 ml of resuspension buffer containing 1 M urea and 0.5% Triton X100 followed by one wash with 7 ml of resuspension buffer without urea or Triton X100. The pellet was finally resuspended in 5 ml of 6M guanidine hydrochloride in Dulbecco's phosphate buffered saline (pH7.1) containing 1 mM EDTA and 2 mM β-mercaptoethanol and sonicated on ice for 3×60 seconds (microtip, power=3.5, Heat Systems XL-2020 model sonicator). The sonicated suspension was incubated at 4° C. for 18 hours and then centrifuged at 14,000 rpm in a microcentrifuge. The supernatent (6 ml) was dialyzed (10,000 MWCO) against 4×4 L of distilled water at 4° C. The contents of the dialysis tubing were transferred to a 150 ml round bottom flask and lyophilized to dryness. The residue (~30 mg) was dissolved in 3 ml of 700% formic acid and 40 mg of cyanogen bromide was added. The flask was flushed once with nitrogen, evacuated, and allowed to stir for 18 hours at room temperature. The contents of the flask were taken to dryness in vacuo at room temperature, the residue resuspended in 5 ml of distilled water and evaporated to dryness again. This was repeated 2 times. The residue was finally dissolved in 2 ml of 0.2% trifluoroacetic acid (TFA). The trinfluoroacetic acid-soluble material was applied in 100 μl aliquots to a Poros R2 column (4.6 mm×100 mm) running at 5 ml/min. with a starting buffer of 98% 0.1% trifluoroacetic acid in water/2% 0.1% TFA in acetonitrile. The hydroxyproline-containing protein was eluted with of gradient of 2% 0.1% TFA/acetonitrile to 40% 0.1% TFA/acetonitrile over 25 column volumes (FIG. 62A). The collagen-mimetic eluted between 18 and 23% 0.1% TFA/acetonitrile. FIG. 62A is a chromatogram of the elution of hydroxyproline containing CM4 from a Poros RP2 column (available from Perseptive Biosystems, Framingham, Mass.). The arrow indicates the peak containing hydroxyproline containing CM4. Fractions were assayed by SDS-PAGE and collagen mimetic-containing fractions were pooled and lyophilized. Lyophilized material was stored at –20° C.

EXAMPLE 20

Purification of Proline-containing Collagen-like Peptide from *E. coli*

The cell pellet from a 500 ml fermentation culture prepared as described in Example 18 above, was resuspended in 20 ml of Dulbecco's phosphate buffered saline (pH 7.1) (PBS) containing 10 mM EDTA, 100 μM PMSF, 0.5 μg/ml E64, and 0.06 μg/ml aprotinin. Lysozyme (2 mg) was added and the suspension incubated at 4° C. for 60 minutes. The suspension was sonicated for 5×60 seconds (microtip, power=3.5, Heat Systems XL-2020 model sonicator). The sonicated suspension was centrifuged at 20,000×g for 15 minutes. The supernatent was adjusted to 1% Triton X100 and incubated for 30 minutes at room temperature with 7 ml of glutathione sepharose 4B pre-equilibrated in PBS. The suspension was centrifuged at 500 rpm for 3 minutes. The supernatent decanted, and the resin washed 3 times with 8 ml of PBS. Bound proteins were eluted with 3 aliquots (2 ml each, 10 minutes gentle rocking at room temperature) of 10 mM glutathione in 50 mM Tris (pH 8.0). Eluants were combined and dialyzed (10,000 MWCO) against 3×4 L of distilled water at 4° C. The contents of the dialysis tubing were transferred to a 150 ml round bottom flask and lyophilized to dryness. The residue was dissolved in 3 ml of 70% formic acid and 4 mg of cyanogen bromide was added. The flask was flushed once with nitrogen, evacuated, and allowed to stir for 18 hours at room temperature. The contents of the flask were taken to dryness in vacuo at room temperature, the residue resuspended in 5 ml of distilled water, and evaporated to dryness again. This was repeated 2 times. The residue was finally dissolved in 2 ml of 0.2% trifluoroacctic acid (TFA). The trifluoroacetic acid-soluble material was applied in 100 μl aliquots to a Poros R2 column (4:6 mm×100 mm) running at 5 ml/min. with a staring buffer of 98% 0.1% trifluoroacetic acid in water/2% 0.1% TFA in acetonitrile. Bound protein was eluted with of gradient of 2% 0.1% TFA/acetonitrile to 40% 0.1% TFA/acetonitrile over 25 column volumes (FIG. 62B). The collagen-mimetic eluted between 24 and 27% 0.1% TFA/acetonitrile. FIG. 62B is a chromatogram of the elution of proline containing CM4 from a Poros RP2 column. The arrow indicates the peak containing proline containing CM4. Fractions were assayed by SDS-PAGE and collagen mimetic-containing fractions were pooled and lyophilized. Lyophilized material was stored at –20° C.

EXAMPLE 21

Figure 63A:
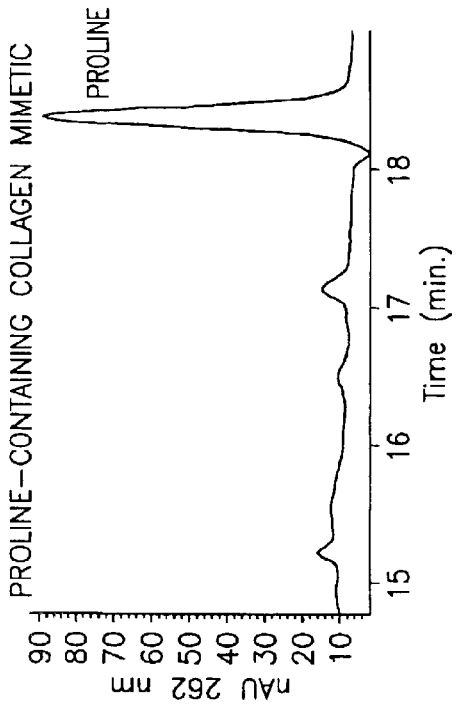
FIG. 63A depicts a chromatogram of a proline amino acid standard (250 pmol).
Figure 63B:
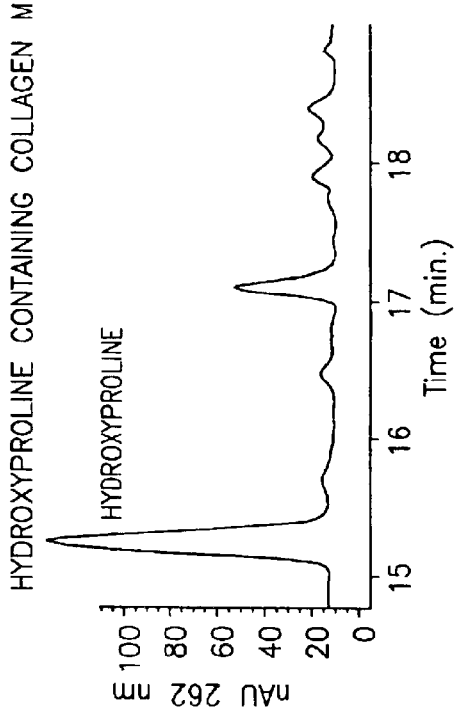
FIG. 63B depicts a chromatogram of a hydroxyproline amino acid standard (250 pmol).
Figure 63C:
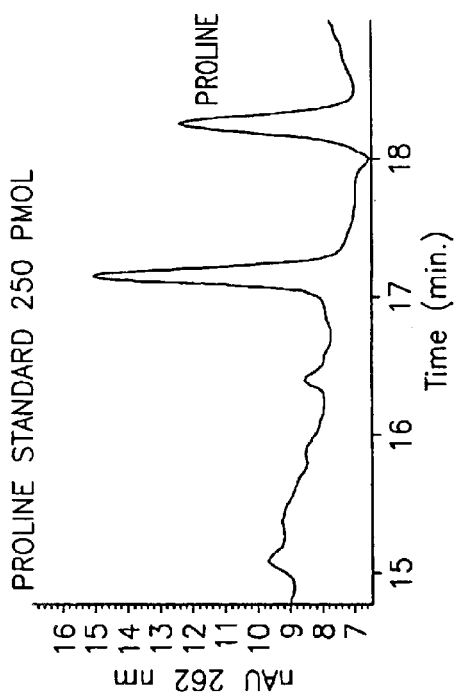
FIG. 63C depicts an amino acid analysis chromatogram of the hydrolysis of proline containing collagen mimetic 4.
Figure 63D:
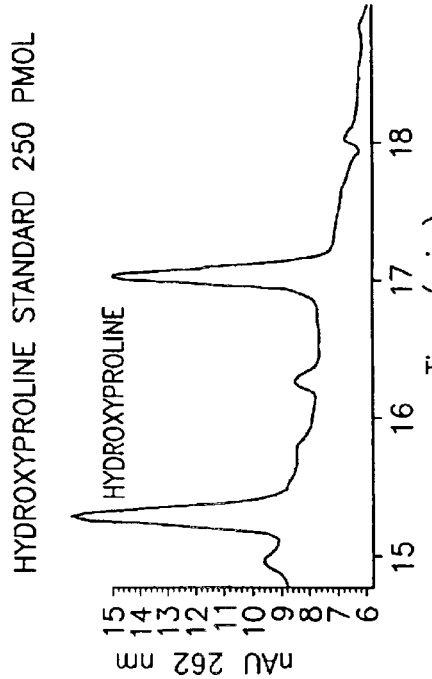
FIG. 63D depicts an amino acid analysis chromatogram of the hydrolysis of hydroxyproline containing collagen mimetic 4.

Amino Acid Analysis of Hydroxyproline-containing Collagen Mimetic and Proline-containing Collagen Mimetic Approximately 30 μg of purified hydroxyproline-containing collagen mimetic and proline-containing collagen mimetic prepared as described in Examples 19 and 20, respectively, were dissolved in 250 μl of 6N hydrochloric acid in glass ampules. The ampules were flushed two times with nitrogen, sealed under vacuum, and incubated at 110° C. for 23 hours. Following hydrolysis, samples were removed from the ampules and taken to dryness in vacuo. The samples were dissolved in 15 μl of 0.1N hydrochloric acid and subjected to amino acid analysis on a Hewlett Packard AminoQuant 1090 amino acid analyzer utilizing standard OPA and FMOC derivitization chemistry. Examples of the results of the amino acid analysis that illustrate the region of the chromatogrms where the secondary amino acids (proline and hydroxyproline) elute are shown in FIGS. 63A through 63D. These Figures also show chromatograms of proline and hydroxyproline amino acid standards. More particularly, FIG. 63A, depicts a chromatogram of a proline amino acid standard (250 pmol). *indicates a contaminating peak; FIG. 63B depicts a chromatogram of a hydroxyproline amino acid standard (250 pool). *indicates a contaminating peak. FIG. 63C depicts an amino analysis chromatogram of the hydrolysis of proline-containing CM4. Only the region of the chromatogram where proline and hydroxyproline elute is shown. *indicates a contaminating peak. FIG. 63D depicts an amino acid analysis chromatogram of the hydrolysis of hydroxyproline-containing CM4. Only the region of the chromatogram where proline and hydroxyproline elute is shown. *indicates a contaminating peak.

EXAMPLE 22

Determination of Proline Starvation Conditions for *E. coli* (Strain JM109 (F-))

Figure 64:
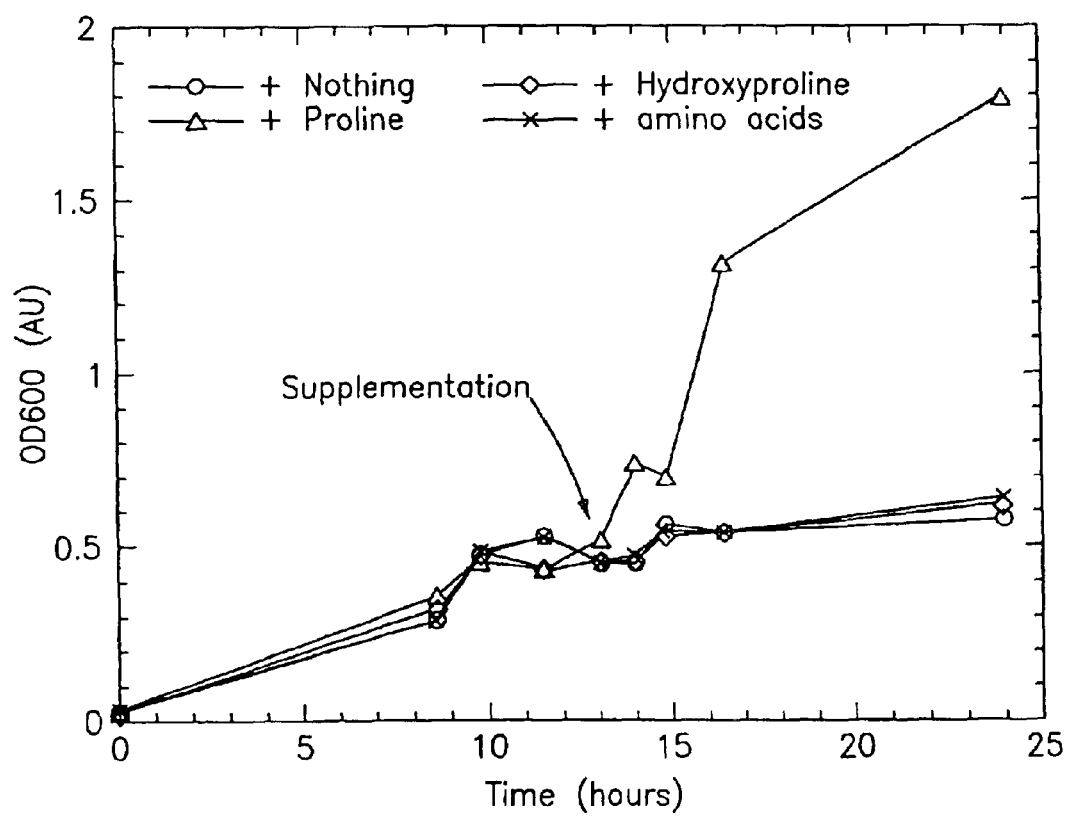
FIG. 64 is a graph of OD600 versus time for cultures of E. coli JM109 (F-) grown to plateau and then supplemented with various amino acids.

A plasmid (pGST-CM4, FIG. 60) containing the gene for collagen mimetic 4 (CM4, FIG. 61) genetically linked to the 3' end of the gene for *S. japonicum* glutathione S-transferase was used to transform by electroporation proline auxotrophic *E. coli* strain JM109 (F-). Transformation cultures were plated on LB agar containing 100 µg/ml ampicillin. After overnight incubation at 37° C., a single colony from a fresh transformation plate was used to inoculate 2 ml of M9 media (1× M9 salts, 0.5% glucose, 1 mM MgCl$_2$, 0.01% thiamine, 200 µg/ml glycine, 200 µg/ml alanine, 100 µg/ml of the other amino acids except proline, and 200 µg/ml carbenicillin) and containing 20 µg/ml proline. After growth at 37° C. with shaking for 8 hours, 1.5 ml was used to inoculate 27 ml of M9 media containing 45 µg/ml proline. After incubation at 37° C. with shaking for 7 hours, the culture was centrifuged, the cell pellet washed with 7 ml of M9 media with no proline, and finally resuspended in 17 ml of M9 media with no proline. This culture was used to inoculate four 35 ml cultures of M9 media containing 4 µg/ml proline at an OD600 of 0.028. Cultures were incubated with shaking at 37° C. and the OD600 monitored. After 13.5 hours growth, the OD600 had plateaued. At this time, one culture was supplemented with proline at 15 µg/ml, one with hydroxyproline at 15 µg/ml, one with all of the amino acids at 15 µg/ml except proline and hydroxyproline, and one culture with nothing. Incubation was continued and the OD600 monitored for a total of 24 hours. FIG. 64 is a graph of OD600 vs. time for cultures of JM109 (F-) grown to plateau and then supplemented with various amino acids. The point at which the cultures were supplemented is indicated with an arrow. Proline starvation is evident since only the culture supplemented with proline continued to grow past plateau.

EXAMPLE 23

Hydroxyproline Incorporation Into Type I (α1) Collagen in *E. coli*

Figure 65:
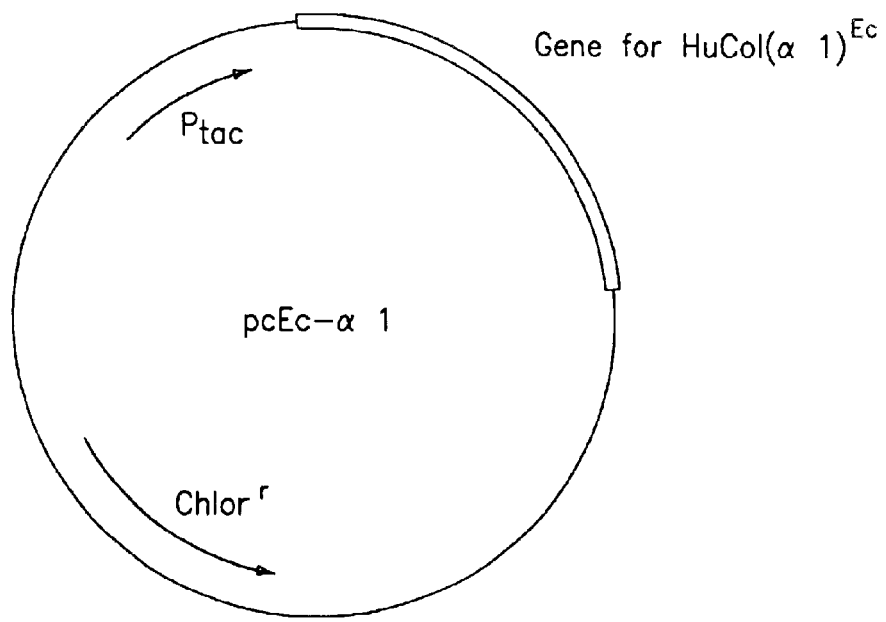
FIG. 65 depicts a plasmid map of pcEc-α1 containing the gene for HuCol(α1)$^{Ec}$.

A plasmid (pHuCol(α1)$^{Ec}$, FIG. 65) containing the gene for Type I (α1) collagen with optimized *E. coli* codon usage (FIG. 39A–39E) (SEQ. ID. NO. 19) under control of the tac promoter and containing the gene for chloramphenicol resistance was used to transform by electroporation proline auxotrophic *E. coli* strain JM109 (F-). Transformation cultures were plated on LB agar containing 20 µg/ml chloramphenicol. After overnight incubation at 37° C., a single colony from a fresh transformation plate was used to inoculate 100 ml of LB media containing 20 µg/ml chloramphenicol. This culture was grown to an OD600nm of 0.5 and 100 µl aliquots transferred to 1.5 ml tubes. The tubes were stored at –80° C. For expression, a tube was thawed on ice and used to inoculate 25 ml of LB media containing 20 µg/ml chloramphenicol. After overnight growth at 37° C., a four ml aliquot was withdrawn, centrifuged, the cell pellet washed once with 1 ml of 2×YT media containing 20 µg/ml chloramphenicol, and the washed cells used to inoculate 1 L of 2×YT medium containing 20 µg/ml chloramphenicol. This culture was grown at 37° C. to an OD600nm of 0.8. The culture was centrifuged and the cell pellet washed once with 100 ml of M9 medium (1× M9 salts, 0.5% glucose, 1 mM MgCl$_2$, 0.01% thiamine, 200 µg/ml glycine, 200 µg/ml alanine, 100 µg/ml of the other amino acids except proline, and 20 µg/ml chloramphenicol). The cells were resuspended in 910 ml of M9 medium (1× M9 salts, 0.5% glucose, 1 mM MgCl$_2$, 0.01% thiamine, 200 µg/ml glycine, 200 µg/ml alanine, 100 µg/ml of the other amino acids except proline, and 20 µg/ml chlorarnphenicol) and allowed to grow at 37° C. for 30 minutes. NaCl (80 ml of 5 M), hydroxyproline (7.5 ml of 2M), and IPTG (500 µl of 1 M) were added and growth continued for 3 hours. Cells were harvested by centrifugation and stored at –20° C.

EXAMPLE 24

Hydroxyproline Incorporation Into Type I (α2) in *E. coli*

Figure 66:
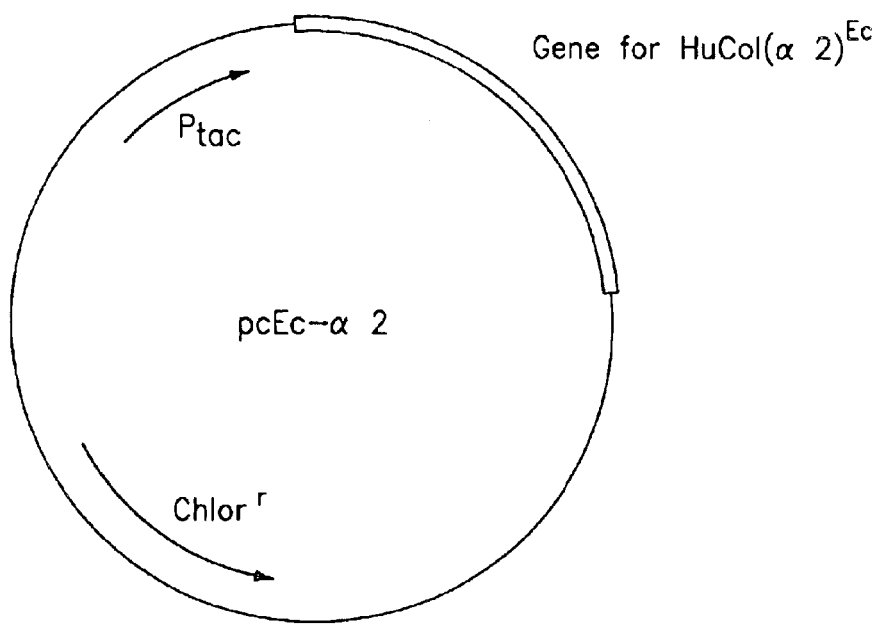
FIG. 66 depicts a plasmid map of pcEc-α2 containing the gene for HuCol(α2)$^{Ec}$

A plasmid (pHuCol(α2)$^{Ec}$, FIG. 66) containing the gene for Type I (α2) collagen with optimized *E. coli* codon usage (FIG. 50A–50E) (SEQ. ID. NO. 31) under control of the tac promoter and containing the gene for chloramphenicol resistance was used to transform by electroporation proline auxotrophic *E. coli* strain JM109 (F-). Transformation cultures were plated on LB agar containing 20 µg/ml chloramphenicol. After overnight incubation at 37° C., a single colony from a fresh transformation plate was used to inoculate 100 ml of LB media containing 20 µg/ml chloramphenicol. This culture was grown to an OD600nm of 0.5 and 100 µl aliquots transferred to 1.5 ml tubes. The tubes were stored at –80° C. For expression, a tube was thawed on ice and used to inoculate 25 ml of LB media containing 20 µg/ml chloramphenicol. After overnight growth at 37° C., a four ml aliquot was withdrawn, centrifuged, the cell pellet washed once with 1 ml of 2×YT media containing 20 µg/ml chloramphenicol, and the washed cells used to inoculate 1 L of 2×YT medium containing 20 µg/ml chloramphenicol. This culture was grown at 37° C. to an OD600nm of 0.8. The culture was centrifuged and the cell pellet washed once with 100 ml of M9 mediurn (1× M9 salts, 0.5% glucose, 1 mM MgCl$_2$, 0.01% thiamine, 200 µg/ml glycine, 200 µg/ml alanine, 100 µµg/ml of the other amino acids except proline, and 20 µg/ml chloramphenicol). The cells were resuspended in 910 ml of M9 medium (1× M9 salts, 0.5% glucose, 1 mM MgCl$_2$, 0.01% thiamine, 200 µg/ml glycine, 200 µg/ml alanine, 100 µg/ml of the other amino acids except proline, and 20 µg/ml chloramphenicol) and allowed to grow at 37° C. for 30 minutes. NaCl (80 ml of 5 M), hydroxyproline (7.5 ml of 2M), and IPTG (500 µl of 1 M) were added and growth continued for 3 hours. Cells were harvested by centrifugation and stored at –20° C.

EXAMPLE 25

Hydroxyproline Incorporation Into a C-termiinal Fragment of Type I (α1) Collagen in *E. coli*

Figure 67:
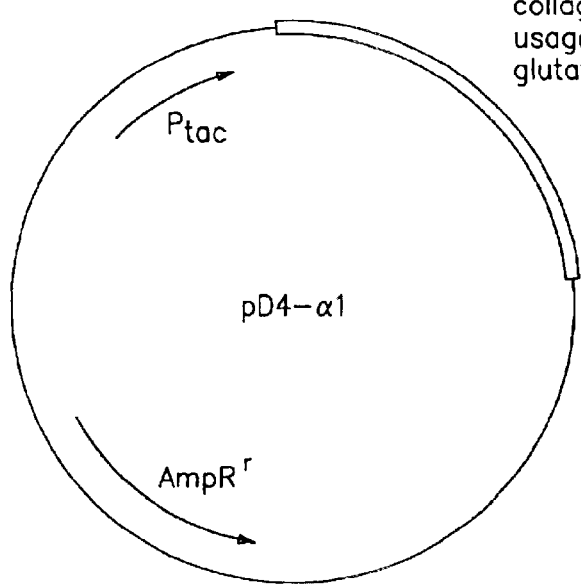
FIG. 67 depicts a plasmid map of pD4-α1 containing the gene for a 219 amino acid C-terminal fragment of Type I (α1) human collagen with optimized E. coli codon usage fused to the gene for glutathione S-tansferase.

A plasmid (pD4-α1, FIG. 67) encoding the gene for the carboxy terminal 219 amino acids of human Type I (α1) collagen with optimized *E. coli* codon usage fused to the 3'-end of the gene for glutathione S-transferase and under control of the tac promoter and containing the gene for ampicillin resistance was used to transform by electroporation proline auxotrophic *E. coli* strain JM109 (F-). Transformation cultures were plated on LB agar containing 100 µg/ml ampicillin. After overnight incubation at 37° C., a single colony from a fresh transformation plate was used to inoculate 100 ml of LB media containing 100 µg/ml ampicillin. This culture was grown to an OD600nm of 0.5 and 100 µl aliquots transferred to 1.5 ml tubes. The tubes were stored at –80° C. For expression, a tube was thawed on ice and used to inoculate 25 ml of LB media containing 400 µg/ml ampicillin. After overnight growth at 37° C., a four ml aliquot was withdrawn, centrifuged, the cell pellet washed once with 1 ml of 2×YT media containing 400 µg/ml ampicillin, and the washed cells used to inoculate 1 L of 2×YT medium containing 400 µg/ml ampicillin. This culture was grown at 37° C. to an OD600nm of 0.8. The culture was centrifuged and the cell pellet washed once with 100 ml of M9 medium (1× M9 salts, 0.5% glucose, 1 mM MgCl$_2$, 0.01% thiamine, 200 µg/ml glycine, 200 µg/ml alanine, 100 µg/ml of the other amino acids except proline, and 400 µµg/ml ampicillin). The cells were resuspended in 910 ml of M9 medium (1× M9 salts, 0.5% glucose, 1 mM MgCl$_2$, 0.01% thiamine, 200 µg/ml glycine, 200 µg/ml alanine, 100 µg/ml of the other amino acids except proline, and 400 µg/ml ampicillin) and allowed to grow at 37° C. for 30 minutes. NaCl (80 ml of 5 M), hydroxyproline (7.5 ml of 2M), and IPTG (500 µl of 1 M) were added and growth continued for 3 hours. Cells were harvested by centrifugation and stored at ~20° C.

EXAMPLE 26

Figure 68:
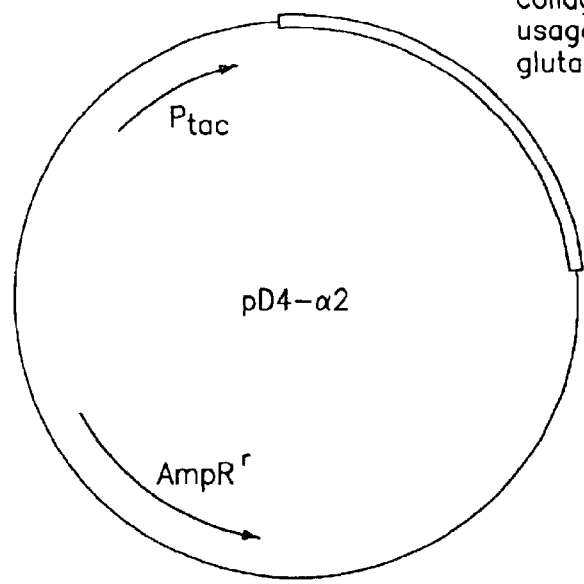
FIG. 68 depicts a plasmid map of pD4-α2 containing the gene for a 207 amino acid C-terminal fragment of Type I (α2) human collagen with optimized E. coli codon usage fused to the gene for glutathione S-transferase.

Hydroxyproline Incorporation Into a C-terminal Fragment of Type I (α2) Collagen in E. coli A plasmid (pD4-α2, FIG. 68) encoding the gene for the carboxy terminal 219 amino acids of human Type I (α2) collagen with optimized E. coli codon usage as constructed in accordance with Example 14A fused to the 3'-end of the gene for glutathione S-transferase and under control of the tac promoter and containing the gene for ampicillin resistance was used to transform by electroporation proline auxotrophic E. coli strain JM109 (F-). Transformation cultures were plated on LB agar containing 100 µg/ml ampicillin. After overnight incubation at 37° C., a single colony from a fresh transformation plate was used to inoculate 100 ml of LB media containing 100 µg/ml ampicillin. This culture was grown to an OD600 nm of 0.5 and 100 µl aliquots transferred to 1.5 ml tubes. The tubes were stored at ~80° C. For expression, a tube was thawed on ice and used to inoculate 25 ml of LB media containing 400 µg/ml ampicillin. After overnight growth at 37° C., a four ml aliquot was withdrawn, centrifuged, the cell pellet washed once with 1 ml of 2×YT media containing 400 µg/ml ampicillin, and the washed cells used to inoculate 1 L of 2×YT medium containing 400 µg/ml ampicillin. This culture was grown at 37° C. to an OD600nm of 0.8. The culture was centrifuged and the cell pellet washed once-with 100 ml of M9 medium (1× M9 salts, 0.5% glucose, 1 mM MgCl$_2$, 0.01% thiamine, 200 µg/ml glycine, 200 µg/ml alanine, 100 µg/ml of the other amino acids except proline, and 400 µg/ml ampicillin). The cells were resuspended in 910 ml of M9 medium (1× M9 salts, 0.5% glucose, 1 mM MgCl$_2$, 0.01% thiamine, 200 µg/ml glycine, 200 µg/ml alanine, 100 µg/ml of the other amino acids except proline, and 400 µg/ml ampicillin) and allowed to grow at 37° C. for 30 minutes. NaCl (80 ml of 5 M), hydroxyproline (7.5 ml of 2M), and IPTG (500 µl of 1 M) were added and growth continued for 3 hours. Cells were harvested by centrifugation and stored at −200° C.

EXAMPLE 27

Purification of Hydroxyproline-containing C-terminal Fragment of Type I (α1) Collagen Cell paste harvested from a 1 L culture grown as in Example 25 was resuspended in 30 ml of lysis buffer (2M urea, 137 mM NaCl, 2.7mM KCl, 4.3 mM Na$_2$HPO$_4$, 1.4 mM KH$_2$PO$_4$, 10 mM EDTA, 10 mM βME, 0.1% Triton X-100, pH 7.4) at 4° C. Lysozyme (chicken egg white) was added to 100 µg/ml and the solution incubated at 4° C. for 30 minutes. The solution was passed twice through a cell disruption press (SLM Instruments, Rochester, N.Y.) and then centrifuged at 30,000×g for 30 minutes. The pellet was resuspended in 30 ml of 50 mM Tris-HCl, pH 7.6, centrifuged at 30,000×g for 30 minutes, and the pellet solubilized in 25 ml of solubilization buffer (8M urea, 137 mM NaCl, 2.7 mM KCl, 4.3 mM Na$_2$HPO$_4$, 1.4 mM KH2PO$_4$, 5 mM EDTA, 5 mM βME). The solution was centrifuged at 30,000×g for 30 minutes and supematent dialyzed against two changes of 4 L of distilled water at 4° C. Following dialysis, the entire mixture was lyophilized. The lyophilized solid was dissolved in 0.1M HCl in a flask with stirring. After addition of a 5-fold excess of crystalline BrCN, the flask was evacuated and filled with nitrogen. Cleavage was allowed to proceed for 24 hrs, at which time the solvent was removed in vacuo. The residue was dissolved in 0.1% trifluoroacetic acid (TFA) and purified by reverse-phase HPLC using a Vydac C4 RP-HPLC column (10×250 mm, 5µ300 Å) on a BioCad Sprint system (Perceptive Biosystems, Framingham, Mass.). Hydroxyproline-containing D4 protein was eluted with a gradient of 15–40% acetonitrile/0.1% TFA over a 45 minute period. Protein D4-α1 eluted at 26% acetonitrile/0.1% TFA.

EXAMPLE 28

Purification of Hydroxyproline-ontaining C-terminal Fragment of Type I (α2) Collagen Cell paste harvested from a 1 L culture grown as in Example 26 was resuspended in 30 ml of lysis buffer (2M urea, 137 mM NaCl, 2.7 mM KCl, 4.3 mM Na$_2$HPO$_4$, 1.4 mM KH$_2$PO$_4$, 10 mM EDTA, 10 mM βME, 0.1% Triton X-100, pH 7.4) at 4° C. Lysozyme (chicken egg white) was added to 100 µg/ml and the solution incubated at 4° C. for 30 minutes. The solution was passed twice through a cell disruption press (SLM Instruments, Rochester, N.Y.) and then centrifuged at 30,000×g for 30 minutes. The pellet was resuspended in 30 ml of 50 mM Tris-HCl, pH 7.6, centrifuged at 30,000×g for 30 minutes, and the pellet solubilized in 25 ml of solubilization buffer (8M urea, 137 mM NaCl, 2.7 mM KCl, 4.3 mM Na$_2$HPO$_4$, 1.4 mM KH$_2$PO$_4$, 5 mM EDTA, 5 mM βME). The solution was centrifuged at 30,00×g for 30 minutes and supematent dialyzed against two changes of 4 L of distilled water at 4° C. Following,dialysis, the entire mixture was lyophilized. The lyophilized solid was dissolved in 0.1M HCl in a flask with stirring. After addition of a 5-fold excess of crystalline BrCN, the flask was evacuated and filled with nitrogen. Cleavage was allowed to proceed for 24 hrs, at which time the solvent was removed in vacuo. The residue was dissolved in 0.1% trifluoroacetic acid (TFA) and purified by reverse-phase HPLC using a Vydac C4 RP-HPLC column (10×250 mm, 5µ, 300 Å) on a BioCad Sprint system (Perceptive Biosystems, Framingham, Mass.). Hydroxyproline-containing D4 protein was eluted with a gradient of 15–40% acetonitrile/0.1% TFA over a 45 minute period. Protein D4-α2 eluted at 25% acetonitrile/0.1% TFA.

EXAMPLE 29

Figure 70:
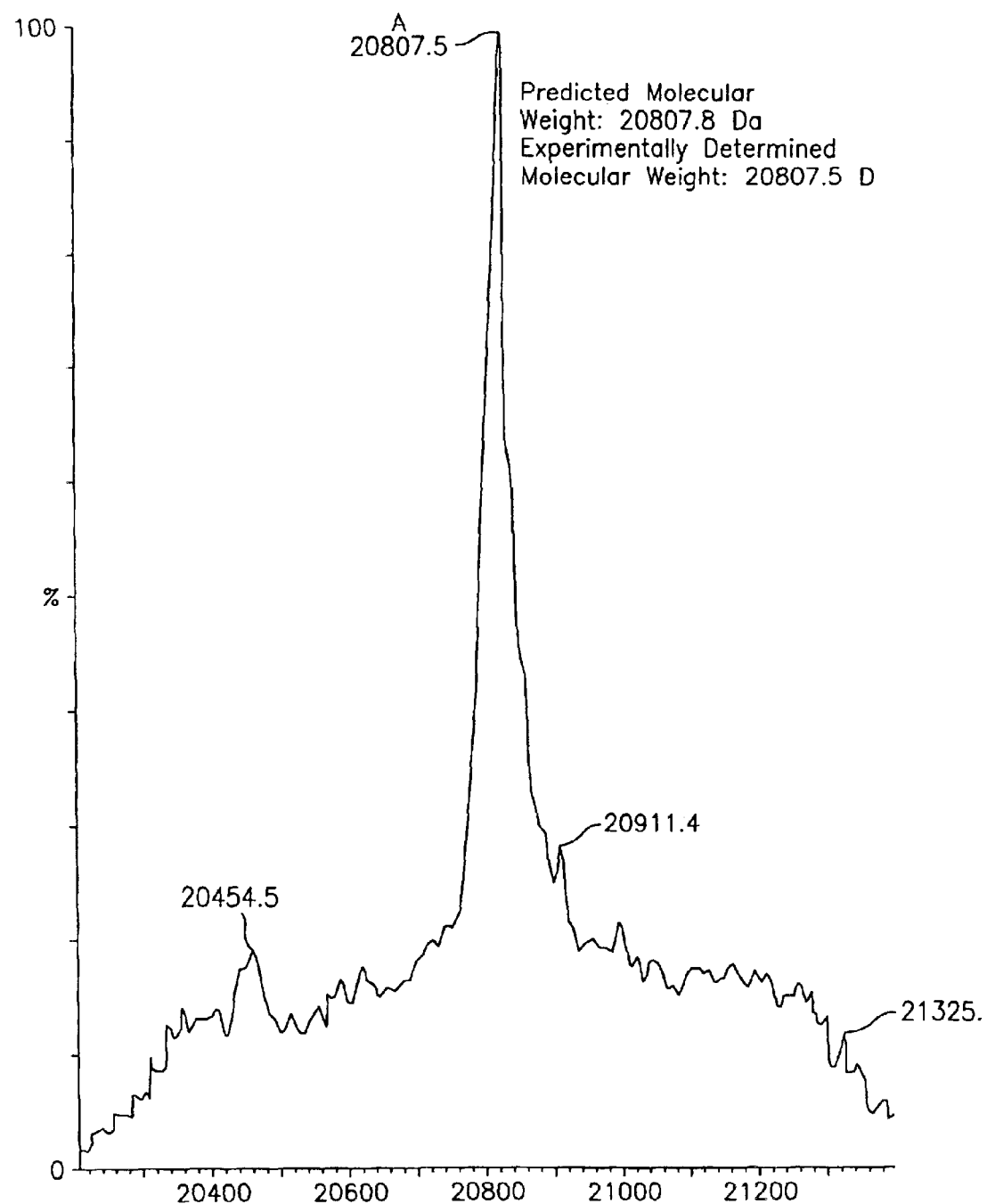
FIG. 70 depicts the mass spectrum of hydroxyproline containing D4-α1.

Amino Acid Composition Analysis of Hydroxyproline-containing C-terminal Fragment of Type I (α1) Collagen Protein D4-α1 (10 µg) purified as in Example 27 was taken to dryness in vacuo in a 1.5 ml microcentrifuge tube. A sample was subjected to amino acid analysis at the W. M. Keck Foundation Biotechnology Resource Laboratory (New Haven, Conn.) on an Applied Biosystems sequencer equipped with an on-line HPLC system. The experimentally determined sequence of the first 13 amino acids (SEQ. ID. NO. 41) and the sequence predicted from the DNA sequence (SEQ. ID. NO. 42) are shown in FIG. 69. A sample of protein D4-α1 was subjected to mass spectral analysis on a VG Biotech BIO-Q quadrople analyzer at M-Scan, Inc. (West Chester, Pa.). The mass spectrum and the predicted molecular weight of protein D4-α1 if it contained 100% hydroxyproline in lieu of proline are given in FIG. 70. The predicted molecular weight of protein D4-α1 containing 100% hydroxyproline in lieu of proline is 20807.8 Da. The experimentally determined molecular weight was 20807.5 Da. chloroform/isoamyl alcohol. After ethanol precipitation, the pellet was resuspended in 10 μL of TE buffer (10 mM Tris HCl (pH 8.0), 1 mM EDTA). Resuspended pellet 4 μL of was ligated overnight at 16° C. with agarose gel-purified EcoRI/Hind III digested pBSKS+ vector (1 μg) using T4 DNA ligase (100 units). One half of the transformation mixture was transformed by heat shock into DH5α cells and 100 μL of the 1.0 mL transformation mixture was plated on Luria Broth (LB) agar plates containing 70 μg/mL ampicillin. Plates were incubated overnight at 37° C. Ampicillin resistant colonies (6–12) were picked and grown overnight in LB media containing 70 μg/mL ampicillin. Plasmid DNA was isolated from each culture by Wizard Minipreps (Promega Corporation, Madison Wis.) and screened for the presence of the approximately 120 base pair insert by digestion with EcoRI and Hind III and running the digestion products on agarose electrophoresis gels. Clones with inserts were confirmed by standard dideoxy termination DNA sequencing. The correct clone was named pBSN4-1.

Oligos N4-3 (SEQ. ID. NO.49) and N4-4 (SEQ. ID. NO.50) FIG. 81) were synthesized, purified, annealed, extended, and cloned into pBSKS+ following exactly the same procedure given above for oligos N4-1 and N4-2. The resulting plasmid was named pBSN4-2A. To clone together the sections of the collagen gene from pBSN4-1 and pBSN4-2A, plasmid pBSN4-1 (1 μg) was digested for 2 hours at 37° C. with Apa L1 and Hind III. The digested vector was purified by agarose gel electrophoresis. Plasmid pBSN4-2A (3 μg) was digested for 2 hours at 37° C. with Apa L1 and Hind III and the insert purified by agarose gel electrophoresis. Apa L1/Hind II-digested pBSN4-1 was ligated with this insert overnight at 16° C. with T4 DNA ligase. One half of the ligation mixture was transformed into DH5α cells and 1/10 of the transformation mixture was plated on LB agar plates containing 70 μg/ml ampicillin. After overnight incubation at 37° C., ampicillin-resistant clones were picked and screened for the presence of insert DNA as described above. Clones were confirmed by dideoxy termination sequencing. The correct clone was named pBSN4-2.

SEQUENCE LISTING (1) GENERAL INFORMATION:

(iii) NUMBER OF SEQUENCES: 50

(2) INFORMATION FOR SEQ ID NO: 1:

(i) SEQUENCE CHARACTERISTICS:
      (A) LENGTH: 3170 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
CAGCTGTCTT ATGGCTATGA TGAGAAATCA ACCGGAGGAA TTTCCGTGCC TGGCCCCATG      60

GGTCCCTCTG GTCCTCGTGG TCTCCCTGGC CCCCCTGGTG CACCTGGTCC CCAAGGCTTC     120

CAAGGTCCCC CTGGTGAGCC TGGCGAGCCT GGAGCTTCAG GTCCCATGGG TCCCCGAGGT     180

CCCCCAGGTC CCCCTGGAAA GAATGGAGAT GATGGGGAAG CTGGAAAACC TGGTCGTCCT     240

GGTGAGCGTG GGCCTCCTGG GCCTCAGGGT GCTCGAGGAT TGCCCGGAAC AGCTGGCCTC     300

CCTGGAATGA AGGGACACAG AGGTTTCAGT GGTTTGGATG GTGCCAAGGG AGATGCTGGT     360

CCTGCTGGTC CTAAGGGTGA GCCTGGCAGC CCTGGTGAAA ATGGAGCTCC TGGTCAGATG     420

GGCCCCCGTG GCCTGCCTGG TGAGAGAGGT CGCCCTGGAG CCCCTGGCCC TGCTGGTGCT     480

CGTGGAAATG ATGGTGCTAC TGGTGCTGCC GGGCCCCCTG GTCCCACCGG CCCCGCTGGT     540

CCTCCTGGCT TCCCTGGTGC TGTTGGTGCT AAGGGTGAAG CTGGTCCCCA AGGGCCCCGA     600

GGCTCTGAAG GTCCCCAGGG TGTGCGTGGT GAGCCTGGCC CCCCTGGCCC TGCTGGTGCT     660

GCTGGCCCTG CTGGAAACCC TGGTGCTGAT GGACAGCCTG GTGCTAAAGG TGCCAATGGT     720

GCTCCTGGTA TTGCTGGTGC TCCTGGCTTC CCTGGTGCCC GAGGCCCCTC TGGACCCCAG     780

GGCCCCGGCG GCCCTCCTGG TCCCAAGGGT AACAGCGGTG AACCTGGTGC TCCTGGCAGC     840
```

-continued

| | | | | | |
|---|---|---|---|---|---|
| AAAGGAGACA | CTGGTGCTAA | GGGAGAGCCT | GGCCCTGTTG | GTGTTCAAGG | ACCCCCTGGC | 900 |
| CCTGCTGGAG | AGGAAGGAAA | GCGAGGAGCT | CGAGGTGAAC | CCGGACCCAC | TGGCCTGCCC | 960 |
| GGACCCCCTG | GCGAGCGTGG | TGGACCTGGT | AGCCGTGGTT | TCCCTGGCGC | AGATGGTGTT | 1020 |
| GCTGGTCCCA | AGGGTCCCGC | TGGTGAACGT | GGTTCTCCTG | GCCCCGCTGG | CCCCAAAGGA | 1080 |
| TCTCCTGGTG | AAGCTGGTCG | TCCCGGTGAA | GCTGGTCTGC | CTGGTGCCAA | GGGTCTGACT | 1140 |
| GGAAGCCCTG | GCAGCCCTGG | TCCTGATGGC | AAAACTGGCC | CCCCTGGTCC | CGCCGGTCAA | 1200 |
| GATGGTCGCC | CCGGACCCCC | AGGCCCACCT | GGTGCCCGTG | GTCAGGCTGG | TGTGATGGGA | 1260 |
| TTCCCTGGAC | CTAAAGGTGC | TGCTGGAGAG | CCCGGCAAGG | CTGGAGAGCG | AGGTGTTCCC | 1320 |
| GGACCCCCTG | GCGCTGTCGG | TCCTGCTGGC | AAAGATGGAG | AGGCTGGAGC | TCAGGGACCC | 1380 |
| CCTGGCCCTG | CTGGTCCCGC | TGGCGAGAGA | GGTGAACAAG | GCCCTGCTGG | CTCCCCCGGA | 1440 |
| TTCCAGGGTC | TCCCTGGTCC | TGCTGGTCCA | CCAGGTGAAG | CAGGCAAACC | TGGTGAACAG | 1500 |
| GGTGTTCCTG | GAGACCTTGG | CGCCCCTGGC | CCCTCTGGAG | CAAGAGGCGA | GAGAGGTTTC | 1560 |
| CCTGGCGAGC | GTGGTGTGCA | AGGTCCCCCT | GGTCCTGCTG | GACCCCGAGG | GGCCAACGGT | 1620 |
| GCTCCCGGCA | ACGATGGTGC | TAAGGGTGAT | GCTGGTGCCC | CTGGAGCTCC | CGGTAGCCAG | 1680 |
| GGCGCCCCTG | GCCTTCAGGG | AATGCCTGGT | GAACGTGGTG | CAGCTGGTCT | TCCAGGGCCT | 1740 |
| AAGGGTGACA | GAGGTGATGC | TGGTCCCAAA | GGTGCTGATG | GCTCTCCTGG | CAAAGATGGC | 1800 |
| GTCCGTGGTC | TGACCGGCCC | CATTGGTCCT | CCTGGCCCTG | CTGGTGCCCC | TGGTGACAAG | 1860 |
| GGTGAAAGTG | GTCCCAGCGG | CCCTGCTGGT | CCCACTGGAG | CTCGTGGTGC | CCCCGGAGAC | 1920 |
| CGTGGTGAGC | CTGGTCCCCC | CGGCCCTGCT | GGCTTTGCTG | GCCCCCCTGG | TGCTGACGGC | 1980 |
| CAACCTGGTG | CTAAAGGCGA | ACCTGGTGAT | GCTGGTGCCA | AGGCGATGC | TGGTCCCCCT | 2040 |
| GGGCCTGCCG | GACCCGCTGG | ACCCCCTGGC | CCCATTGGTA | ATGTTGGTGC | TCCTGGAGCC | 2100 |
| AAAGGTGCTC | GGGCAGCGCT | GGTCCCCCTG | GTGCTACTGG | TTTCCCTGGT | GCTGCTGGCC | 2160 |
| GAGTCGGTCC | TCCTGGCCCC | TCTGGAAATG | CTGGACCCCC | TGGCCCTCCT | GGTCCTGCTG | 2220 |
| GCAAAGAAGG | CGGCAAAGGT | CCCCGTGGTG | AGACTGGCCC | TGCTGGACGT | CCTGGTGAAG | 2280 |
| TTGGTCCCCC | TGGTCCCCCT | GGCCCTGCTG | GCGAGAAAGG | ATCCCTGGT | GCTGATGGTC | 2340 |
| CTGCTGGTGC | TCCTGGTACT | CCCGGGCCTC | AAGGTATTGC | TGGACAGCGT | GGTGTGGTCG | 2400 |
| GCCTGCCTGG | TCAGAGAGGA | GAGAGAGGCT | TCCCTGGTCT | TCCTGGCCCC | TCTGGTGAAC | 2460 |
| CTGGCAAACA | AGGTCCCTCT | GGAGCAAGTG | GTGAACGTGG | TCCCCCCGGT | CCCATGGGCC | 2520 |
| CCCCTGGATT | GGCTGGACCC | CCTGGTGAAT | CTGGACGTGA | GGGGCTCCT | GCTGCCGAAG | 2580 |
| GTTCCCCTGG | ACGAGACGGT | TCTCCTGGCG | CCAAGGGTGA | CCGTGGTGAG | ACCGGCCCCG | 2640 |
| CTGGACCCCC | TGGTGCTCCT | GGTGCTCCTG | GTGCCCCTGG | CCCCGTTGGC | CCTGCTGGCA | 2700 |
| AGAGTGGTGA | TCGTGGTGAG | ACTGGTCCTG | CTGGTCCCGC | CGGTCCCGTC | GGCCCCGCTG | 2760 |
| GCGCCCGTGG | CCCCGCCGGA | CCCCAAGGCC | CCCGTGGTGA | CAAGGGTGAG | ACAGGCGAAC | 2820 |
| AGGGCGACAG | AGGCATAAAG | GGTCACCGTG | GCTTCTCTGG | CCTCCAGGGT | CCCCCTGGCC | 2880 |
| CTCCTGGCTC | TCCTGGTGAA | CAAGGTCCCT | CTGGAGCCTC | TGGTCCTGCT | GGTCCCCGAG | 2940 |
| GTCCCCCTGG | CTCTGCTGGT | GCTCCTGGCA | AAGATGGACT | CAACGGTCTC | CCTGGCCCCA | 3000 |
| TTGGGCCCCC | TGGTCCTCGC | GGTCGCACTG | GTGATGCTGG | TCCTGTTGGT | CCCCCCGGCC | 3060 |
| CTCCTGGACC | TCCTGGTCCC | CCTGGTCCTC | CCAGCGCTGG | TTTCGACTTC | AGCTTCCTCC | 3120 |
| CCCAGCCACC | TCAAGAGAAG | GCTCACGATG | GTGGCCGCTA | CTACCGGGCT | | 3170 |

(2) INFORMATION FOR SEQ ID NO: 2:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

```
CAGCTGTCTT ATGGCTATGA TGAGAAATCA ACCGGAGGAA TTTCCGTGCC TGGCCCCATG      60

GGTCCCTCTG GTCCTCGTGG TCTCCCTGGC CCCCCTGGTG CACCTGGTCC CCAAGGCTTC     120

CAAGGTCCCC CTGGTGAGCC TGGCGAGCCT GGAGCTTCAG GTCCCATGGG TCCCCGAGGT     180

CCCCCAGGTC CCCCTGGAAA GAATGGAGAT GATGGGGAAG CTGGAAAACC TGGTCGTCCT     240
```

(2) INFORMATION FOR SEQ ID NO: 3:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
GGATCCATGG GGCTCGCTGG CCCACCGGGC GAACCGGGTC CGCCAGGCCC GAAAGGTCCG      60

CGTGGCGATA GCGGGCTCCC GGGCGATTCC TAATGGATCC                           100
```

(2) INFORMATION FOR SEQ ID NO: 4:

(i) SEQUENCE CHARACTERISTICS:
        (A) LENGTH: 21 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 4:

```
Gly Leu Ala Gly Pro Pro Gly Glu Pro Gly Pro Pro Gly Pro Lys Gly
1               5                  10                  15

Pro Arg Gly Asp Ser
            20
```

(2) INFORMATION FOR SEQ ID NO: 5:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
CAGCGGGCCA GGAAGAAGAA TAAGAACTGC CGGCGCCACT CGCTCTATGT GGACTTCAGC      60

GATGTGGGCT GGAATGACTG GATTGTGGCC CCACCAGGCT ACCAGGCCTT CTACTGCCAT     120

GGGGACTGCC CCTTTCCACT GGCTGACCAC CTCAACTCAA CCAACCATGC CATTGTGCAG     180

ACCCTGGTCA ATTCTGTCAA TTCCAGTATC CCCAAAGCCT GTTGTGTGCC CACTGAACTG     240

AGTGCCATCT CCATGCTGTA CCTGGATGAG TATGATAAGG TGGTACTGAA AAATTATCAG     300
```

-continued

```
GAGATGGTAG TAGAGGGATG TGGGTGCCGC                                        330
```

(2) INFORMATION FOR SEQ ID NO: 6:

(i) SEQUENCE CHARACTERISTICS:
        (A) LENGTH: 1169 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 6:

```
Gln Leu Ser Tyr Gly Tyr Asp Glu Lys Ser Thr Gly Gly Ile Ser Val
  1               5                  10                  15

Pro Gly Pro Met Gly Pro Ser Gly Pro Arg Gly Leu Pro Gly Pro Pro
             20                  25                  30

Gly Ala Pro Gly Pro Gln Gly Phe Gln Gly Pro Pro Gly Glu Pro Gly
         35                  40                  45

Glu Pro Gly Ala Ser Gly Pro Met Gly Pro Arg Gly Pro Pro Gly Pro
 50                  55                  60

Pro Gly Lys Asn Gly Asp Asp Gly Glu Ala Gly Lys Pro Gly Arg Pro
 65                  70                  75                  80

Gly Glu Arg Gly Pro Pro Gly Pro Gln Gly Ala Arg Gly Leu Pro Gly
             85                  90                  95

Thr Ala Gly Leu Pro Gly Met Lys Gly His Arg Gly Phe Ser Gly Leu
            100                 105                 110

Asp Gly Ala Lys Gly Asp Ala Gly Pro Ala Gly Pro Lys Gly Glu Pro
            115                 120                 125

Gly Ser Pro Gly Glu Asn Gly Ala Pro Gly Gln Met Gly Pro Arg Gly
        130                 135                 140

Leu Pro Gly Glu Arg Gly Arg Pro Gly Ala Pro Gly Pro Ala Gly Ala
145                 150                 155                 160

Arg Gly Asn Asp Gly Ala Thr Gly Ala Ala Gly Pro Pro Gly Pro Thr
            165                 170                 175

Gly Pro Ala Gly Pro Pro Gly Phe Pro Gly Ala Val Gly Ala Lys Gly
            180                 185                 190

Glu Ala Gly Pro Gln Gly Pro Arg Gly Ser Glu Gly Pro Gln Gly Val
        195                 200                 205

Arg Gly Glu Pro Gly Pro Pro Gly Pro Ala Gly Ala Ala Gly Pro Ala
210                 215                 220

Gly Asn Pro Gly Ala Asp Gly Gln Pro Gly Ala Lys Gly Ala Asn Gly
225                 230                 235                 240

Ala Pro Gly Ile Ala Gly Ala Pro Gly Phe Pro Gly Ala Arg Gly Pro
            245                 250                 255

Ser Gly Pro Gln Gly Pro Gly Gly Pro Pro Gly Pro Lys Gly Asn Ser
        260                 265                 270

Gly Glu Pro Gly Ala Pro Gly Ser Lys Gly Asp Thr Gly Ala Lys Gly
        275                 280                 285

Glu Pro Gly Pro Val Gly Val Gln Gly Pro Pro Gly Pro Ala Gly Glu
        290                 295                 300

Glu Gly Lys Arg Gly Ala Arg Gly Glu Pro Gly Pro Thr Gly Leu Pro
305                 310                 315                 320

Gly Pro Pro Gly Glu Arg Gly Gly Pro Gly Ser Arg Gly Phe Pro Gly
            325                 330                 335

Ala Asp Gly Val Ala Gly Pro Lys Gly Pro Ala Gly Glu Arg Gly Ser
```

-continued

```
            340             345             350
Pro Gly Pro Ala Gly Pro Lys Gly Ser Pro Gly Glu Ala Gly Arg Pro
                355                 360                 365
Gly Glu Ala Gly Leu Pro Gly Ala Lys Gly Leu Thr Gly Ser Pro Gly
    370                 375                 380
Ser Pro Gly Pro Asp Gly Lys Thr Gly Pro Pro Gly Pro Ala Gly Gln
385                 390                 395                 400
Asp Gly Arg Pro Gly Pro Pro Gly Pro Pro Gly Ala Arg Gly Gln Ala
                405                 410                 415
Gly Val Met Gly Phe Pro Gly Pro Lys Gly Ala Ala Gly Glu Pro Gly
            420                 425                 430
Lys Ala Gly Glu Arg Gly Val Pro Gly Pro Pro Gly Ala Val Gly Pro
                435                 440                 445
Ala Gly Lys Asp Gly Glu Ala Gly Ala Gln Gly Pro Pro Gly Pro Ala
            450                 455                 460
Gly Pro Ala Gly Glu Arg Gly Glu Gln Gly Pro Ala Gly Ser Pro Gly
465                 470                 475                 480
Phe Gln Gly Leu Pro Gly Pro Ala Gly Pro Pro Gly Glu Ala Gly Lys
                485                 490                 495
Pro Gly Glu Gln Gly Val Pro Gly Asp Leu Gly Ala Pro Gly Pro Ser
                500                 505                 510
Gly Ala Arg Gly Glu Arg Gly Phe Pro Gly Glu Arg Gly Val Gln Gly
            515                 520                 525
Pro Pro Gly Pro Ala Gly Pro Arg Gly Ala Asn Gly Ala Pro Gly Asn
            530                 535                 540
Asp Gly Ala Lys Gly Asp Ala Gly Ala Pro Gly Ala Pro Gly Ser Gln
545                 550                 555                 560
Gly Ala Pro Gly Leu Gln Gly Met Pro Gly Glu Arg Gly Ala Ala Gly
                565                 570                 575
Leu Pro Gly Pro Lys Gly Asp Arg Gly Asp Ala Gly Pro Lys Gly Ala
                580                 585                 590
Asp Gly Ser Pro Gly Lys Asp Gly Val Arg Gly Leu Thr Gly Pro Ile
            595                 600                 605
Gly Pro Pro Gly Pro Ala Gly Ala Pro Gly Asp Lys Gly Glu Ser Gly
        610                 615                 620
Pro Ser Gly Pro Ala Gly Pro Thr Gly Ala Arg Gly Ala Pro Gly Asp
625                 630                 635                 640
Arg Gly Glu Pro Gly Pro Pro Gly Pro Ala Gly Phe Ala Gly Pro Pro
                645                 650                 655
Gly Ala Asp Gly Gln Pro Gly Ala Lys Gly Glu Pro Gly Asp Ala Gly
                660                 665                 670
Ala Lys Gly Asp Ala Gly Pro Pro Gly Pro Ala Gly Pro Ala Gly Pro
            675                 680                 685
Pro Gly Pro Ile Gly Asn Val Gly Ala Pro Gly Ala Lys Gly Ala Arg
        690                 695                 700
Gly Ser Ala Gly Pro Pro Gly Ala Thr Gly Phe Pro Gly Ala Ala Gly
705                 710                 715                 720
Arg Val Gly Pro Pro Gly Pro Ser Gly Asn Ala Gly Pro Pro Gly Pro
                725                 730                 735
Pro Gly Pro Ala Gly Lys Glu Gly Gly Lys Gly Pro Arg Gly Glu Thr
            740                 745                 750
Gly Pro Ala Gly Arg Pro Gly Glu Val Gly Pro Pro Gly Pro Pro Gly
        755                 760                 765
```

-continued

```
Pro Ala Gly Glu Lys Gly Ser Pro Gly Ala Asp Gly Pro Ala Gly Ala
    770                 775                 780
Pro Gly Thr Pro Gly Pro Gln Gly Ile Ala Gly Gln Arg Gly Val Val
785                 790                 795                 800
Gly Leu Pro Gly Gln Arg Gly Glu Arg Gly Phe Pro Gly Leu Pro Gly
                805                 810                 815
Pro Ser Gly Glu Pro Gly Lys Gln Gly Pro Ser Gly Ala Ser Gly Glu
            820                 825                 830
Arg Gly Pro Pro Gly Pro Met Gly Pro Pro Gly Leu Ala Gly Pro Pro
        835                 840                 845
Gly Glu Ser Gly Arg Glu Gly Ala Pro Ala Ala Glu Gly Ser Pro Gly
    850                 855                 860
Arg Asp Gly Ser Pro Gly Ala Lys Gly Asp Arg Gly Glu Thr Gly Pro
865                 870                 875                 880
Ala Gly Pro Pro Gly Ala Xaa Gly Ala Xaa Gly Ala Pro Gly Pro Val
                885                 890                 895
Gly Pro Ala Gly Lys Ser Gly Asp Arg Gly Glu Thr Gly Pro Ala Gly
            900                 905                 910
Pro Ala Gly Pro Val Gly Pro Ala Gly Ala Arg Gly Pro Ala Gly Pro
        915                 920                 925
Gln Gly Pro Arg Gly Asp Lys Gly Glu Thr Gly Glu Gln Gly Asp Arg
    930                 935                 940
Gly Ile Lys Gly His Arg Gly Phe Ser Gly Leu Gln Gly Pro Pro Gly
945                 950                 955                 960
Pro Pro Gly Ser Pro Gly Glu Gln Gly Pro Ser Gly Ala Ser Gly Pro
                965                 970                 975
Ala Gly Pro Arg Gly Pro Pro Gly Ser Ala Gly Ala Pro Gly Lys Asp
            980                 985                 990
Gly Leu Asn Gly Leu Pro Gly Pro Ile Gly Pro Pro Gly Pro Arg Gly
        995                 1000                1005
Arg Thr Gly Asp Ala Gly Pro Val Gly Pro Pro Gly Pro Pro Gly Pro
    1010                1015                1020
Pro Gly Pro Pro Gly Pro Pro Ser Ala Gly Phe Asp Phe Ser Phe Leu
1025                1030                1035                1040
Pro Gln Pro Pro Gln Glu Lys Ala His Asp Gly Gly Arg Tyr Tyr Arg
                1045                1050                1055
Ala Arg Ser Gln Arg Ala Arg Lys Lys Asn Lys Asn Cys Arg Arg His
            1060                1065                1070
Ser Leu Tyr Val Asp Phe Ser Asp Val Gly Trp Asn Asp Trp Ile Val
        1075                1080                1085
Ala Pro Pro Gly Tyr Gln Ala Phe Tyr Cys His Gly Asp Cys Pro Phe
    1090                1095                1100
Pro Leu Ala Asp His Leu Asn Ser Thr Asn His Ala Ile Val Gln Thr
1105                1110                1115                1120
Leu Val Asn Ser Val Asn Ser Ser Ile Pro Lys Ala Cys Cys Val Pro
                1125                1130                1135
Thr Glu Leu Ser Ala Ile Ser Met Leu Tyr Leu Asp Glu Tyr Asp Lys
            1140                1145                1150
Val Val Leu Lys Asn Tyr Gln Glu Met Val Val Glu Gly Cys Gly Cys
        1155                1160                1165
Arg
```

(2) INFORMATION FOR SEQ ID NO: 7:

(i) SEQUENCE CHARACTERISTICS:
        (A) LENGTH: 3531 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
GGGAAGGATT TCCATTTCCC AGCTGTCTTA TGGCTATGAT GAGAAATCAA CCGGAGGAAT      60
TTCCGTGCCT GGCCCCATGG GTCCCTCTGG TCCTCGTGGT CTCCCTGGCC CCCTGGTGC      120
ACCTGGTCCC CAAGGCTTCC AAGGTCCCCC TGGTGAGCCT GGCGAGCCTG GAGCTTCAGG     180
TCCCATGGGT CCCCGAGGTC CCCCAGGTCC CCTGGAAAAG AATGGAGATG ATGGGGAAGC     240
TGGAAAACCT GGTCGTCCTG GTGAGCGTGG GCCTCCTGGG CCTCAGGGTG CTCGAGGATT     300
GCCCGGAACA GCTGGCCTCC CTGGAATGAA GGGACACAGA GGTTTCAGTG GTTTGGATGG     360
TGCCAAGGGA GATGCTGGTC CTGCTGGTCC TAAGGGTGAG CCTGGCAGCC TGGTGAAAA      420
TGGAGCTCCT GGTCAGATGG GCCCCCGTGG CCTGCCTGGT GAGAGAGGTC GCCCTGGAGC     480
CCCTGGCCCT GCTGGTGCTC GTGGAAATGA TGGTGCTACT GGTGCTGCCG GGCCCCCTGG     540
TCCCACCGGC CCCGCTGGTC CTCCTGGCTT CCCTGGTGCT GTTGGTGCTA AGGGTGAAGC     600
TGGTCCCCAA GGGCCCCGAG GCTCTGAAGG TCCCCAGGGT GTGCGTGGTG AGCCTGGCCC     660
CCCTGGCCCT GCTGGTGCTG CTGGCCCTGC TGGAAACCCT GGTGCTGATG ACAGCCTGG      720
TGCTAAAGGT GCCAATGGTG CTCCTGGTAT TGCTGGTGCT CCTGGCTTCC CTGGTGCCCG     780
AGGCCCCTCT GGACCCCAGG GCCCCGGCGG CCCTCCTGGT CCCAAGGGTA ACAGCGGTGA     840
ACCTGGTGCT CCTGGCAGCA AGGAGACAC TGGTGCTAAG GGAGAGCCTG GCCCTGTTGG      900
TGTTCAAGGA CCCCCTGGCC CTGCTGGAGA GGAAGGAAAG CGAGGAGCTC GAGGTGAACC     960
CGGACCCACT GGCCTGCCCG GACCCCCTGG CGAGCGTGGT GGACCTGGTA GCCGTGGTTT    1020
CCCTGGCGCA GATGGTGTTG CTGGTCCCAA GGGTCCCGCT GGTGAACGTG GTTCTCCTGG    1080
CCCCGCTGGC CCCAAAGGAT CTCCTGGTGA AGCTGGTCGT CCCGGTGAAG CTGGTCTGCC    1140
TGGTGCCAAG GGTCTGACTG GAAGCCCTGG CAGCCCTGGT CCTGATGGCA AAACTGGCCC    1200
CCCTGGTCCC GCCGGTCAAG ATGGTCGCCC CGGACCCCCA GGCCCACCTG GTGCCCGTGG    1260
TCAGGCTGGT GTGATGGGAT CCCTGGACC TAAAGGTGCT GCTGGAGAGC CCGGCAAGGC     1320
TGGAGAGCGA GGTGTTCCCG GACCCCCTGG CGCTGTCGGT CCTGCTGGCA AGATGGAGA     1380
GGCTGGAGCT CAGGGACCCC CTGGCCCTGC TGGTCCCGCT GGCGAGAGAG GTGAACAAGG    1440
CCCTGCTGGC TCCCCCGGAT TCCAGGGTCT CCCTGGTCCT GCTGGTCCTC CAGGTGAAGC    1500
AGGCAAACCT GGTGAACAGG GTGTTCCTGG AGACCTTGGC GCCCCTGGCC CCTCTGGAGC    1560
AAGAGGCGAG AGAGGTTTCC CTGGCGAGCG TGGTGTGCAA GGTCCCCCTG GTCCTGCTGG    1620
ACCCCGAGGG GCCAACGGTG CTCCCGGCAA CGATGGTGCT AAGGGTGATG CTGGTGCCCC    1680
TGGAGCTCCC GGTAGCCAGG GCGCCCCTGG CCTTCAGGGA ATGCCTGGTG AACGTGGTGC    1740
AGCTGGTCTT CCAGGGCCTA AGGGTGACAG AGGTGATGCT GGTCCCAAAG GTGCTGATGG    1800
CTCTCCTGGC AAAGATGGCG TCCGTGGTCT GACCGGCCCC ATTGGTCCTC CTGGCCCTGC    1860
TGGTGCCCCT GGTGACAAGG GTGAAAGTGG TCCCAGCGGC CCTGCTGGTC CCACTGGAGC    1920
TCGTGGTGCC CCCGGAGACC GTGGTGAGCC TGGTCCCCCC GGCCCTGCTG GCTTTGCTGG    1980
CCCCCCTGGT GCTGACGGCC AACCTGGTGC TAAAGGCGAA CCTGGTGATG CTGGTGCCAA    2040
```

```
AGGCGATGGG TCCCCCTGGG CCTGCCGGAC CCGCTGGACC CCCTGGCCCC ATTGGTAATG    2100

TTGGTGCTCC TGGAGCCAAA GGTGCTCGCG GCAGCGCTGG TCCCCCTGGT GCTACTGGTT    2160

TCCCTGGTGC TGCTGGCCGA GTCGGTCCTC CTGGCCCCTC TGGAAATGCT GGACCCCCTG    2220

GCCCTCCTGG TCCTGCTGGC AAAGAAGGCG GCAAAGGTCC CCGTGGTGAG ACTGGCCCTG    2280

CTGGACGTCC TGGTGAAGTT GGTCCCCCTG GTCCCCCTGG CCCTGCTGGC GAGAAAGGAT    2340

CCCCTGGTGC TGATGGTCCT GCTGGTGCTC CTGGTACTCC CGGGCCTCAA GGTATTGCTG    2400

GACAGCGTGG TGTGGTCGGC CTGCCTGGTC AGAGAGGAGA GAGAGGCTTC CCTGGTCTTC    2460

CTGGCCCCTC TGGTGAACCT GGCAAACAAG GTCCCTCTGG AGCAAGTGGT GAACGTGGTC    2520

CCCCCGGTCC CATGGGCCCC CCTGGATTGG CTGGACCCCC TGGTGAATCT GGACGTGAGG    2580

GGGCTCCTGC TGCCGAAGGT TCCCCTGGAC GAGACGGTTC TCCTGGCGCC AAGGGTGACC    2640

GTGGTGAGAC CGGCCCCGCT GGACCCCCTG GTGCTCTGGT GCTCTGGTGC CCCTGGCCCC    2700

GTTGGCCCTG CTGGCAAGAG TGGTGATCGT GGTGAGACTG GTCCTGCTGG TCCCGCCGGT    2760

CCCGTCGGCC CCGCTGGCGC CCGTGGCCCC GCCGGACCCC AAGGCCCCCG TGGTGACAAG    2820

GGTGAGACAG GCGAACAGGG CGACAGAGGC ATAAAGGGTC ACCGTGGCTT CTCTGGCCTC    2880

CAGGGTCCCC CTGGCCCTCC TGGCTCTCCT GGTGAACAAG GTCCCTCTGG AGCCTCTGGT    2940

CCTGCTGGTC CCCGAGGTCC CCCTGGCTCT GCTGGTGCTC CTGGCAAAGA TGGACTCAAC    3000

GGTCTCCCTG GCCCCATTGG GCCCCCTGGT CCTCGCGGTC GCACTGGTGA TGCTGGTCCT    3060

GTTGGTCCCC CCGGCCCTCC TGGACCTCCT GGTCCCCCTG GTCCTCCCAG CGCTGGTTTC    3120

GACTTCAGCT TCCTCCCCCA GCCACCTCAA GAGAAGGCTC ACGATGGTGG CCGCTACTAC    3180

CGGGCTAGAT CCCAGCGGGC CAGGAAGAAG AATAAGAACT GCCGGCGCCA CTCGCTCTAT    3240

GTGGACTTCA GCGATGTGGG CTGGAATGAC TGGATTGTGG CCCCACCAGG CTACCAGGCC    3300

TTCTACTGCC ATGGGGACTG CCCCTTTCCA CTGGCTGACC ACCTCAACTC AACCAACCAT    3360

GCCATTGTGC AGACCCTGGT CAATTCTGTC AATTCCAGTA TCCCCAAAGC CTGTTGTGTG    3420

CCCACTGAAC TGAGTGCCAT CTCCATGCTG TACCTGGATG AGTATGATAA GGTGGTACTG    3480

AAAAATTATC AGGAGATGGT AGTAGAGGGA TGTGGGTGCC GCTAAAAGCT T             3531
```

(2) INFORMATION FOR SEQ ID NO: 8:

(i) SEQUENCE CHARACTERISTICS:
        (A) LENGTH: 1171 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 8:

```
Gln Leu Ser Tyr Gly Tyr Asp Glu Lys Ser Thr Gly Gly Ile Ser Val
1               5                  10                  15

Pro Gly Pro Met Gly Pro Ser Gly Pro Arg Gly Leu Pro Gly Pro Pro
                20                  25                  30

Gly Ala Pro Gly Pro Gln Gly Phe Gln Gly Pro Pro Gly Glu Pro Gly
            35                  40                  45

Glu Pro Gly Ala Ser Gly Pro Met Gly Pro Arg Gly Pro Pro Gly Pro
        50                  55                  60

Pro Gly Lys Asn Gly Asp Asp Gly Glu Ala Gly Lys Pro Gly Arg Pro
65                  70                  75                  80
```

-continued

```
Gly Glu Arg Gly Pro Pro Gly Pro Gln Gly Ala Arg Gly Leu Pro Gly
                85                  90                  95

Thr Ala Gly Leu Pro Gly Met Lys Gly His Arg Gly Phe Ser Gly Leu
            100                 105                 110

Asp Gly Ala Lys Gly Asp Ala Gly Pro Ala Gly Pro Lys Gly Glu Pro
            115                 120                 125

Gly Ser Pro Gly Glu Asn Gly Ala Pro Gly Gln Met Gly Pro Arg Gly
        130                 135                 140

Leu Pro Gly Glu Arg Gly Arg Pro Gly Ala Pro Gly Pro Ala Gly Ala
145                 150                 155                 160

Arg Gly Asn Asp Gly Ala Thr Gly Ala Ala Gly Pro Pro Gly Pro Thr
                165                 170                 175

Gly Pro Ala Gly Pro Pro Gly Phe Pro Gly Ala Val Gly Ala Lys Gly
            180                 185                 190

Glu Ala Gly Pro Gln Gly Pro Arg Gly Ser Glu Gly Pro Gln Gly Val
            195                 200                 205

Arg Gly Glu Pro Gly Pro Pro Gly Pro Ala Gly Ala Ala Gly Pro Ala
        210                 215                 220

Gly Asn Pro Gly Ala Asp Gly Gln Pro Gly Ala Lys Gly Ala Asn Gly
225                 230                 235                 240

Ala Pro Gly Ile Ala Gly Ala Pro Gly Phe Pro Gly Ala Arg Gly Pro
                245                 250                 255

Ser Gly Pro Gln Gly Pro Gly Gly Pro Pro Gly Pro Lys Gly Asn Ser
            260                 265                 270

Gly Glu Pro Gly Ala Pro Gly Ser Lys Gly Asp Thr Gly Ala Lys Gly
            275                 280                 285

Glu Pro Gly Pro Val Gly Val Gln Gly Pro Pro Gly Pro Ala Gly Glu
        290                 295                 300

Glu Gly Lys Arg Gly Ala Arg Gly Glu Pro Gly Pro Thr Gly Leu Pro
305                 310                 315                 320

Gly Pro Pro Gly Glu Arg Gly Gly Pro Gly Ser Arg Gly Phe Pro Gly
                325                 330                 335

Ala Asp Gly Val Ala Gly Pro Lys Gly Pro Ala Gly Glu Arg Gly Ser
            340                 345                 350

Pro Gly Pro Ala Gly Pro Lys Gly Ser Pro Gly Glu Ala Gly Arg Pro
            355                 360                 365

Gly Glu Ala Gly Leu Pro Gly Ala Lys Gly Leu Thr Gly Ser Pro Gly
        370                 375                 380

Ser Pro Gly Pro Asp Gly Lys Thr Gly Pro Pro Gly Pro Ala Gly Gln
385                 390                 395                 400

Asp Gly Arg Pro Gly Pro Pro Gly Pro Pro Gly Ala Arg Gly Gln Ala
                405                 410                 415

Gly Val Met Gly Phe Pro Gly Pro Lys Gly Ala Ala Gly Glu Pro Gly
            420                 425                 430

Lys Ala Gly Glu Arg Gly Val Pro Gly Pro Pro Gly Ala Val Gly Pro
            435                 440                 445

Ala Gly Lys Asp Gly Glu Ala Gly Ala Gln Gly Pro Pro Gly Pro Ala
        450                 455                 460

Gly Pro Ala Gly Glu Arg Gly Glu Gln Gly Pro Ala Gly Ser Pro Gly
465                 470                 475                 480

Phe Gln Gly Leu Pro Gly Pro Ala Gly Pro Pro Gly Glu Ala Gly Lys
                485                 490                 495

Pro Gly Glu Gln Gly Val Pro Gly Asp Leu Gly Ala Pro Gly Pro Ser
```

-continued

```
                500                 505                 510
Gly Ala Arg Gly Glu Arg Gly Phe Pro Gly Arg Gly Val Gln Gly
        515                 520                 525
Pro Pro Gly Pro Ala Gly Pro Arg Gly Ala Asn Gly Ala Pro Gly Asn
    530                 535                 540
Asp Gly Ala Lys Gly Asp Ala Gly Ala Pro Gly Ala Pro Gly Ser Gln
545                 550                 555                 560
Gly Ala Pro Gly Leu Gln Gly Met Pro Gly Glu Arg Gly Ala Ala Gly
                565                 570                 575
Leu Pro Gly Pro Lys Gly Asp Arg Gly Asp Ala Gly Pro Lys Gly Ala
            580                 585                 590
Asp Gly Ser Pro Gly Lys Asp Gly Val Arg Gly Leu Thr Gly Pro Ile
            595                 600                 605
Gly Pro Pro Gly Pro Ala Gly Ala Pro Gly Asp Lys Gly Glu Ser Gly
        610                 615                 620
Pro Ser Gly Pro Ala Gly Pro Thr Gly Ala Arg Gly Ala Pro Gly Asp
625                 630                 635                 640
Arg Gly Glu Pro Gly Pro Pro Gly Pro Ala Gly Phe Ala Gly Pro Pro
                645                 650                 655
Gly Ala Asp Gly Gln Pro Gly Ala Lys Gly Glu Pro Gly Asp Ala Gly
            660                 665                 670
Ala Lys Gly Asp Ala Gly Pro Pro Gly Pro Ala Gly Pro Ala Gly Pro
        675                 680                 685
Pro Gly Pro Ile Gly Asn Val Gly Ala Pro Gly Ala Lys Gly Ala Arg
        690                 695                 700
Gly Ser Ala Gly Pro Pro Gly Ala Thr Gly Phe Pro Gly Ala Ala Gly
705                 710                 715                 720
Arg Val Gly Pro Pro Gly Pro Ser Gly Asn Ala Gly Pro Pro Gly Pro
                725                 730                 735
Pro Gly Pro Ala Gly Lys Glu Gly Gly Lys Gly Pro Arg Gly Glu Thr
            740                 745                 750
Gly Pro Ala Gly Arg Pro Gly Glu Val Gly Pro Pro Gly Pro Pro Gly
        755                 760                 765
Pro Ala Gly Glu Lys Gly Ser Pro Gly Ala Asp Gly Pro Ala Gly Ala
    770                 775                 780
Pro Gly Thr Pro Gly Pro Gln Gly Ile Ala Gly Gln Arg Gly Val Val
785                 790                 795                 800
Gly Leu Pro Gly Gln Arg Gly Glu Arg Gly Phe Pro Gly Leu Pro Gly
                805                 810                 815
Pro Ser Gly Glu Pro Gly Lys Gln Gly Pro Ser Gly Ala Ser Gly Glu
            820                 825                 830
Arg Gly Pro Pro Gly Pro Met Gly Pro Pro Gly Leu Ala Gly Pro Pro
        835                 840                 845
Gly Glu Ser Gly Arg Glu Gly Ala Pro Gly Ala Glu Gly Ser Pro Gly
        850                 855                 860
Arg Asp Gly Ser Pro Gly Ala Lys Gly Asp Arg Gly Glu Thr Gly Pro
865                 870                 875                 880
Ala Gly Pro Pro Gly Ala Pro Gly Ala Pro Gly Ala Pro Gly Pro Val
                885                 890                 895
Gly Pro Ala Gly Lys Ser Gly Asp Arg Gly Glu Thr Gly Pro Ala Gly
            900                 905                 910
Pro Ala Gly Pro Val Gly Pro Ala Gly Ala Arg Gly Pro Ala Gly Pro
        915                 920                 925
```

```
Gln Gly Pro Arg Gly Asp Lys Gly Glu Thr Gly Glu Gln Gly Asp Arg
    930                 935                 940
Gly Ile Lys Gly His Arg Gly Phe Ser Gly Leu Gln Gly Pro Pro Gly
945                 950                 955                 960
Pro Pro Gly Ser Pro Gly Glu Gln Gly Pro Ser Gly Ala Ser Gly Pro
                965                 970                 975
Ala Gly Pro Arg Gly Pro Pro Gly Ser Ala Gly Ala Pro Gly Lys Asp
            980                 985                 990
Gly Leu Asn Gly Leu Pro Gly Pro Ile Gly Pro Pro Gly Pro Arg Gly
        995                 1000                1005
Arg Thr Gly Asp Ala Gly Pro Val Gly Pro Pro Gly Pro Pro Gly Pro
    1010                1015                1020
Pro Gly Pro Pro Gly Pro Ser Ala Gly Phe Asp Phe Ser Phe Leu
1025                1030                1035                1040
Pro Gln Pro Pro Gln Glu Lys Ala His Asp Gly Gly Arg Tyr Tyr Arg
                1045                1050                1055
Ala Arg Ser Ala Leu Asp Thr Asn Tyr Cys Phe Ser Ser Thr Glu Lys
            1060                1065                1070
Asn Cys Cys Val Arg Gln Leu Tyr Ile Asp Phe Arg Lys Asp Leu Gly
        1075                1080                1085
Trp Lys Trp Ile His Glu Pro Lys Gly Tyr His Ala Asn Phe Cys Leu
    1090                1095                1100
Gly Pro Cys Pro Tyr Ile Trp Ser Leu Asp Thr Gln Tyr Ser Lys Val
1105                1110                1115                1120
Leu Ala Leu Tyr Asn Gln His Asn Pro Gly Ala Ser Ala Ala Pro Cys
                1125                1130                1135
Cys Val Pro Gln Ala Leu Glu Pro Leu Pro Ile Val Tyr Tyr Val Gly
            1140                1145                1150
Arg Lys Pro Lys Val Glu Gln Leu Ser Asn Met Ile Val Arg Ser Cys
        1155                1160                1165
Lys Cys Ser
    1170

(2) INFORMATION FOR SEQ ID NO: 9:

(i) SEQUENCE CHARACTERISTICS:
        (A) LENGTH: 3541 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GGGAAGGATT TCCATTTCCC AGCTGTCTTA TGGCTATGAT GAGAAATCAA CCGGAGGAAT    60

TTCCGTGCCT GGCCCCATGG GTCCCTCTGG TCCTCGTGGT CTCCCTGGCC CCCCTGGTGC   120

ACCTGGTCCC CAAGGCTTCC AAGGTCCCCC TGGTGAGCCT GGCGAGCCTG GAGCTTCAGG   180

TCCCATGGGT CCCCGAGGTC CCCCAGGTCC CCCTGGAAAG AATGGAGATG ATGGGGAAGC   240

TGGAAAACCT GGTCGTCCTG GTGAGCGTGG GCCTCCTGGG CCTCAGGGTG CTCGAGGATT   300

GCCCGGAACA GCTGGCCTCC CTGGAATGAA GGGACACAGA GGTTTCAGTG GTTTGGATGG   360

TGCCAAGGGA GATGCTGGTC CTGCTGGTCC TAAGGGTGAG CCTGGCAGCC TGGTGAAAA    420

TGGAGCTCCT GGTCAGATGG GCCCCCGTGG CCTGCCTGGT GAGAGAGGTC GCCCTGGAGC   480

CCCTGGCCCT GCTGGTGCTC GTGGAAATGA TGGTGCTACT GGTGCTGCCG GGCCCCCTGG   540
```

```
TCCCACCGGC CCCGCTGGTC CTCCTGGCTT CCCTGGTGCT GTTGGTGCTA AGGGTGAAGC    600

TGGTCCCCAA GGGCCCCGAG GCTCTGAAGG TCCCCAGGGT GTGCGTGGTG AGCCTGGCCC    660

CCCTGGCCCT GCTGGTGCTG CTGGCCCTGC TGGAAACCCT GGTGCTGATG GACAGCCTGG    720

TGCTAAAGGT GCCAATGGTG CTCCTGGTAT TGCTGGTGCT CCTGGCTTCC CTGGTGCCCG    780

AGGCCCCTCT GGACCCCAGG GCCCCGGCGG CCCTCCTGGT CCCAAGGGTA ACAGCGGTGA    840

ACCTGGTGCT CCTGGCAGCA AGGAGACAC TGGTGCTAAG GGAGAGCCTG GCCCTGTTGG    900

TGTTCAAGGA CCCCCTGGCC CTGCTGGAGA GGAAGGAAAG CGAGGAGCTC GAGGTGAACC    960

CGGACCCACT GGCCTGCCCG ACCCCCTGG CGAGCGTGGT GGACCTGGTA GCCGTGGTTT   1020

CCCTGGCGCA GATGGTGTTG CTGGTCCCAA GGGTCCCGCT GGTGAACGTG GTTCTCCTGG   1080

CCCCGCTGGC CCCAAAGGAT CTCCTGGTGA AGCTGGTCGT CCCGGTGAAG CTGGTCTGCC   1140

TGGTGCCAAG GGTCTGACTG GAAGCCCTGG CAGCCCTGGT CCTGATGGCA AAACTGGCCC   1200

CCCTGGTCCC GCCGGTCAAG ATGGTCGCCC CGGACCCCCA GGCCCACCTG GTGCCCGTGG   1260

TCAGGCTGGT GTGATGGGAT TCCCTGGACC TAAAGGTGCT GCTGGAGAGC CCGGCAAGGC   1320

TGGAGAGCGA GGTGTTCCCG ACCCCCTGG CGCTGTCGGT CCTGCTGGCA AGATGGAGA    1380

GGCTGGAGCT CAGGGACCCC CTGGCCCTGC TGGTCCCGCT GGCGAGAGAG GTGAACAAGG   1440

CCCTGCTGGC TCCCCCGGAT TCCAGGGTCT CCCTGGTCCT GCTGGTCCTC CAGGTGAAGC   1500

AGGCAAACCT GGTGAACAGG GTGTTCCTGG AGACCTTGGC GCCCCTGGCC CCTCTGGAGC   1560

AAGAGGCGAG AGAGGTTTCC CTGGCGAGCG TGGTGTGCAA GGTCCCCCTG GTCCTGCTGG   1620

ACCCCGAGGG GCCAACGGTG CTCCCGGCAA CGATGGTGCT AAGGGTGATG CTGGTGCCCC   1680

TGGAGCTCCC GGTAGCCAGG GCGCCCCTGG CCTTCAGGGA ATGCCTGGTG AACGTGGTGC   1740

AGCTGGTCTT CCAGGGCCTA AGGGTGACAG AGGTGATGCT GGTCCCAAAG GTGCTGATGG   1800

CTCTCCTGGC AAAGATGGCG TCCGTGGTCT GACCGGCCCC ATTGGTCCTC CTGGCCCTGC   1860

TGGTGCCCCT GGTGACAAGG GTGAAAGTGG TCCCAGCGGC CCTGCTGGTC CCACTGGAGC   1920

TCGTGGTGCC CCCGGAGACC GTGGTGAGCC TGGTCCCCCC GGCCCTGCTG GCTTTGCTGG   1980

CCCCCCTGGT GCTGACGGCC AACCTGGTGC TAAAGGCGAA CCTGGTGATG CTGGTGCCAA   2040

AGGCGATGCT GGTCCCCCTG GCCTGCCGG ACCCGCTGGA CCCCCTGGCC CCATTGGTAA   2100

TGTTGGTGCT CCTGGAGCCA AGGTGCTCG CGGCAGCGCT GGTCCCCCTG GTGCTACTGG   2160

TTTCCCTGGT GCTGCTGGCC GAGTCGGTCC TCCTGGCCCC TCTGGAAATG CTGGACCCCC   2220

TGGCCCTCCT GGTCCTGCTG GCAAAGAAGG CGGCAAAGGT CCCCGTGGTG AGACTGGCCC   2280

TGCTGGACGT CCTGGTGAAG TTGGTCCCCC TGGTCCCCCT GGCCCTGCTG GCGAGAAAGG   2340

ATCCCCTGGT GCTGATGGTC CTGCTGGTGC TCCTGGTACT CCCGGGCCTC AAGGTATTGC   2400

TGGACAGCGT GGTGTGGTCG GCCTGCCTGG TCAGAGAGGA GAGAGAGGCT TCCCTGGTCT   2460

TCCTGGCCCC TCTGGTGAAC TGGCAAACA AGGTCCCTCT GGAGCAAGTG GTGAACGTGG   2520

TCCCCCCGGT CCCATGGGCC CCCTGGATT GGCTGGACCC CCTGGTGAAT CTGGACGTGA   2580

GGGGCTCCT GCTGCCGAAG GTTCCCCTGG ACGAGACGGT TCTCCTGGCG CCAAGGGTGA   2640

CCGTGGTGAG ACCGGCCCCG CTGGACCCCC TGGTGCTCCT GGTGCTCCTG GTGCCCCTGG   2700

CCCCGTTGGC CCTGCTGGCA AGAGTGGTGA TCGTGGTGAG ACTGGTCCTG CTGGTCCCGC   2760

CGGTCCCGTC GGCCCCGCTG GCGCCCGTGG CCCCGCCGGA CCCCAAGGCC CCGTGGTGA    2820

CAAGGGTGAG ACAGGCGAAC AGGGCGACAG AGGCATAAAG GGTCACCGTG GCTTCTCTGG   2880
```

-continued

```
CCTCCAGGGT CCCCCTGGCC CTCCTGGCTC TCCTGGTGAA CAAGGTCCCT CTGGAGCCTC    2940

TGGTCCTGCT GGTCCCCGAG GTCCCCCTGG CTCTGCTGGT GCTCCTGGCA AAGATGGACT    3000

CAACGGTCTC CCTGGCCCCA TTGGGCCCCC TGGTCCTCGC GGTCGCACTG GTGATGCTGG    3060

TCCTGTTGGT CCCCCCGGCC CTCCTGGACC TCCTGGTCCC CCTGGTCCTC CCAGCGCTGG    3120

TTTCGACTTC AGCTTCCTCC CCCAGCCACC TCAAGAGAAG GCTCACGATG GTGGCCGCTA    3180

CTACCGGGCT AGATCTGCCC TGGACACCAA CTATTGCTTC AGCTCCACGG AGAAGAACTG    3240

CTGCGTGCGG CAGCTGTACA TTGACTTCCG CAAGGACCTC GGCTGGAAGT GGATCCACGA    3300

GCCCAAGGGC TACCATGCCA ACTTCTGCCT CGGGCCCTGC CCCTACATTT GGAGCCTGGA    3360

CACGCAGTAC AGCAAGGTCC TGGCCCTGTA CAACCAGCAT AACCCGGGCG CCTCGGCGGC    3420

GCCGTGCTGC GTGCCGCAGG CGCTGGAGCC GCTGCCCATC GTGTACTACG TGGGCCGCAA    3480

GCCCAAGGTG GAGCAGCTGT CCAACATGAT CGTGCGCTCC TGCAAGTGCA GCTGATCTAG    3540

A                                                                    3541
```

(2) INFORMATION FOR SEQ ID NO: 10:

(i) SEQUENCE CHARACTERISTICS:
        (A) LENGTH: 1388 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 10:

```
Gln Leu Ser Tyr Gly Tyr Asp Glu Lys Ser Thr Gly Gly Ile Ser Val
1               5                   10                  15

Pro Gly Pro Met Gly Pro Ser Gly Pro Arg Gly Leu Pro Gly Pro Pro
                20                  25                  30

Gly Ala Pro Gly Pro Gln Gly Phe Gln Gly Pro Pro Gly Glu Pro Gly
            35                  40                  45

Glu Pro Gly Ala Ser Gly Pro Met Gly Pro Arg Gly Pro Pro Gly Pro
    50                  55                  60

Pro Gly Lys Asn Gly Asp Asp Gly Glu Ala Gly Lys Pro Gly Arg Pro
65                  70                  75                  80

Gly Glu Arg Gly Pro Pro Gly Pro Gln Gly Ala Arg Gly Leu Pro Gly
                85                  90                  95

Thr Ala Gly Leu Pro Gly Met Lys Gly His Arg Gly Phe Ser Gly Leu
                100                 105                 110

Asp Gly Ala Lys Gly Asp Ala Gly Pro Ala Gly Pro Lys Gly Glu Pro
            115                 120                 125

Gly Ser Pro Gly Glu Asn Gly Ala Pro Gly Gln Met Gly Pro Arg Gly
    130                 135                 140

Leu Pro Gly Glu Arg Gly Arg Pro Gly Ala Pro Gly Pro Ala Gly Ala
145                 150                 155                 160

Arg Gly Asn Asp Gly Ala Thr Gly Ala Ala Gly Pro Pro Gly Pro Thr
                165                 170                 175

Gly Pro Ala Gly Pro Pro Gly Phe Pro Gly Ala Val Gly Ala Lys Gly
            180                 185                 190

Glu Ala Gly Pro Gln Gly Pro Arg Gly Ser Glu Gly Pro Gln Gly Val
        195                 200                 205

Arg Gly Glu Pro Gly Pro Pro Gly Pro Ala Gly Ala Ala Gly Pro Ala
    210                 215                 220
```

-continued

```
Gly Asn Pro Gly Ala Asp Gly Gln Pro Gly Ala Lys Gly Asn Gly
225                 230                 235                 240

Ala Pro Gly Ile Ala Gly Ala Pro Gly Phe Pro Gly Ala Arg Gly Pro
            245                 250                 255

Ser Gly Pro Gln Gly Pro Gly Gly Pro Gly Pro Lys Gly Asn Ser
            260                 265                 270

Gly Glu Pro Gly Ala Pro Gly Ser Lys Gly Asp Thr Gly Ala Lys Gly
            275                 280                 285

Glu Pro Gly Pro Val Gly Val Gln Gly Pro Gly Pro Ala Gly Glu
        290                 295                 300

Glu Gly Lys Arg Gly Ala Arg Gly Glu Pro Gly Thr Gly Leu Pro
305                 310                 315                 320

Gly Pro Pro Gly Glu Arg Gly Pro Gly Ser Arg Gly Phe Pro Gly
                325                 330                 335

Ala Asp Gly Val Ala Gly Pro Lys Gly Pro Ala Gly Glu Arg Gly Ser
            340                 345                 350

Pro Gly Pro Ala Gly Pro Lys Gly Ser Pro Gly Glu Ala Gly Arg Pro
        355                 360                 365

Gly Glu Ala Gly Leu Pro Gly Ala Lys Gly Leu Thr Gly Ser Pro Gly
370                 375                 380

Ser Pro Gly Pro Asp Gly Lys Thr Gly Pro Pro Gly Pro Ala Gly Gln
385                 390                 395                 400

Asp Gly Arg Pro Gly Pro Gly Pro Pro Gly Ala Arg Gly Gln Ala
                405                 410                 415

Gly Val Met Gly Phe Pro Gly Pro Lys Gly Ala Ala Gly Glu Pro Gly
            420                 425                 430

Lys Ala Gly Glu Arg Gly Val Pro Gly Pro Pro Gly Ala Val Gly Pro
        435                 440                 445

Ala Gly Lys Asp Gly Glu Ala Gly Ala Gln Gly Pro Pro Gly Pro Ala
450                 455                 460

Gly Pro Ala Gly Glu Arg Gly Glu Gln Gly Pro Ala Gly Ser Pro Gly
465                 470                 475                 480

Phe Gln Gly Leu Pro Gly Pro Ala Gly Pro Pro Gly Glu Ala Gly Lys
            485                 490                 495

Pro Gly Glu Gln Gly Val Pro Gly Asp Leu Gly Ala Pro Gly Pro Ser
        500                 505                 510

Gly Ala Arg Gly Glu Arg Gly Phe Pro Gly Glu Arg Gly Val Gln Gly
            515                 520                 525

Pro Pro Gly Pro Ala Gly Pro Arg Gly Ala Asn Gly Ala Pro Gly Asn
530                 535                 540

Asp Gly Ala Lys Gly Asp Ala Gly Ala Pro Gly Ala Pro Gly Ser Gln
545                 550                 555                 560

Gly Ala Pro Gly Leu Gln Gly Met Pro Gly Glu Arg Gly Ala Ala Gly
            565                 570                 575

Leu Pro Gly Pro Lys Gly Asp Arg Gly Asp Ala Gly Pro Lys Gly Ala
        580                 585                 590

Asp Gly Ser Pro Gly Lys Asp Gly Val Arg Gly Leu Thr Gly Pro Ile
            595                 600                 605

Gly Pro Pro Gly Pro Ala Gly Ala Pro Gly Asp Lys Gly Glu Ser Gly
            610                 615                 620

Pro Ser Gly Pro Ala Gly Pro Thr Gly Ala Arg Gly Ala Pro Gly Asp
625                 630                 635                 640

Arg Gly Glu Pro Gly Pro Pro Gly Pro Ala Gly Phe Ala Gly Pro Pro
```

-continued

```
                645                 650                 655
Gly Ala Asp Gly Gln Pro Gly Ala Lys Gly Glu Pro Gly Asp Ala Gly
                660                 665                 670
Ala Lys Gly Asp Ala Gly Pro Pro Gly Pro Ala Gly Pro Ala Gly Pro
                675                 680                 685
Pro Gly Pro Ile Gly Asn Val Gly Ala Pro Gly Ala Lys Gly Ala Arg
                690                 695                 700
Gly Ser Ala Gly Pro Pro Gly Ala Thr Gly Phe Pro Gly Ala Ala Gly
705                 710                 715                 720
Arg Val Gly Pro Pro Gly Pro Ser Gly Asn Ala Gly Pro Pro Gly Pro
                725                 730                 735
Pro Gly Pro Ala Gly Lys Glu Gly Gly Lys Gly Pro Arg Gly Glu Thr
                740                 745                 750
Gly Pro Ala Gly Arg Pro Gly Glu Val Gly Pro Pro Gly Pro Pro Gly
                755                 760                 765
Pro Ala Gly Glu Lys Gly Ser Pro Gly Ala Asp Gly Pro Ala Gly Ala
                770                 775                 780
Pro Gly Thr Pro Gly Pro Gln Gly Ile Ala Gly Gln Arg Gly Val Val
785                 790                 795                 800
Gly Leu Pro Gly Gln Arg Gly Glu Arg Gly Phe Pro Gly Leu Pro Gly
                805                 810                 815
Pro Ser Gly Glu Pro Gly Lys Gln Gly Pro Ser Gly Ala Ser Gly Glu
                820                 825                 830
Arg Gly Pro Pro Gly Pro Met Gly Pro Pro Gly Leu Ala Gly Pro Pro
                835                 840                 845
Gly Glu Ser Gly Arg Glu Gly Ala Pro Gly Ala Glu Gly Ser Pro Gly
                850                 855                 860
Arg Asp Gly Ser Pro Gly Ala Lys Gly Asp Arg Gly Glu Thr Gly Pro
865                 870                 875                 880
Ala Gly Pro Pro Gly Ala Pro Gly Ala Pro Gly Ala Pro Gly Pro Val
                885                 890                 895
Gly Pro Ala Gly Lys Ser Gly Asp Arg Gly Glu Thr Gly Pro Ala Gly
                900                 905                 910
Pro Ala Gly Pro Val Gly Pro Ala Gly Ala Arg Gly Pro Ala Gly Pro
                915                 920                 925
Gln Gly Pro Arg Gly Asp Lys Gly Glu Thr Gly Glu Gln Gly Asp Arg
                930                 935                 940
Gly Ile Lys Gly His Arg Gly Phe Ser Gly Leu Gln Gly Pro Pro Gly
945                 950                 955                 960
Pro Pro Gly Ser Pro Gly Glu Gln Gly Pro Ser Gly Ala Ser Gly Pro
                965                 970                 975
Ala Gly Pro Arg Gly Pro Pro Gly Ser Ala Gly Ala Pro Gly Lys Asp
                980                 985                 990
Gly Leu Asn Gly Leu Pro Gly Pro Ile Gly Pro Pro Gly Pro Arg Gly
                995                 1000                1005
Arg Thr Gly Asp Ala Gly Pro Val Gly Pro Pro Gly Pro Pro Gly Pro
                1010                1015                1020
Pro Gly Pro Pro Gly Pro Pro Ser Ala Gly Phe Asp Phe Ser Phe Leu
1025                1030                1035                1040
Pro Gln Pro Pro Gln Glu Lys Ala His Asp Gly Gly Arg Tyr Tyr Arg
                1045                1050                1055
Ala Arg Ser Asp Glu Ala Ser Gly Ile Gly Pro Glu Val Pro Asp Asp
                1060                1065                1070
```

-continued

```
Arg Asp Phe Glu Pro Ser Leu Gly Pro Val Cys Pro Phe Arg Cys Gln
        1075                1080                1085

Cys His Leu Arg Val Val Gln Cys Ser Asp Leu Gly Leu Asp Lys Val
        1090                1095                1100

Pro Lys Asp Leu Pro Pro Asp Thr Thr Leu Leu Asp Leu Gln Asn Asn
1105                1110                1115                1120

Lys Ile Thr Glu Ile Lys Asp Gly Asp Phe Lys Asn Leu Lys Asn Leu
                1125                1130                1135

His Ala Leu Ile Leu Val Asn Asn Lys Ile Ser Lys Val Ser Pro Gly
            1140                1145                1150

Ala Phe Thr Pro Leu Val Lys Leu Glu Arg Leu Tyr Leu Ser Lys Asn
            1155                1160                1165

Gln Leu Lys Glu Leu Pro Glu Lys Met Pro Lys Thr Leu Gln Glu Leu
        1170                1175                1180

Arg Ala His Glu Asn Glu Ile Thr Lys Val Arg Lys Val Thr Phe Asn
1185                1190                1195                1200

Gly Leu Asn Gln Met Ile Val Ile Glu Leu Gly Thr Asn Pro Leu Lys
            1205                1210                1215

Ser Ser Gly Ile Glu Asn Gly Ala Phe Gln Gly Met Lys Lys Leu Ser
            1220                1225                1230

Tyr Ile Arg Ile Ala Asp Thr Asn Ile Thr Ser Ile Pro Gln Gly Leu
            1235                1240                1245

Pro Pro Ser Leu Thr Glu Leu His Leu Asp Gly Asn Lys Ile Ser Arg
        1250                1255                1260

Val Asp Ala Ala Ser Leu Lys Gly Leu Asn Asn Leu Ala Lys Leu Gly
1265                1270                1275                1280

Leu Ser Phe Asn Ser Ile Ser Ala Val Asp Asn Gly Ser Leu Ala Asn
            1285                1290                1295

Thr Pro His Leu Arg Glu Leu His Leu Asp Asn Asn Lys Leu Thr Arg
            1300                1305                1310

Val Pro Gly Gly Leu Ala Glu His Lys Tyr Ile Gln Val Val Tyr Leu
        1315                1320                1325

His Asn Asn Asn Ile Ser Val Val Gly Ser Ser Asp Phe Cys Pro Pro
    1330                1335                1340

Gly His Asn Thr Lys Lys Ala Ser Tyr Ser Gly Val Ser Leu Phe Ser
1345                1350                1355                1360

Asn Pro Val Gln Tyr Trp Glu Ile Gln Pro Ser Thr Phe Arg Cys Val
            1365                1370                1375

Tyr Val Arg Ser Ala Ile Gln Leu Gly Asn Tyr Lys
            1380                1385
```

(2) INFORMATION FOR SEQ ID NO: 11:

(i) SEQUENCE CHARACTERISTICS:
        (A) LENGTH: 1107 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 11:

```
Gln Leu Ser Tyr Gly Tyr Asp Glu Lys Ser Thr Gly Gly Ile Ser Val
1               5                   10                  15

Pro Gly Pro Met Gly Pro Ser Gly Pro Arg Gly Leu Pro Gly Pro Pro
            20                  25                  30
```

```
Gly Ala Pro Gly Pro Gln Gly Phe Gln Gly Pro Pro Gly Glu Pro Gly
         35                  40                  45

Glu Pro Gly Ala Ser Gly Pro Met Gly Pro Arg Gly Pro Pro Gly Pro
 50                  55                  60

Pro Gly Lys Asn Gly Asp Asp Gly Glu Ala Gly Lys Pro Gly Arg Pro
65                  70                  75                  80

Gly Glu Arg Gly Pro Pro Gly Pro Gln Gly Ala Arg Gly Leu Pro Gly
                 85                  90                  95

Thr Ala Gly Leu Pro Gly Met Lys Gly His Arg Gly Phe Ser Gly Leu
             100                 105                 110

Asp Gly Ala Lys Gly Asp Ala Gly Pro Ala Gly Pro Lys Gly Glu Pro
         115                 120                 125

Gly Ser Pro Gly Glu Asn Gly Ala Pro Gly Gln Met Gly Pro Arg Gly
     130                 135                 140

Leu Pro Gly Glu Arg Gly Arg Pro Gly Ala Pro Gly Pro Ala Gly Ala
145                 150                 155                 160

Arg Gly Asn Asp Gly Ala Thr Gly Ala Ala Gly Pro Pro Gly Pro Thr
                 165                 170                 175

Gly Pro Ala Gly Pro Pro Gly Phe Pro Gly Ala Val Gly Ala Lys Gly
             180                 185                 190

Glu Ala Gly Pro Gln Gly Pro Arg Gly Ser Glu Gly Pro Gln Gly Val
         195                 200                 205

Arg Gly Glu Pro Gly Pro Pro Gly Pro Ala Gly Ala Ala Gly Pro Ala
         210                 215                 220

Gly Asn Pro Gly Ala Asp Gly Gln Pro Gly Ala Lys Gly Ala Asn Gly
225                 230                 235                 240

Ala Pro Gly Ile Ala Gly Ala Pro Gly Phe Pro Gly Ala Arg Gly Pro
                 245                 250                 255

Ser Gly Pro Gln Gly Pro Gly Gly Pro Pro Gly Pro Lys Gly Asn Ser
             260                 265                 270

Gly Glu Pro Gly Ala Pro Gly Ser Lys Gly Asp Thr Gly Ala Lys Gly
         275                 280                 285

Glu Pro Gly Pro Val Gly Val Gln Gly Pro Pro Gly Pro Ala Gly Glu
290                 295                 300

Glu Gly Lys Arg Gly Ala Arg Gly Glu Pro Gly Pro Thr Gly Leu Pro
305                 310                 315                 320

Gly Pro Pro Gly Glu Arg Gly Gly Pro Gly Ser Arg Gly Phe Pro Gly
                 325                 330                 335

Ala Asp Gly Val Ala Gly Pro Lys Gly Pro Ala Gly Glu Arg Gly Ser
             340                 345                 350

Pro Gly Pro Ala Gly Pro Lys Gly Ser Pro Gly Glu Ala Gly Arg Pro
         355                 360                 365

Gly Glu Ala Gly Leu Pro Gly Ala Lys Gly Leu Thr Gly Ser Pro Gly
     370                 375                 380

Ser Pro Gly Pro Asp Gly Lys Thr Gly Pro Pro Gly Pro Ala Gly Gln
385                 390                 395                 400

Asp Gly Arg Pro Gly Pro Pro Gly Pro Pro Gly Ala Arg Gly Gln Ala
                 405                 410                 415

Gly Val Met Gly Phe Pro Gly Pro Lys Gly Ala Ala Gly Glu Pro Gly
             420                 425                 430

Lys Ala Gly Glu Arg Gly Val Pro Gly Pro Pro Gly Ala Val Gly Pro
         435                 440                 445
```

-continued

```
Ala Gly Lys Asp Gly Glu Ala Gly Ala Gln Gly Pro Pro Gly Pro Ala
    450                 455                 460
Gly Pro Ala Gly Glu Arg Gly Glu Gln Gly Pro Ala Gly Ser Pro Gly
465                 470                 475                 480
Phe Gln Gly Leu Pro Gly Pro Ala Gly Pro Pro Gly Glu Ala Gly Lys
                485                 490                 495
Pro Gly Glu Gln Gly Val Pro Gly Asp Leu Gly Ala Pro Gly Pro Ser
            500                 505                 510
Gly Ala Arg Gly Glu Arg Gly Phe Pro Gly Glu Arg Gly Val Gln Gly
        515                 520                 525
Pro Pro Gly Pro Ala Gly Pro Arg Gly Ala Asn Gly Ala Pro Gly Asn
530                 535                 540
Asp Gly Ala Lys Gly Asp Ala Gly Ala Pro Gly Ala Pro Gly Ser Gln
545                 550                 555                 560
Gly Ala Pro Gly Leu Gln Gly Met Pro Gly Glu Arg Gly Ala Ala Gly
                565                 570                 575
Leu Pro Gly Pro Lys Gly Asp Arg Gly Asp Ala Gly Pro Lys Gly Ala
            580                 585                 590
Asp Gly Ser Pro Gly Lys Asp Gly Val Arg Gly Leu Thr Gly Pro Ile
        595                 600                 605
Gly Pro Pro Gly Pro Ala Gly Ala Pro Gly Asp Lys Gly Glu Ser Gly
610                 615                 620
Pro Ser Gly Pro Ala Gly Pro Thr Gly Ala Arg Gly Ala Pro Gly Asp
625                 630                 635                 640
Arg Gly Glu Pro Gly Pro Pro Gly Pro Ala Gly Phe Ala Gly Pro Pro
                645                 650                 655
Gly Ala Asp Gly Gln Pro Gly Ala Lys Gly Glu Pro Gly Asp Ala Gly
            660                 665                 670
Ala Lys Gly Asp Ala Gly Pro Pro Gly Pro Ala Gly Pro Ala Gly Pro
        675                 680                 685
Pro Gly Pro Ile Gly Asn Val Gly Ala Pro Gly Ala Lys Gly Ala Arg
690                 695                 700
Gly Ser Ala Gly Pro Pro Gly Ala Thr Gly Phe Pro Gly Ala Ala Gly
705                 710                 715                 720
Arg Val Gly Pro Pro Gly Pro Ser Gly Asn Ala Gly Pro Pro Gly Pro
                725                 730                 735
Pro Gly Pro Ala Gly Lys Glu Gly Lys Gly Pro Arg Gly Glu Thr
            740                 745                 750
Gly Pro Ala Gly Arg Pro Gly Glu Val Gly Pro Pro Gly Pro Pro Gly
        755                 760                 765
Pro Ala Gly Glu Lys Gly Ser Pro Gly Ala Asp Gly Pro Ala Gly Ala
    770                 775                 780
Pro Gly Thr Pro Gly Pro Gln Gly Ile Ala Gly Gln Arg Gly Val Val
785                 790                 795                 800
Gly Leu Pro Gly Gln Arg Gly Glu Arg Gly Phe Pro Gly Leu Pro Gly
                805                 810                 815
Pro Ser Gly Glu Pro Gly Lys Gln Gly Pro Ser Gly Ala Ser Gly Glu
            820                 825                 830
Arg Gly Pro Pro Gly Pro Met Gly Pro Pro Gly Leu Ala Gly Pro Pro
        835                 840                 845
Gly Glu Ser Gly Arg Glu Gly Ala Pro Gly Ala Glu Gly Ser Pro Gly
    850                 855                 860
Arg Asp Gly Ser Pro Gly Ala Lys Gly Asp Arg Gly Glu Thr Gly Pro
```

```
                 865                 870                 875                 880
Ala Gly Pro Pro Gly Ala Pro Gly Ala Pro Gly Ala Pro Gly Pro Val
                885                 890                 895

Gly Pro Ala Gly Lys Ser Gly Asp Arg Gly Glu Thr Gly Pro Ala Gly
                900                 905                 910

Pro Ala Gly Pro Val Gly Pro Ala Gly Ala Arg Gly Pro Ala Gly Pro
                915                 920                 925

Gln Gly Pro Arg Gly Asp Lys Gly Glu Thr Gly Glu Gln Gly Asp Arg
                930                 935                 940

Gly Ile Lys Gly His Arg Gly Phe Ser Gly Leu Gln Gly Pro Pro Gly
945                 950                 955                 960

Pro Pro Gly Ser Pro Gly Glu Gln Gly Pro Ser Gly Ala Ser Gly Pro
                965                 970                 975

Ala Gly Pro Arg Gly Pro Pro Gly Ser Ala Gly Ala Pro Gly Lys Asp
                980                 985                 990

Gly Leu Asn Gly Leu Pro Gly Pro Ile Gly Pro Pro Gly Pro Arg Gly
                995                 1000                1005

Arg Thr Gly Asp Ala Gly Pro Val Gly Pro Pro Gly Pro Pro Gly Pro
                1010                1015                1020

Pro Gly Pro Pro Gly Pro Pro Ser Ala Gly Phe Asp Phe Ser Phe Leu
1025                1030                1035                1040

Pro Gln Pro Pro Gln Glu Lys Ala His Asp Gly Gly Arg Tyr Tyr Arg
                1045                1050                1055

Ala Arg Ser Pro Lys Asp Leu Pro Pro Asp Thr Thr Leu Leu Asp Leu
                1060                1065                1070

Gln Asn Asn Lys Ile Thr Glu Ile Lys Asp Gly Asp Phe Lys Asn Leu
                1075                1080                1085

Lys Asn Leu His Ala Leu Ile Leu Val Asn Asn Lys Ile Ser Lys Val
                1090                1095                1100

Ser Pro Gly
1105

(2) INFORMATION FOR SEQ ID NO: 12:

(i) SEQUENCE CHARACTERISTICS:
        (A) LENGTH: 4167 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

CAGCTGTCTT ATGGCTATGA TGAGAAATCA ACCGGAGGAA TTTCCGTGCC TGGCCCCATG        60

GGTCCCTCTG GTCCTCGTGG TCTCCCTGGC CCCCCTGGTG CACCTGGTCC CCAAGGCTTC       120

CAAGGTCCCC CTGGTGAGCC TGGCGAGCCT GGAGCTTCAG GTCCCATGGG TCCCCGAGGT       180

CCCCCAGGTC CCCCTGGAAA GAATGGAGAT GATGGGAAG CTGGAAAACC TGGTCGTCCT        240

GGTGAGCGTG GGCCTCCTGC GCCTCAGGGT GCTCGAGGAT TGCCCGGAAC AGCTGGCCTC       300

CCTGGAATGA AGGGACACAG AGGTTTCAGT GGTTTGGATG GTGCCAAGGG AGATGCTGGT       360

CCTGCTGGTC CTAAGGGTGA GCCTGGCAGC CCTGGTGAAA ATGGAGCTCC TGGTCAGATG       420

GGCCCCCGTG GCCTGCCTGG TGAGAGAGGT CGCCCTGGAG CCCCTGGCCC TGCTGGTGCT       480

CGTGGAAATG ATGGTGCTAC TGGTGCTGCC GGGCCCCCTG GTCCCACCGG CCCCGCTGGT       540

CCTCCTGGCT TCCCTGGTGC TGTTGGTGCT AAGGGTGAAG CTGGTCCCCA AGGGCCCCGA       600
```

```
                                              -continued

GGCTCTGAAG GTCCCCAGGG TGTGCGTGGT GAGCCTGGCC CCCCTGGCCC TGCTGGTGCT     660

GCTGGCCCTG CTGGAAACCC TGGTGCTGAT GGACAGCCTG GTGCTAAAGG TGCCAATGGT     720

GCTCCTGGTA TTGCTGGTGC TCCTGGCTTC CCTGGTGCCC GAGGCCCCTC TGGACCCCAG     780

GGCCCCGGCG GCCCTCCTGG TCCCAAGGGT AACAGCGGTG AACCTGGTGC TCCTGGCAGC     840

AAAGGAGACA CTGGTGCTAA GGGAGAGCCT GGCCCTGTTG GTGTTCAAGG ACCCCCTGGC     900

CCTGCTGGAG AGCAAGGAAA GCGAGGAGCT CGAGGTGAAC CCGGACCCAC TGGCCTGCCC     960

GGACCCCCTG GCGAGCGTGG TGGACCTGGT AGCCGTGGTT TCCCTGGCGC AGATGGTGTT    1020

GCTGGTCCCA AGGGTCCCGC TGGTGAACGT GGTTCTCCTG GCCCCGCTGG CCCCAAAGGA    1080

TCTCCTCGTG AAGCTGGTCG TCCCGGTGAA GCTGGTCTGC CTGGTGCCAA GGGTCTGACT    1140

GGAAGCCCTG GCAGCCCTGG TCCTGATGGC AAAACTGGCC CCCTGGTCC CGCCGGTCAA     1200

GATGGTCGCC CCGGACCCCC AGGCCCACCT GGTGCCCGTG GTCAGGCTGG TGTGATGGGA    1260

TTCCCTGGAC CTAAAGGTGC TGCTCGAGAG CCCGGCAAGG CTGGAGAGCG AGGTGTTCCC    1320

GGACCCCCTC GCGCTGTCGG TCCTGCTGGC AAAGATGGAG AGGCTGGAGC TCAGGGACCC    1380

CCTGGCCCTG CTGGTCCCGC TGGCGAGAGA GGTGAACAAG GCCCTGCTGG CTCCCCCGGA    1440

TTCCAGGGTC TCCCTGGTCC TGCTGGTCCT CCAGGTGAAG CAGGCAAACC TGGTGAACAG    1500

GGTGTTCCTG GAGACCTTGG CGCCCCTGGC CCCTCTGGAG CAAGAGGCGA GAGAGGTTTC    1560

CCTGGCGAGC GTGGTGTGCA AGGTCCCCCT GGTCCTGCTG GACCCCGAGG GGCCAACGGT    1620

GCTCCCGCCA ACGATGCTGC TAAGGGTGAT GCTGGTGCCC CTGGAGCTCC CGGTAGCCAG    1680

GGCGCCCCTG GCCTTCAGGG AATGCCTGGT GAACGTGGTG CAGCTGGTCT TCCAGGGCCT    1740

AAGGGTGACA GAGGTGATGC TGGTCCCAAA GGTGCTGATG GCTCTCCTGG CAAAGATGGC    1800

GTCCGTGGTC TGACCGACCC CATTGGTCCT CCTGGCCCTG CTGGTGCCCC TGGTGACAAG    1860

GGTGAAAGTG GTCCCAGCGG CCCTGCTGGT CCCACTGGAG CTCGTGGTGC CCCCGGAGAC    1920

CGTGGTGAGC CTGGTCCCCC CGGCCCTGCT GGCTTTGCTG GCCCCCCTGG TGCTGACGGC    1980

CAACCTGGTG CTAAAGGCGA ACCTGGTGAT GCTGGTGCCA AAGGCGATGC TGGTCCCCCT    2040

GGGCCTGCCG GACCCGCTGG ACCCCCTGGC CCCATTGGTA ATGTTGGTGC TCCTGGAGCC    2100

AAACGTGCTC GCGGCAGCGC TGGTCCCCCT GGTGCTACTG GTTTCCCTGG TGCTGCTGGC    2160

CGAGTCGGTC CTCCTGGCCC CTCTGGAAAT GCTGGACCCC CTGGCCCTCC TGGTCCTGCT    2220

GGCAAAGAAG GCGGCAAAGG TCCCCGTGGT GAGACTGGCC CTGCTGGACG TCCTGGTGAA    2280

GTTGGTCCCC CTGGTCCCCC TGGCCCTGCT GGCGAGAAAG GATCCCCTGG TGCTGATGGT    2340

CCTGCTGGTG CTCCTGGTAC TCCCGGGCCT CAAGGTATTG CTGGACAGCG TGGTGTGGTC    2400

GGCCTGCCTG GTCAGAGAGG AGAGAGAGGC TTCCCTGGTC TTCTTGGCCC CTCTGGTGAA    2460

CCTGGCAAAC AAGGTCCCTC TGGAGCAAGT GGTGAACGTG GTCCCCCCGG TCCCATGGGC    2520

CCCCCTGGAT TGGCTGGACC CCCTGGTGAA TCTGGACGTG AGGGGCTCC TGCTGCCGAA     2580

GGTTCCCCTG GACGAGACGG TTCTCCTGGC GCCAAGGGTG ACCGTGGTGA GACCGGCCCC    2640

GCTGGACCCC CTGGTGCTCC TGGTGCTCCT GGTGCCCCTG GCCCCGTTGG CCCTGCTGGC    2700

AAGAGTGGTG ATCGTGGTGA GACTGGTCCT GCTGGTCCCG CCGGTCCCGT CGGCCCCGCT    2760

GGCGCCCGTG GCCCCGCCGG ACCCCAAGGC CCCCGTGGTG ACAAGGGTGA GACAGGCGAA    2820

CAGGGCGACA GAGGCATAAA GGGTCACCGT GGCTTCTCTG GCCTCCAGGG TCCCCCTGGC    2880

CCTCCTGGCT CTCCTGGTGA ACAAGGTCCC TCTGGAGCCT CTGGTCCTGC TGGTCCCCGA    2940
```

```
GGTCCCCCTG GCTCTGCTGG TGCTCCTGGC AAAGATGGAC TCAACGGTCT CCCTGGCCCC      3000

ATTGGGCCCC CTGGTCCTCG CGGTCGCACT GGTGATGCTG GTCCTGTTGG TCCCCCCGGC      3060

CCTCCTGGAC CTCCTGGTCC CCCTGGTCCT CCCAGCGCTG GTTTCGACTT CAGCTTCCTC      3120

CCCCAGCCAC CTCAAGAGAA GGCTCACGAT GGTGGCCGCT ACTACCGGGC TAGATCCGAT      3180

GAGGCTTCTG GGATAGCCCC AGAAGTTCCT GATGACCGCG ACTTCGAGCC CTCCCTAGGC      3240

CCAGTGTGCC CCTTCCGCTG TCAATGCCAT CTTCGAGTGG TCCAGTGTTC TGATTTGGGT      3300

CTGGACAAAG TGCCAAAGGA TCTTCCCCCT GACACAACTC TGCTAGACCT GCAAACAAC       3360

AAAATAACCG AAATCAAAGA TGGAGACTTT AAGAACCTGA AGAACCTTCA CGCATTGATT      3420

CTTGTCAACA ATAAAATTAG CAAAGTTAGT CCTGGAGCAT TTACACCTTT GGTGAAGTTG      3480

GAACGACTTT ATCTGTCCAA GAATCAGCTG AAGGAATTGC CAGAAAAAAT GCCCAAAACT      3540

CTTCAGGAGC TGCGTGCCCA TGAGAATGAG ATCACCAAAG TGCGAAAAGT TACTTTCAAT      3600

GGACTGAACC AGATGATTGT CATAGAACTG GGCACCAATC CGCTGAAGAG CTCAGGAATT      3660

GAAAATGGGG CTTTCCAGGG AATGAAGAAG CTCTCCTACA TCCGCATTGC TGATACCAAT      3720

ATCACCAGCA TTCCTCAAGG TCTTCCTCCT TCCCTTACGG AATTACATCT TGATGGCAAC      3780

AAAATCAGCA GAGTTGATGC AGCTAGCCTG AAAGGACTGA ATAATTTGGC TAAGTTGGGA      3840

TTGAGTTTCA ACAGCATCTC TGCTGTTGAC AATGGCTCTC TGGCCAACAC GCCTCATCTG      3900

AGGGAGCTTC ACTTGGACAA CAACAAGCTT ACCAGAGTAC CTGGTGGGCT GGCAGAGCAT      3960

AAGTACATCC AGGTTGTCTA CCTTCATAAC AACAATATCT CTGTAGTTGG ATCAAGTGAC      4020

TTCTGCCCAC CTGGACACAA CACCAAAAAG GCTTCTTATT CGGGTGTGAG TCTTTTCAGC      4080

AACCCGGTCC AGTACTGGGA GATACAGCCA TCCACCTTCA GATGTGTCTA CGTGCGCTCT      4140

GCCATTCAAC TCGGAAACTA TAAGTAA                                         4167

(2) INFORMATION FOR SEQ ID NO: 13:

(i) SEQUENCE CHARACTERISTICS:
        (A) LENGTH: 3349 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GGGAAGGATT TCCATTTCCC AGCTGTCTTA TGGCTATGAT GAGAAATCAA CCGGAGGAAT        60

TTCCGTGCCT GGCCCCATGG GTCCCTCTGG TCCTCGTGGT CTCCCTGGCC CCCTGGTGC        120

ACCTGGTCCC CAAGGCTTCC AAGGTCCCCC TGGTGAGCCT GGCGAGCCTG GAGCTTCAGG       180

TCCCATGGGT CCCCGAGGTC CCCCAGGTCC CCTGGAAAG AATGGAGATG ATGGGGAAGC        240

TGGAAAACCT GGTCGTCCTG GTGAGCGTGG GCCTCCTGGG CCTCAGGGTG CTCGAGGATT       300

GCCCGGAACA GCTGGCCTCC CTGGAATGAA GGGACACAGA GGTTTCAGTG GTTTGGATGG       360

TGCCAAGGGA GATGCTGGTC CTGCTGGTCC TAAGGGTGAG CCTGGCAGCC TGGTGAAAA       420

TGGAGCTCCT GGTCAGATGG GCCCCCGTGG CCTGCCTGGT GAGAGAGGTC GCCCTGGAGC       480

CCCTGGCCCT GCTGGTGCTC GTGGAAATGA TGGTGCTACT GGTGCTGCCG GCCCCCTGG       540

TCCCACCGGC CCCGCTGGTC CTCCTGGCTT CCCTGGTGCT GTTGGTGCTA AGGGTGAAGC       600

TGGTCCCCAA GGGCCCCGAG GCTCTGAAGG TCCCCAGGGT GTGCGTGGTG AGCCTGGCCC       660

CCCTGGCCCT GCTGGTGCTG CTGGCCCTGC TGGAAACCCT GGTGCTGATG GACAGCCTGG       720
```

```
TGCTAAAGGT GCCAATGGTG CTCCTGGTAT TGCTGGTGCT CCTGGCTTCC CTGGTGCCCG    780
AGGCCCCTCT GGACCCCAGG GCCCCGGCGG CCCTCCTGGT CCCAAGGGTA ACAGCGGTGA    840
ACCTGGTGCT CCTGGCAGCA AAGGAGACAC TGGTGCTAAG GGAGAGCCTG GCCCTGTTGG    900
TGTTCAAGGA CCCCCTGGCC CTGCTGGAGA GGAAGGAAAG CGAGGAGCTC GAGGTGAACC    960
CGGACCCACT GGCCTGCCCG GACCCCCTGG CGAGCGTGGT GGACCTGGTA GCCGTGGTTT   1020
CCCTGGCGCA GATGGTGTTG CTGGTCCCAA GGGTCCCGCT GGTGAACGTG GTTCTCCTGG   1080
CCCCGCTGGC CCCAAAGGAT CTCCTGGTGA AGCTGGTCGT CCCGGTGAAG CTGGTCTGCC   1140
TGGTGCCAAG GGTCTGACTG GAAGCCCTGG CAGCCCTGGT CCTGATGGCA AAACTGGCCC   1200
CCCTGGTCCC GCCGGTCAAG ATGGTCGCCC CGGACCCCCA GGCCCACCTG GTGCCCGTGG   1260
TCAGGCTGGT GTGATGGGAT TCCCTGGACC TAAAGGTGCT GCTGGAGAGC CCGGCAAGGC   1320
TGGAGAGCGA GGTGTTCCCG ACCCCCTGG CGCTGTCGGT CCTGCTGGCA AGATGGAGA    1380
GGCTGGAGCT CAGGGACCCC CTGGCCCTGC TGGTCCCGCT GGCGAGAGAG GTGAACAAGG   1440
CCCTGCTGGC TCCCCCGGAT TCCAGGGTCT CCCTGGTCCT GCTGGTCCTC CAGGTGAAGC   1500
AGGCAAACCT GGTGAACAGG GTGTTCCTGG AGACCTTGGC GCCCCTGGCC CCTCTGGAGC   1560
AAGAGGCGAG AGAGGTTTCC CTGGCGAGCG TGGTGTGCAA GGTCCCCCTG GTCCTGCTGG   1620
ACCCCGAGGG GCCAACGGTG CTCCCGGCAA CGATGGTGCT AAGGGTGATG CTGGTGCCCC   1680
TGGAGCTCCC GGTAGCCAGG GCGCCCCTGG CCTTCAGGGA ATGCCTGGTG AACGTGGTGC   1740
AGCTGGTCTT CCAGGGCCTA AGGGTGACAG AGGTGATGCT GGTCCCAAAG GTGCTGATGG   1800
CTCTCCTGGC AAAGATGGCG TCCGTGGTCT GACCGGCCCC ATTGGTCCTC CTGGCCCTGC   1860
TGGTGCCCCT GGTGACAAGG GTGAAAGTGG TCCCAGCGGC CCTGCTGGTC CCACTGGAGC   1920
TCGTGGTGCC CCCGGAGACC GTGGTGAGCC TGGTCCCCCC GGCCCTGCTG GCTTTGCTGG   1980
CCCCCCTGGT GCTGACGGCC AACCTGGTGC TAAAGGCGAA CCTGGTGATG CTGGTGCCAA   2040
AGGCGATGCT GGTCCCCCTG GGCCTGCCGG ACCCGCTGGA CCCCCTGGCC CCATTGGTAA   2100
TGTTGGTGCT CCTGGAGCCA AAGGTGCTCG CGGCAGCGCT GGTCCCCCTG GTGCTACTGG   2160
TTTCCCTGGT GCTGCTGGCC GAGTCGGTCC TCCTGGCCCC TCTGGAAATG CTGGACCCCC   2220
TGGCCCTCCT GGTCCTGCTG GCAAAGAAGG CGGCAAAGGT CCCCGTGGTG AGACTGGCCC   2280
TGCTGGACGT CCTGGTGAAG TTGGTCCCCC TGGTCCCCCT GGCCCTGCTG GCGAGAAAGG   2340
ATCCCCTGGT GCTGATGGTC CTGCTGGTGC TCCTGGTACT CCCGGGCCTC AAGGTATTGC   2400
TGGACAGCGT GGTGTGGTCG GCCTGCCTGG TCAGAGAGGA GAGAGAGGCT TCCCTGGTCT   2460
TCCTGGCCCC TCTGGTGAAC CTGGCAAACA AGGTCCCTCT GGAGCAAGTG GTGAACGTGG   2520
TCCCCCCGGT CCCATGGGCC CCCTGGATT GGCTGGACCC CCTGGTGAAT CTGGACGTGA    2580
GGGGGCTCCT GCTGCCGAAG GTTCCCCTGG ACGAGACGGT TCTCCTGGCG CCAAGGGTGA   2640
CCGTGGTGAG ACCGGCCCCG CTGGACCCCC TGGTGCTCCT GGTGCTCCTG GTGCCCCTGG   2700
CCCCGTTGGC CCTGCTGGCA AGAGTGGTGA TCGTGGTGAG ACTGGTCCTG CTGGTCCCGC   2760
CGGTCCCGTC GGCCCCGCTG GCGCCCGTGG CCCCGCCGGA CCCCAAGGCC CCGTGGTGA    2820
CAAGGGTGAG ACAGGCGAAC AGGGCGACAG AGGCATAAAG GGTCACCGTG GCTTCTCTGG   2880
CCTCCAGGGT CCCCCTGGCC CTCCTGGCTC TCCTGGTGAA CAAGGTCCCT CTGGAGCCTC   2940
TGGTCCTGCT GGTCCCCGAG GTCCCCCTGG CTCTGCTGGT GCTCCTGGCA AGATGGACT    3000
CAACGGTCTC CCTGGCCCCA TTGGGCCCCC TGGTCCTCGC GGTCGCACTG GTGATGCTGG   3060
TCCTGTTGGT CCCCCCGGCC CTCCTGGACC TCCTGGTCCC CTGGTCCTC CCAGCGCTGG   3120
```

| | |
|---|---|
| TTTCGACTTC AGCTTCCTCC CCCAGCCACC TCAAGAGAAG GCTCACGATG GTGGCCGCTA | 3180 |
| CTACCGGGCT AGATCTCCAA AGGATCTTCC CCCTGACACA ACTCTGCTAG ACCTGCAAAA | 3240 |
| CAACAAAATA ACCGAAATCA AAGATGGAGA CTTTAAGAAC CTGAAGAACC TTCACGCATT | 3300 |
| GATTCTTGTC AACAATAAAA TTAGCAAAGT TAGTCCTGGA TAACTGCAG | 3349 |

(2) INFORMATION FOR SEQ ID NO: 14:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

| | |
|---|---|
| ATCGAGGGAA GGATTTCAGA ATTCGGATCC TCTAGAGTCG ACCTGCAGGC AAGCTTG | 57 |

(2) INFORMATION FOR SEQ ID NO: 15:

(i) SEQUENCE CHARACTERISTICS:
        (A) LENGTH: 3171 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

| | |
|---|---|
| CAGCTGTCTT ATGGCTATGA TGAGAAATCA ACCGGAGGAA TTTCCGTGCC TGGCCCCATG | 60 |
| GGTCCCTCTG GTCCTCGTGG TCTCCCTGGC CCCCCTGGTG CACCTGGTCC CCAAGGCTTC | 120 |
| CAAGGTCCCC CTGGTGAGCC TGGCGAGCCT GGAGCTTCAG GTCCCATGGG TCCCCGAGGT | 180 |
| CCCCCAGGTC CCCCTGGAAA GAATGGAGAT GATGGGGAAG CTGGAAAACC TGGTCGTCCT | 240 |
| GGTGAGCGTG GGCCTCCTGG GCCTCAGGGT GCTCGAGGAT TGCCCGGAAC AGCTGGCCTC | 300 |
| CCTGGAATGA AGGGACACAG AGGTTTCAGT GGTTTGGATG GTGCCAAGGG AGATGCTGGT | 360 |
| CCTGCTGGTC CTAAGGGTGA GCCTGGCAGC CCTGGTGAAA ATGGAGCTCC TGGTCAGATG | 420 |
| GGCCCCCGTG GCCTGCCTGG TGAGAGAGGT CGCCCTGGAG CCCCTGGCCC TGCTGGTGCT | 480 |
| CGTGGAAATG ATGGTGCTAC TGGTGCTGCC GGGCCCCCTG GTCCCACCGG CCCCGCTGGT | 540 |
| CCTCCTGGCT TCCCTGGTGC TGTTGGTGCT AAGGGTGAAG CTGGTCCCCA GGGCCCCGA | 600 |
| GGCTCTGAAG GTCCCCAGGG TGTGCGTGGT GAGCCTGGCC CCCCTGGCCC TGCTGGTGCT | 660 |
| GCTGGCCCTG CTGGAAACCC TGGTGCTGAT GGACAGCCTG GTGCTAAAGG TGCCAATGGT | 720 |
| GCTCCTGGTA TTGCTGGTGC TCCTGGCTTC CCTGGTGCCC GAGGCCCCTC TGGACCCCAG | 780 |
| GGCCCCGGCG CCCCTCCTGG TCCCAAGGGT AACAGCGGTG AACCTGGTGC TCCTGGCAGC | 840 |
| AAAGGAGACA CTGGTGCTAA GGGAGAGCCT GGCCCTGTTG GTGTTCAAGG ACCCCCTGGC | 900 |
| CCTGCTGGAG AGGAAGGAAA GCGAGGAGCT CGAGGTGAAC CCGGACCCAC TGGCCTGCCC | 960 |
| GGACCCCCTG GCGAGCGTGG TGGACCTGGT AGCCGTGGTT TCCCTGGCGC AGATGGTGTT | 1020 |
| GCTGGTCCCA AGGGTCCCGC TGGTGAACGT GGTTCTCCTG GCCCCGCTGG CCCCAAAGGA | 1080 |
| TCTCCTGGTG AAGCTGGTCG TCCCGGTGAA GCTGGTCTGC CTGGTGCCAA GGGTCTGACT | 1140 |
| GGAAGCCCTG GCAGCCCTGG TCCTGATGGC AAAACTGGCC CCCCTGGTCC CGCCGGTCAA | 1200 |
| GATGGTCGCC CCGGACCCCC AGGCCCACCT GGTGCCCGTG GTCAGGCTGG TGTGATGGGA | 1260 |

```
                                    -continued

TTCCCTGGAC CTAAAGGTGC TGCTGGAGAG CCCGGCAAGG CTGGAGAGCG AGGTGTTCCC      1320

GGACCCCCTG GCGCTGTCGG TCCTGCTGGC AAAGATGGAG AGGCTGGAGC TCAGGGACCC      1380

CCTGGCCCTG CTGGTCCCGC TGGCGAGAGA GGTGAACAAG GCCCTGCTGG CTCCCCCGGA      1440

TTCCAGGGTC TCCCTGGTCC TGCTGGTCCT CCAGGTGAAG CAGGCAAACC TGGTGAACAG      1500

GGTGTTCCTG GAGACCTTGG CGCCCCTGGC CCCTCTGGAG CAAGAGGCGA GAGAGGTTTC      1560

CCTGGCGAGC GTGGTGTGCA AGGTCCCCCT GGTCCTGCTG ACCCCGAGG GGCCAACGGT       1620

GCTCCCGGCA ACGATGGTGC TAAGGGTGAT GCTGGTGCCC CTGGAGCTCC CGGTAGCCAG      1680

GGCGCCCCTG GCCTTCAGGG AATGCCTGGT GAACGTGGTG CAGCTGGTCT TCCAGGGCCT      1740

AAGGGTGACA GAGGTGATGC TGGTCCCAAA GGTGCTGATG GCTCTCCTGG CAAAGATGGC      1800

GTCCGTGGTC TGACCGGCCC CATTGGTCCT CCTGGCCCTG CTGGTGCCCC TGGTGACAAG      1860

GGTGAAAGTG GTCCCAGCGG CCCTGCTGGT CCCACTGGAG CTCGTGGTGC CCCCGGAGAC     1920

CGTGGTGAGC CTGGTCCCCC CGGCCCTGCT GGCTTTGCTG GCCCCCCTGG TGCTGACGGC      1980

CAACCTGGTG CTAAAGGCGA ACCTGGTGAT GCTGGTGCCA AAGGCGATGC TGGTCCCCCT      2040

GGGCCTGCCG GACCCGCTGG ACCCCCTGGC CCCATTGGTA ATGTTGGTGC TCCTGGAGCC     2100

AAAGGTGCTC GCGGCAGCGC TGGTCCCCCT GGTGCTACTG GTTTCCCTGG TGCTGCTGGC      2160

CGAGTCGGTC CTCCTGGCCC CTCTGGAAAT GCTGGACCCC CTGGCCCTCC TGGTCCTGCT      2220

GGCAAAGAAG GCGGCAAAGG TCCCCGTGGT GAGACTGGCC CTGCTGGACG TCCTGGTGAA      2280

GTTGGTCCCC CTGGTCCCCC TGGCCCTGCT GGCGAGAAAG GATCCCCTGG TGCTGATGGT      2340

CCTGCTGGTG CTCCTGGTAC TCCCGGGCCT CAAGGTATTG CTGGACAGCG TGGTGTGGTC      2400

GGCCTGCCTG GTCAGAGAGG AGAGAGAGGC TTCCCTGGTC TTCCTGGCCC CTCTGGTGAA      2460

CCTGGCAAAC AAGGTCCCTC TGGAGCAAGT GGTGAACGTG GTCCCCCCGG TCCCATGGGC     2520

CCCCCTGGAT TGGCTGGACC CCCTGGTGAA TCTGGACGTG AGGGGCTCC TGCTGCCGAA      2580

GGTTCCCCTG GACGAGACGG TTCTCCTGGC GCCAAGGGTG ACCGTGGTGA GACCGGCCCC      2640

GCTGGACCCC CTGGTGCTCC TGGTGCTCCT GGTGCCCCTG GCCCCGTTGG CCCTGCTGGC      2700

AAGAGTGGTG ATCGTGGTGA GACTGGTCCT GCTGGTCCCG CCGGTCCCGT CGGCCCCGCT      2760

GGCGCCCGTG GCCCCGCCGG ACCCCAAGGC CCCCGTGGTG ACAAGGGTGA GACAGGCGAA      2820

CAGGGCGACA GAGGCATAAA GGGTCACCGT GGCTTCTCTG GCCTCCAGGG TCCCCCTGGC      2880

CCTCCTGGCT CTCCTGGTGA ACAAGGTCCC TCTGGAGCCT CTGGTCCTGC TGGTCCCCGA      2940

GGTCCCCCTG GCTCTGCTGG TGCTCCTGGC AAAGATGGAC TCAACGGTCT CCCTGGCCCC      3000

ATTGGGCCCC CTGGTCCTCG CGGTCGCACT GGTGATGCTG GTCCTGTTGG TCCCCCCGGC      3060

CCTCCTGGAC CTCCTGGTCC CCCTGGTCCT CCCAGCGCTG GTTTCGACTT CAGCTTCCTC      3120

CCCCAGCCAC CTCAAGAGAA GGCTCACGAT GGTGGCCGCT ACTACCGGGC T              3171

(2) INFORMATION FOR SEQ ID NO: 16:

(i) SEQUENCE CHARACTERISTICS:
         (A) LENGTH: 1057 amino acids
         (B) TYPE: amino acid
         (C) STRANDEDNESS: single
         (D) TOPOLOGY: unknown (ii) MOLECULE TYPE: peptide (xi) SEQUENCE DESCRIPTION: SEQ ID NO: 16:

Gln Leu Ser Tyr Gly Tyr Asp Glu Lys Ser Thr Gly Gly Ile Ser Val
1               5                   10                  15
```

-continued

```
Pro Gly Pro Met Gly Pro Ser Gly Pro Arg Gly Leu Pro Gly Pro Pro
            20                  25                  30
Gly Ala Pro Gly Pro Gln Gly Phe Gln Gly Pro Pro Gly Glu Pro Gly
            35                  40                  45
Glu Pro Gly Ala Ser Gly Pro Met Gly Pro Arg Gly Pro Pro Gly Pro
 50                  55                  60
Pro Gly Lys Asn Gly Asp Asp Gly Glu Ala Gly Lys Pro Gly Arg Pro
 65                  70                  75                  80
Gly Glu Arg Gly Pro Pro Gly Pro Gln Gly Ala Arg Gly Leu Pro Gly
                85                  90                  95
Thr Ala Gly Leu Pro Gly Met Lys Gly His Arg Gly Phe Ser Gly Leu
            100                 105                 110
Asp Gly Ala Lys Gly Asp Ala Gly Pro Ala Gly Pro Lys Gly Glu Pro
            115                 120                 125
Gly Ser Pro Gly Glu Asn Gly Ala Pro Gly Gln Met Gly Pro Arg Gly
        130                 135                 140
Leu Pro Gly Glu Arg Gly Arg Pro Gly Ala Pro Gly Pro Ala Gly Ala
145                 150                 155                 160
Arg Gly Asn Asp Gly Ala Thr Gly Ala Ala Gly Pro Pro Gly Pro Thr
                165                 170                 175
Gly Pro Ala Gly Pro Pro Gly Phe Pro Gly Ala Val Gly Ala Lys Gly
            180                 185                 190
Glu Ala Gly Pro Gln Gly Pro Arg Gly Ser Glu Gly Pro Gln Gly Val
            195                 200                 205
Arg Gly Glu Pro Gly Pro Pro Gly Pro Ala Gly Ala Ala Gly Pro Ala
        210                 215                 220
Gly Asn Pro Gly Ala Asp Gly Gln Pro Gly Ala Lys Gly Ala Asn Gly
225                 230                 235                 240
Ala Pro Gly Ile Ala Gly Ala Pro Gly Phe Pro Gly Ala Arg Gly Pro
                245                 250                 255
Ser Gly Pro Gln Gly Pro Gly Gly Pro Pro Gly Pro Lys Gly Asn Ser
            260                 265                 270
Gly Glu Pro Gly Ala Pro Gly Ser Lys Gly Asp Thr Gly Ala Lys Gly
            275                 280                 285
Glu Pro Gly Pro Val Gly Val Gln Gly Pro Pro Gly Pro Ala Gly Glu
        290                 295                 300
Glu Gly Lys Arg Gly Ala Arg Gly Glu Pro Gly Pro Thr Gly Leu Pro
305                 310                 315                 320
Gly Pro Pro Gly Glu Arg Gly Gly Pro Gly Ser Arg Gly Phe Pro Gly
                325                 330                 335
Ala Asp Gly Val Ala Gly Pro Lys Gly Pro Ala Gly Glu Arg Gly Ser
            340                 345                 350
Pro Gly Pro Ala Gly Pro Lys Gly Ser Pro Gly Glu Ala Gly Arg Pro
            355                 360                 365
Gly Glu Ala Gly Leu Pro Gly Ala Lys Gly Leu Thr Gly Ser Pro Gly
        370                 375                 380
Ser Pro Gly Pro Asp Gly Lys Thr Gly Pro Pro Gly Pro Ala Gly Gln
385                 390                 395                 400
Asp Gly Arg Pro Gly Pro Pro Gly Pro Pro Gly Ala Arg Gly Gln Ala
                405                 410                 415
Gly Val Met Gly Phe Pro Gly Pro Lys Gly Ala Ala Gly Glu Pro Gly
            420                 425                 430
```

```
Lys Ala Gly Glu Arg Gly Val Pro Gly Pro Pro Gly Ala Val Gly Pro
            435                 440                 445
Ala Gly Lys Asp Gly Glu Ala Gly Ala Gln Gly Pro Pro Gly Pro Ala
450                 455                 460
Gly Pro Ala Gly Glu Arg Gly Glu Gln Gly Pro Ala Gly Ser Pro Gly
465                 470                 475                 480
Phe Gln Gly Leu Pro Gly Pro Ala Gly Pro Gly Glu Ala Gly Lys
            485                 490                 495
Pro Gly Glu Gln Gly Val Pro Gly Asp Leu Gly Ala Pro Gly Pro Ser
            500                 505                 510
Gly Ala Arg Gly Glu Arg Gly Phe Pro Gly Glu Arg Gly Val Gln Gly
            515                 520                 525
Pro Pro Gly Pro Ala Gly Pro Arg Gly Ala Asn Gly Ala Pro Gly Asn
530                 535                 540
Asp Gly Ala Lys Gly Asp Ala Gly Ala Pro Gly Ala Pro Gly Ser Gln
545                 550                 555                 560
Gly Ala Pro Gly Leu Gln Gly Met Pro Gly Glu Arg Gly Ala Ala Gly
            565                 570                 575
Leu Pro Gly Pro Lys Gly Asp Arg Gly Asp Ala Gly Pro Lys Gly Ala
            580                 585                 590
Asp Gly Ser Pro Gly Lys Asp Gly Val Arg Gly Leu Thr Gly Pro Ile
            595                 600                 605
Gly Pro Pro Gly Pro Ala Gly Ala Pro Gly Asp Lys Gly Glu Ser Gly
            610                 615                 620
Pro Ser Gly Pro Ala Gly Pro Thr Gly Ala Arg Gly Ala Pro Gly Asp
625                 630                 635                 640
Arg Gly Glu Pro Gly Pro Pro Gly Pro Ala Gly Phe Ala Gly Pro Pro
            645                 650                 655
Gly Ala Asp Gly Gln Pro Gly Ala Lys Gly Glu Pro Gly Asp Ala Gly
            660                 665                 670
Ala Lys Gly Asp Ala Gly Pro Pro Gly Pro Ala Gly Pro Ala Gly Pro
            675                 680                 685
Pro Gly Pro Ile Gly Asn Val Gly Ala Pro Gly Ala Lys Gly Ala Arg
            690                 695                 700
Gly Ser Ala Gly Pro Pro Gly Ala Thr Gly Phe Pro Gly Ala Ala Gly
705                 710                 715                 720
Arg Val Gly Pro Pro Gly Pro Ser Gly Asn Ala Gly Pro Pro Gly Pro
            725                 730                 735
Pro Gly Pro Ala Gly Lys Glu Gly Lys Gly Pro Arg Gly Glu Thr
            740                 745                 750
Gly Pro Ala Gly Arg Pro Gly Glu Val Gly Pro Pro Gly Pro Pro Gly
            755                 760                 765
Pro Ala Gly Glu Lys Gly Ser Pro Gly Ala Asp Gly Pro Ala Gly Ala
            770                 775                 780
Pro Gly Thr Pro Gly Pro Gln Gly Ile Ala Gly Gln Arg Gly Val Val
785                 790                 795                 800
Gly Leu Pro Gly Gln Arg Gly Glu Arg Gly Phe Pro Gly Leu Pro Gly
            805                 810                 815
Pro Ser Gly Glu Pro Gly Lys Gln Gly Pro Ser Gly Ala Ser Gly Glu
            820                 825                 830
Arg Gly Pro Pro Gly Pro Met Gly Pro Pro Gly Leu Ala Gly Pro Pro
            835                 840                 845
Gly Glu Ser Gly Arg Glu Gly Ala Pro Ala Ala Glu Gly Ser Pro Gly
```

-continued

```
          850             855             860
Arg Asp Gly Ser Pro Gly Ala Lys Gly Asp Arg Gly Glu Thr Gly Pro
865                     870             875                 880

Ala Gly Pro Pro Gly Ala Pro Gly Ala Pro Gly Ala Pro Gly Pro Val
                885             890                 895

Gly Pro Ala Gly Lys Ser Gly Asp Arg Gly Glu Thr Gly Pro Ala Gly
            900             905                 910

Pro Ala Gly Pro Val Gly Pro Ala Gly Ala Arg Gly Pro Ala Gly Pro
            915             920             925

Gln Gly Pro Arg Gly Asp Lys Gly Glu Thr Gly Glu Gln Gly Asp Arg
930                     935             940

Gly Ile Lys Gly His Arg Gly Phe Ser Gly Leu Gln Gly Pro Pro Gly
945                 950             955                 960

Pro Pro Gly Ser Pro Gly Glu Gln Gly Pro Ser Gly Ala Ser Gly Pro
                965             970             975

Ala Gly Pro Arg Gly Pro Pro Gly Ser Ala Gly Ala Pro Gly Lys Asp
            980             985             990

Gly Leu Asn Gly Leu Pro Gly Pro Ile Gly Pro Pro Gly Pro Arg Gly
            995             1000            1005

Arg Thr Gly Asp Ala Gly Pro Val Gly Pro Pro Gly Pro Pro Gly Pro
    1010            1015            1020

Pro Gly Pro Pro Gly Pro Pro Ser Ala Gly Phe Asp Phe Ser Phe Leu
1025            1030            1035                1040

Pro Gln Pro Pro Gln Glu Lys Ala His Asp Gly Gly Arg Tyr Tyr Arg
                1045            1050                1055

Ala
```

(2) INFORMATION FOR SEQ ID NO: 17:

(i) SEQUENCE CHARACTERISTICS:
        (A) LENGTH: 46 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Region
        (B) LOCATION: 1..2
        (D) OTHER INFORMATION: /note= "Amino acid sequence for
           glutathione S-transferase"

(ix) FEATURE:
        (A) NAME/KEY: Region
        (B) LOCATION: 19..20
        (D) OTHER INFORMATION: /note= "338 repeats of the
           following triplet Gly-X-y wherein about 35% of the X and
           Y positions are occupied by proline and
           4-hydroxyproline. "

(xi) SEQUENCE DESCRIPTION: SEQ ID NO: 17:

```
Xaa Met Gln Leu Ser Tyr Gly Tyr Asp Glu Lys Ser Thr Gly Gly Ile
1               5                   10                  15

Ser Val Pro Xaa Ser Ala Gly Phe Asp Phe Ser Phe Leu Pro Gln Pro
                20              25                  30

Pro Gln Glu Lys Ala His Asp Gly Gly Arg Tyr Tyr Arg Ala
                35              40                  45
```

(2) INFORMATION FOR SEQ ID NO: 18:

```
    (i) SEQUENCE CHARACTERISTICS:
        (A) LENGTH: 31 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Region
        (B) LOCATION: 1..2
        (D) OTHER INFORMATION: /note= "Amino acid sequence for
            glutathione S-transferase."

(ix) FEATURE:
        (A) NAME/KEY: Region
        (B) LOCATION: 4..5
        (D) OTHER INFORMATION: /note= "338 repeats of the
            following triplet Gly-X-Y wherein about 35% of the X and
            Y positions are occupied by proline and
            4-hydroxyproline. "

(xi) SEQUENCE DESCRIPTION: SEQ ID NO: 18:

Xaa Met Gly Xaa Tyr Ser Ala Gly Phe Asp Phe Ser Phe Leu Pro Gln
 1               5                  10                  15

Pro Pro Gln Glu Lys Ala His Asp Gly Gly Arg Tyr Tyr Arg Ala
            20                  25                  30

(2) INFORMATION FOR SEQ ID NO: 19:

(i) SEQUENCE CHARACTERISTICS:
        (A) LENGTH: 3171 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 19:

CAGCTGAGCT ATGGCTATGA TGAAAAAAGC ACCGGCGGCA TCAGCGTGCC GGGCCCGATG      60

GGTCCGAGCG GCCCTCGTGG CCTGCCGGGC CCGCCAGGTG CGCCCGGTCC GCAGGGCTTT    120

CAGGGTCCGC CGGGCGAACC GGGCGAACCT GGTGCGAGCG GCCCGATGGG CCCGCGCGGC    180

CCGCCGGGTC CGCCAGGCAA AAACGGCGAT GATGGCGAAG CGGGCAAACC GGGACGTCCG    240

GGTGAACGTG GCCCCCCGGG CCCGCAGGGC GCGCGCGGAC TGCCGGGTAC TGCGGGACTG    300

CCGGGCATGA AAGGCCACCG CGGTTTCTCT GGTCTGGATG GTGCGAAAGG TGATGCGGGT    360

CCGGCGGGTC CGAAAGGTGA GCCGGGCAGC CCGGGCGAAA ACGGCGCGCC GGGTCAGATG    420

GGCCCGCGTG GCCTGCCTGG TGAACGCGGT CGCCCGGGCG CCCCGGGCCC AGCTGGCGCA    480

CGTGGCAACG ATGGTGCGAC CGGTGCGGCC GGTCCACCGG GCCCGACGGG CCCGGCGGGT    540

CCCCCGGGCT TTCCGGGTGC GGTGGGTGCG AAAGGCGAAG CAGGTCCGCA GGGGCCGCGC    600

GGGAGCGAGG GTCCTCAGGG CGTTCGTGGT GAACCGGGCC CGCCGGGCCC GGCGGGTGCG    660

GCGGGCCCGG CTGGTAACCC TGGCGCGGAC GGTCAGCCAG GTGCGAAAGG TGCCAACGGC    720

GCGCCGGGTA TTGCAGGTGC ACCGGGCTTC CCGGGTGCCC GCGGCCCGTC GGCCCGCAG    780

GGCCCGGGCG GCCCGCCCGG CCCGAAAGGG AACAGCGGTG AACCGGGTGC GCCAGGCAGC    840

AAAGGCGACA CCGGTGCGAA AGGTGAACCG GGCCCAGTGG GTGTTCAAGG CCCGCCGGGC    900

CCGGCGGGCG AGGAAGGCAA ACGCGGTGCT CGCGGTGAAC CGGGCCCGAC CGGCCTGCCT    960

GGCCCGCCGG GAGAACGTGG TGGCCCGGGT AGCCGCGGTT TTCCGGGCGC GGATGGTGTG   1020

GCGGGCCCGA AAGGTCCGGC GGGTGAACGT GGTAGCCCGG GCCCGGCGGG CCCAAAAGGC   1080
```

```
AGCCCGGGCG AGGCAGGACG TCCGGGTGAA GCGGGTCTCC CGGGCGCCAA AGGTCTGACC    1140

GGCTCTCCGG GCAGCCCGGG TCCGGATGGC AAAACGGGCC CGCCTGGTCC GGCCGGCCAG    1200

GATGGTCGCC CGGGCCCGCC GGGCCCGCCG GGTGCCCGTG GTCAGGCGGG TGTCATGGGC    1260

TTTCCAGGCC CCAAAGGTGC GGCGGGTGAA CCGGGCAAAG CGGGCGAACG CGGTGTCCCG    1320

GGTCCGCCGG GCGCTGTCGG GCCGGCGGGC AAAGATGGCG AAGCGGGCGC GCAAGGCCCG    1380

CCGGGACCAG CGGGTCCGGC GGGCGAGCGC GGTGAACAGG GCCCGGCAGG CAGCCCGGGT    1440

TTCCAGGGTC TGCCGGGCCC TGCGGGTCCA CCGGGTGAAG CGGGCAAACC GGGGGAACAA    1500

GGTGTGCCGG GCGACCTGGG CGCCCCAGGC CCGAGCGGCG CGCGCGGCGA ACGCGGTTTC    1560

CCGGGCGAAC GTGGTGTGCA GGGCCCGCCC GGCCCGGCTG GTCCGCGCGG CGCCAACGGC    1620

GCGCCGGGCA ACGATGGTGC GAAAGGTGAT GCGGGTGCCC CAGGTGCGCC GGGCAGCCAG    1680

GGCGCCCCGG GGCTGCAAGG CATGCCGGGT GAACGTGGTG CCGCGGGTCT ACCGGGTCCG    1740

AAAGGCGACC GCGGTGATGC GGGTCCAAAA GGTGCGGATG GCTCCCCTGG CAAAGATGGC    1800

GTTCGTGGTC TGACCGGCCC GATCGGCCCG CCGGGCCCGG CAGGTGCCCC GGGTGACAAA    1860

GGTGAAAGCG GTCCGAGCGG CCCAGCGGGC CCCACTGGTG CGCGTGGTGC CCCGGGCGAC    1920

CGTGGTGAAC CGGGTCCGCC GGGCCCGGCG GGCTTTGCGG GCCCGCCAGG CGCTGACGGC    1980

CAGCCGGGTG CGAAAGGCGA ACCGGGGGAT GCGGGTGCTA AAGGCGACGC GGGTCCGCCG    2040

GGCCCTGCCG GCCCGGCGGG CCCGCCAGGC CCGATTGGCA ACGTGGGTGC GCCGGGTGCC    2100

AAAGGTGCGC GCGGCAGCGC TGGTCCGCCG GGCGCGACCG GTTTCCCCGG TGCGGCGGGG    2160

CGCGTGGGTC CGCCAGGCCC GAGCGGTAAC GCGGGTCCGC CAGGTCCGCC TGGCCCGGCT    2220

GGCAAAGAGG GCGGCAAAGG TCCGCGTGGT GAAACCGGCC CTGCGGGACG TCCAGGTGAA    2280

GTGGGTCCGC CGGGCCCGCC GGGCCCGGCG GGCGAAAAAG GTAGCCCGGG TGCGGATGGT    2340

CCCGCCGGTG CGCCAGGCAC GCCGGGTCCG CAAGGTATCG CTGGCCAGCG TGGTGTCGTC    2400

GGGCTGCCGG GTCAGCGCGG CGAACGCGGC TTTCCGGGTC TGCCGGGCCC GAGCGGTGAG    2460

CCGGGCAAAC AGGGTCCATC TGGCGCGAGC GGTGAACGTG GCCCGCCGGG TCCCATGGGC    2520

CCGCCGGGTC TGGCGGGCCC TCCGGGTGAA AGCGGTCGTG AAGGCGCGCC GGGTGCCGAA    2580

GGCAGCCCAG GCCGCGACGG TAGCCCGGGG GCCAAAGGGG ATCGTGGTGA AACCGGCCCG    2640

GCGGGCCCCC CGGGTGCACC GGGCGCGCCG GGTGCCCCAG GCCCGGTGGG CCCGGCGGGC    2700

AAAAGCGGTG ATCGTGGTGA GACCGGTCCG GCGGGCCCGG CCGGTCCGGT GGGCCCAGCG    2760

GGCGCCCGTG GCCCGGCCGG TCCGCAGGGC CGCGGGGTG ACAAAGGTGA AACGGGCGAA    2820

CAGGGCGACC GTGGCATTAA AGGCCACCGT GGCTTCAGCG GCCTGCAGGG TCCACCGGGC    2880

CCGCCGGGCA GTCGGGTGA ACAGGGTCCG TCCGGAGCCA GCGGGCCGGC GGGCCCACGC    2940

GGTCCGCCGG GCAGCGCGGG CGCGCCGGGC AAAGACGGTC TGAACGGTCT GCCGGGCCCG    3000

ATCGGCCCGC CGGGCCCACG CGGCCGCACC GGTGATGCGG GTCCGGTGGG TCCCCCGGGC    3060

CCGCCGGGCC CGCCAGGCCC GCCGGGACCG CCGAGCGCGG GTTTCGACTT CAGCTTCCTG    3120

CCGCAGCCGC CGCAGGAGAA AGCGCACGAC GGCGGTCGCT ACTACCGTGC G            3171
```

(2) INFORMATION FOR SEQ ID NO: 20:

(i) SEQUENCE CHARACTERISTICS:
        (A) LENGTH: 1057 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 20:

```
Gln Leu Ser Tyr Gly Tyr Asp Glu Lys Ser Thr Gly Ile Ser Val
1               5                   10                  15

Pro Gly Pro Met Gly Pro Ser Gly Pro Arg Gly Leu Pro Gly Pro Pro
                20              25                  30

Gly Ala Pro Gly Pro Gln Gly Phe Gln Gly Pro Pro Gly Glu Pro Gly
            35              40                  45

Glu Pro Gly Ala Ser Gly Pro Met Gly Pro Arg Gly Pro Pro Gly Pro
    50              55                  60

Pro Gly Lys Asn Gly Asp Asp Gly Glu Ala Gly Lys Pro Gly Arg Pro
65              70                  75                  80

Gly Glu Arg Gly Pro Pro Gly Pro Gln Gly Ala Arg Gly Leu Pro Gly
                85                  90                  95

Thr Ala Gly Leu Pro Gly Met Lys Gly His Arg Gly Phe Ser Gly Leu
            100                 105                 110

Asp Gly Ala Lys Gly Asp Ala Gly Pro Ala Gly Pro Lys Gly Glu Pro
            115                 120                 125

Gly Ser Pro Gly Glu Asn Gly Ala Pro Gly Gln Met Gly Pro Arg Gly
    130                 135                 140

Leu Pro Gly Glu Arg Gly Arg Pro Gly Ala Pro Gly Pro Ala Gly Ala
145                 150                 155                 160

Arg Gly Asn Asp Gly Ala Thr Gly Ala Ala Gly Pro Pro Gly Pro Thr
                165                 170                 175

Gly Pro Ala Gly Pro Pro Gly Phe Pro Gly Ala Val Gly Ala Lys Gly
            180                 185                 190

Glu Ala Gly Pro Gln Gly Pro Arg Gly Ser Glu Gly Pro Gln Gly Val
        195                 200                 205

Arg Gly Glu Pro Gly Pro Pro Gly Pro Ala Gly Ala Ala Gly Pro Ala
        210                 215                 220

Gly Asn Pro Gly Ala Asp Gly Gln Pro Gly Ala Lys Gly Ala Asn Gly
225                 230                 235                 240

Ala Pro Gly Ile Ala Gly Ala Pro Gly Phe Pro Gly Ala Arg Gly Pro
                245                 250                 255

Ser Gly Pro Gln Gly Pro Gly Gly Pro Pro Gly Pro Lys Gly Asn Ser
            260                 265                 270

Gly Glu Pro Gly Ala Pro Gly Ser Lys Gly Asp Thr Gly Ala Lys Gly
        275                 280                 285

Glu Pro Gly Pro Val Gly Val Gln Gly Pro Pro Gly Pro Ala Gly Glu
    290                 295                 300

Glu Gly Lys Arg Gly Ala Arg Gly Glu Pro Gly Pro Thr Gly Leu Pro
305                 310                 315                 320

Gly Pro Pro Gly Glu Arg Gly Gly Pro Gly Ser Arg Gly Phe Pro Gly
                325                 330                 335

Ala Asp Gly Val Ala Gly Pro Lys Gly Pro Ala Gly Glu Arg Gly Ser
            340                 345                 350

Pro Gly Pro Ala Gly Pro Lys Gly Ser Pro Gly Glu Ala Gly Arg Pro
        355                 360                 365

Gly Glu Ala Gly Leu Pro Gly Ala Lys Gly Leu Thr Gly Ser Pro Gly
    370                 375                 380

Ser Pro Gly Pro Asp Gly Lys Thr Gly Pro Pro Gly Pro Ala Gly Gln
385                 390                 395                 400
```

```
Asp Gly Arg Pro Gly Pro Pro Gly Pro Pro Gly Ala Arg Gly Gln Ala
            405                 410                 415
Gly Val Met Gly Phe Pro Gly Pro Lys Gly Ala Ala Gly Glu Pro Gly
            420                 425                 430
Lys Ala Gly Glu Arg Gly Val Pro Gly Pro Pro Gly Ala Val Gly Pro
            435                 440                 445
Ala Gly Lys Asp Gly Glu Ala Gly Ala Gln Gly Pro Pro Gly Pro Ala
            450                 455                 460
Gly Pro Ala Gly Glu Arg Gly Glu Gln Gly Pro Ala Gly Ser Pro Gly
465                 470                 475                 480
Phe Gln Gly Leu Pro Gly Pro Ala Gly Pro Pro Gly Glu Ala Gly Lys
                485                 490                 495
Pro Gly Glu Gln Gly Val Pro Gly Asp Leu Gly Ala Pro Gly Pro Ser
                500                 505                 510
Gly Ala Arg Gly Glu Arg Gly Phe Pro Gly Glu Arg Gly Val Gln Gly
                515                 520                 525
Pro Pro Gly Pro Ala Gly Pro Arg Gly Ala Asn Gly Ala Pro Gly Asn
        530                 535                 540
Asp Gly Ala Lys Gly Asp Ala Gly Ala Pro Gly Ala Pro Gly Ser Gln
545                 550                 555                 560
Gly Ala Pro Gly Leu Gln Gly Met Pro Gly Glu Arg Gly Ala Ala Gly
                565                 570                 575
Leu Pro Gly Pro Lys Gly Asp Arg Gly Asp Ala Gly Pro Lys Gly Ala
                580                 585                 590
Asp Gly Ser Pro Gly Lys Asp Gly Val Arg Gly Leu Thr Gly Pro Ile
                595                 600                 605
Gly Pro Pro Gly Pro Ala Gly Ala Pro Gly Asp Lys Gly Glu Ser Gly
        610                 615                 620
Pro Ser Gly Pro Ala Gly Pro Thr Gly Ala Arg Gly Ala Pro Gly Asp
625                 630                 635                 640
Arg Gly Glu Pro Gly Pro Pro Gly Pro Ala Gly Phe Ala Gly Pro Pro
                645                 650                 655
Gly Ala Asp Gly Gln Pro Gly Ala Lys Gly Glu Pro Gly Asp Ala Gly
                660                 665                 670
Ala Lys Gly Asp Ala Gly Pro Pro Gly Pro Ala Gly Pro Ala Gly Pro
                675                 680                 685
Pro Gly Pro Ile Gly Asn Val Gly Ala Pro Gly Ala Lys Gly Ala Arg
        690                 695                 700
Gly Ser Ala Gly Pro Pro Gly Ala Thr Gly Phe Pro Gly Ala Ala Gly
705                 710                 715                 720
Arg Val Gly Pro Pro Gly Pro Ser Gly Asn Ala Gly Pro Pro Gly Pro
                725                 730                 735
Pro Gly Pro Ala Gly Lys Glu Gly Gly Lys Gly Pro Arg Gly Glu Thr
                740                 745                 750
Gly Pro Ala Gly Arg Pro Gly Glu Val Gly Pro Pro Gly Pro Pro Gly
                755                 760                 765
Pro Ala Gly Glu Lys Gly Ser Pro Gly Ala Asp Gly Pro Ala Gly Ala
                770                 775                 780
Pro Gly Thr Pro Gly Pro Gln Gly Ile Ala Gly Gln Arg Gly Val Val
785                 790                 795                 800
Gly Leu Pro Gly Gln Arg Gly Glu Arg Gly Phe Pro Gly Leu Pro Gly
                805                 810                 815
Pro Ser Gly Glu Pro Gly Lys Gln Gly Pro Ser Gly Ala Ser Gly Glu
```

```
                820             825              830
Arg Gly Pro Pro Gly Pro Met Gly Pro Pro Gly Leu Ala Gly Pro Pro
        835                 840                 845
Gly Glu Ser Gly Arg Glu Gly Ala Pro Gly Ala Glu Gly Ser Pro Gly
    850                 855                 860
Arg Asp Gly Ser Pro Gly Ala Lys Gly Asp Arg Gly Glu Thr Gly Pro
865                 870                 875                 880
Ala Gly Pro Pro Gly Ala Pro Gly Ala Pro Gly Ala Pro Gly Pro Val
                885                 890                 895
Gly Pro Ala Gly Lys Ser Gly Asp Arg Gly Glu Thr Gly Pro Ala Gly
            900                 905                 910
Pro Ala Gly Pro Val Gly Pro Ala Gly Ala Arg Gly Pro Ala Gly Pro
        915                 920                 925
Gln Gly Pro Arg Gly Asp Lys Gly Glu Thr Gly Glu Gln Gly Asp Arg
    930                 935                 940
Gly Ile Lys Gly His Arg Gly Phe Ser Gly Leu Gln Gly Pro Pro Gly
945                 950                 955                 960
Pro Pro Gly Ser Pro Gly Glu Gln Gly Pro Ser Gly Ala Ser Gly Pro
                965                 970                 975
Ala Gly Pro Arg Gly Pro Pro Gly Ser Ala Gly Ala Pro Gly Lys Asp
            980                 985                 990
Gly Leu Asn Gly Leu Pro Gly Pro Ile Gly Pro Pro Gly Pro Arg Gly
        995                1000                1005
Arg Thr Gly Asp Ala Gly Pro Val Gly Pro Pro Gly Pro Pro Gly Pro
    1010                1015                1020
Pro Gly Pro Pro Gly Pro Pro Ser Ala Gly Phe Asp Phe Ser Phe Leu
1025                1030                1035                1040
Pro Gln Pro Pro Gln Glu Lys Ala His Asp Gly Gly Arg Tyr Tyr Arg
                1045                1050                1055
Ala
```

(2) INFORMATION FOR SEQ ID NO: 21:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

```
GGAATTCATG CAGCTGAGCT ATGGCTATGA TGAAAAAAGC ACCGGCGGCA TCAGCGTGCC      60

GGGCCCGATG GGTCCGAGC                                                   79
```

(2) INFORMATION FOR SEQ ID NO: 22:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

```
GGCCCGGGCT ACCCAGGCTC GCCGGGCGCA CCGGACGGCC CGGGCGGTCC AGCGGGGCCA      60

GCATTATTCG AACCC                                                       75
```

(2) INFORMATION FOR SEQ ID NO: 23:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

```
GGAATTCCGG GTCCGCAGGG CTTTCAGGGT CCGCCGGGCG AACCTGGTGC GAGCGGCCCG     60
ATGGGCCCGC GCGGCCCGCC C                                              81
```

(2) INFORMATION FOR SEQ ID NO: 24:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

```
TACCCGGGCG CGCCGGGCGG CCCAGGCGGT CCGTTTTTGC CGCTACTACC GTTCGCCCGT     60
TTGGCCCTGC AGGCATTATT CGAACCC                                        87
```

(2) INFORMATION FOR SEQ ID NO: 25:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

```
CAGCTGAGCT ATGGCTATGA TGAAAAAAGC ACCGGCGGCA TCAGCGTGCC GGGCCCGATG     60
GGTCCGAGCG GCCCTCGTGG CCTGCCGGGC CGCCAGGTG CGCCCGGTCC G              111
```

(2) INFORMATION FOR SEQ ID NO: 26:

(i) SEQUENCE CHARACTERISTICS:
        (A) LENGTH: 37 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 26:

```
Gln Leu Ser Tyr Gly Tyr Asp Glu Lys Ser Thr Gly Gly Ile Ser Val
1               5                   10                  15
Pro Gly Pro Met Gly Pro Ser Gly Pro Arg Gly Leu Pro Gly Pro Pro
            20                  25                  30
Gly Ala Pro Gly Pro
        35
```

(2) INFORMATION FOR SEQ ID NO: 27:

(i) SEQUENCE CHARACTERISTICS:
        (A) LENGTH: 240 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

CAGCTGAGCT ATGGCTATGA TGAAAAAAGC ACCGGCGGCA TCAGCGTGCC GGGCCCGATG      60

GGTCCGAGCG GCCCTCGTGG CCTGCCGGGC CCGCCAGGTG CGCCCGGTCC GCAGGGCTTT     120

CAGGGTCCGC CGGGCGAACC GGGCGAACCT GGTGCGAGCG GCCCGATGGG CCCGCGCGGC     180

CCGCCGGGTC CGCCAGGCAA AAACGGCGAT GATGGCGAAG CGGGCAAACC GGGACGTCCG     240

(2) INFORMATION FOR SEQ ID NO: 28:

(i) SEQUENCE CHARACTERISTICS:
        (A) LENGTH: 80 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 28:

Gln Leu Ser Tyr Gly Tyr Asp Glu Lys Ser Thr Gly Gly Ile Ser Val
1               5                   10                  15

Pro Gly Pro Met Gly Pro Ser Gly Pro Arg Gly Leu Pro Gly Pro Pro
                20                  25                  30

Gly Ala Pro Gly Pro Gln Gly Phe Gln Gly Pro Pro Gly Glu Pro Gly
            35                  40                  45

Glu Pro Gly Ala Ser Gly Pro Met Gly Pro Arg Gly Pro Pro Gly Pro
    50                  55                  60

Pro Gly Lys Asn Gly Asp Asp Gly Glu Ala Gly Lys Pro Gly Arg Pro
65                  70                  75                  80

(2) INFORMATION FOR SEQ ID NO: 29:

(i) SEQUENCE CHARACTERISTICS:
        (A) LENGTH: 3120 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

CAGTATGATG GAAAAGGAGT TGGACTTGGC CCTGGACCAA TGGGCTTAAT GGGACCTAGA      60

GGCCCACCTG GTGCAGCTGG AGCCCCAGGC CCTCAAGGTT TCCAAGGACC TGCTGGTGAG     120

CCTGGTGAAC CTGGTCAAAC TGGTCCTGCA GGTGCTCGTG GTCCAGCTGG CCCTCCTGGC     180

AAGGCTGGTG AAGATGGTCA CCCTGGAAAA CCCGGACGAC TGGTGAGAG AGGAGTTGTT     240

GGACCACAGG GTGCTCGTGG TTTCCCTGGA ACTCCTGGAC TTCCTGGCTT CAAAGGCATT     300

AGGGGACACA ATGGTCTGGA TGGATTGAAG GGACAGCCCG GTGCTCCTGG TGTGAAGGGT     360

GAACCTGGTG CCCCTGGTGA AAATGGAACT CCAGGTCAAA CAGGAGCCCG TGGGCTTCCT     420

GGTGAGAGAG GACGTGTTGG TGCCCCTGGC CCAGCTGGTG CCCGTGGCAG TGATGGAAGT     480

GTGGGTCCCG TGGGTCCTGC TGGTCCCATT GGGTCTGCTG GCCCTCCAGG CTTCCCAGGT     540

GCCCCTGGCC CCAAGGGTGA AATTGGAGCT GTTGGTAACG CTGGTCCTGC TGGTCCCGCC     600

GGTCCCCGTG GTGAAGTGGG TCTTCCAGGC CTCTCCGGCC CCGTTGGACC TCCTGGTAAT     660

| | |
|---|---|
| CCTGGAGCAA ACGGCCTTAC TGGTGCCAAG GGTGCTGCTG GCCTTCCCGG CGTTGCTGGG | 720 |
| GCTCCCGGCC TCCCTGGACC CCGCGGTATT CCTGGCCCTG TTGGTGCTGC CGGTGCTACT | 780 |
| GGTGCCAGAG GACTTGTTGG TGAGCCTGGT CCAGCTGGCT CCAAAGGAGA GAGCGGTAAC | 840 |
| AAGGGTGAGC CCGGCTCTGC TGGGCCCCAA GGTCCTCCTG GTCCCAGTGG TGAAGAAGGA | 900 |
| AAGAGAGGCC CTAATGGGGA AGCTGGATCT GCCGGCCCTC CAGGACCTCC TGGGCTGAGA | 960 |
| GGTAGTCCTG GTTCTCGTGG TCTTCCTGGA GCTGATGGCA GAGCTGGCGT CATGGGCCCT | 1020 |
| CCTGGTAGTC GTGGTGCAAG TGGCCCTGCT GGAGTCCGAG GACCTAATGG AGATGCTGGT | 1080 |
| CGCCCTGGGG AGCCTGGTCT CATGGGACCC AGAGGTCTTC CTGGTTCCCC TGGAAATATC | 1140 |
| GGCCCCGCTG GAAAAGAAGG TCCTGTCGGC CTCCCTGGCA TCGACGGCAG GCCTGGCCCA | 1200 |
| ATTGGCCCAG CTGGAGCAAG AGGAGAGCCT GGCAACATTG GATTCCCTGG ACCCAAAGGC | 1260 |
| CCCACTGGTG ATCCTGGCAA AAACGGTGAT AAAGGTCATG CTGGTCTTGC TGGTGCTCGG | 1320 |
| GGTGCTCCAG GTCCTGATGG AAACAATGGT GCTCAGGGAC CTCCTGGACC ACAGGGTGTT | 1380 |
| CAAGGTGGAA AAGGTGAACA GGGTCCCGCT GGTCCTCCAG GCTTCCAGGG TCTGCCTGGC | 1440 |
| CCCTCAGGTC CCGCTGGTGA AGTTGGCAAA CCAGGAGAAA GGGGTCTCCA TGGTGAGTTT | 1500 |
| GGTCTCCCTG GTCCTGCTGG TCCAAGAGGG AACGCGGTC CCCAGGTGA GAGTGGTGCT | 1560 |
| GCCGGTCCTA CTGGTCCTAT GGAAGCCGA GGTCCTTCTG GACCCCAGG GCCTGATGGA | 1620 |
| AACAAGGGTG AACCTGGTGT GGTTGGTGCT GTGGGCACTG CTGGTCCATC TGGTCCTAGT | 1680 |
| GGACTCCCAG GAGAGAGGGG TGCTGCTGGC ATACCTGGAG GCAAGGGAGA AAAGGGTGAA | 1740 |
| CCTGGTCTCA GAGGTGAAAT TGGTAACCCT GGCAGAGATG GTGCTCGTGG TGCTCATGGT | 1800 |
| GCTGTAGGTG CCCCTGGTCC TGCTGGAGCC ACAGGTGACC GGGGCGAAGC TGGGGCTGCT | 1860 |
| GGTCCTGCTG GTCCTGCTGG TCCTCGGGGA AGCCCTGGTG AACGTGGCGA GGTCGGTCCT | 1920 |
| GCTGGCCCCA ACGGATTTGC TGGTCCGGCT GGTGCTGCTG GTCAACCGGG TGCTAAAGGA | 1980 |
| GAAAGAGGAG CCAAAGGGCC TAAGGGTGAA AACGGTGTTG TTGGTCCCAC AGGCCCCGTT | 2040 |
| GGAGCTGCTG GCCCAGCTGG TCCAAATGGT CCCCCCGGTC CTGCTGGAAG TCGTGGTGAT | 2100 |
| GGAGGCCCCC CTGGTATGAC TGGTTTCCCT GGTGCTGCTG GACGGACTGG TCCCCCAGGA | 2160 |
| CCCTCTGGTA TTTCTGGCCC TCCTGGTCCC CCTGGTCCTG CTGGGAAAGA AGGGCTTCGT | 2220 |
| GGTCCTCGTG GTGACCAAGG TCCAGTTGGC CGAACTGGAG AAGTAGGTGC AGTTGGTCCC | 2280 |
| CCTGGCTTCG CTGGTGAGAA GGGTCCCTCT GGAGAGGCTG GTACTGCTGG ACCTCCTGGC | 2340 |
| ACTCCAGGTC CTCAGGGTCT TCTTGGTGCT CCTGGTATTC TGGGTCTCCC TGGCTCGAGA | 2400 |
| GGTGAACGTG GTCTACCTGG TGTTGCTGGT GCTGTGGGTG AACCTGGTCC TCTTGGCATT | 2460 |
| GCCGGCCCTC CTGGGGCCCG TGGTCCTCCT GGTGCTGTGG GTAGTCCTGG AGTCAACGGT | 2520 |
| GCTCCTGGTG AAGCTGGTCG TGATGGCAAC CCTGGGAACG ATGGTCCCCC AGGTCGCGAT | 2580 |
| GGTCAACCCG GACACAAGGG AGAGCGCGGT TACCCTGGCA ATATTGGTCC CGTTGGTGCT | 2640 |
| GCAGGTGCAC CTGGTCCTCA TGGCCCCGTG GGTCCTGCTG GCAAACATGG AAACCGTGGT | 2700 |
| GAAACTGGTC CTTCTGGTCC TGTTGGTCCT GCTGGTGCTG TTGGCCCAAG AGGTCCTAGT | 2760 |
| GGCCCACAAG GCATTCGTGG CGATAAGGGA GAGCCCGGTG AAAAGGGGCC CAGAGGTCTT | 2820 |
| CCTGGCTTAA AGGGACACAA TGGATTGCAA GGTCTGCCTG GTATCGCTGG TCACCATGGT | 2880 |
| GATCAAGGTG CTCCTGGCTC CGTGGGTCCT GCTGGTCCTA GGGGCCCTGC TGGTCCTTCT | 2940 |
| GGCCCTGCTG GAAAAGATGG TCGCACTGGA CATCCTGGTA CGGTTGGACC TGCTGGCATT | 3000 |
| CGAGGCCCTC AGGGTCACCA AGGCCCTGCT GGCCCCCCTG GTCCCCCTGG CCCTCCTGGA | 3060 |

-continued

CCTCCAGGTG TAAGCGGTGG TGGTTATGAC TTTGGTTACG ATGGAGACTT CTACAGGGCT   3120

(2) INFORMATION FOR SEQ ID NO: 30:

(i) SEQUENCE CHARACTERISTICS:
        (A) LENGTH: 1040 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 30:

```
Gln Tyr Asp Gly Lys Gly Val Gly Leu Gly Pro Gly Pro Met Gly Leu
 1               5                  10                  15

Met Gly Pro Arg Gly Pro Pro Gly Ala Gly Ala Pro Gly Pro Gln
             20                  25                  30

Gly Phe Gln Gly Pro Ala Gly Glu Pro Gly Glu Pro Gly Gln Thr Gly
             35                  40                  45

Pro Ala Gly Ala Arg Gly Pro Ala Gly Pro Pro Gly Lys Ala Gly Glu
 50                  55                  60

Asp Gly His Pro Gly Lys Pro Gly Arg Pro Gly Glu Arg Gly Val Val
 65                  70                  75                  80

Gly Pro Gln Gly Ala Arg Gly Phe Pro Gly Thr Pro Gly Leu Pro Gly
                 85                  90                  95

Phe Lys Gly Ile Arg Gly His Asn Gly Leu Asp Gly Leu Lys Gly Gln
                100                 105                 110

Pro Gly Ala Pro Gly Val Lys Gly Glu Pro Gly Ala Pro Gly Glu Asn
            115                 120                 125

Gly Thr Pro Gly Gln Thr Gly Ala Arg Gly Leu Pro Gly Glu Arg Gly
            130                 135                 140

Arg Val Gly Ala Pro Gly Pro Ala Gly Ala Arg Gly Ser Asp Gly Ser
145                 150                 155                 160

Val Gly Pro Val Gly Pro Ala Gly Pro Ile Gly Ser Ala Gly Pro Pro
                165                 170                 175

Gly Phe Pro Gly Ala Pro Gly Pro Lys Gly Glu Ile Gly Ala Val Gly
                180                 185                 190

Asn Ala Gly Pro Ala Gly Pro Ala Gly Pro Arg Gly Glu Val Gly Leu
            195                 200                 205

Pro Gly Leu Ser Gly Pro Val Gly Pro Pro Gly Asn Pro Gly Ala Asn
210                 215                 220

Gly Leu Thr Gly Ala Lys Gly Ala Ala Gly Leu Pro Gly Val Ala Gly
225                 230                 235                 240

Ala Pro Gly Leu Pro Gly Pro Arg Gly Ile Pro Gly Pro Val Gly Ala
                245                 250                 255

Ala Gly Ala Thr Gly Ala Arg Gly Leu Val Gly Glu Pro Gly Pro Ala
                260                 265                 270

Gly Ser Lys Gly Glu Ser Gly Asn Lys Gly Glu Pro Gly Ser Ala Gly
            275                 280                 285

Pro Gln Gly Pro Pro Gly Pro Ser Gly Glu Glu Gly Lys Arg Gly Pro
290                 295                 300

Asn Gly Glu Ala Gly Ser Ala Gly Pro Pro Gly Pro Pro Gly Leu Arg
305                 310                 315                 320

Gly Ser Pro Gly Ser Arg Gly Leu Pro Gly Ala Asp Gly Arg Ala Gly
                325                 330                 335
```

-continued

```
Val Met Gly Pro Pro Gly Ser Arg Gly Ala Ser Gly Pro Ala Gly Val
            340                 345                 350

Arg Gly Pro Asn Gly Asp Ala Gly Arg Pro Gly Glu Pro Gly Leu Met
        355                 360                 365

Gly Pro Arg Gly Leu Pro Gly Ser Pro Gly Asn Ile Gly Pro Ala Gly
    370                 375                 380

Lys Glu Gly Pro Val Gly Leu Pro Gly Ile Asp Gly Arg Pro Gly Pro
385                 390                 395                 400

Ile Gly Pro Ala Gly Ala Arg Gly Glu Pro Gly Asn Ile Gly Phe Pro
                405                 410                 415

Gly Pro Lys Gly Pro Thr Gly Asp Pro Gly Lys Asn Gly Asp Lys Gly
            420                 425                 430

His Ala Gly Leu Ala Gly Ala Arg Gly Ala Pro Gly Pro Asp Gly Asn
        435                 440                 445

Asn Gly Ala Gln Gly Pro Pro Gly Pro Gln Gly Val Gln Gly Gly Lys
    450                 455                 460

Gly Glu Gln Gly Pro Ala Gly Pro Pro Gly Phe Gln Gly Leu Pro Gly
465                 470                 475                 480

Pro Ser Gly Pro Ala Gly Glu Val Gly Lys Pro Gly Glu Arg Gly Leu
                485                 490                 495

His Gly Glu Phe Gly Leu Pro Gly Pro Ala Gly Pro Arg Gly Glu Arg
            500                 505                 510

Gly Pro Pro Gly Glu Ser Gly Ala Ala Gly Pro Thr Gly Pro Ile Gly
        515                 520                 525

Ser Arg Gly Pro Ser Gly Pro Pro Gly Pro Asp Gly Asn Lys Gly Glu
    530                 535                 540

Pro Gly Val Val Gly Ala Val Gly Thr Ala Gly Pro Ser Gly Pro Ser
545                 550                 555                 560

Gly Leu Pro Gly Glu Arg Gly Ala Ala Gly Ile Pro Gly Gly Lys Gly
                565                 570                 575

Glu Lys Gly Glu Pro Gly Leu Arg Gly Glu Ile Gly Asn Pro Gly Arg
            580                 585                 590

Asp Gly Ala Arg Gly Ala His Gly Ala Val Gly Ala Pro Gly Pro Ala
        595                 600                 605

Gly Ala Thr Gly Asp Arg Gly Glu Ala Gly Ala Ala Gly Pro Ala Gly
    610                 615                 620

Pro Ala Gly Pro Arg Gly Ser Pro Gly Glu Arg Gly Glu Val Gly Pro
625                 630                 635                 640

Ala Gly Pro Asn Gly Phe Ala Gly Pro Ala Gly Ala Ala Gly Gln Pro
                645                 650                 655

Gly Ala Lys Gly Glu Arg Gly Ala Lys Gly Pro Lys Gly Glu Asn Gly
            660                 665                 670

Val Val Gly Pro Thr Gly Pro Val Gly Ala Ala Gly Pro Ala Gly Pro
        675                 680                 685

Asn Gly Pro Pro Gly Pro Ala Gly Ser Arg Gly Asp Gly Gly Pro Pro
    690                 695                 700

Gly Met Thr Gly Phe Pro Gly Ala Ala Gly Arg Thr Gly Pro Pro Gly
705                 710                 715                 720

Pro Ser Gly Ile Ser Gly Pro Pro Gly Pro Pro Gly Pro Ala Gly Lys
                725                 730                 735

Glu Gly Leu Arg Gly Pro Arg Gly Asp Gln Gly Pro Val Gly Arg Thr
            740                 745                 750

Gly Glu Val Gly Ala Val Gly Pro Pro Gly Phe Ala Gly Glu Lys Gly
```

|  | 755 |  |  |  | 760 |  |  |  | 765 |  |  |
|---|---|---|---|---|---|---|---|---|---|---|---|
| Pro | Ser | Gly | Glu | Ala | Gly | Thr | Ala | Gly | Pro | Pro | Gly |
|  |  | Thr | Pro | Gly | Pro |  |  |  |  |  |  |
|  |  | 770 |  |  | 775 |  |  |  | 780 |  |  |

Pro Ser Gly Glu Ala Gly Thr Ala Gly Pro Gly Thr Pro Gly Pro
770                     775                 780

Gln Gly Leu Leu Gly Ala Pro Gly Ile Leu Gly Leu Pro Gly Ser Arg
785                 790                 795                 800

Gly Glu Arg Gly Leu Pro Gly Val Ala Gly Ala Val Gly Glu Pro Gly
            805                 810                 815

Pro Leu Gly Ile Ala Gly Pro Gly Ala Arg Gly Pro Pro Gly Ala
                820             825             830

Val Gly Ser Pro Gly Val Asn Gly Ala Pro Gly Glu Ala Gly Arg Asp
            835             840             845

Gly Asn Pro Gly Asn Asp Gly Pro Gly Arg Asp Gly Gln Pro Gly
850             855             860

His Lys Gly Glu Arg Gly Tyr Pro Gly Asn Ile Gly Pro Val Gly Ala
865             870             875             880

Ala Gly Ala Pro Gly Pro His Gly Pro Val Gly Pro Ala Gly Lys His
                885             890             895

Gly Asn Arg Gly Glu Thr Gly Pro Ser Gly Pro Val Gly Pro Ala Gly
            900             905             910

Ala Val Gly Pro Arg Gly Pro Ser Gly Pro Gln Gly Ile Arg Gly Asp
            915             920             925

Lys Gly Glu Pro Gly Glu Lys Gly Pro Arg Gly Leu Pro Gly Leu Lys
930             935             940

Gly His Asn Gly Leu Gln Gly Leu Pro Gly Ile Ala Gly His His Gly
945             950             955             960

Asp Gln Gly Ala Pro Gly Ser Val Gly Pro Ala Gly Pro Arg Gly Pro
            965             970             975

Ala Gly Pro Ser Gly Pro Ala Gly Lys Asp Gly Arg Thr Gly His Pro
            980             985             990

Gly Thr Val Gly Pro Ala Gly Ile Arg Gly Pro Gln Gly His Gln Gly
            995             1000            1005

Pro Ala Gly Pro Pro Gly Pro Pro Gly Pro Pro Gly Pro Pro Gly Val
    1010            1015            1020

Ser Gly Gly Gly Tyr Asp Phe Gly Tyr Asp Gly Asp Phe Tyr Arg Ala
1025            1030            1035            1040

(2) INFORMATION FOR SEQ ID NO: 31:

(i) SEQUENCE CHARACTERISTICS:
  (A) LENGTH: 3120 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 31:

```
CAGTACGACG GTAAAGGCGT AGGCCTGGGT CCGGGTCCGA TGGGCCTGAT GGGTCCACGT      60

GGCCCACCGG GTGCAGCAGG TGCGCCGGGT CCGCAGGGCT TCCAAGGTCC GGCGGGTGAA     120

CCGGGCGAAC CGGGTCAGAC GGGTCCGGCG GGTGCTCGCG GTCCGGCTGG CCCACCGGGC     180

AAAGCTGGCG AAGACGGTCA CCCGGGTAAG CCAGGCCGCC CGGGCGAACG TGGCGTCGTG     240

GGTCCGCAAG GTGCGCGTGG TTTCCCGGGC ACGCCGGGTC TGCCGGGTTT CAAAGGCATT     300

CGTGGTCACA ACGGTCTGGA CGGTCTGAAA GGCCAACCGG GTGCTCCGGG CGTCAAAGGC     360

GAACCGGGTG CCCCAGGCGA AAACGGTACG CCGGGCCAGA CTGGTGCGCG TGGTCTGCCG     420
```

-continued

```
GGTGAACGCG GCCGTGTTGG CGCTCCGGGT CCGGCTGGCG CGCGTGGCAG CGATGGCTCC      480

GTCGGTCCGG TTGGCCCTGC GGGTCCGATT GGTTCCGCTG GCCCTCCGGG TTTCCCGGGT      540

GCGCCGGGTC CGAAGGGTGA GATCGGCGCG GTTGGCAACG CAGGCCCGGC TGGTCCAGCC      600

GGCCCTCGTG GCGAAGTCGG TCTGCCGGGT CTGAGCGGTC CGGTAGGCCC ACCGGGTAAC      660

CCGGGCGCAA ACGGCCTGAC GGGTGCAAAA GGTGCGGCTG GCCTGCCGGG CGTTGCCGGT      720

GCCCCGGGCC TGCCGGGTCC GCGCGGTATT CCGGGTCCGG TAGGCGCAGC CGGTGCAACT      780

GGTGCCCGTG GCCTGGTTGG CGAACCGGGT CCGGCGGGTT CTAAAGGCGA AAGCGGTAAC      840

AAAGGTGAGC CGGGTTCCGC GGGCCCGCAG GGTCCGCCGG GTCCGAGCGG CGAAGAAGGT      900

AAACGTGGTC CGAACGGCGA GGCTGGTTCC GCAGGCCCTC CGGGTCCGCC GGGTCTGCGT      960

GGCAGCCCGG GTAGCCGTGG CCTGCCGGGC GCGGACGGCC GTGCGGGCGT GATGGGTCCG      1020

CCGGGTTCCC GTGGTGCCTC TGGTCCGGCT GGTGTCCGTG GTCCGAATGG CGACGCGGGC      1080

CGTCCGGGTG AACCGGGCCT GATGGGTCCG CGTGGCCTGC CGGGTAGCCC GGGTAACATT      1140

GGTCCGGCGG GTAAGGAGGG TCCGGTAGGT CTGCCGGGTA TTGATGGTCG TCCGGGTCCG      1200

ATCGGCCCTG CGGGCGCTCG TGGCGAGCCG GGTAACATCG GTTTTCCGGG TCCGAAGGGT      1260

CCGACGGGCG ACCCGGGCAA GAACGGTGAT AAAGGCCATG CAGGTCTGGC AGGTGCCCGT      1320

GGTGCACCGG GTCCGGATGG TAACAATGGT GCGCAGGGTC CGCCGGGTCC GCAGGGCGTA      1380

CAGGGTGGCA AAGGTGAACA GGGTCCGGCA GGCCCACCGG GCTTCCAGGG TCTGCCGGGT      1440

CCGAGCGGCC CGGCTGGTGA AGTGGGCAAA CCGGGCGAAC GTGGCCTCCA TGGCGAGTTT      1500

GGCCTGCCGG GTCCGCCGGG TCCGCGTGGT GAGCGCGGCC CTCCGGGCGA ATCCGGCGCG      1560

GCAGGTCCGA CCGGCCCGAT TGGTTCCCGT GGTCCGAGCG GCCACCGGG TCCGGACGGC       1620

AACAAAGGCG AGCCGGGTGT TGTTGGTGCT GTTGGTACCG CCGGCCCGTC TGGTCCGAGC      1680

GGTCTGCCGG GCGAACGCGG TGCCGCTGGT ATTCCGGGCG GCAAAGGTGA AAAAGGTGAA      1740

CCGGGTCTGC GCGGTGAGAT TGGCAACCCG GGCCGTGACG GTGCTCGCGG TGCACACGGC      1800

GCGGTTGGCG CACCGGGTCC GGCAGGCGCG ACTGGTGATC GTGGCGAAGC TGGTGCAGCG      1860

GGTCCGGCGG GTCCGGCCGG CCCTCGCGGT TCCCCGGGCG AACGCGGCGA AGTCGGCCCG      1920

GCTGGCCCGA ATGGCTTTGC TGGCCCAGCG GGCGCTGCGG GCCAACCGGG TGCGAAAGGT      1980

GAGCGCGGTG CCAAAGGCCC GAAAGGTGAA AATGGTGTAG TTGGTCCGAC GGGTCCGGTT      2040

GGTGCGGCTG GTCCGGCTGG CCCGAATGGT CCGCCGGGTC CGGCAGGCAG CCGTGGCGAT      2100

GGTGGCCCAC CGGGCATGAC CGGTTTCCCT GGCGCGGCCG GTCGCACCGG CCCGCCGGGT      2160

CCGTCTGGCA TTTCTGGCCC ACCGGGTCCG CCGGGTCCGG CGGGCAAAGA AGGTCTGCGT      2220

GGCCCACGCG GCGACCAGGG TCCGGTGGGC CGTACCGGCG AAGTCGGTGC TGTTGGCCCT      2280

CCGGGCTTTG CGGGTGAGAA AGGTCCGAGC GGTGAAGCTG GCACCGCAGG CCCGCCGGGT      2340

ACGCCGGGTC CGCAAGGTCT GCTGGGTGCT CCGGGTATCC TGGGCCTGCC GGGCTCCCGT      2400

GGCGAACGCG GTCTGCCGGG CGTTGCAGGC GCTGTAGGCG AACCGGGTCC GCTGGGTATC      2460

GCGGGTCCGC CGGGTGCGCG TGGTCCGCCG GGTGCCGTGG GCTCTCCGGG TGTTAACGGC      2520

GCCCCTGGTG AAGCGGGCCG CGACGGCAAT CCGGGCAACG ATGGTCCGCC GGGTCGTGAT      2580

GGTCAGCCGG GTCACAAAGG TGAGCGTGGC TACCGGGTA ACATCGGTCC GGTTGGTGCG       2640

GCCGGCGCTC CGGGTCCGCA CGGTCCGGTA GGCCCAGCCG GCAAACACGG TAACCGTGGT      2700

GAAACGGGTC CGTCCGGTCC GGTAGGTCCG GCGGGTGCTG TTGGTCCACG CGGCCCGTCC      2760
```

-continued

```
GGCCCGCAGG GTATTCGCGG TGACAAAGGC GAACCGGGCG AAAAAGGTCC GCGTGGTCTG    2820

CCGGGCCTTA AGGGCCACAA CGGTCTGCAA GGTCTGCCGG GTATCGCGGG TCACCACGGT    2880

GATCAGGGTG CTCCGGGTTC CGTTGGTCCG GCCGGTCCGC GTGGCCCGGC TGGTCCGTCT    2940

GGTCCGGCCG GTAAAGACGG CCGTACGGGC CACCCGGGTA CGGTGGGTCC GGCCGGCATT    3000

CGCGGTCCGC AAGGTCACCA GGGTCCGGCC GGTCCGCCGG GTCCGCCGGG TCCGCCGGGT    3060

CCGCCGGGTG TTAGCGGTGG CGGTTATGAT TTTGGTTATG ACGGTGATTT CTATCGTGCG    3120
```

(2) INFORMATION FOR SEQ ID NO: 32:

(i) SEQUENCE CHARACTERISTICS:
        (A) LENGTH: 1040 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 32:

```
Gln Tyr Asp Gly Lys Gly Val Gly Leu Gly Pro Gly Pro Met Gly Leu
1               5                   10                  15

Met Gly Pro Arg Gly Pro Pro Gly Ala Ala Gly Ala Pro Gly Pro Gln
            20                  25                  30

Gly Phe Gln Gly Pro Ala Gly Glu Pro Gly Glu Pro Gly Gln Thr Gly
        35                  40                  45

Pro Ala Gly Ala Arg Gly Pro Ala Gly Pro Pro Gly Lys Ala Gly Glu
    50                  55                  60

Asp Gly His Pro Gly Lys Pro Gly Arg Pro Gly Glu Arg Gly Val Val
65                  70                  75                  80

Gly Pro Gln Gly Ala Arg Gly Phe Pro Gly Thr Pro Gly Leu Pro Gly
                85                  90                  95

Phe Lys Gly Ile Arg Gly His Asn Gly Leu Asp Gly Leu Lys Gly Gln
            100                 105                 110

Pro Gly Ala Pro Gly Val Lys Gly Glu Pro Gly Ala Pro Gly Glu Asn
        115                 120                 125

Gly Thr Pro Gly Gln Thr Gly Ala Arg Gly Leu Pro Gly Glu Arg Gly
    130                 135                 140

Arg Val Gly Ala Pro Gly Pro Ala Gly Ala Arg Gly Ser Asp Gly Ser
145                 150                 155                 160

Val Gly Pro Val Gly Pro Ala Gly Pro Ile Gly Ser Ala Gly Pro Pro
                165                 170                 175

Gly Phe Pro Gly Ala Pro Gly Pro Lys Gly Glu Ile Gly Ala Val Gly
            180                 185                 190

Asn Ala Gly Pro Ala Gly Pro Ala Gly Pro Arg Gly Glu Val Gly Leu
        195                 200                 205

Pro Gly Leu Ser Gly Pro Val Gly Pro Pro Gly Asn Pro Gly Ala Asn
    210                 215                 220

Gly Leu Thr Gly Ala Lys Gly Ala Ala Gly Leu Pro Gly Val Ala Gly
225                 230                 235                 240

Ala Pro Gly Leu Pro Gly Pro Arg Gly Ile Pro Gly Pro Val Gly Ala
                245                 250                 255

Ala Gly Ala Thr Gly Ala Arg Gly Leu Val Gly Glu Pro Gly Pro Ala
            260                 265                 270

Gly Ser Lys Gly Glu Ser Gly Asn Lys Gly Glu Pro Gly Ser Ala Gly
        275                 280                 285
```

```
Pro Gln Gly Pro Pro Gly Pro Ser Gly Glu Glu Gly Lys Arg Gly Pro
    290                 295                 300
Asn Gly Glu Ala Gly Ser Ala Gly Pro Pro Gly Pro Pro Gly Leu Arg
305                 310                 315                 320
Gly Ser Pro Gly Ser Arg Gly Leu Pro Gly Ala Asp Gly Arg Ala Gly
                325                 330                 335
Val Met Gly Pro Pro Gly Ser Arg Gly Ala Ser Gly Pro Ala Gly Val
            340                 345                 350
Arg Gly Pro Asn Gly Asp Ala Gly Arg Pro Gly Glu Pro Gly Leu Met
        355                 360                 365
Gly Pro Arg Gly Leu Pro Gly Ser Pro Gly Asn Ile Gly Pro Ala Gly
    370                 375                 380
Lys Glu Gly Pro Val Gly Leu Pro Gly Ile Asp Gly Arg Pro Gly Pro
385                 390                 395                 400
Ile Gly Pro Ala Gly Ala Arg Gly Glu Pro Gly Asn Ile Gly Phe Pro
                405                 410                 415
Gly Pro Lys Gly Pro Thr Gly Asp Pro Gly Lys Asn Gly Asp Lys Gly
            420                 425                 430
His Ala Gly Leu Ala Gly Ala Arg Gly Ala Pro Gly Pro Asp Gly Asn
        435                 440                 445
Asn Gly Ala Gln Gly Pro Pro Gly Pro Gln Gly Val Gln Gly Gly Lys
450                 455                 460
Gly Glu Gln Gly Pro Ala Gly Pro Pro Gly Phe Gln Gly Leu Pro Gly
465                 470                 475                 480
Pro Ser Gly Pro Ala Gly Glu Val Gly Lys Pro Gly Glu Arg Gly Leu
                485                 490                 495
His Gly Glu Phe Gly Leu Pro Gly Pro Ala Gly Pro Arg Gly Glu Arg
            500                 505                 510
Gly Pro Pro Gly Glu Ser Gly Ala Ala Gly Pro Thr Gly Pro Ile Gly
        515                 520                 525
Ser Arg Gly Pro Ser Gly Pro Pro Gly Pro Asp Gly Asn Lys Gly Glu
    530                 535                 540
Pro Gly Val Val Gly Ala Val Gly Thr Ala Gly Pro Ser Gly Pro Ser
545                 550                 555                 560
Gly Leu Pro Gly Glu Arg Gly Ala Ala Gly Ile Pro Gly Gly Lys Gly
                565                 570                 575
Glu Lys Gly Glu Pro Gly Leu Arg Gly Glu Ile Gly Asn Pro Gly Arg
            580                 585                 590
Asp Gly Ala Arg Gly Ala His Gly Ala Val Gly Ala Pro Gly Pro Ala
        595                 600                 605
Gly Ala Thr Gly Asp Arg Gly Glu Ala Gly Ala Ala Gly Pro Ala Gly
    610                 615                 620
Pro Ala Gly Pro Arg Gly Ser Pro Gly Glu Arg Gly Glu Val Gly Pro
625                 630                 635                 640
Ala Gly Pro Asn Gly Phe Ala Gly Pro Ala Gly Ala Ala Gly Gln Pro
                645                 650                 655
Gly Ala Lys Gly Glu Arg Gly Ala Lys Gly Pro Lys Gly Glu Asn Gly
            660                 665                 670
Val Val Gly Pro Thr Gly Pro Val Gly Ala Ala Gly Pro Ala Gly Pro
        675                 680                 685
Asn Gly Pro Pro Gly Pro Ala Gly Ser Arg Gly Asp Gly Gly Pro Pro
    690                 695                 700
Gly Met Thr Gly Phe Pro Gly Ala Ala Gly Arg Thr Gly Pro Pro Gly
```

```
                    705                 710                 715                 720
Pro Ser Gly Ile Ser Gly Pro Pro Gly Pro Pro Gly Pro Ala Gly Lys
                725                 730                 735

Glu Gly Leu Arg Gly Pro Arg Gly Asp Gln Gly Pro Val Gly Arg Thr
                740                 745                 750

Gly Glu Val Gly Ala Val Gly Pro Pro Gly Phe Ala Gly Glu Lys Gly
                755                 760                 765

Pro Ser Gly Glu Ala Gly Thr Ala Gly Pro Pro Gly Thr Pro Gly Pro
            770                 775                 780

Gln Gly Leu Leu Gly Ala Pro Gly Ile Leu Gly Leu Pro Gly Ser Arg
785                 790                 795                 800

Gly Glu Arg Gly Leu Pro Gly Val Ala Gly Ala Val Gly Glu Pro Gly
                805                 810                 815

Pro Leu Gly Ile Ala Gly Pro Pro Gly Ala Arg Gly Pro Pro Gly Ala
                820                 825                 830

Val Gly Ser Pro Gly Val Asn Gly Ala Pro Gly Glu Ala Gly Arg Asp
            835                 840                 845

Gly Asn Pro Gly Asn Asp Gly Pro Pro Gly Arg Asp Gly Gln Pro Gly
850                 855                 860

His Lys Gly Glu Arg Gly Tyr Pro Gly Asn Ile Gly Pro Val Gly Ala
865                 870                 875                 880

Ala Gly Ala Pro Gly Pro His Gly Pro Val Gly Pro Ala Gly Lys His
                885                 890                 895

Gly Asn Arg Gly Glu Thr Gly Pro Ser Gly Pro Val Gly Pro Ala Gly
                900                 905                 910

Ala Val Gly Pro Arg Gly Pro Ser Gly Pro Gln Gly Ile Arg Gly Asp
                915                 920                 925

Lys Gly Glu Pro Gly Glu Lys Gly Pro Arg Gly Leu Pro Gly Leu Lys
            930                 935                 940

Gly His Asn Gly Leu Gln Gly Leu Pro Gly Ile Ala Gly His His Gly
945                 950                 955                 960

Asp Gln Gly Ala Pro Gly Ser Val Gly Pro Ala Gly Pro Arg Gly Pro
                965                 970                 975

Ala Gly Pro Ser Gly Pro Ala Gly Lys Asp Gly Arg Thr Gly His Pro
                980                 985                 990

Gly Thr Val Gly Pro Ala Gly Ile Arg Gly Pro Gln Gly His Gln Gly
                995                1000                1005

Pro Ala Gly Pro Pro Gly Pro Pro Gly Pro Pro Gly Pro Pro Gly Val
            1010                1015                1020

Ser Gly Gly Gly Tyr Asp Phe Gly Tyr Asp Gly Asp Phe Tyr Arg Ala
1025                1030                1035                1040

(2) INFORMATION FOR SEQ ID NO: 33:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

GGAATTCATG CAGTATGATG GCAAAGGCGT CGGCCTCGGC CCGGGCCCAA TGGGCCTCAT      60

GGGCCCGCGC GGCCCA                                                     76
```

(2) INFORMATION FOR SEQ ID NO: 34:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

```
CCGGGCGCGC CGGGTGGCCC ACGTCGACCG CGGGGTCCGG GCGTTCCAAA GGTCCCGGGA      60

CGGCCAATTA TTCGAACCC                                                  79
```

(2) INFORMATION FOR SEQ ID NO: 35:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

```
GGAATTCGCC GGTGAGCCGG GTGAACCGGG CCAAACGGGT CCGGCAGGTC CACGTGGTCC      60

AGCGGGCCCG CCTGGCAAGG CG                                              82
```

(2) INFORMATION FOR SEQ ID NO: 36:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

```
CCGGGCGGAC CGTTCCGCCC ACTTCTACCG GTGGGACCGT TTGGCCCGGC GGGCCACTCG      60

CACCGCATCA CATTATTCGA ACCC                                            84
```

(2) INFORMATION FOR SEQ ID NO: 37:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

```
CAGTATGATG GCAAAGGCGT CGGCCTCGGC CCGGGCCCAA TGGGCCTCAT GGGCCCGCGC      60

GGCCCACCGG GTGCAGCTGG CGCCCCAGGC CCGCAAGGTT TCCAGGGCCC TGCCGGTGAG     120

CCGGGTGAAC CGGGCCAAAC GGGTCCGGCA GGTGCACGTG GTCCAGCGGG CCCGCCTGGC     180

AAGGCGGGTG AAGATGGCCA CCCTGGCAAA CCGGGCCGCC CGGGTGAGCG TGGCGTAGTG     240
```

(2) INFORMATION FOR SEQ ID NO: 38:

(i) SEQUENCE CHARACTERISTICS:
        (A) LENGTH: 80 amino acids
        (B) TYPE: amino acid
        (C) STRANDEDNESS: single (D) TOPOLOGY: unknown (ii) MOLECULE TYPE: peptide (xi) SEQUENCE DESCRIPTION: SEQ ID NO: 38:

Gln Tyr Asp Gly Lys Gly Val Gly Leu Gly Pro Gly Pro Met Gly Leu
1               5                   10                  15

Met Gly Pro Arg Gly Pro Pro Gly Ala Ala Gly Ala Pro Gly Pro Gln
                20                  25                  30

Gly Phe Gln Gly Pro Ala Gly Glu Pro Gly Glu Pro Gly Gln Thr Gly
            35                  40                  45

Pro Ala Gly Ala Arg Gly Pro Ala Gly Pro Pro Gly Lys Ala Gly Glu
        50                  55                  60

Asp Gly His Pro Gly Lys Pro Gly Arg Pro Gly Glu Arg Gly Val Val
65                  70                  75                  80

(2) INFORMATION FOR SEQ ID NO: 39:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

ATGGGGCTCG CTGGCCCACC GGGCGAACCG GGTCCGCCAG GCCCGAAAGG TCCGCGTGGC      60

GATAGCGGGC TCGCTGGCCC ACCGGGCGAA CCGGGTCCGC CAGGCCCGAA AGGTCCGCGT     120

GGCGATAGCG GGCTCGCTGG CCCACCGGGC GAACCGGGTC CGCCAGGCCC GAAAGGTCCG     180

CGTGGCGATA GCGGGCTCGC TGGCCCACCG GGCGAACCGG GTCCGCCAGG CCCGAAAGGT     240

CCGCGTGGCG ATAGCGGGCT CCCGGGCGAT TCCTAA                              276

(2) INFORMATION FOR SEQ ID NO: 40:

(i) SEQUENCE CHARACTERISTICS:
        (A) LENGTH: 91 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 40:

Met Gly Leu Ala Gly Pro Pro Gly Glu Pro Gly Pro Pro Gly Pro Lys
1               5                   10                  15

Gly Pro Arg Gly Asp Ser Gly Leu Ala Gly Pro Pro Gly Glu Pro Gly
                20                  25                  30

Pro Pro Gly Pro Lys Gly Pro Arg Gly Asp Ser Gly Leu Ala Gly Pro
            35                  40                  45

Pro Gly Glu Pro Gly Pro Pro Gly Pro Lys Gly Pro Arg Gly Asp Ser
        50                  55                  60

Gly Leu Ala Gly Pro Pro Gly Glu Pro Gly Pro Pro Gly Pro Lys Gly
65                  70                  75                  80

Pro Arg Gly Asp Ser Gly Leu Pro Gly Asp Ser
                85                  90

(2) INFORMATION FOR SEQ ID NO: 41:

(i) SEQUENCE CHARACTERISTICS:

```
        (A) LENGTH: 13 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 41:

Gly Pro Pro Gly Leu Ala Gly Pro Pro Gly Glu Ser Gly
1               5                   10

(2) INFORMATION FOR SEQ ID NO: 42:

(i) SEQUENCE CHARACTERISTICS:
        (A) LENGTH: 13 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 2..3
        (D) OTHER INFORMATION: /product= "4-hydroxyproline"

(ix) FEATURE:
        (A) NAME/KEY: Modified-site
        (B) LOCATION: 8..9
        (D) OTHER INFORMATION: /product= "Xaa = 4-hydroxyproline"

(xi) SEQUENCE DESCRIPTION: SEQ ID NO: 42:

Gly Xaa Xaa Gly Leu Ala Gly Xaa Xaa Gly Glu Ser Gly
1               5                   10

(2) INFORMATION FOR SEQ ID NO: 43:

(i) SEQUENCE CHARACTERISTICS:
        (A) LENGTH: 660 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 43:

ATGGGCCCGC CGGGTCTGGC GGGCCCTCCG GGTGAAAGCG GTCGTGAAGG CGCGCCGGGT      60

GCCGAAGGCA GCCCAGGCCG CGACGGTAGC CCGGGGGCCA AGGGGATCG TGGTGAAACC      120

GGCCCGGCGG GCCCCCCGGG TGCACCGGGC GCGCCGGGTG CCCCAGGCCC GGTGGGCCCG     180

GCGGGCAAAA GCGGTGATCG TGGTGAGACC GGTCCGGCGG GCCCGGCCGG TCCGGTGGGC     240

CCAGCGGGCG CCCGTGGCCC GGCCGGTCCG CAGGGCCCGC GGGGTGACAA AGGTGAAACG     300

GGCGAACAGG GCGACCGTGG CATTAAAGGC CACCGTGGCT TCAGCGGCCT GCAGGGTCCA     360

CCGGGCCCGC CGGGCAGTCC GGGTGAACAG GGTCCGTCCG GAGCCAGCGG GCCGGCGGGC     420

CCACGCGGTC CGCCGGGCAG CGCGGGCGCG CCGGGCAAAG ACGGTCTGAA CGGTCTGCCG     480

GGCCCGATCG GCCCGCCGGG CCCACGCGGC CGCACCGGTG ATGCGGGTCC GGTGGGTCCC     540

CCGGGCCCGC CGGGCCCGCC AGGCCCGCCG GGACCGCCGA GCGCGGGTTT CGACTTCAGC     600

TTCCTGCCGC AGCCGCCGCA GGAGAAAGCG CACGACGGCG GTCGCTACTA CCGTGCGTAA     660

(2) INFORMATION FOR SEQ ID NO: 44:

(i) SEQUENCE CHARACTERISTICS:
        (A) LENGTH: 219 amino acids
        (B) TYPE: amino acid
```

(C) STRANDEDNESS: single
(D) TOPOLOGY: unknown (ii) MOLECULE TYPE: peptide (xi) SEQUENCE DESCRIPTION: SEQ ID NO: 44:

```
Met Gly Pro Pro Gly Leu Ala Gly Pro Pro Gly Glu Ser Gly Arg Glu
1               5                   10                  15
Gly Ala Pro Gly Ala Glu Gly Ser Pro Gly Arg Asp Gly Ser Pro Gly
            20                  25                  30
Ala Lys Gly Asp Arg Gly Glu Thr Gly Pro Ala Gly Pro Pro Gly Ala
        35                  40                  45
Pro Gly Ala Pro Gly Ala Pro Gly Pro Val Gly Pro Ala Gly Lys Ser
    50                  55                  60
Gly Asp Arg Gly Glu Thr Gly Pro Ala Gly Pro Ala Gly Pro Val Gly
65                  70                  75                  80
Pro Ala Gly Ala Arg Gly Pro Ala Gly Pro Gln Gly Pro Arg Gly Asp
                85                  90                  95
Lys Gly Glu Thr Gly Glu Gln Gly Asp Arg Gly Ile Lys Gly His Arg
            100                 105                 110
Gly Phe Ser Gly Leu Gln Gly Pro Pro Gly Pro Pro Gly Ser Pro Gly
        115                 120                 125
Glu Gln Gly Pro Ser Gly Ala Ser Gly Pro Ala Gly Pro Arg Gly Pro
    130                 135                 140
Pro Gly Ser Ala Gly Ala Pro Gly Lys Asp Gly Leu Asn Gly Leu Pro
145                 150                 155                 160
Gly Pro Ile Gly Pro Pro Gly Pro Arg Gly Arg Thr Gly Asp Ala Gly
                165                 170                 175
Pro Val Gly Pro Pro Gly Pro Pro Gly Pro Pro Gly Pro Pro Gly Pro
            180                 185                 190
Pro Ser Ala Gly Phe Asp Phe Ser Phe Leu Pro Gln Pro Pro Gln Glu
        195                 200                 205
Lys Ala His Asp Gly Gly Arg Tyr Tyr Arg Ala
    210                 215
```

(2) INFORMATION FOR SEQ ID NO: 45:

(i) SEQUENCE CHARACTERISTICS:
(A) LENGTH: 627 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 45:

```
ATGGGCTCTC CGGGTGTTAA CGGCGCCCCT GGTGAAGCGG GCCGCGACGG CAATCCGGGC      60
AACGATGGTC CGCCGGGTCG TGATGGTCAG CCGGGTCACA AGGTGAGCG  TGGCTACCCG     120
GGTAACATCG GTCCGGTTGG TGCGGCCGGC GCTCCGGGTC CGCACGGTCC GGTAGGCCCA     180
GCCGGCAAAC ACGGTAACCG TGGTGAAACG GGTCCGTCCG GTCCGGTAGG TCCGGCGGGT     240
GCTGTTGGTC CACGCGGCCC GTCCGGCCCG CAGGGTATTC GCGGTGACAA AGGCGAACCG     300
GGCGAAAAAG GTCCGCGTGG TCTGCCGGGC CTTAAGGGCC ACAACGGTCT GCAAGGTCTG     360
CCGGGTATCG CGGGTCACCA CGGTGATCAG GGTGCTCCGG GTTCCGTTGG TCCGGCCGGT     420
CCGCGTGGCC CGGCTGGTCC GTCTGGTCCG GCCGGTAAAG ACGGCCGTAC GGGCCACCCG     480
GGTACGGTGG GTCCGGCCGG CATTCGCGGT CCGCAAGGTC ACCAGGGTCC GGCGGGTCCG     540
```

```
CCGGGTCCGC CGGGTCCGCC GGGTCCGCCG GGTGTTAGCG GTGGCGGTTA TGATTTTGGT    600

TATGACGGTG ATTTCTATCG TGCGTAA                                        627
```

(2) INFORMATION FOR SEQ ID NO: 46:

(i) SEQUENCE CHARACTERISTICS:
        (A) LENGTH: 219 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 46:

```
Met Gly Pro Pro Gly Leu Ala Gly Pro Pro Gly Glu Ser Gly Arg Glu
1               5                   10                  15

Gly Ala Pro Gly Ala Glu Gly Ser Pro Gly Arg Asp Gly Ser Pro Gly
            20                  25                  30

Ala Lys Gly Asp Arg Gly Glu Thr Gly Pro Ala Gly Pro Pro Gly Ala
        35                  40                  45

Pro Gly Ala Pro Gly Ala Pro Gly Pro Val Gly Pro Ala Gly Lys Ser
    50                  55                  60

Gly Asp Arg Gly Glu Thr Gly Pro Ala Gly Pro Ala Gly Pro Val Gly
65                  70                  75                  80

Pro Ala Gly Ala Arg Gly Pro Ala Gly Pro Gln Gly Pro Arg Gly Asp
                85                  90                  95

Lys Gly Glu Thr Gly Glu Gln Gly Asp Arg Gly Ile Lys Gly His Arg
            100                 105                 110

Gly Phe Ser Gly Leu Gln Gly Pro Pro Gly Pro Pro Gly Ser Pro Gly
        115                 120                 125

Glu Gln Gly Pro Ser Gly Ala Ser Gly Pro Ala Gly Pro Arg Gly Pro
    130                 135                 140

Pro Gly Ser Ala Gly Ala Pro Gly Lys Asp Gly Leu Asn Gly Leu Pro
145                 150                 155                 160

Gly Pro Ile Gly Pro Pro Gly Pro Arg Gly Arg Thr Gly Asp Ala Gly
                165                 170                 175

Pro Val Gly Pro Pro Gly Pro Pro Gly Pro Pro Gly Pro Pro Gly Pro
            180                 185                 190

Pro Ser Ala Gly Phe Asp Phe Ser Phe Leu Pro Gln Pro Pro Gln Glu
        195                 200                 205

Lys Ala His Asp Gly Gly Arg Tyr Tyr Arg Ala
    210                 215
```

(2) INFORMATION FOR SEQ ID NO: 47:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 47:

```
GGAATTCTCC CATGGGCCCG CCGGGTCTGG CGGGCCCTCC GGGTGAAAGC GGTCGTGAAG    60

GCGCGCCGGG TGCCGAAGGC AGCCCAGGCC GCGAC                                95
```

(2) INFORMATION FOR SEQ ID NO: 48:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 48:

CTTCCGTCGG GTCCGGCGCT GCCATCGGGC CCCCGGTTTC CCCTAGCACC ACTTTGGCCG      60

GGCCGCCCGG GGGGCCCACG TGGCATTATT CGAACCC                              97

(2) INFORMATION FOR SEQ ID NO: 49:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 49:

GGAATTCGGT GCACCGGGCG CGCCGGGTGC CCCAGGCCCG GTGGGCCCGG CGGGCAAAAG      60

CGGTGATCGT GGCGAGACCG GTCCGGCGGG C                                    91

(2) INFORMATION FOR SEQ ID NO: 50:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 50:

CTCTGGCCAG GCCGCCCGGG CCGGCCAGGC CACCCGGGTC GCCCGCGGGC ACCGGGCCGG      60

CCAGGCGTCC CGGGCGCCAT TATTCGAACC C                                    91

What is claimed is:

1. Nucleic acid comprising the sequence shown in SEQ. ID. NO. 31.

2. Nucleic acid comprising the sequence shown in SEQ. ID. NO. 45.

* * * * *